United States Patent
Yu et al.

(10) Patent No.: US 9,775,830 B2
(45) Date of Patent: *Oct. 3, 2017

(54) DIHYDROPYRAZOLES

(71) Applicant: Merck Patent GmbH, Darmstadt (DE)

(72) Inventors: Henry Yu, Wellesley, MA (US); Thomas E. Richardson, Chapel Hill, NC (US); Robert James Foglesong, Durham, NC (US); Lizbeth Celeste Deselm, Melrose, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/342,550

(22) Filed: Nov. 3, 2016

(65) Prior Publication Data

US 2017/0071910 A1 Mar. 16, 2017

Related U.S. Application Data

(63) Continuation of application No. 14/300,945, filed on Jun. 10, 2014, now Pat. No. 9,517,227, which is a
(Continued)

(51) Int. Cl.
| | |
|---|---|
| C07D 231/12 | (2006.01) |
| A61K 31/423 | (2006.01) |
| A61K 31/427 | (2006.01) |
| A61K 31/415 | (2006.01) |
| A61K 31/4155 | (2006.01) |
| C07D 401/04 | (2006.01) |
| C07D 401/06 | (2006.01) |
| C07D 403/06 | (2006.01) |
| C07D 405/04 | (2006.01) |
| C07D 405/06 | (2006.01) |
| C07D 405/14 | (2006.01) |
| C07D 409/04 | (2006.01) |

(Continued)

(52) U.S. Cl.
CPC .......... *A61K 31/415* (2013.01); *A61K 9/0014* (2013.01); *A61K 9/0019* (2013.01); *A61K 9/0031* (2013.01); *A61K 9/0048* (2013.01); *A61K 9/0078* (2013.01); *A61K 9/06* (2013.01); *A61K 9/19* (2013.01); *A61K 9/2018* (2013.01); *A61K 9/2059* (2013.01); *A61K 9/48* (2013.01); *A61K 31/4155* (2013.01); *A61K 31/423* (2013.01); *A61K 31/427* (2013.01); *A61K 31/437* (2013.01); *A61K 31/4709* (2013.01); *A61K 31/506* (2013.01); *A61K 31/5377* (2013.01); *A61K 45/06* (2013.01); *A61K 47/06* (2013.01); *C07D 231/06* (2013.01); *C07D 231/12* (2013.01); *C07D 401/04* (2013.01); *C07D 401/06* (2013.01); *C07D 401/10* (2013.01); *C07D 403/04* (2013.01); *C07D 403/06* (2013.01); *C07D 403/10* (2013.01); *C07D 405/04* (2013.01); *C07D 405/06* (2013.01); *C07D 405/10* (2013.01); *C07D 405/14* (2013.01); *C07D 409/04* (2013.01); *C07D 409/06* (2013.01); *C07D 413/06* (2013.01); *C07D 413/10* (2013.01); *C07D 417/10* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,250,185 A | 2/1981 | Gaughan | |
| 6,653,338 B2 * | 11/2003 | El Tayer | C07K 5/06139 514/411 |

(Continued)

FOREIGN PATENT DOCUMENTS

| | | |
|---|---|---|
| CN | 101243048 A1 | 7/2006 |
| EP | 0035792 A2 | 9/1981 |

(Continued)

OTHER PUBLICATIONS

Acharya et al., Synthesis and antimalarial evaluation of 1, 3, 5-trisubstituted pyrazolines, European Journal of Medicinal Chemistry, 45: 430-438 (2010).

(Continued)

*Primary Examiner* — Kamal Saeed
(74) *Attorney, Agent, or Firm* — Dwight D. Kim; EMD Serono Research and Development Institute

(57) ABSTRACT

Novel dihydropyrazole derivatives of formula (I)

(I)

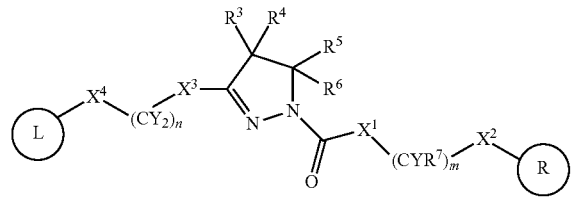

wherein L, R, $R^3$, $R^4$, $R^5$, $R^6$, $R^7$, $X^1$, $X^2$, $X^3$, $X^4$, Y, m and n have the meaning according to the claims, are positive allosteric modulators of the FSH receptor, and can be employed, inter alia, for the treatment of fertility disorders.

4 Claims, No Drawings

Related U.S. Application Data continuation-in-part of application No. 13/533,759, filed on Jun. 26, 2012, now Pat. No. 8,791,114.

(60) Provisional application No. 61/503,694, filed on Jul. 1, 2011.

(51) Int. Cl.

| | | |
|---|---|---|
| *C07D 409/06* | (2006.01) | |
| *C07D 413/06* | (2006.01) | |
| *A61K 31/437* | (2006.01) | |
| *A61K 31/4709* | (2006.01) | |
| *A61K 31/506* | (2006.01) | |
| *A61K 31/5377* | (2006.01) | |
| *A61K 45/06* | (2006.01) | |
| *C07D 231/06* | (2006.01) | |
| *C07D 401/10* | (2006.01) | |
| *C07D 403/04* | (2006.01) | |
| *C07D 403/10* | (2006.01) | |
| *C07D 405/10* | (2006.01) | |
| *C07D 413/10* | (2006.01) | |
| *C07D 417/10* | (2006.01) | |
| *C07D 471/04* | (2006.01) | |
| *A61K 9/00* | (2006.01) | |
| *A61K 47/06* | (2006.01) | |
| *A61K 9/06* | (2006.01) | |
| *A61K 9/19* | (2006.01) | |
| *A61K 9/20* | (2006.01) | |
| *A61K 9/48* | (2006.01) | |

(56) References Cited

U.S. PATENT DOCUMENTS

| | | |
|---|---|---|
| 6,831,083 B2 | 12/2004 | Fujiwara |
| 8,404,685 B2 | 3/2013 | Dorsch |
| 2004/0147562 A1 | 7/2004 | Solow-Cordero et al. |
| 2008/0269206 A1 | 10/2008 | Russell et al. |
| 2010/0137394 A1 | 6/2010 | Brunton et al. |
| 2011/0071153 A1 | 3/2011 | Dorsch et al. |

FOREIGN PATENT DOCUMENTS

| | | |
|---|---|---|
| EP | 1270567 A1 | 1/2003 |
| WO | 0132173 A1 | 5/2001 |
| WO | 0209706 A1 | 2/2002 |
| WO | 03079973 A2 | 10/2003 |
| WO | 2007019933 A1 | 2/2007 |
| WO | 2007038425 A2 | 4/2007 |
| WO | 2008121877 A2 | 10/2008 |
| WO | 2010136438 A1 | 12/2010 |

OTHER PUBLICATIONS

Kini et al., Synthesis, antitubercular activity and docking study of novel cyclic substituted diphenyl ether derivatives, European Journal of Medicinal Chemistry, 44: 492-500 (2009).
Patani et al., Chemical Reviews, 96: 3147-3176 (1996).
Baumstark et al. Journal of Heterocyclic Chemistry, vol. 27, pp. 291-294 (1990).
Biscoe et al. J. Am. Soc. 130: 6686-6687 (2008).
Bundgaard H. Design of Prodrugs, Elsevier 1985.
Bundgaard H. A Textbook of Drug Design and Development, Harwood Academic Publishers, Chapter 5: 131-191, (1991).
Carmacho et al. Journal of Medicinal Chemistry, 47(23) pp. 5641-5650 (2004).
Chan et al. Chemical Abstracts Service, Columbus, Ohio, US XP002685759 (2002).
Cignarella et al. Synthesis, pp. 320-321 (1989).
Fors et al. J. Am. Chem. Soc. 130: 13552-13554 (2008).
Gembus et al. Organic & Biomolecular Chemistry, vol. 8, pp. 3287-3293 (2010).
Mahe et al. Angewandte Chemie International Edition, 49(39) pp. 7072-7075 (2010).
Oliveira Baptista et al. Journal of the Chemical Society, Perkin Transactions 1, pp. 1477-1500 (1977).
Wermuth et al. The Practice of Medicinal Chemistry, Academic Press, Chapter 31: 671-696, (1996).
Yanofsky et.al. J. Biol. Chem. 281(19): 13226-13233 (2006).
Yoshida et al. Int. J. Pharm. 115, 61-67 (1995).

\* cited by examiner

DIHYDROPYRAZOLES

PRIORITY CLAIM

This application is a continuation application of U.S. application Ser. No. 14/300,945, filed on Jun. 10, 2014, which is a continuation application of U.S. application Ser. No. 13/533,759, filed on Jun. 26, 2012, which claims the benefit of U.S. Provisional application Ser. No. 61/503,694 filed on Jul. 1, 2011. The entire contents of the aforementioned applications are hereby incorporated by reference.

FIELD OF THE INVENTION

The present invention relates to compounds of formula (I)

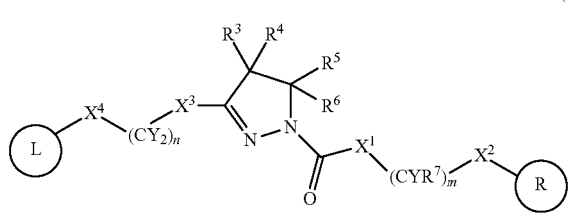

wherein L, R, $R^3$, $R^4$, $R^5$, $R^6$, $R^7$, $X^1$, $X^2$, $X_3$, $X^4$, Y, m and n have the meaning according to the claims, and/or physiologically acceptable salts thereof. The compounds of formulas (I) can be used as positive allosteric modulators of the follicle stimulating hormone receptor (FSHR). Objects of the invention are also pharmaceutical compositions comprising the compounds of formula (I), and the use of the compounds of formula (I) for the treatment of fertility disorders.

BACKGROUND

Gonadotropins serve important functions in a variety of bodily functions including metabolism, temperature regulation and the reproductive process. Gonadotropins act on specific gonadal cell types to initiate ovarian and testicular differentiation and steroidogenesis. The gonadotropin FSH (follicle stimulating hormone) is released from the anterior pituitary under the influence of gonadotropin-releasing hormone and estrogens, and from the placenta during pregnancy. FSH is a heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. In the female, FSH plays a pivotal role in the stimulation of follicle development and maturation and in addition, it is the major hormone regulating secretion of estrogens, whereas LH induces ovulation. In the male, FSH is responsible for the integrity of the seminiferous tubules and acts on Sertoli cells to support gametogenesis.

The hormones are relatively large (28-38 kDa) and are composed of a common α-subunit non-covalently bound to a distinct n-subunit that confers receptor binding specificity. The cellular receptor for these hormones is expressed on testicular Sertoli cells and ovarian granulosa cells. The FSH receptor is known to be members of the G protein-coupled class of membrane-bound receptors, which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: a hydrophilic amino-terminal region, considered to be the amino-terminal extracellular domain; seven hydrophobic segments of membrane-spanning length, considered to be the transmembrane domain; and a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β-2-adrenergic, rhodopsin, and substance K receptors, by the large size of the hydrophilic amino-terminal domain, which is involved in hormone binding.

Annually in the U.S. there are 2.4 million couples experiencing infertility that are potential candidates for treatment. FSH, either extracted from urine or produced by recombinant DNA technology, is a parenterally-administered protein product used by specialists for ovulation induction and for controlled ovarial hyperstimulation. Whereas ovulation induction is directed at achieving a single follicle to ovulate, controlled ovarial hyperstimulation is directed at harvesting multiple oocytes for use in various in-vitro assisted reproductive technologies, e.g. in-vitro fertilization (IVF). FSH is also used clinically to treat male hypogonadism and male infertility, e.g. some types of failure of spermatogenesis.

FSHR is a highly specific target in the ovarian follicle growth process and is exclusively expressed in the ovary. However, the use of FSH is limited by its high cost, lack of oral dosing, and need of extensive monitoring by specialist physicians. Hence, identification of a non-peptidic small molecule substitute for FSH that could potentially be developed for oral administration is desirable. Low molecular weight FSH mimetics with agonistic properties are disclosed in the international applications WO 2002/09706 and WO 2010/136438 as well as the U.S. Pat. No. 6,653,338. There is still a need for low molecular weight hormone mimetics that selectively activate FSHR.

SUMMARY OF THE INVENTION

The invention had the object of finding novel compounds having valuable properties, in particular those which can be used for the preparation of medicaments.

It has been surprisingly found that the compounds according to the invention and salts thereof have very valuable pharmacological properties while being well tolerated. In particular, they act as FSHR agonists. The invention relates to compounds of formula (I)

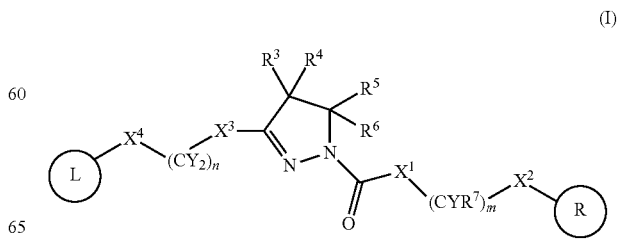

wherein

R, L denote $Ar^1$ or $Het^1$;

$R^1$ denotes Hal, A, —$(CY_2)_p$—OY, —$(CY_2)_p$—$NY_2$, COOY, $CONY_2$, NHCOY, CN, $SO_2Y$, -E-$(CY_2)_p$—$Ar^2$, -E-$(CY_2)_p$-$Het^1$ or -E-$(CY_2)_p$-$Het^3$;

$R^2$ denotes Hal, A, —$(CY_2)_p$—OY, —$(CY_2)_p$—$NY_2$, COOY, $CONY_2$, —CONY-Cyc, $NO_2$, CN, SY, SOY, $SO_2Y$, $SO_2NY_2$, $NHSO_2Y$, alkenyl or -E-$(CY_2)_p$—$Ar^2$;

$R^3$, $R^4$, $R^5$, $R^6$ denote independently from one another H, A or $Ar^2$;

$R^7$ denotes Y, OY or $NY_2$;

$X^1$, $X^2$, $X^3$, $X^4$ denote independently from one another O, NY or a single bond,
   with the proviso that m denotes 0 if $X^1$ and $X^2$ denote a single bond;

E denotes —C≡C—, $SO_2$, —$SO_2$—NY—, O, NY or a single bond;

Y denotes H or A;

A denotes unbranched or branched alkyl having 1-10 C atoms,
   in which 1-7 H atoms can be replaced by Hal;

Cyc denotes cycloalkyl having 3-7 C atoms,
   in which 1-4 H atoms can be replaced independently from one another by Hal or A;

$Ar^1$ denotes a saturated, unsaturated or aromatic, mono- or bicyclic carbocycle having 3-10 C atoms,
   which can be substituted by at least one substituent selected from the group of $R^1$, $R^2$ and —C≡C—$C(A)_2OH$, or which can be fused to Cyc, $Het^1$ or $Het^3$;

$Ar^2$ denotes an aromatic, mono- or bicyclic carbocycle having 6-10 C atoms, which can be substituted by at least one substituent selected from the group of Hal, A and —$(CY_2)_p$—OY;

$Het^1$ denotes an unsaturated or aromatic monocyclic heterocycle having 3-7 C atoms and 1-4 N, O and/or S atoms,
   which can be substituted by at least one substituent selected from the group of Hal, A, —$(CY_2)_p$—OY, —$(CY_2)_p$—$NY_2$, —$(CY_2)_p$—$Ar^2$, —$(CY_2)_p$-$Het^2$, $Het^3$ and CN;

$Het^2$ denotes an aromatic monocyclic heterocycle having 5-7 C atoms and 1-3 N atoms,
   which can be substituted by at least one substituent selected from the group of Hal, A and —$(CY_2)_p$—OY;

$Het^3$ denotes a saturated monocyclic heterocycle having 3-7 C atoms and 1-4 N, O and/or S atoms,
   which can be substituted by at least one substituent selected from the group of Hal, A, —$(CY_2)_p$—OY, —$(CY_2)_p$—$NY_2$, COOY, COY, —$CONY_2$, =O and CN;

Hal denotes F, Cl, Br or I; and m, n, p denote independently from one another 0, 1, 2, 3 or 4;

and/or physiologically acceptable salts thereof.

For the sake of clarity, R and L denote both either $Ar^1$ or $Het^1$. R and L, respectively, can be bound on, substituted at and/or fused via any (ring) atom unless stated otherwise. The fusion of Cyc, $Het^1$ or $Het^3$ to the carbocycle in the $Ar^1$ definition refers to a condensed ring system, wherein another ring system is constructed on the mono- or bicyclic carbocycle with the result of a bi- or tricyclic carbocycle.

DETAILED DESCRIPTION OF THE INVENTION

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Y_2$) the expression of such substituent may differ from each other (e.g. methyl and ethyl). It shall be understood accordingly that a multiple substitution by any radical of the invention (e.g. $R^2$ in sub-formula I-B) may involve identical or different radicals (e.g. OA and/or Hal). Hence, if individual radicals occur a number of times within a compound, the radicals adopt the meanings indicated, independently of one another. In case of a multiple substitution, the radical could be alternatively designated with R', R", R''', R'''' etc.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, "A" denotes unbranched or branched alkyl having 1-10 C atoms, in which 1-7 H atoms may be replaced by Hal. A more preferred "A" denotes unbranched or branched alkyl having 1-5 C atoms, in which 1-3 atoms may be replaced by F and/or Cl. Most preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It is a highly preferred embodiment of the invention that "A" denotes methyl. It shall be understood that the respective denotation of "A" is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "Cyc" denotes cycloalkyl having 3-7 C atoms, in which 1-4 H atoms may be replaced independently of one another by Hal and/or A. More preferred is $C_3$-$C_5$-cycloalkyl, i.e. cyclopropyl, cyclobutyl or cyclopentyl. Moreover, the definition of "A" shall also comprise cycloalkyls and it is to be applied mutatis mutandis to "Cyc". It shall be understood that the respective denotation of "Cyc" is independently of one another in any radical of the invention.

The term "alkenyl" refers to unbranched or branched alkenyl having 1, 2, 3, 4, 5 or 6 C atoms, i.e. $C_2$-$C_6$-alkenyls. Alkenyls have at least one C—C double bond. Example of suitable alkenyls are allyl, vinyl, propenyl, —$CH_2CH$=$CH_2$, —CH=CH—$CH_3$, —C(=$CH_2$)—$CH_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl.

The term "aryl" or "carboaryl" for the purposes of this invention refers to a mono- or polycyclic aromatic hydrocarbon systems having 3 to 14, preferably 4 to 10, more preferably 5 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise in-danyl, indenyl or 1,2,3,4-tetrahydronaphthyl. Preferred "carboaryls" of the invention are optionally substituted phenyl, naphthyl and biphenyl, more preferably optionally substituted monocylic carboaryl having 5-8 C atoms, most preferably optionally substituted phenyl, highly preferably optionally substituted phenyl if defined in terms of $R^1$ and/or $R^2$ radical.

In another embodiment of the invention, a "carbocycle", including, but not limited to, carboaryl, is defined as "Ar", including "$Ar^1$" and "$Ar^2$". Examples of suitable "Ar" radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

"$Ar^1$" preferably denotes a saturated, unsaturated or aromatic, mono- or bicyclic carbocycle having 3-10 C atoms, which can be substituted by at least one substituent selected from the group of $(R^1)_q$, $(R^2)_l$ and —C≡C—C(A)$_2$OH, or which can be fused to Cyc, $Het^1$ or $Het^3$. In a more preferred embodiment of the invention, "$Ar^1$" denotes a saturated, unsaturated or aromatic, mono- or bicyclic carbocycle having 3-10 C atoms, which is substituted by at least one substituent selected from the group of $R^1$, $R^2$ and —C≡C—C(A)$_2$OH, or which is fused to Cyc, $Het^1$ or $Het^3$. In another more preferred embodiment of the invention, "$Ar^1$" denotes an aromatic, monocyclic carbocycle having 5-8 C atoms, which can be mono-, di- or trisubstituted by at least one substituent selected from the group of $R^1$ and $R^2$. It is most preferred that "$Ar^1$" denotes an aromatic, monocyclic carbocycle having 5-8 C atoms, which is mono-, di- or trisubstituted by at least one substituent selected from the group of $R^1$ and $R^2$. In a highly preferred embodiment of the invention, "$Ar^1$" denotes phenyl, which can be mono- or disubstituted by $R^1$ and $R^2$. It shall be understood that the respective denotation of "$Ar^1$" is independently of one another in any radical of the invention.

"$Ar^2$" preferably denotes an aromatic, mono- or bicyclic carbocycle having 6-10 C atoms, which can be substituted by at least one substituent selected from the group of Hal, A and —(CY$_2$)$_p$—OY. In a more preferred embodiment of the invention, "$Ar^2$" denotes phenyl. It shall be understood that the respective denotation of "$Ar^2$" is independently of one another in any radical of the invention.

The term "heteroaryl" for the purposes of this invention refers to a 2-15, preferably 2-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, 3 or 4, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that "heteroaryl" in the realms of "$Het^1$" represents an unsaturated or aromatic monocyclic heterocycle having 3-7 C atoms and 1-4 N, O and/or S atoms, which can be substituted by at least one substituent selected from the group of Hal, A, —(CY$_2$)$_p$—OY, —(CY$_2$)$_p$—NY$_2$, —(CY$_2$)$_p$—Ar$^2$,
—(CY$_2$)$_p$-Het$^2$, Het$^3$ and CN. In a more preferred embodiment of the invention, "$Het^1$" denotes an unsaturated or aromatic monocyclic heterocycle having 3-6 C atoms and 1-3 N, O and/or S atoms, which can be substituted by at least one substituent selected from the group of Hal, A and OA. It is most preferred that "$Het^1$" denotes an unsaturated or aromatic monocyclic heterocycle having 3-6 C atoms and 1-3 N, O and/or S atoms, which is substituted by at least one substituent selected from the group of Hal, A and OA. In another most preferred embodiment of the invention, "$Het^1$" denotes pyrrolyl, furyl, thiophenyl, imidazolyl, pyrazyl, isoxazyl, thiazyl or pyridyl, which can be mono- or disubstituted by at least one substituent selected from the group of Hal, A and OA. It is particularly preferred that "$Het^1$" can be monosubstituted by A. It shall be understood that the respective denotation of "$Het^1$" is independently of one another in any radical of the invention.

It is preferred that "heteroaryl" in the realms of "$Het^2$" represents an aromatic monocyclic heterocycle having 5-7 C atoms and 1-3 N atoms, which can be substituted by at least one substituent selected from the group of Hal, A and —(CY$_2$)$_p$—OY. In a more preferred embodiment of the invention, "$Het^2$" denotes pyridyl.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated. In the case of a cyclic system consisting of at least two rings the rings may be fused or spiro or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyclyl radical. The bonding to the compounds of the general formula (I) can be effected via any possible ring member of the heterocyclyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In a preferred aspect of the invention, "$Het^3$" denotes a saturated monocyclic heterocycle having 3-7 C atoms and 1-4 N, O and/or S atoms, which can be substituted by at least one substituent selected from the group of Hal, A, —(CY$_2$)$_p$—OY, —(CY$_2$)$_p$—NY$_2$, COOY, COY, —CONY$_2$, =O and CN. In a more preferred embodiment of the invention, "$Het^3$" denotes a saturated monocyclic heterocycle having 3-6 C atoms and 1-2 N and/or O atoms, which can be substituted by at least one substituent selected from the group of Hal, COA and =O. In a most preferred embodiment of the invention, "$Het^3$" denotes pyrrolidinyl, tetrahydrofuryl, oxazolidinyl, dioxalanyl, piperazinyl, morpholinyl or dioxanyl, which can be mono- or disubstituted by at least one substituent selected from the group of Hal, COA and =O. It shall be understood that the respective denotation of "$Het^3$" is independently of one another in any radical of the invention.

The term "alkyloxy", "alkoxy" or "OA" for the purposes of this invention refers to an alkyl radical according to above definition that is attached to an oxygen atom. The attachment to the compounds of the general formula (I) is via the oxygen atom. Examples are methoxy, ethoxy and n-propyloxy, propoxy and isopropoxy. Preferred is "$C_1$-$C_4$-alkyloxy" having the indicated number of carbon atoms.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl (haloalkyl) or alkoxy group (e.g. CF₃ and CF₃O). It shall be understood that the respective denotation of "Hal" is independently of one another in any radical of the invention.

It is a preferred embodiment of the present invention that both R and L denote Ar¹, which can be substituted as defined above. In a more preferred embodiment of the invention, R denotes Ar¹, which can be substituted by R¹. It is most preferred that R denotes phenyl, which is monosubstituted in meta position by R¹. In another more preferred embodiment of the invention, L denotes Ar¹, which can be substituted by R². It is most preferred that L denotes phenyl, which is disubstituted in meta and para position by R².

It is a preferred embodiment of the R¹ radical according to the present invention to be Hal, A, —(CY₂)$_p$—OY, —(CY₂)$_p$—NY₂, COOY, CONY₂, NHCOY, CN, SO₂Y, -E-(CY₂)$_p$—Ar², -E-(CY₂)$_p$-Het¹ or -E-(CY₂)$_p$-Het³, more preferably Hal, A, —(CY₂)$_p$—OY, —(CY₂)$_p$—NY₂, CONY₂, NHCOA, CN, SO₂A, -E-(CY₂)$_p$—Ar², Het¹ or -E-Het³, most preferably Hal, A, CN, -E-phenyl or Het³, highly preferably Hal, CN or O-phenyl.

It is a preferred embodiment of the R² radical according to the present invention to be Hal, A, —(CY₂)$_p$—OY, —(CY₂)$_p$—NY₂, COOY, CONY₂, —CONY-Cyc, NO₂, CN, SY, SOY, SO₂Y, SO₂NY₂, NHSO₂Y, alkenyl or -E-(CY₂)$_p$—Ar², more preferably Hal, A, —(CY₂)$_p$—OY, —(CY₂)$_p$—NY₂, CONY₂, —CONH-Cyc, NO₂, CN, SA, SOA, SO₂A, SO₂NY₂, NHSO₂A, alkenyl, -E-(CY₂)$_p$—Ar² or Het¹, most preferably Hal, A, OA, NH₂, CN, SA, SO₂A, SO₂NH₂, O-phenyl or Het¹, or in another most preferred aspect Hal, A, —(CY₂)$_p$—OY, CONY₂, SA, NHSO₂A, -E-(CY₂)$_p$—Ar² or Het¹, highly preferably OA.

It is a preferred embodiment of the R³, R⁴, R⁵, R⁶ radicals according to the present invention to be independently from one another H, A or Ar², more preferably they denote independently from one another H or A, most preferably R³, R⁴ denote H and R⁵, R⁶ denote A, or R³, R⁴ denote A and R⁵, R⁶ denote H.

It is a preferred embodiment of the R⁷ radical according to the present invention to be H, OA or NA₂, more preferably H or OA.

It is a preferred embodiment of the X¹, X², X³, X⁴ radicals according to the present invention to be independently from one another O, NY or a single bond with the proviso that m denotes 0 if X¹ and X² denote a single bond, more preferably they denote independently from one another O, NH or a single bond with the proviso that m denotes 0 if X¹ and X² denote a single bond, preferably they denote a single bond and m denotes 0.

It is a preferred embodiment of the E radical according to the present invention to be —C≡C—, SO₂, —SO₂—NY—, O, NY or a single bond, more preferably —C≡C—, SO₂, —SO₂—NH—, O or a single bond, most preferably O or a single bond.

In an aspect of the invention, Y denotes H or A.

It is a preferred embodiment of the m, n, p indices according to the present invention to be independently from one another 0, 1, 2, 3 or 4, more preferably they denote independently from one another 0, 1, 2 or 3, most preferably they denote independently from one another 0, 1 or 2, highly preferably they denote independently from one another 0 or 1, particularly preferably they denote independently from one another 0. It shall be understood that the respective denotation of "p" is independently of one another in any radical of the invention.

It is a preferred embodiment of the q index according to the present invention to be 0, 1, 2, 3 or 4, more preferably 1, 2, 3 or 4, most preferably 1, 2 or 3, highly preferably 1 or 2.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means, the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another preferred embodiment of the present invention, dihydropyrazole derivatives of sub-formula (I-A) are provided

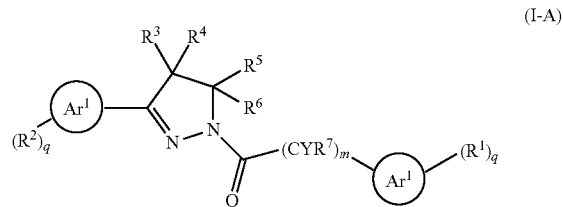

(I-A)

wherein
R¹ denotes Hal, A, —(CY₂)$_p$—OY, —(CY₂)$_p$—NY₂, CONY₂, NHCOA, CN, SO₂A, -E-(CY₂)$_p$—Ar², Het¹ or -E-Het³;
R² denotes Hal, A, —(CY₂)$_p$—OY, —(CY₂)$_p$—NY₂, CONY₂, —CONH-Cyc, NO₂, CN, SA, SOA, SO₂A, SO₂NY₂, NHSO₂A, alkenyl, -E-(CY₂)$_p$—Ar² or Het¹;
R³, R⁴, R⁵, R⁶ denote independently from one another H or A;
R⁷ denotes H, OA or NA₂;
E denotes —C≡C—, SO₂, —SO₂—NH—, O or a single bond;
Y denotes H or A;
A denotes unbranched or branched alkyl having 1-5 C atoms, in which 1-3 H atoms can be replaced by Hal;
Cyc denotes cycloalkyl having 3-5 C atoms;
Ar¹ denotes an aromatic, monocyclic carbocycle having 5-8 C atoms;
Ar² denotes phenyl;
Het¹ denotes an unsaturated or aromatic monocyclic heterocycle having 3-6 C atoms and 1-3 N, O and/or S atoms, which can be substituted by at least one substituent selected from the group of Hal, A and OA;
Het³ denotes a saturated monocyclic heterocycle having 3-6 C atoms and 1-2 N and/or O atoms, which can be substituted by at least one substituent selected from the group of Hal, COA and =O;
Hal denotes F, Cl, Br or I; and
m, p, q denote independently from one another 0, 1, 2 or 3;
and/or physiologically acceptable salts thereof.

It is a preferred embodiment of the m index according to the present invention to be 0 or 1. It is another preferred embodiment of the q index according to the present invention to be 1, 2 or 3, more preferably 1 or 2.

In a more preferred embodiment of the present invention, dihydropyrazole derivatives of sub-formula (I-B) are provided

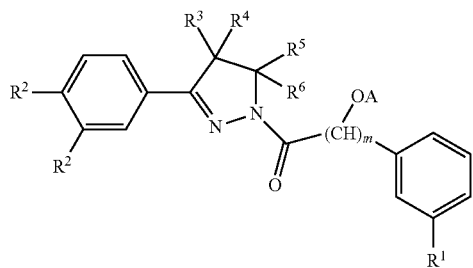
(I-B)

wherein
R$^1$ denotes Hal, A, CN, -E-phenyl or Het$^3$;
R$^2$ denotes Hal, A, OA, NH$_2$, CN, SA, SO$_2$A, SO$_2$NH$_2$, O-phenyl or Het$^1$;
R$^3$, R$^4$ denote H, and
R$^5$, R$^6$ denote A, or vice versa;
E denotes O or a single bond;
A denotes unbranched or branched alkyl having 1-5 C atoms;
Het$^1$ denotes pyrrolyl, furyl, thiophenyl, imidazolyl, pyrazyl, isoxazyl, thiazyl or pyridyl, which can be mono- or disubstituted by at least one substituent selected from the group of Hal, A and OA;
Het$^3$ denotes pyrrolidinyl, tetrahydrofuryl, oxazolidinyl, dioxalanyl, piperazinyl, morpholinyl or dioxanyl, which can be mono- or disubstituted by at least one substituent selected from the group of Hal, COA and =O;
Hal denotes F, Cl or Br; and
m denotes 0 or 1;
and/or physiologically acceptable salts thereof.

Most preferred embodiments are those compounds of formulae (I), (I-A) and (I-B) listed in Table 1.

TABLE 1

Compounds of formulae (I), (I-A), (I-B). Assay A: Example 10; Assay B: Example 11.

| No. | Name | Assay A | Assay B |
|---|---|---|---|
| 1 |  | 16.70 μM | 0.878 μM |
| 2 |  | 41.50% | |

TABLE 1-continued

Compounds of formulae (I), (I-A), (I-B). Assay A: Example 10; Assay B: Example 11.

| No. | Name | Assay A | Assay B |
|---|---|---|---|
| 3 | | 40.30 μM | 0.656 μM |
| 4 | | 6.00% | |
| 5 | | 6.00% | |
| 6 | | 11.00% | |

TABLE 1-continued

Compounds of formulae (I), (I-A), (I-B). Assay A: Example 10; Assay B: Example 11.

| No. | Name | Assay A | Assay B |
|---|---|---|---|
| 7 | | | |
| 8 | | | |
| 9 | | | |

TABLE 1-continued

Compounds of formulae (I), (I-A), (I-B). Assay A: Example 10; Assay B: Example 11.

| No. | Name | Assay A | Assay B |
|---|---|---|---|
| 10 | (3-(3,4-dimethoxyphenyl)-4,5-dihydro-1H-pyrazol-1-yl)(3-methoxyphenyl)methanone | | |
| 11 | (3-(3,4-dimethoxyphenyl)-4,5-dihydro-1H-pyrazol-1-yl)(3,5-dimethoxyphenyl)methanone | | |
| 12 | (3-(3,4-dimethoxyphenyl)-4,5-dihydro-1H-pyrazol-1-yl)(4-fluorophenyl)methanone | | |

TABLE 1-continued
Compounds of formulae (I), (I-A), (I-B). Assay A: Example 10; Assay B: Example 11.
| No. | Name | Assay A | Assay B |
|---|---|---|---|
| 13 | 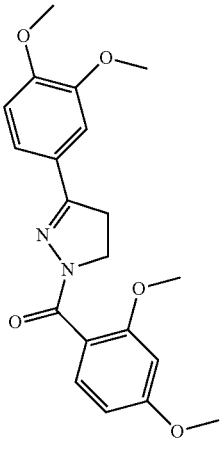 [SMILES: COc1ccc(C(=O)N2CCC(c3ccc(OC)c(OC)c3)=N2)c(OC)c1] | | |
| 14 | 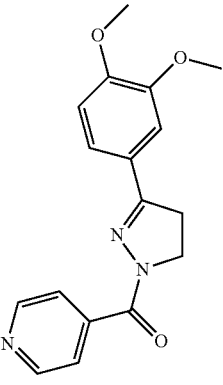 [SMILES: COc1ccc(C2=NN(C(=O)c3ccncc3)CC2)cc1OC] | | |
| 15 | 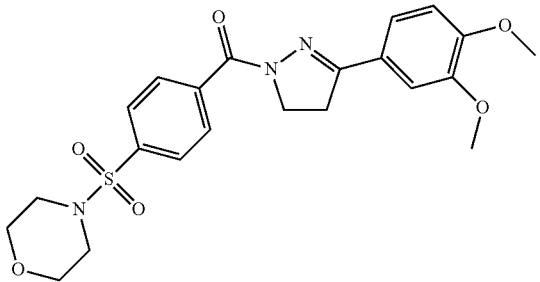 [SMILES: COc1ccc(C2=NN(C(=O)c3ccc(S(=O)(=O)N4CCOCC4)cc3)CC2)cc1OC] | | |
| 16 | 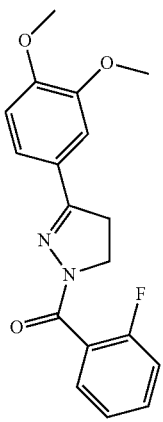 [SMILES: COc1ccc(C2=NN(C(=O)c3ccccc3F)CC2)cc1OC] | | |

TABLE 1-continued

Compounds of formulae (I), (I-A), (I-B). Assay A: Example 10; Assay B: Example 11.

| No. | Name | Assay A | Assay B |
|-----|------|---------|---------|
| 17 | | | |
| 18 | | | |
| 19 | | | |
| 20 | | | |

TABLE 1-continued
Compounds of formulae (I), (I-A), (I-B). Assay A: Example 10; Assay B: Example 11.
| No. | Name | Assay A | Assay B |
|---|---|---|---|
| 21 | 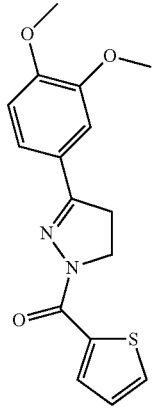 [SMILES: COc1ccc(C2=NN(C(=O)c3cccs3)CC2)cc1OC] | | |
| 22 | 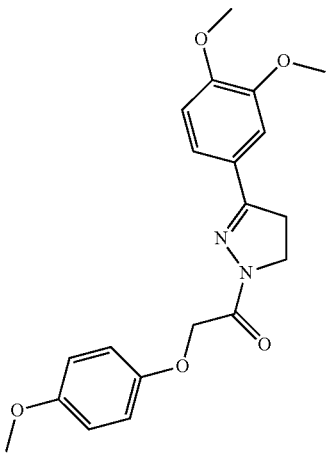 | | |
| 23 | 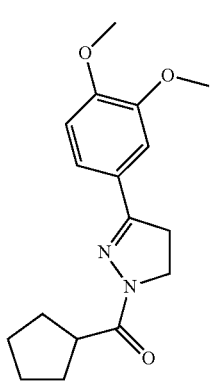 [SMILES: COc1ccc(C2=NN(C(=O)C3CCCC3)CC2)cc1OC] | | |

TABLE 1-continued

Compounds of formulae (I), (I-A), (I-B). Assay A: Example 10; Assay B: Example 11.

| No. | Name | Assay A | Assay B |
|---|---|---|---|
| 24 | | | |
| 25 | | | |
| 26 | | | |
| 27 | | | |

TABLE 1-continued
Compounds of formulae (I), (I-A), (I-B). Assay A: Example 10; Assay B: Example 11.
| No. | Name | Assay A | Assay B |
|---|---|---|---|
| 28 | 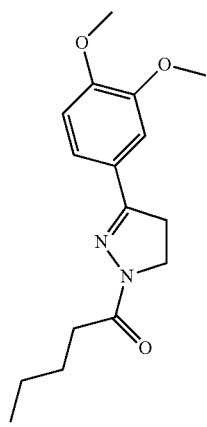 [SMILES: CCCCC(=O)N1CCC(c2ccc(OC)c(OC)c2)=N1] | | |
| 29 | 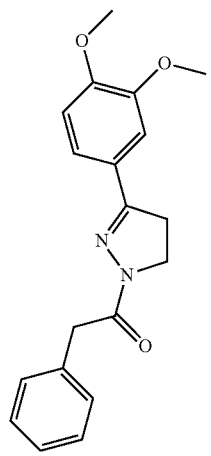 [SMILES: COc1ccc(C2=NN(C(=O)Cc3ccccc3)CC2)cc1OC] | | |
| 30 | 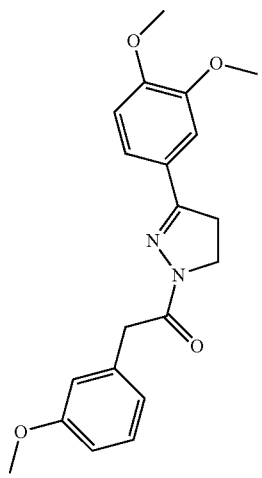 | | |

TABLE 1-continued
Compounds of formulae (I), (I-A), (I-B). Assay A: Example 10; Assay B: Example 11.
| No. | Name | Assay A | Assay B |
|---|---|---|---|
| 31 | 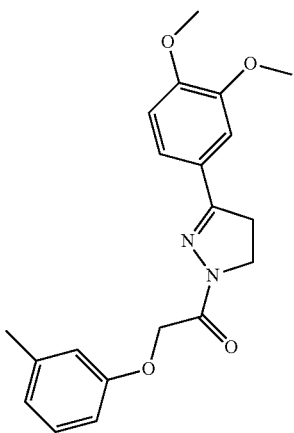 | | |
| 32 | 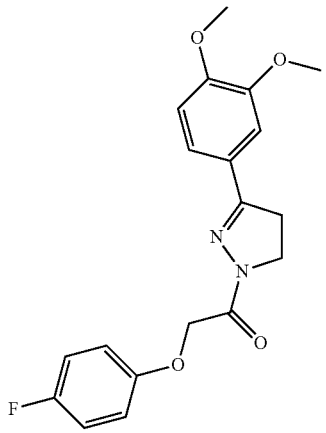 [SMILES: COc1ccc(C2=NN(C(=O)COc3ccc(F)cc3)CC2)cc1OC] | | |
| 33 | 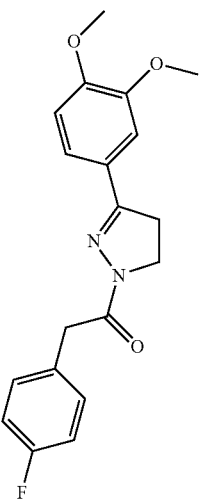 [SMILES: COc1ccc(C2=NN(C(=O)Cc3ccc(F)cc3)CC2)cc1OC] | | |

TABLE 1-continued

Compounds of formulae (I), (I-A), (I-B). Assay A: Example 10; Assay B: Example 11.

| No. | Name | Assay A | Assay B |
|-----|------|---------|---------|
| 34  |      |         |         |
| 35  |      |         |         |
| 36  |      |         | 40.50%  |
| 37  |      |         |         |
| 38  |      |         |         |
| 39  |      |         |         |
| 40  |      |         |         |

TABLE 1-continued
Compounds of formulae (I), (I-A), (I-B). Assay A: Example 10; Assay B: Example 11.
| No. | Name | Assay A | Assay B |
|---|---|---|---|
| 41 | 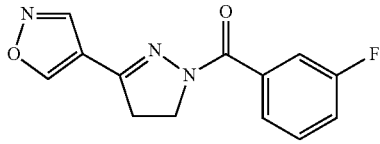 [SMILES: O=C(c1cccc(F)c1)N1CCC(c2cnoc2)=N1] | | |
| 42 | 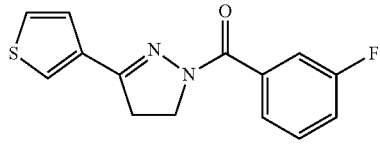 [SMILES: O=C(c1cccc(F)c1)N1CCC(c2ccsc2)=N1] | | |
| 43 | 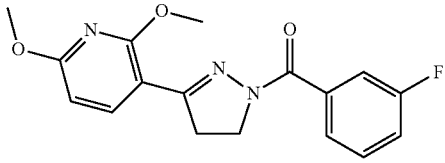 [SMILES: COc1ccc(C2=NN(C(=O)c3cccc(F)c3)CC2)c(OC)n1] | 17.50% | |
| 44 | 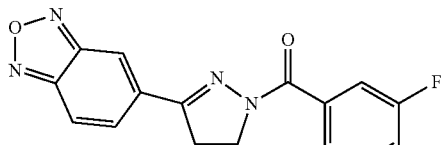 | | |
| 45 | 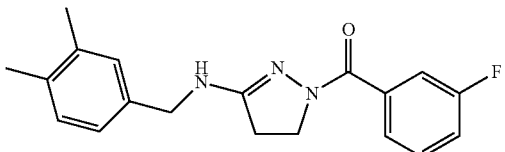 | 4.00% | |
| 46 | 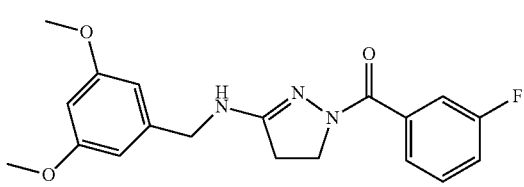 [SMILES: COc1cc(CNC2=NN(C(=O)c3cccc(F)c3)CC2)cc(OC)c1] | | |
| 47 | 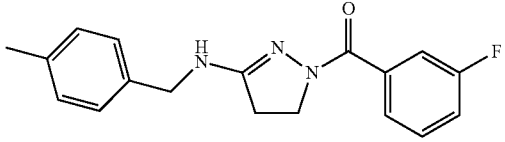 [SMILES: Cc1ccc(CNC2=NN(C(=O)c3cccc(F)c3)CC2)cc1] | | |
| 48 | 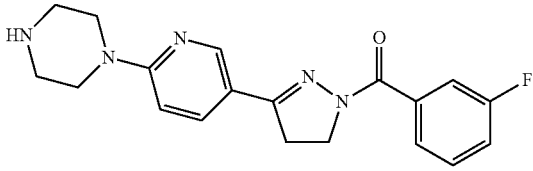 [SMILES: O=C(c1cccc(F)c1)N1CCC(c2ccc(N3CCNCC3)nc2)=N1] | 4.24% | |
| 49 | 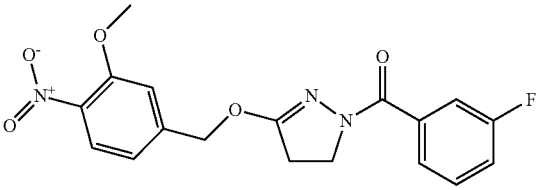 [SMILES: COc1cc(COC2=NN(C(=O)c3cccc(F)c3)CC2)ccc1[N+](=O)[O-]] | | |

TABLE 1-continued
Compounds of formulae (I), (I-A), (I-B). Assay A: Example 10; Assay B: Example 11.
| No. | Name | Assay A | Assay B |
|---|---|---|---|
| 50 | 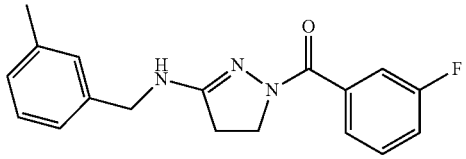 [SMILES: Cc1cccc(CNC2=NN(C(=O)c3cccc(F)c3)CC2)c1] | | |
| 51 | 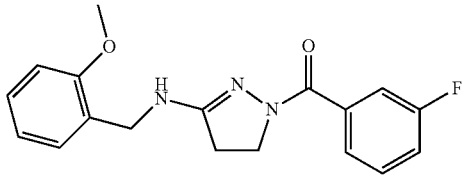 [SMILES: COc1ccccc1CNC1=NN(C(=O)c2cccc(F)c2)CC1] | | |
| 52 | 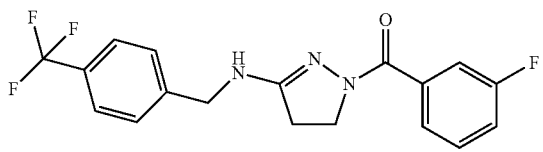 [SMILES: O=C(c1cccc(F)c1)N1CCC(NCc2ccc(C(F)(F)F)cc2)=N1] | | |
| 53 | 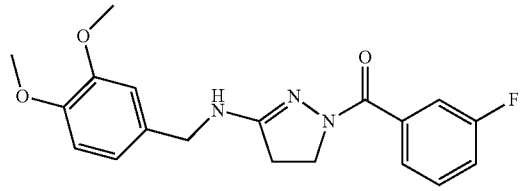 [SMILES: COc1ccc(CNC2=NN(C(=O)c3cccc(F)c3)CC2)cc1OC] | | |
| 54 | 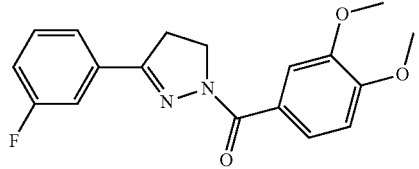 [SMILES: COc1ccc(C(=O)N2CCC(c3cccc(F)c3)=N2)cc1OC] | | |
| 55 | 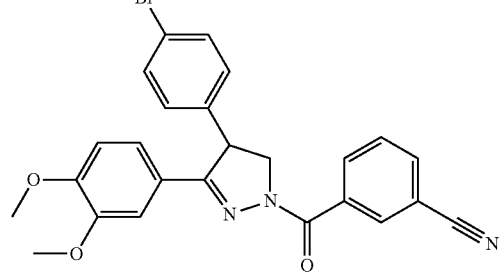 | | |
| 56 | 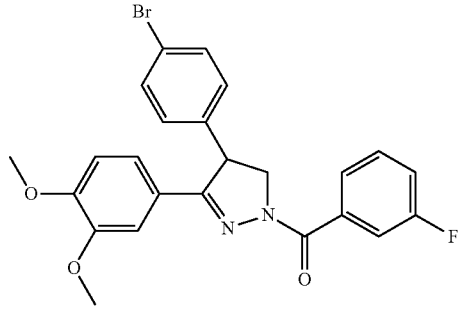 [SMILES: COc1ccc(C2=NN(C(=O)c3cccc(F)c3)CC2c2ccc(Br)cc2)cc1OC] | | |

TABLE 1-continued

Compounds of formulae (I), (I-A), (I-B). Assay A: Example 10; Assay B: Example 11.

| No. | Name | Assay A | Assay B |
|---|---|---|---|
| 57 | | | |
| 58 | | | |
| 59 | | | |
| 60 | | | |
| 61 | | 9.75 μM | 0.465 μM |
| 62 | | 6.49 μM | 0.0981 μM |

TABLE 1-continued

Compounds of formulae (I), (I-A), (I-B). Assay A: Example 10; Assay B: Example 11.

| No. | Name | Assay A | Assay B |
| --- | --- | --- | --- |
| 63 | | 25.90% | |
| 64 | | 11.00 μM | 0.348 μM |
| 65 | | 21.00 μM | 5.090 μM |
| 66 | | 15.40% | |
| 67 | | 21.00 μM | 0.814 μM |
| 68 | | 11.50% | |

TABLE 1-continued

Compounds of formulae (I), (I-A), (I-B). Assay A: Example 10; Assay B: Example 11.

| No. | Name | Assay A | Assay B |
| --- | --- | --- | --- |
| 69 | | 33.50% | |
| 70 | | 39.00 μM | 0.110 μM |
| 71 | | 14.70% | |
| 72 | | 40.00% | |
| 73 | | 5.48% | |
| 74 | | 34.00% | |

TABLE 1-continued
Compounds of formulae (I), (I-A), (I-B). Assay A: Example 10; Assay B: Example 11.
| No. | Name | Assay A | Assay B |
|---|---|---|---|
| 75 | 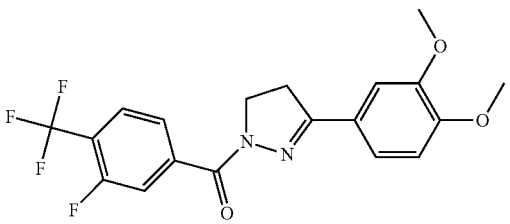 [SMILES: COc1ccc(C2=NN(C(=O)c3ccc(C(F)(F)F)c(F)c3)CC2)cc1OC] | 5.70 μM | |
| 76 | 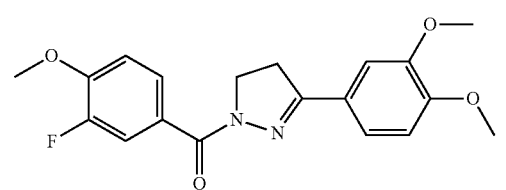 | 24.00% | |
| 77 | 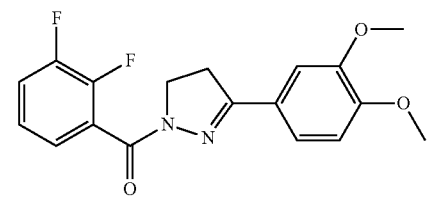 [SMILES: COc1ccc(C2=NN(C(=O)c3cccc(F)c3C)CC2)cc1OC] | 8.61 μM | 0.729 μM |
| 78 | 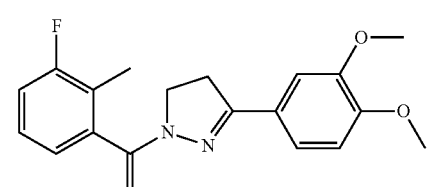 | 16.00% | |
| 79 | 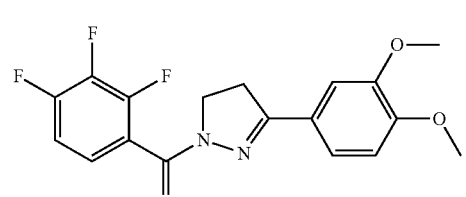 | 35.00% | |
| 80 | 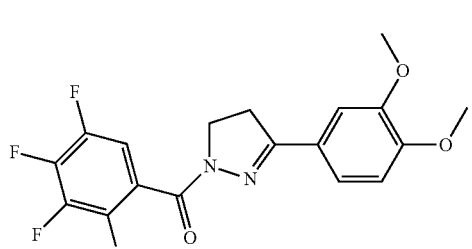 | 28.00 μM | 1.190 μM |
| 81 | 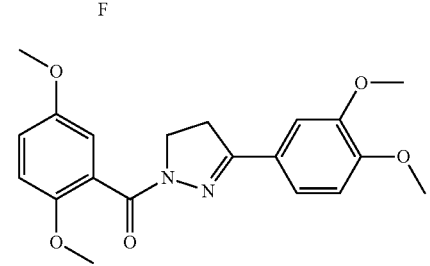 | 8.12% | |

TABLE 1-continued
Compounds of formulae (I), (I-A), (I-B). Assay A: Example 10; Assay B: Example 11.
| No. | Name | Assay A | Assay B |
|---|---|---|---|
| 82 | 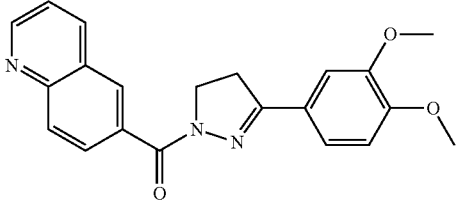 [SMILES: COc1ccc(C2=NN(C(=O)c3ccc4ncccc4c3)CC2)cc1OC] | | |
| 83 | 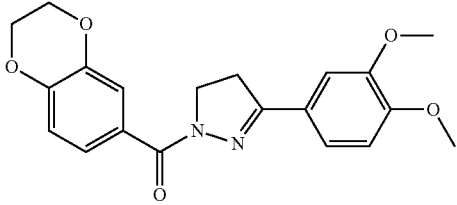 [SMILES: COc1ccc(C2=NN(C(=O)c3ccc4c(c3)OCCO4)CC2)cc1OC] | | 33.00% |
| 84 | 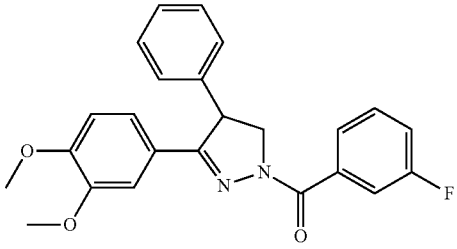 [SMILES: COc1ccc(C2=NN(C(=O)c3cccc(F)c3)CC2c2ccccc2)cc1OC] | | |
| 85 | 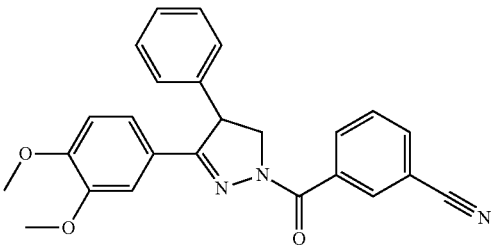 [SMILES: COc1ccc(C2=NN(C(=O)c3cccc(C#N)c3)CC2c2ccccc2)cc1OC] | | |
| 86 | 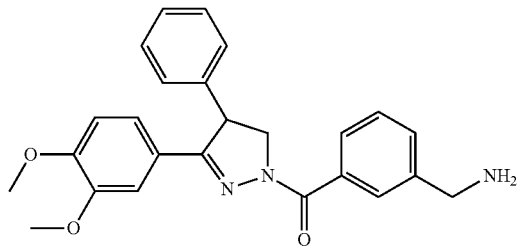 [SMILES: COc1ccc(C2=NN(C(=O)c3cccc(CN)c3)CC2c2ccccc2)cc1OC] | | 21.80% |
| 87 | 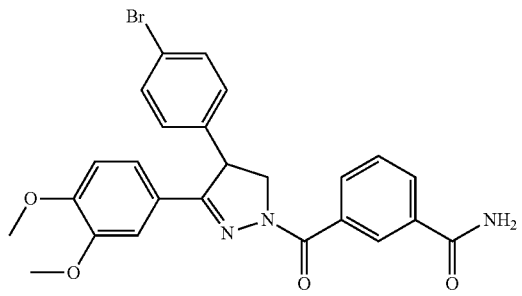 [SMILES: COc1ccc(C2=NN(C(=O)c3cccc(C(N)=O)c3)CC2c2ccc(Br)cc2)cc1OC] | | |

TABLE 1-continued

Compounds of formulae (I), (I-A), (I-B). Assay A: Example 10; Assay B: Example 11.

| No. | Name | Assay A | Assay B |
|-----|------|---------|---------|
| 88 | | | |
| 89 | | | |
| 90 | | | |
| 91 | | 27.00% | |
| 92 | | 22.00% | |

TABLE 1-continued
Compounds of formulae (I), (I-A), (I-B). Assay A: Example 10; Assay B: Example 11.
| No. | Name | Assay A | Assay B |
|-----|------|---------|---------|
| 93 | 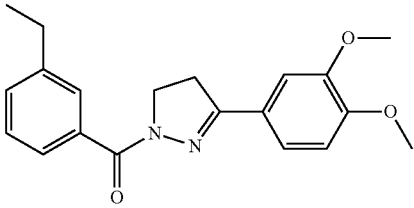 [SMILES: CCc1cccc(C(=O)N2CCC(c3ccc(OC)c(OC)c3)=N2)c1] | 27.00 μM | 0.726 μM |
| 94 | 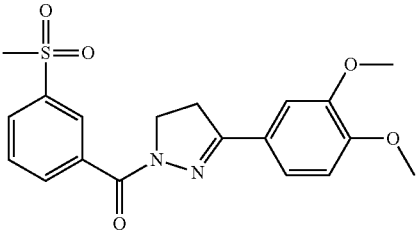 | 29.00% | |
| 95 | 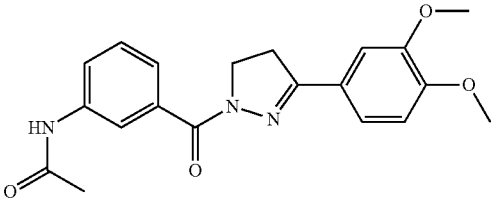 [SMILES: COc1ccc(C2=NN(C(=O)c3cccc(NC(C)=O)c3)CC2)cc1OC] | 4.00% | |
| 96 | 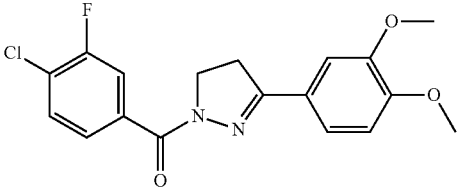 [SMILES: COc1ccc(C2=NN(C(=O)c3ccc(Cl)c(F)c3)CC2)cc1OC] | 44.00% | |
| 97 | 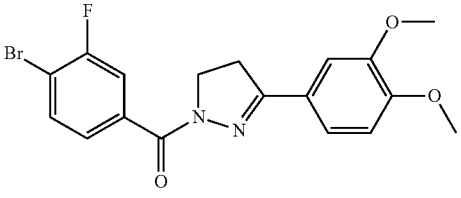 [SMILES: COc1ccc(C2=NN(C(=O)c3ccc(Br)c(F)c3)CC2)cc1OC] | 29.00% | |
| 98 | 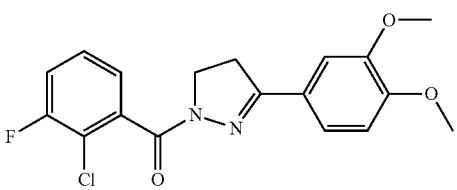 [SMILES: COc1ccc(C2=NN(C(=O)c3cccc(F)c3Cl)CC2)cc1OC] | 26.00% | |
| 99 | 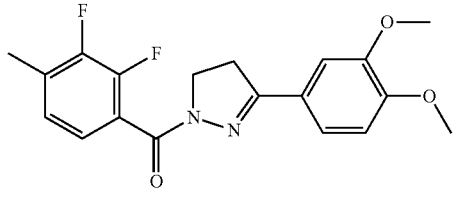 | 22.00% | |

TABLE 1-continued

Compounds of formulae (I), (I-A), (I-B). Assay A: Example 10; Assay B: Example 11.

| No. | Name | Assay A | Assay B |
|-----|------|---------|---------|
| 100 | | 5.00% | |
| 101 | | 14.00% | |
| 102 | | 15.00% | |
| 103 | | 24.00% | |
| 104 | | 20.00% | |
| 105 | | 22.00% | |
| 106 | | 1.00% | |

TABLE 1-continued

Compounds of formulae (I), (I-A), (I-B). Assay A: Example 10; Assay B: Example 11.

| No. | Name | Assay A | Assay B |
|---|---|---|---|
| 107 | | 8.00% | |
| 108 | | 19.00% | |
| 109 | | 2.00% | |
| 110 | | | |
| 111 | | 2.00% | |
| 112 | | 3.00% | |
| 113 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 114 | | | |
| 115 | | 28.00% | |
| 116 | | 1.00% | |
| 117 | | 4.00% | |
| 118 | | 5.00% | |
| 119 | | 21.00% | |
| 120 | | 23.00% | |

TABLE 1-continued

Compounds of formulae (I), (I-A), (I-B). Assay A: Example 10; Assay B: Example 11.

| No. | Name | Assay A | Assay B |
|-----|------|---------|---------|
| 121 | | | 16.00% |
| 122 | | | |
| 123 | | | |
| 124 | | | |
| 125 | | | 25.00% |
| 126 | | | |
| 127 | | | |

TABLE 1-continued

Compounds of formulae (I), (I-A), (I-B). Assay A: Example 10; Assay B: Example 11.

| No. | Name | Assay A | Assay B |
|---|---|---|---|
| 128 | | 28.00% | |
| 129 | | 35.00 μM | 0.363 μM |
| 130 | | | |
| 131 | | 23.00 μM | 0.413 μM |
| 132 | | 41.50 μM | 0.025 μM |
| 133 | | | |
| 134 | | 28.70% | |

TABLE 1-continued

Compounds of formulae (I), (I-A), (I-B). Assay A: Example 10; Assay B: Example 11.

| No. | Name | Assay A | Assay B |
|---|---|---|---|
| 135 | | | |
| 136 | | 30.00 μM | 0.106 μM |
| 137 | | 36.50% | |
| 138 | | 19.80% | |
| 139 | | 16.00% | |
| 140 | | 7.75% | |

TABLE 1-continued

Compounds of formulae (I), (I-A), (I-B). Assay A: Example 10; Assay B: Example 11.

| No. | Name | Assay A | Assay B |
|-----|------|---------|---------|
| 141 | | 23.50% | |
| 142 | | | |
| 143 | | 4.47% | |
| 144 | | | |
| 145 | | 7.35% | |
| 146 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 147 | | 49.00% | |
| 148 | | 2.88 μM | 3.400 μM |
| 149 | | 0.382 μM | |
| 150 | | 34.90% | |
| 151 | | 37.90% | |
| 152 | | 26.90% | |
| 153 | | 23.40% | |

TABLE 1-continued
Compounds of formulae (I), (I-A), (I-B). Assay A: Example 10; Assay B: Example 11.
| No. | Name | Assay A | Assay B |
|---|---|---|---|
| 154 | 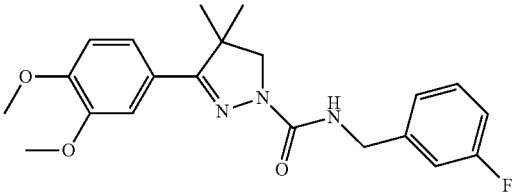 [SMILES: COc1ccc(C2=NN(C(=O)NCc3cccc(F)c3)CC2(C)C)cc1OC] | | 6.93% |
| 155 | 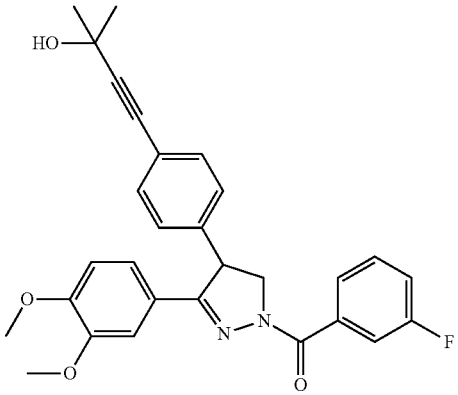 [SMILES: COc1ccc(C2=NN(C(=O)c3cccc(F)c3)CC2c2ccc(C#CC(C)(C)O)cc2)cc1OC] | | |
| 156 | 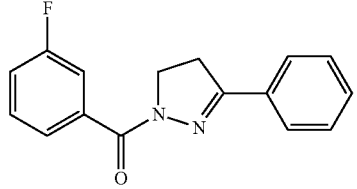 [SMILES: O=C(c1cccc(F)c1)N1CCC(c2ccccc2)=N1] | | |
| 157 | 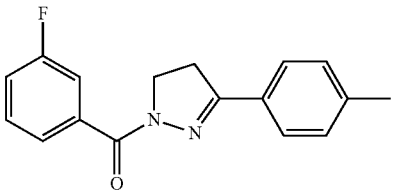 [SMILES: Cc1ccc(C2=NN(C(=O)c3cccc(F)c3)CC2)cc1] | | |
| 158 | 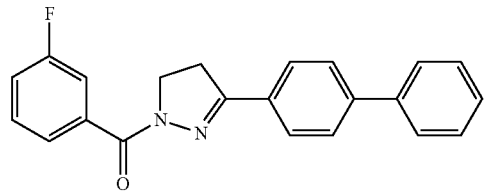 [SMILES: O=C(c1cccc(F)c1)N1CCC(c2ccc(-c3ccccc3)cc2)=N1] | | |
| 159 | 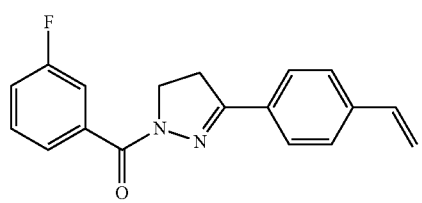 [SMILES: C=Cc1ccc(C2=NN(C(=O)c3cccc(F)c3)CC2)cc1] | | |

TABLE 1-continued
Compounds of formulae (I), (I-A), (I-B). Assay A: Example 10; Assay B: Example 11.
| No. | Name | Assay A | Assay B |
|---|---|---|---|
| 160 | 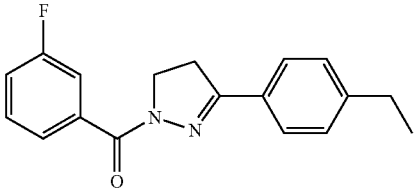 [SMILES: CCc1ccc(C2=NN(C(=O)c3cccc(F)c3)CC2)cc1] | | |
| 161 | 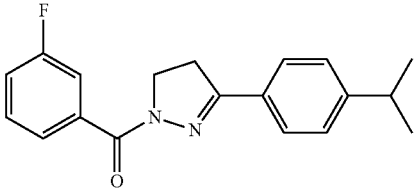 [SMILES: CC(C)c1ccc(C2=NN(C(=O)c3cccc(F)c3)CC2)cc1] | | |
| 162 | 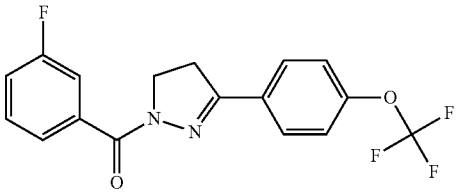 [SMILES: O=C(c1cccc(F)c1)N1CCC(c2ccc(OC(F)(F)F)cc2)=N1] | | |
| 163 | 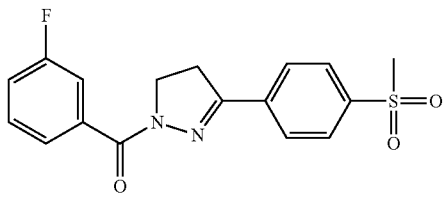 [SMILES: CS(=O)(=O)c1ccc(C2=NN(C(=O)c3cccc(F)c3)CC2)cc1] | | |
| 164 | 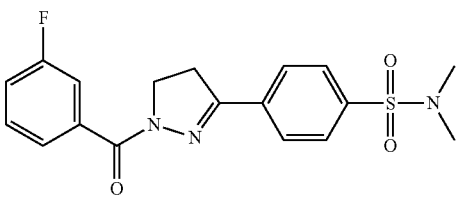 [SMILES: CN(C)S(=O)(=O)c1ccc(C2=NN(C(=O)c3cccc(F)c3)CC2)cc1] | | |
| 165 | 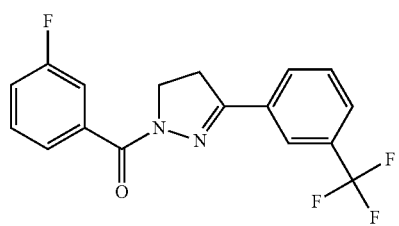 [SMILES: O=C(c1cccc(F)c1)N1CCC(c2cccc(C(F)(F)F)c2)=N1] | | |
| 166 | 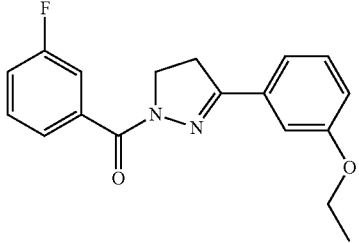 [SMILES: CCOc1cccc(C2=NN(C(=O)c3cccc(F)c3)CC2)c1] | | |

TABLE 1-continued
Compounds of formulae (I), (I-A), (I-B). Assay A: Example 10; Assay B: Example 11.
| No. | Name | Assay A | Assay B |
|---|---|---|---|
| 167 | 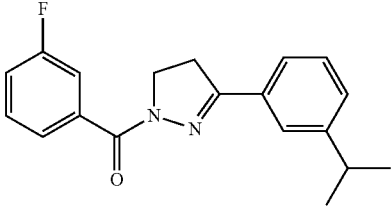 | | |
| 168 | 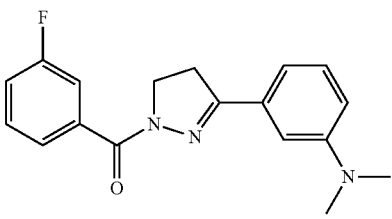 [SMILES: CC(C)c1cccc(C2=NN(C(=O)c3cccc(F)c3)CC2)c1] | | |
| 169 | 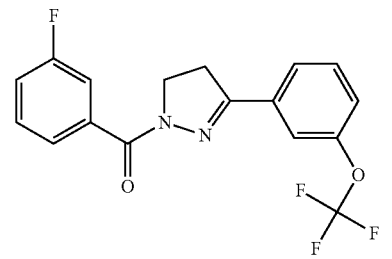 [SMILES: O=C(c1cccc(F)c1)N1CCC(c2cccc(OC(F)(F)F)c2)=N1] | | |
| 170 | 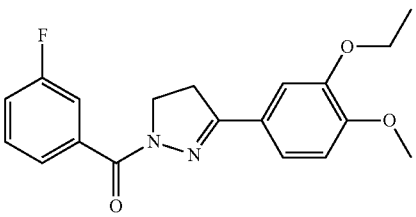 [SMILES: CCOc1cc(C2=NN(C(=O)c3cccc(F)c3)CC2)ccc1OC] | | |
| 171 | 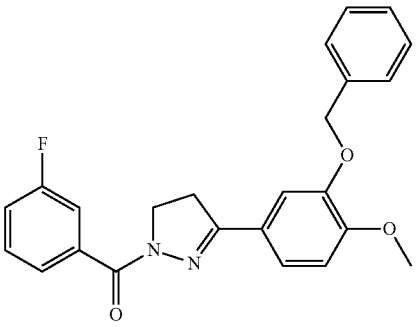 [SMILES: COc1ccc(C2=NN(C(=O)c3cccc(F)c3)CC2)cc1OCc1ccccc1] | | |
| 172 | 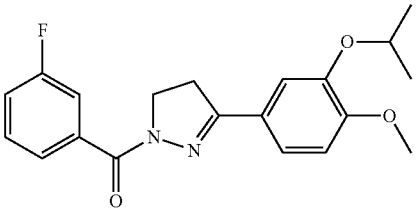 [SMILES: COc1ccc(C2=NN(C(=O)c3cccc(F)c3)CC2)cc1OC(C)C] | | |

TABLE 1-continued

Compounds of formulae (I), (I-A), (I-B). Assay A: Example 10; Assay B: Example 11.

| No. | Name | Assay A | Assay B |
|-----|------|---------|---------|
| 173 | | | |
| 174 | | | |
| 175 | | | |
| 176 | | | 3% |
| 177 | | | 36.50% |
| 178 | | | 3.61% |

TABLE 1-continued

Compounds of formulae (I), (I-A), (I-B). Assay A: Example 10; Assay B: Example 11.

| No. | Name | Assay A | Assay B |
|-----|------|---------|---------|
| 179 | | | 34.00 μM |
| 180 | | | |
| 181 | | | |
| 182 | | | |
| 183 | | | |
| 184 | | | |

TABLE 1-continued

Compounds of formulae (I), (I-A), (I-B). Assay A: Example 10; Assay B: Example 11.

| No. | Name | Assay A | Assay B |
|---|---|---|---|
| 185 | | 4.50 µM | |
| 186 | | 25.00% | |
| 187 | | 20.00% | |
| 188 | | | |
| 189 | | 28.00 µM | |
| 190 | | 12.00% | |
| 191 | | | |

TABLE 1-continued

Compounds of formulae (I), (I-A), (I-B). Assay A: Example 10; Assay B: Example 11.

| No. | Name | Assay A | Assay B |
|---|---|---|---|
| 192 | | | |
| 193 | | 40.00% | |
| 194 | | | |
| 195 | | 16.00% | |
| 196 | | 46.00% | |
| 197 | | 23.00% | |
| 198 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 199 | | 34.30 μM | |
| 200 | | | |
| 201 | | | |
| 202 | | | |
| 203 | | | |
| 204 | | 8.25 μM | |
| 205 | | 30.00 μM | |
| 206 | | 29.00% | |

83
84
TABLE 1-continued
Compounds of formulae (I), (I-A), (I-B). Assay A: Example 10; Assay B: Example 11.
| No. | Name | Assay A | Assay B |
|---|---|---|---|
| 207 | 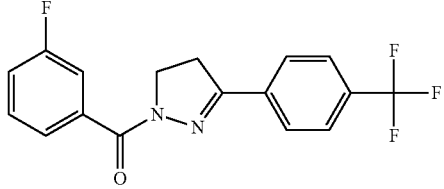 [SMILES: O=C(c1cccc(F)c1)N1CCC(c2ccc(C(F)(F)F)cc2)=N1] | 44.50 μM | |
| 208 | 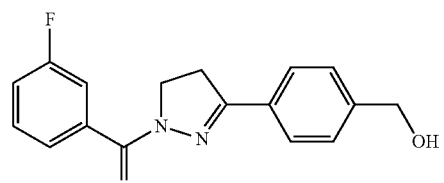 | 19.10% | |
| 209 | 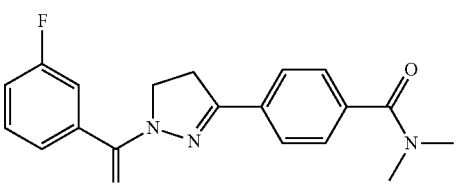 | | |
| 210 | 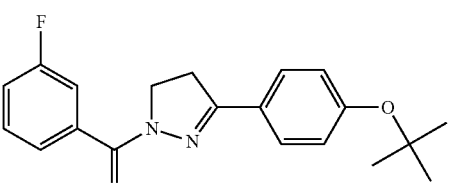 | 7.39 μM | |
| 211 | 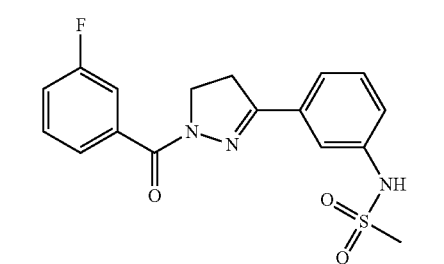 [SMILES: CS(=O)(=O)Nc1cccc(C2=NN(C(=O)c3cccc(F)c3)CC2)c1] | 8.39% | |
| 212 | 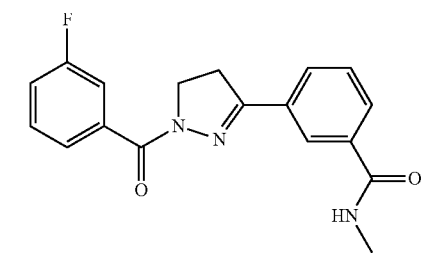 [SMILES: CNC(=O)c1cccc(C2=NN(C(=O)c3cccc(F)c3)CC2)c1] | | |

TABLE 1-continued

Compounds of formulae (I), (I-A), (I-B). Assay A: Example 10; Assay B: Example 11.

| No. | Name | Assay A | Assay B |
|-----|------|---------|---------|
| 213 | | | |
| 214 | | | 1.10 μM |
| 215 | | | |
| 216 | | | |
| 217 | | | |

TABLE 1-continued

Compounds of formulae (I), (I-A), (I-B). Assay A: Example 10; Assay B: Example 11.

| No. | Name | Assay A | Assay B |
|---|---|---|---|
| 218 | | | |
| 219 | | 22.40% | |
| 220 | | | |
| 221 | | 13.30% | |
| 222 | | | |
| 223 | | 31.20 μM | |
| 224 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 225 | | 15.30% | |
| 226 | | | |
| 227 | | | |
| 228 | | 37.80% | 0.134 μM |
| 229 | | 35.90% | 0.032 μM |
| 230 | | 2.20 μM | 0.128 μM |

TABLE 1-continued

Compounds of formulae (I), (I-A), (I-B). Assay A: Example 10; Assay B: Example 11.

| No. | Name | Assay A | Assay B |
|---|---|---|---|
| 231 | | 23.80 μM | 1.150 μM |
| 232 | | 38.70 μM | 0.572 μM |
| 233 | | 27.80 μM | 0.216 μM |
| 234 | | 22.40 μM | 0.699 μM |
| 235 | | 35.70 μM | 0.538 μM |
| 236 | | 25.30 μM | 1.730 μM |

TABLE 1-continued

Compounds of formulae (I), (I-A), (I-B). Assay A: Example 10; Assay B: Example 11.

| No. | Name | Assay A | Assay B |
| --- | --- | --- | --- |
| 237 | | 35.00 μM | 0.598 μM |
| 238 | | 5.00% | |
| 239 | | 4.47% | |
| 240 | | 11.50% | |
| 241 | | 31.00 μM | 0.342 μM |
| 242 | | | |
| 243 | | | |

TABLE 1-continued

Compounds of formulae (I), (I-A), (I-B). Assay A: Example 10; Assay B: Example 11.

| No. | Name | Assay A | Assay B |
|---|---|---|---|
| 244 | | | |
| 245 | | | |
| 246 | | 25.00% | |
| 247 | | 35.20 μM | |
| 248 | | | |
| 249 | | 38.70% | |
| 250 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 251 | | 27.10 μM | |
| 252 | | | |
| 253 | | | |
| 254 | | | |
| 255 | | 35.00 μM | |
| 256 | | 35.20% | |

TABLE 1-continued

Compounds of formulae (I), (I-A), (I-B). Assay A: Example 10; Assay B: Example 11.

| No. | Name | Assay A | Assay B |
|-----|------|---------|---------|
| 257 | | 33.20 μM | |
| 258 | | 40.90% | |
| 259 | | 30.00 μM | |
| 260 | | | |
| 261 | | 42.50% | |
| 262 | | 16.10% | |
| 263 | | 24.40% | |

TABLE 1-continued

Compounds of formulae (I), (I-A), (I-B). Assay A: Example 10; Assay B: Example 11.

| No. | Name | Assay A | Assay B |
|---|---|---|---|
| 264 | | 37.80% | |
| 265 | | 16.50% | |
| 266 | | | |
| 267 | | | |
| 268 | | | |
| 269 | | | |

TABLE 1-continued

Compounds of formulae (I), (I-A), (I-B). Assay A: Example 10; Assay B: Example 11.

| No. | Name | Assay A | Assay B |
|---|---|---|---|
| 270 | | 17.00% | |
| 271 | | 43.00% | |
| 282 | | 27.00 μM | |
| 273 | | 35.00% | |
| 274 | | 25.00 μM | |
| 275 | | 24.00 μM | |

TABLE 1-continued

Compounds of formulae (I), (I-A), (I-B). Assay A: Example 10; Assay B: Example 11.

| No. | Name | Assay A | Assay B |
|---|---|---|---|
| 276 | | 46.00% | |
| 277 | | | 2.00 μM |
| 278 | | | |
| 279 | | 20.00% | |
| 280 | | 24.00% | |
| 281 | | | |

TABLE 1-continued

Compounds of formulae (I), (I-A), (I-B). Assay A: Example 10; Assay B: Example 11.

| No. | Name | Assay A | Assay B |
|-----|------|---------|---------|
| 282 | | | |
| 283 | | 26.00% | |
| 284 | | 26.00% | |
| 285 | | 35.00% | |
| 286 | | 37.00% | |
| 287 | | 11.00% | |

TABLE 1-continued

Compounds of formulae (I), (I-A), (I-B). Assay A: Example 10; Assay B: Example 11.

| No. | Name | Assay A | Assay B |
|---|---|---|---|
| 288 | | 10.00% | |
| 289 | | | |
| 290 | | 9.00% | 5.40 μM |
| 291 | | 38.00% | 144.00% |
| 292 | | 29.00 μM | 186.00% |

Highly preferred embodiments are the compounds selected from the group of

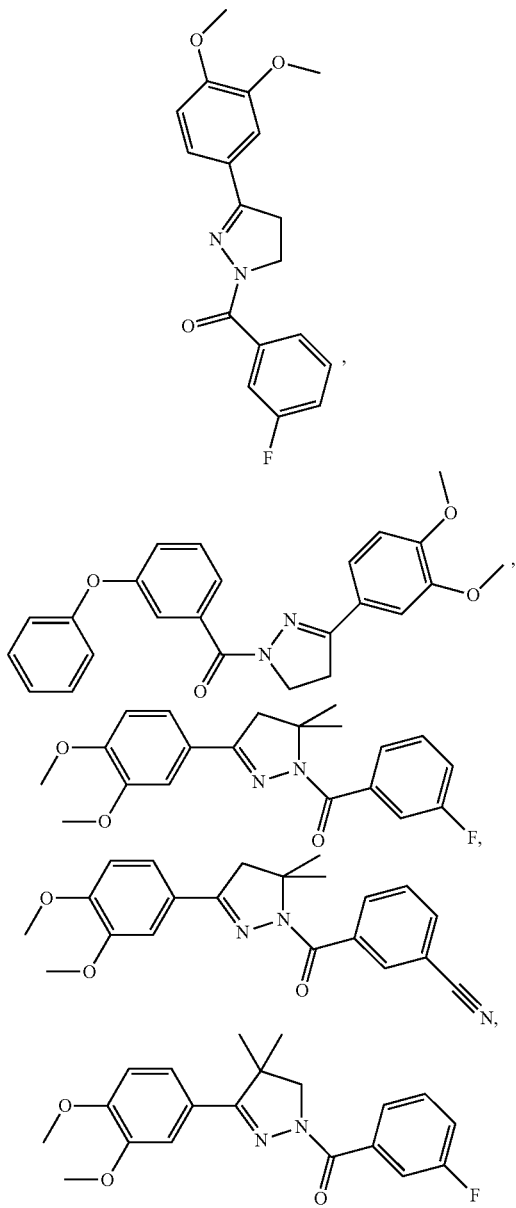

and/or physiologically acceptable salts thereof.

The dihydropyrazole derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to water, THF, tert. butanol, tert. amylalcohol, NMP, triethylamine and/or dioxane.

Depending on the conditions used, the reaction time is between a few minutes and 14 days, the reaction temperature is between about −30° C. and 140° C., normally between −10° C. and 130° C., preferably between 30° C. and 125° C.

The present invention also relates to a process for manufacturing compounds of formula (I) comprising the steps of:

(a) reacting a compound of formula (II)

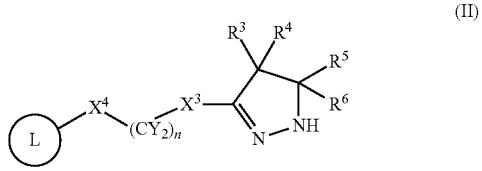

wherein

L, $R^3$, $R^4$, $R^5$, $R^6$, $X^3$, $X^4$, Y and n have the meaning as defined above or below, with a compound of formula (III)

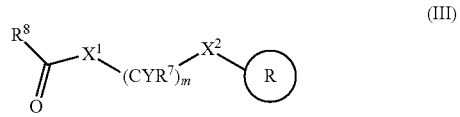

wherein $R^8$ denotes Hal or OH, and

R, $R^7$, $X^1$, $X^2$, Y, Hal and m have the meaning as defined above or below, to yield a compound of formula (I)

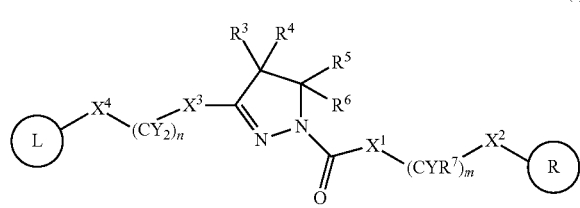

(I)

wherein
L, R, $R^3$, $R^4$, $R^5$, $R^6$, $R^7$, $X^1$, $X^2$, $X^3$, $X^4$, Y, m and n have the meaning as defined above or below,
and optionally
(b) converting a base or an acid of the compound of formula (I) into a salt thereof.

The dihydropyrazole derivatives of formula (I) are accessible via the route above. The starting materials, including the compounds of formulae (II) and (III), are usually known to the skilled artisan, or they can be easily prepared by known methods. Accordingly, any compound of formulae (II) and (III) can be purified, provided as intermediate product and used as starting material for the preparation of compounds of formula (I).

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or an sufonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of PdO catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zink organyles (Negishi coupling) and tin organyles (Stille coupling) are useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (Fors et al. JACS 130: 13552 (2008)) as well as for O-arylation by using Cu catalysis and Pd catalysis.

In the final step of the processes above, a salt of the compound according to formulae (I) to (III), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for modulating an FSH receptor, particularly in the presence of FSH. The term "modulation" denotes any change in FSHR-mediated signal transduction, which is based on the action of the specific inventive compounds capable to interact with the FSHR target in such a manner that makes recognition, binding and activating possible. The compounds are characterized by such a high affinity to FSHR, which ensures a reliable binding and preferably a positive allosteric modulation of FSHR. More preferably, the substances are mono-specific in order to guarantee an exclusive and directed recognition with the single FSHR target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

A preferred object of the present invention relates to a method for modulating an FSH receptor, preferably in a positive allosteric manner, wherein a system capable of expressing the FSH receptor, preferably expressing the FSH receptor, is contacted, preferably in the presence of FSH, with at least one compound of formula (I)

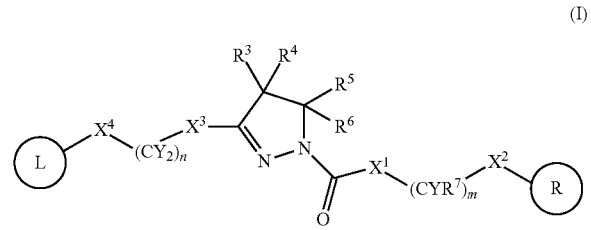

(I)

wherein

R, L denote independently from one another $Ar^1$, $Het^1$, A or OY;

$R^1$ denotes Hal, A, $-(CY_2)_p-OY$, $-(CY_2)_p-NY_2$, COOY, $CONY_2$, NHCOY, CN, $SO_2Y$, -E-$(CY_2)_p-Ar^2$, -E-$(CY_2)_p$-$Het^1$ or -E-$(CY_2)_p$-$Het^3$;

$R^2$ denotes Hal, A, $-(CY_2)_p-OY$, $-(CY_2)_p-NY_2$, COY, COOY, $CONY_2$, $-CONY$-Cyc, $-O$-Cyc, $NO_2$, CN, SY, SOY, $SO_2Y$, $SO_2NY_2$, $NHSO_2Y$, alkenyl or -E-$(CY_2)_p-Ar^2$;

$R^3$, $R^4$, $R^5$, $R^6$ denote independently from one another H, A or $Ar^2$;

$R^7$ denotes Y, OY or $NY_2$;

$X^1$, $X^2$, $X^3$, $X^4$ denote independently from one another O, NY or a single bond;

E denotes $-C\equiv C-$, $SO_2$, $-SO_2-NY-$, O, NY or a single bond;

Y denotes H or A;

A denotes unbranched or branched alkyl having 1-10 C atoms,
in which 1-7 H atoms can be replaced by Hal;

Cyc denotes cycloalkyl having 3-7 C atoms,
in which 1-4 H atoms can be replaced independently from one another by Hal or A;

$Ar^1$ denotes a saturated, unsaturated or aromatic, mono- or bicyclic carbocycle having 3-10 C atoms,
which can be substituted by at least one substituent selected from the group of $R^1$, $R^2$ and $-C\equiv C-C(A)_2OH$, and/or which can be fused to Cyc, $Het^1$ or $Het^3$;

$Ar^2$ denotes an aromatic, mono- or bicyclic carbocycle having 6-10 C atoms, which can be substituted by at least one substituent selected from the group of Hal, A and $-(CY_2)_p-OY$;

$Het^1$ denotes an unsaturated or aromatic mono- or bicyclic heterocycle having 3-8 C atoms and 1-4 N, O and/or S atoms,
which can be substituted by at least one substituent selected from the group of Hal, A, $-(CY_2)_p-OY$, $-(CY_2)_p-NY_2$, $-(CY_2)_p-Ar^2$, $-CO-Ar^2$, $SO_2-Ar^2$, $-(CY_2)_p$-$Het^2$, $Het^3$ and CN;

$Het^2$ denotes an aromatic monocyclic heterocycle having 5-7 C atoms and 1-3 N atoms,
which can be substituted by at least one substituent selected from the group of Hal, A and $-(CY_2)_p-OY$;

$Het^3$ denotes a saturated monocyclic heterocycle having 3-7 C atoms and 1-4 N, O and/or S atoms,
which can be substituted by at least one substituent selected from the group of Hal, A, $-(CY_2)_p-OY$, $-(CY_2)_p-NY_2$, COOY, COY, $-CONY_2$, $=O$ and CN;

Hal denotes F, Cl, Br or I; and m, n, p denote independently from one another 0, 1, 2, 3 or 4;

and/or physiologically acceptable salts thereof, under conditions such that said FSH receptor is modulated, preferably in a positive allosteric manner.

Although a cellular system is preferred in the scope of the invention, an in-vitro translation system can be alternatively used which is based on the protein synthesis without living cells. The cellular system is defined to be any subject provided that the subject comprises cells. Hence, the cellular system can be selected from the group of single cells, cell cultures, tissues, organs and animals. The prior teaching of the present specification concerning the compounds of formula (I), including any preferred embodiment thereof, is valid and applicable without restrictions to the compounds according to formula (I) and their salts when used in the method for modulating FSHR.

The compounds according to the invention preferably exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect. It is preferred that the compounds of the invention have an FSHR agonist activity, as expressed by an $EC_{50}$ standard, of less than 1000 nM, more preferably less than 500 nM. "$EC_{50}$" is the effective concentration of a compound at which 50% of the maximal response of that obtained with FSH would be obtained.

As discussed herein, these signaling pathways are relevant for various diseases, preferably fertility disorders. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably agonists, more preferably positive allosteric modulators, of the signaling pathways described herein, preferably of the FSHR-mediated signaling pathway. The compounds of the invention are supposed to bind to the intracellular receptor domain without a competitive interaction with FSH, but they act as an allosteric enhancer of FSH on its receptor. The non-competitive interaction refers to the nature of the agonist activity exhibited by the compounds of the invention, wherein the compounds activate FSHR without substantially reducing the magnitude of binding of FSH to FSHR.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate FSHR activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing FSHR-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. The in-vitro use is preferably applied to samples of humans suffering from fertility disorders. Testing of several specific compounds and/or derivatives thereof makes the selection of that active ingredient possible that is best suited for the treatment of the human subject. The in-vivo dose rate of the chosen derivative is advantageously pre-adjusted to the FSHR susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the modulation of FSHR activity if expedient.

The invention furthermore relates to a medicament comprising at least one compound according to the invention and/or pharmaceutically usable derivatives, salts, solvates and stereoisomers thereof, including mixtures thereof in all ratios. Preferably, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with FSHR activity, in such a way that a pathogenic modification of their overall condition or of the condition of particular regions of the organism could establish at least temporarily.

Consequently, the invention also relates to a pharmaceutical composition comprising as active ingredient an effective amount of at least one compound according to formula (I) and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The present compounds are suitable for combination with known fertility-inducing agents. Preferably, the other active pharmaceutical ingredient is selected from the group of FSH, α-FSH (Gonal F), β-FSH, LH, hMG and 2-(4-(2-chloro-1,2-diphenylethenyl)-phenoxy)-N,N-diethyl-ethanamine citrate (Chlomifene citrate). Further ovulation adjuncts are known to those of skill in the art (cf. e.g. WO 2002/09706, which is incorporated herein by reference) and are useful with the compounds of the present invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by FSHR activity. It is particularly preferred that the diseases are fertility disorders. It shall be understood that the host of the compound is included in the present scope of protection according to the present invention.

Particular preference is given to the stimulation of follicular development, ovulation induction, controlled ovarial hyperstimulation, assisted reproductive technology, including in-vitro fertilization, male hypogonadism and male infertility, including some types of failure of spermatogenesis.

The invention also relates to the use of compounds according to formula (I) and/or physiologically acceptable salts thereof for the prophylactic or therapeutic treatment and/or monitoring of diseases that are caused, mediated and/or propagated by FSHR activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by FSHR activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds according to formula (I) and/or physiologically acceptable salts thereof for use in the prophylactic or therapeutic treatment and/or monitoring of diseases that are caused, mediated and/or propagated by FSHR activity.

Another preferred object of the invention concerns compounds of formula (I)

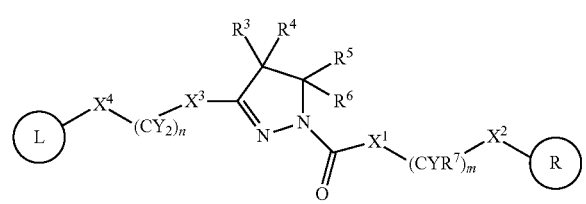

(I)

wherein
R, L denote independently from one another $Ar^1$, $Het^1$, A or OY;
$R^1$ denotes Hal, A, —$(CY_2)_p$—OY, —$(CY_2)_p$—$NY_2$, COOY, $CONY_2$, NHCOY, CN, $SO_2Y$, -E-$(CY_2)_p$—$Ar^2$, -E-$(CY_2)_p$-$Het^1$ or -E-$(CY_2)_p$-$Het^3$;
$R^2$ denotes Hal, A, —$(CY_2)_p$—OY, —$(CY_2)_p$—$NY_2$, COOY, $CONY_2$, —CONY-Cyc, —O-Cyc, $NO_2$, CN, SY, SOY, $SO_2Y$, $SO_2NY_2$, $NHSO_2Y$, alkenyl or -E-$(CY_2)_p$—$Ar^2$;
$R^3$, $R^4$, $R^5$, $R^6$ denote independently from one another H, A or $Ar^2$;
$R^7$ denotes Y, OY or $NY_2$;
$X^1$, $X^2$, $X^3$, $X^4$ denote independently from one another O, NY or a single bond;
E denotes —C≡C—, $SO_2$, —$SO_2$—NY—, O, NY or a single bond;
Y denotes H or A;
A denotes unbranched or branched alkyl having 1-10 C atoms, in which 1-7 H atoms can be replaced by Hal;
Cyc denotes cycloalkyl having 3-7 C atoms,
in which 1-4 H atoms can be replaced independently from one another by Hal or A;
$Ar^1$ denotes a saturated, unsaturated or aromatic, mono- or bicyclic carbocycle having 3-10 C atoms,
which can be substituted by at least one substituent selected from the group of $R^1$, $R^2$ and —C≡C—C(A)$_2$OH, and/or which can be fused to Cyc, $Het^1$ or $Het^3$;
$Ar^2$ denotes an aromatic, mono- or bicyclic carbocycle having 6-10 C atoms, which can be substituted by at least one substituent selected from the group of Hal, A and —$(CY_2)_p$—OY;
$Het^1$ denotes an unsaturated or aromatic mono- or bicyclic heterocycle having 3-8 C atoms and 1-4 N, O and/or S atoms,
which can be substituted by at least one substituent selected from the group of Hal, A, —$(CY_2)_p$—OY, —$(CY_2)_p$—$NY_2$, —$(CY_2)_p$—$Ar^2$, —CO—$Ar^2$, $SO_2$—$Ar^2$, —$(CY_2)_p$-$Het^2$, $Het^3$ and CN;
$Het^2$ denotes an aromatic monocyclic heterocycle having 5-7 C atoms and 1-3 N atoms,
which can be substituted by at least one substituent selected from the group of Hal, A and —$(CY_2)_p$—OY;
$Het^3$ denotes a saturated monocyclic heterocycle having 3-7 C atoms and 1-4 N, O and/or S atoms,
which can be substituted by at least one substituent selected from the group of Hal, A, —$(CY_2)_p$—OY, —$(CY_2)_p$—$NY_2$, COOY, COY, —$CONY_2$, =O and CN;
Hal denotes F, Cl, Br or I; and
m, n, p denote independently from one another 0, 1, 2, 3 or 4;
and/or physiologically acceptable salts thereof for use in the prophylactic or therapeutic treatment and/or monitoring of fertility disorders.

The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of fertility disorders.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with FSHR activity in advance or to treat the arising and continuing symptoms. The disorders as concerned by the invention are preferably fertility disorders.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by FSHR activity, wherein an effective amount of at least one compound of formula (I) and/or physiologically acceptable salts thereof is administered to a mammal in need of such treatment. It is another preferred object of the invention to provide a method for treating fertility disorders, wherein an effective amount of at least one compound of formula (I) and/or physiologically acceptable salts thereof is administered to a mammal in need of such treatment. The preferred treatment is an oral administration. In another preferred aspect, the method of treatment aims to achieve ovulation induction and/or controlled ovarian hyperstimulation. In still another preferred aspect, the method of treatment forms the basis for a method for in-vitro fertilization comprising the steps of: (a) treating a mammal according to the method of treatment as described above, (b) collecting ova from said mammal, (c) fertilizing said ova, and (d) implanting said fertilized ova into a host mammal. The host mammal can be either the treated mammal (i.e. the patient) or a surrogate. The prior teaching of the invention and its embodiments is valid and applicable without restrictions to the methods of treatment if expedient.

In the scope of the present invention, novel dihydropyrazole compounds of formula (I) are provided for the first time. The low molecular weight compounds of the invention are strong and selective modulators of the FSH receptor. Their selectivity to the FSH receptor is 10-fold over the LH receptor and even 100-fold over the TSH receptor while the $IC_{50}$ amounts to more than 10 µM on unrelated G protein-coupled receptors (GPCR) or non-GPCR targets. The current invention comprises the use of present dihydropyrazole derivatives in the regulation and/or modulation of the FSHR signal cascade, which can be advantageously applied as research tool, for diagnosis and/or in treatment of any disorder arising from FSHR signaling.

For example, the compounds of the invention are useful in-vitro as unique tools for understanding the biological role of FSH, including the evaluation of the many factors thought to influence, and be influenced by, the production of FSH and the interaction of FSH with the FSHR (e. g. the mechanism of FSH signal transduction/receptor activation). The present compounds are also useful in the development of other compounds that interact with FSHR since the present compounds provide important structure-activity relationship (SAR) information that facilitate that development. Compounds of the present invention that bind to FSHR can be used as reagents for detecting FSHR on living cells, fixed cells, in biological fluids, in tissue homogenates, in purified, natural biological materials, etc. For example, by labeling such compounds, one can identify cells having FSHR on their surfaces. In addition, based on their ability to bind FSHR, compounds of the present invention can be used in in-situ staining, FACS (fluorescence-activated cell sorting), western blotting, ELISA (enzyme-linked immunoadsorptive assay), etc., receptor purification, or in purifying cells expressing FSHR on the cell surface or inside permeabilized cells.

The compounds of the invention can also be utilized as commercial research reagents for various medical research and diagnostic uses. Such uses can include but are not limited to: use as a calibration standard for quantifying the activities of candidate FSH agonists in a variety of functional assays; use as blocking reagents in random compound screening, i.e. in looking for new families of FSH receptor ligands, the compounds can be used to block recovery of the presently claimed FSH compounds; use in the co-crystallization with FSHR receptor, i.e. the compounds of the present invention will allow formation of crystals of the compound bound to FSHR, enabling the determination of receptor/compound structure by x-ray crystallography; other research and diagnostic applications, wherein FSHR is preferably activated or such activation is conveniently calibrated against a known quantity of an FSH agonist, etc.; use in assays as probes for determining the expression of FSHR on the surface of cells; and developing assays for detecting compounds which bind to the same site as the FSHR binding ligands.

The low molecular weight inhibitors can be applied either themselves and/or in combination with physical measurements for diagnostics of treatment effectiveness. Medicaments and pharmaceutical compositions containing said compounds and the use of said compounds to treat FSHR-mediated conditions is a promising, novel approach for a broad spectrum of therapies causing a direct and immediate improvement in the state of health, whether in man and animal. The impact is of special benefit to efficiently combat infertility, either alone or in combination with other fertility-inducing treatments. In particular, the compounds of the invention potentiate the native FSH effect for both ovulation induction and assisted reproductive technology. The orally bioavailable and active new chemical entities of the invention improve convenience for patients and compliance for physicians. The PK properties permit an administration twice daily.

The compounds of the invention have Log P lower than 4, a solubility of more than 5 mg/ml in an acceptable vehicle (preferably more than 10 mg/ml), and they are active in the primary screen (0.1 nM CHO cells+FSHR; inactive in absence of FSHR), secondary screen (preferably 10-100 nM), chimeric receptor (TSHR/FSHR) screen (preferably 50-500 nM), granulosa cell aromatase assay (preferably 1-10 nM) and ovulation induction assay (preferably 0.5-50 mg/kg bid). Due to the surprisingly strong, selective and positive allosteric modulation of FSHR, the compounds of the invention can be advantageously administered at lower doses compared to other less potent or selective agonists of prior art while still achieving equivalent or even superior desired biological effects. In addition, such a dose reduction advantageously leads to less or even no medicinal adverse effects. Neither hERG nor any toxic effects could be observed in-vitro or in-vivo.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

It is to be understood that this invention is not limited to the particular compounds, pharmaceutical compositions, uses and methods described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved. Similarly, the features of any claim can be combined with the features of one or more other claims.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.

Standard Description of Analytical Equipment

NMR Spectra were acquired on a Varian $^{Unity}$Inova 400 MHz NMR spectrometer equipped with an Automation Triple Broadband (ATB) probe. The ATB probe was simultaneously tuned to $^1$H, $^{19}$F and $^{13}$O. For typical $^1$H NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to 1 second. Spectra were collected at 25° C. $^1$H NMR Spectra are typically processed with 0.2 Hz line broadening and zero-filling to 131072 points prior to Fourier transformation.

Method A (Rapid LC): A Shimadzu Shim-pack XR-ODS, 3.0×30 mm, 2.2 µm, was used at a temperature of 50° C. and at a flow rate of 1.5 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B).

Method B (Polar Stop-Gap): An Agilent Zorbax Bonus RP, 2.1×50 mm, 3.5 µm, was used at a temperature of 50° C. and at a flow rate of 0.8 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Preparative HPLC—was performed using a system controlled by Chromeleon software and consisting of two Varian PrepStar Model 218 Pumps, a Varian ProStar Model 320 UV/Vis detector, a SEDEX 55 ELSD detector, and a Gilson 215 liquid handler. Typical HPLC—mobile phases consist of water and methanol. The standard column is a Varian Dynamax 21.4 mm diameter Microsorb Guard-8 C18 column.

Example 1: Synthetic Route Towards [3-(3,4-dimethoxy-phenyl)-5,5-dimethyl-4,5-dihydro-pyrazol-1-yl]-phenyl-methanones

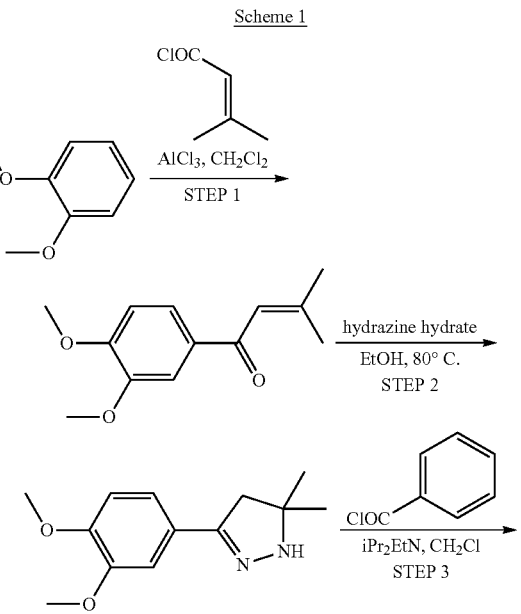

Scheme 1

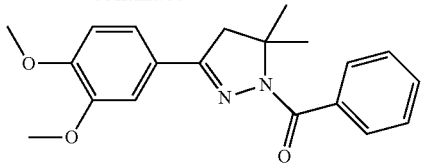

It shall be understood that the phenyl moiety (radical R) can be substituted in accordance with the Ar¹ definition as demonstrated below.

Step 1

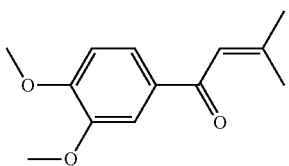 [SMILES: COc1ccc(C(=O)C=C(C)C)cc1OC]

1-(3,4-dimethoxy-phenyl)-3-methyl-but-2-en-1-one. A round bottom flask equipped with a stir bar and nitrogen inlet was charged with veratrole (2.5 mL, 20 mmol), 3,3-dimethyl acryloyl chloride (2.2 mL, 20 mmol) and dry $CH_2Cl_2$ (100 mL). The solution was cooled to 0° C. and $AlCl_3$ (2.6 g, 20 mmol) was added portionwise. On completion of addition, the cooling bath was removed and the reaction was allowed 3 h. TLC showed consumption of SM. It was added to saturated $NH_4Cl$ (100 mL) and stirred vigourously for 15 min. The phases were separated and the $CH_2Cl_2$ phase was washed with saturated $Na_2CO_3$ (100 mL), washed with brine, (100 mL), dried ($Na_2SO_4$) and the solvent was evaporated under reduced pressure. The material was used as is in the next step. Amount obtained: 4.3 g, 19.5 mmol, 98% yield. LC-MS (ESI) m/e 221 (M+H). ¹H NMR (400 MHz, CHLOROFORM-d) δ ppm 2.02 (s, 3H) 2.20 (s, 3H) 3.96 (s, 6H) 6.73 (s, 1H) 6.89 (d, J=8.20 Hz, 1H) 7.53-7.60 (m, 2H).

Step 2

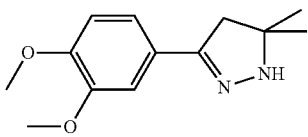

3-(3,4-Dimethoxy-phenyl)-5,5-dimethyl-4,5-dihydro-1H-pyrazole. A 100 mL round bottom flask equipped with a stir bar, Vigreux column and nitrogen inlet was charged with 1-(3,4-dimethoxy-phenyl)-3-methyl-but-2-en-1-one (1.4 g, 10 mmol), EtOH (40 mL) and hydrazine monohydrate (0.58 mL, 12 mmol). The mixture was heated at 80° C. for 2 h. LC-MS and TLC analysis showed consumption of SM. The solvent was evaporated under reduced pressure and trace hydrazine and EtOH was removed under high vacuum for 30 min. The material was used as in the next step. Amount obtained: 2.3 g, 10 mmol, 100% yield. LC-MS (ESI) m/e 235 (M+H).

Step 3

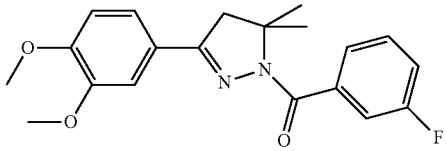 [SMILES: COc1ccc(C2=NN(C(=O)c3cccc(F)c3)C(C)(C)C2)cc1OC]

[3-(3,4-Dimethoxy-phenyl)-5,5-dimethyl-4,5-dihydro-pyrazol-1-yl]-(3-fluoro-phenyl)-methanone (129). A scintillation vial equipped with a stir bar was charged with 3-(3,4-dimethoxy-phenyl)-5,5-dimethyl-4,5-dihydro-1H-pyrazole (469 mg, 2 mmol), Hunigs base (1 mL, 6 mmol) and dry $CH_2Cl_2$ (10 mL). To this mixture was added 3-fluorobenzoyl chloride (0.23 mL, 2 mmol) and the reaction was stirred at RT for 3 h. LC-MS indicated consumption of SM. The mixture was diluted with $CH_2Cl_2$ (50 mL) and added to water (50 mL). The phases were separated and the $CH_2Cl_2$ phase was washed with saturated $Na_2CO_3$ (50 mL), brine (50 mL), dried ($Na_2SO_4$) and the solvent was evaporated under reduced pressure. The material was purified using a 40 g silica cartridge eluting with heptane-EtOAc, gradient 0 to 50% EtOAc. Amount obtained: 350 mg, 1 mmol, 50% yield. LC-MS (ESI) m/e 357 (M+H). ¹H NMR (400 MHz, CHLOROFORM-d) δ ppm 1.79 (s, 6H) 3.17 (s, 2H) 3.88 (s, 3H) 3.93 (s, 3H) 6.87 (d, J=8.35 Hz, 1H) 7.10 (dd, J=8.32, 1.83 Hz, 1H) 7.15 (td, J=8.33, 2.03 Hz, 1H) 7.28 (d, J=1.76 Hz, 1H) 7.38 (td, J=7.92, 5.88 Hz, 1H) 7.62-7.69 (m, 2H).

The following compounds were prepared with the same procedure as [3-(3,4-Dimethoxy-phenyl)-5,5-dimethyl-4,5-dihydro-pyrazol-1-yl]-(3-fluoro-phenyl)-methanone (129):

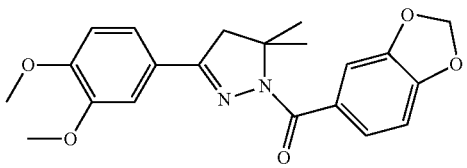 [SMILES: COc1ccc(C2=NN(C(=O)c3ccc4c(c3)OCO4)C(C)(C)C2)cc1OC]

[1,3]Dioxol-5-yl-[3-(3,4-dimethoxy-phenyl)-5,5-dimethyl-4,5-dihydro-pyrazol-1-yl]-methanone (131). Amount obtained: 382 mg, 1 mmol, 50% yield. LC-MS (ESI) m/e 383 (M+H). ¹H NMR (400 MHz, CHLOROFORM-d) δ ppm 1.77 (s, 6H) 3.14 (s, 2H) 3.90 (s, 3H) 3.93 (s, 3H) 6.02 (s, 2H) 6.86 (dd, J=14.91, 8.27 Hz, 2H) 7.12 (dd, J=8.30, 1.85 Hz, 1H) 7.30 (d, J=1.76 Hz, 1H) 7.46 (d, J=1.46 Hz, 1H) 7.53 (dd, J=8.20, 1.56 Hz, 1H).

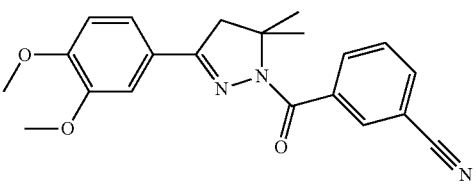 [SMILES: COc1ccc(C2=NN(C(=O)c3cccc(C#N)c3)C(C)(C)C2)cc1OC]

3-[3-(3,4-Dimethoxy-phenyl)-5,5-dimethyl-4,5-dihydro-pyrazole-1-carbonyl]-benzonitrile (132). Amount obtained: 471 mg, 1.2 mmol, 60% yield. LC-MS (ESI) m/e 364 (M+H). ¹H NMR (400 MHz, CHLOROFORM-d) δ ppm 1.80 (s, 6H) 3.19 (s, 2H) 3.91 (s, 3H) 3.93 (s, 3H) 6.88 (d, J=8.30 Hz, 1H) 7.09 (dd, J=8.27, 1.78 Hz, 1H) 7.27-7.28 (m, 1H) 7.54 (t, J=7.83 Hz, 1H) 7.73 (d, J=7.71 Hz, 1H) 8.12 (d, J=7.91 Hz, 1H) 8.30 (s, 1H).

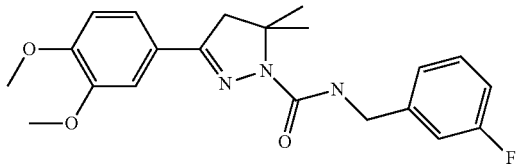 [SMILES: COc1ccc(C2=NN(C(=O)NCc3cccc(F)c3)C(C)(C)C2)cc1OC]

3-(3,4-Dimethoxy-phenyl)-5,5-dimethyl-4,5-dihydro-pyrazole-1-carboxylic acid 3-fluoro-benzylamide (133). Amount obtained: 33 mg, 0.09 mmol, 4% yield. LC-MS (ESI) m/e 386 (M+H). $^1$H NMR (400 MHz, CHLOROFORM-d) δ ppm 1.66 (s, 6H) 3.11 (s, 2H) 3.92 (s, 3H) 3.93 (s, 3H) 4.53 (d, J=6.25 Hz, 2H) 6.47 (t, J=5.93 Hz, 1H) 6.87 (d, J=8.35 Hz, 1H) 6.92-6.99 (m, 1H) 7.08 (dd, J=8.42, 1.59 Hz, 2H) 7.14 (d, J=7.61 Hz, 1H) 7.25-7.34 (m, 2H).

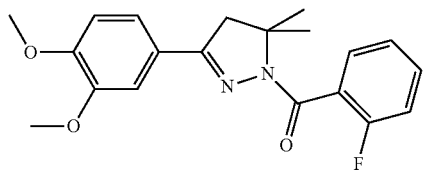 [SMILES: COc1ccc(C2=NN(C(=O)c3ccccc3F)C(C)(C)C2)cc1OC]

[3-(3,4-Dimethoxy-phenyl)-5,5-dimethyl-4,5-dihydro-pyrazol-1-yl]-(2-fluoro-phenyl)-methanone (228). Amount obtained: 17.4 mg, 0.05 mmol, 2% yield. LC-MS (ESI) 357 (M+H); $^1$H NMR (400 MHz, CHLOROFORM-d) δ ppm 1.78-1.82 (m, 6H) 3.19 (s, 2H) 3.81 (s, 3H) 3.90 (s, 3H) 6.83 (d, J=8.35 Hz, 1H) 7.02-7.11 (m, 2H) 7.14-7.22 (m, 2H) 7.36-7.44 (m, 1H) 7.52-7.57 (m, 1H).

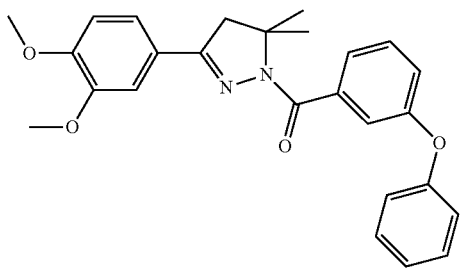 [SMILES: COc1ccc(C2=NN(C(=O)c3cccc(Oc4ccccc4)c3)C(C)(C)C2)cc1OC]

[3-(3,4-Dimethoxy-phenyl)-5,5-dimethyl-4,5-dihydro-pyrazol-1-yl]-(3-phenoxy-phenyl)-methanone (229). Amount obtained: 196.8 mg, 0.46 mmol, 46% yield. LC-MS (ESI) 431 (M+H); $^1$H NMR (400 MHz, CHLOROFORM-d) δ ppm 1.78 (s, 6H) 3.14 (s, 2H) 3.83 (s, 3H) 3.92 (s, 3H) 6.85 (d, J=8.30 Hz, 1H) 7.01-7.16 (m, 5H) 7.27 (s, 1H) 7.31 (t, J=7.93 Hz, 2H) 7.39 (t, J=7.93 Hz, 1H) 7.59-7.68 (m, 2H).

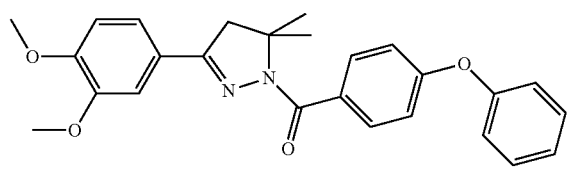 [SMILES: COc1ccc(C2=NN(C(=O)c3ccc(Oc4ccccc4)cc3)C(C)(C)C2)cc1OC]

[3-(3,4-Dimethoxy-phenyl)-5,5-dimethyl-4,5-dihydro-pyrazol-1-yl]-(4-phenoxy-phenyl)-methanone (230). Amount obtained: 151.7 mg, 0.35 mmol, 35% yield. LC-MS (ESI) 431 (M+H); $^1$H NMR (400 MHz, CHLOROFORM-d) δ ppm 1.79 (s, 6H) 3.16 (s, 2H) 3.89 (s, 3H) 3.93 (s, 3H) 6.87 (d, J=8.35 Hz, 1H) 7.01 (d, J=8.74 Hz, 2H) 7.07 (d, J=7.76 Hz, 2H) 7.10-7.19 (m, 2H) 7.29 (d, J=1.71 Hz, 1H) 7.37 (t, J=7.91 Hz, 2H) 7.93 (d, J=8.74 Hz, 2H).

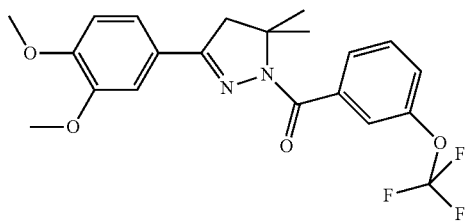 [SMILES: COc1ccc(C2=NN(C(=O)c3cccc(OC(F)(F)F)c3)C(C)(C)C2)cc1OC]

[3-(3,4-Dimethoxy-phenyl)-5,5-dimethyl-4,5-dihydro-pyrazol-1-yl]-(3-trifluoromethoxy-phenyl)-methanone (231). Amount obtained: 151.7 mg, 0.36 mmol, 36% yield. LC-MS (ESI) 423 (M+H); $^1$H NMR (400 MHz, CHLOROFORM-d) δ ppm 1.79 (s, 6H) 3.18 (s, 2H) 3.87 (s, 3H) 3.93 (s, 3H) 6.87 (d, J=8.35 Hz, 1H) 7.09 (dd, J=8.32, 1.88 Hz, 1H) 7.28 (d, J=1.81 Hz, 1H) 7.31 (d, J=8.05 Hz, 1H) 7.45 (t, J=8.08 Hz, 1H) 7.81-7.87 (m, 2H).

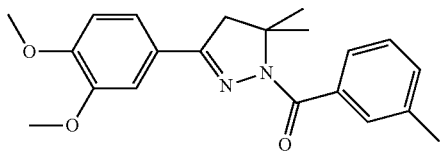

[3-(3,4-Dimethoxy-phenyl)-5,5-dimethyl-4,5-dihydro-pyrazol-1-yl]-m-tolyl-methanone (232). Amount obtained: 295 mg, 0.84 mmol, 42% yield. LC-MS (ESI) 353 (M+H); $^1$H NMR (400 MHz, CHLOROFORM-d) δ ppm 1.79 (s, 6H) 2.40 (s, 3H) 3.15 (s, 2H) 3.87 (s, 3H) 3.92 (s, 3H) 6.86 (d, J=8.35 Hz, 1H) 7.09 (dd, J=8.27, 1.88 Hz, 1H) 7.28-7.32 (m, 3H) 7.67 (d, J=7.08 Hz, 1H) 7.72 (s, 1H).

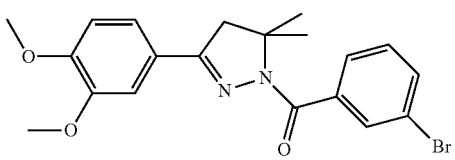 [SMILES: COc1ccc(C2=NN(C(=O)c3cccc(Br)c3)C(C)(C)C2)cc1OC]

(3-Bromo-phenyl)-[3-(3,4-dimethoxy-phenyl)-5,5-dimethyl-4,5-dihydro-pyrazol-1-yl]methanone (233). Amount obtained: 1.6 g, 3.76 mmol, 75% yield. LC-MS (ESI) 417 & 419 (M+H); $^1$H NMR (400 MHz, CHLOROFORM-d) δ ppm 1.79 (s, 6H) 3.17 (s, 2H) 3.92 (s, 3H) 3.93 (s, 3H) 6.87 (d, J=8.30 Hz, 1H) 7.06 (dd, J=8.30, 1.85 Hz, 1H) 7.30 (t, J=7.96 Hz, 1H) 7.34 (d, J=1.71 Hz, 1H) 7.58 (d, J=7.96 Hz, 1H) 7.82 (d, J=7.76 Hz, 1H) 8.14 (s, 1H).

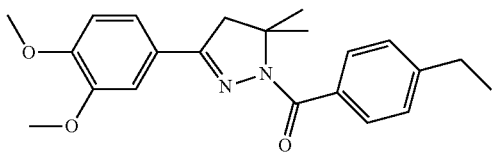 [SMILES: CCc1ccc(C(=O)N2N=C(c3ccc(OC)c(OC)c3)CC2(C)C)cc1]

[3-(3,4-Dimethoxy-phenyl)-5,5-dimethyl-4,5-dihydro-pyrazol-1-yl]-(4-ethyl-phenyl)-methanone (259). Amount obtained: 89.6 mg, 0.24 mmol, 12% yield. LC-MS (ESI) 367 (M+H); $^1$H NMR (400 MHz, CHLOROFORM-d) δ ppm 1.27 (t, J=7.61 Hz, 3H) 1.79 (s, 6H) 2.71 (q, J=7.60 Hz, 2H) 3.15 (s, 2H) 3.89 (s, 3H) 3.92 (s, 3H) 6.87 (d, J=8.35 Hz, 1H) 7.12 (dd, J=8.30, 1.85 Hz, 1H) 7.23 (d, J=8.10 Hz, 2H) 7.29 (d, J=1.71 Hz, 1H) 7.84 (d, J=8.20 Hz, 2H).

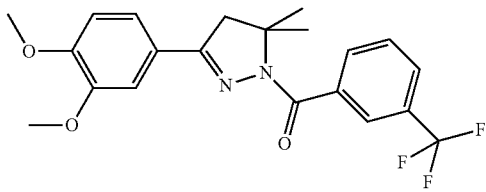 [SMILES: COc1ccc(C2=NN(C(=O)c3cccc(C(F)(F)F)c3)C(C)(C)C2)cc1OC]

[3-(3,4-Dimethoxy-phenyl)-5,5-dimethyl-4,5-dihydro-pyrazol-1-yl]-(3-trifluoromethyl-phenyl)-methanone (234). Amount obtained: 222 mg, 0.55 mmol, 27% yield. LC-MS (ESI) 407 (M+H); $^1$H NMR (400 MHz, CHLOROFORM-d) δ ppm 1.81 (s, 6H) 3.19 (s, 2H) 3.87 (s, 3H) 3.93 (s, 3H) 6.86 (d, J=8.30 Hz, 1H) 7.05 (dd, J=8.27, 1.88 Hz, 1H) 7.32 (d, J=1.81 Hz, 1H) 7.56 (t, J=7.81 Hz, 1H) 7.71 (d, J=7.76 Hz, 1H) 8.09 (d, J=7.81 Hz, 1H) 8.30 (s, 1H).

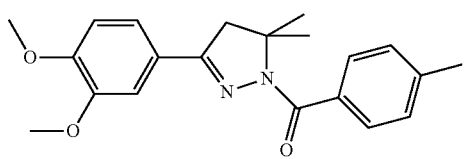

[3-(3,4-Dimethoxy-phenyl)-5,5-dimethyl-4,5-dihydro-pyrazol-1-yl]-p-tolyl-methanone (235). Amount obtained: 119 mg, 0.34 mmol, 17% yield. LC-MS (ESI) 353 (M+H); $^1$H NMR (400 MHz, CHLOROFORM-d) δ ppm 1.78 (s, 6H) 2.41 (s, 3H) 3.15 (s, 2H) 3.89 (s, 3H) 3.92 (s, 3H) 6.87 (d, J=8.35 Hz, 1H) 7.11 (dd, J=8.25, 1.22 Hz, 1H) 7.21 (d, J=7.96 Hz, 2H) 7.29 (s, 1H) 7.81 (d, J=8.00 Hz, 2H).

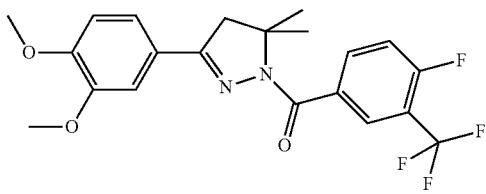 [SMILES: COc1ccc(C2=NN(C(=O)c3ccc(F)c(C(F)(F)F)c3)C(C)(C)C2)cc1OC]

[3-(3,4-Dimethoxy-phenyl)-5,5-dimethyl-4,5-dihydro-pyrazol-1-yl]-(4-fluoro-3-trifluoromethyl-phenyl)-methanone (236). Amount obtained: 69.6 mg, 0.16 mmol, 16% yield. LC-MS (ESI) 425 (M+H); $^1$H NMR (400 MHz, CHLOROFORM-d) δ ppm 1.79 (s, 6H) 3.19 (s, 2H) 3.89 (s, 3H) 3.93 (s, 3H) 6.87 (d, J=8.35 Hz, 1H) 7.06 (dd, J=8.25, 1.90 Hz, 1H) 7.22-7.26 (m, 1H) 7.31 (d, J=1.76 Hz, 1H) 8.12-8.18 (m, 1H) 8.38 (dd, J=6.98, 1.61 Hz, 1H).

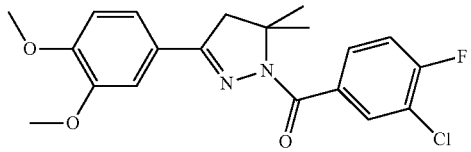 [SMILES: COc1ccc(C2=NN(C(=O)c3ccc(F)c(Cl)c3)C(C)(C)C2)cc1OC]

(3-Chloro-4-fluoro-phenyl)-[3-(3,4-dimethoxy-phenyl)-5,5-dimethyl-4,5-dihydro-pyrazol-1-yl]-methanone (237). Amount obtained: 83.3 mg, 0.21 mmol, 21% yield. LC-MS (ESI) 391 (M+H); $^1$H NMR (400 MHz, CHLOROFORM-d) δ ppm 1.78 (s, 6H) 3.17 (s, 2H) 3.91 (s, 3H) 3.93 (s, 3H) 6.88 (d, J=8.30 Hz, 1H) 7.08 (dd, J=8.27, 1.73 Hz, 1H) 7.18 (t, J=8.71 Hz, 1H) 7.32 (d, J=1.66 Hz, 1H) 7.83 (ddd, J=8.50, 4.77, 2.05 Hz, 1H) 8.12 (dd, J=7.30, 1.98 Hz, 1H).

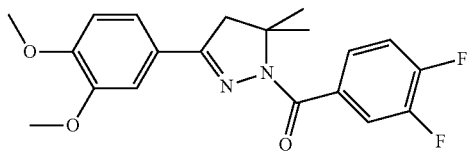 [SMILES: COc1ccc(C2=NN(C(=O)c3ccc(F)c(F)c3)C(C)(C)C2)cc1OC]

(3,4-Difluoro-phenyl)-[3-(3,4-dimethoxy-phenyl)-5,5-dimethyl-4,5-dihydro-pyrazol-1-yl]-methanone (246). Amount obtained: 100 mg, 0.27 mmol, 27% yield. LC-MS (ESI) 375 (M+H); $^1$H NMR (400 MHz, CHLOROFORM-d) δ ppm 1.78 (s, 6H) 3.17 (s, 2H) 3.90 (s, 3H) 3.93 (s, 3H) 6.88 (d, J=8.35 Hz, 1H) 7.11 (dd, J=8.30, 1.90 Hz, 1H) 7.15-7.24 (m, 1H) 7.28 (br. s., 1H) 7.71 (ddd, J=6.43, 4.33, 2.22 Hz, 1H) 7.84 (ddd, J=11.53, 7.94, 2.00 Hz, 1H).

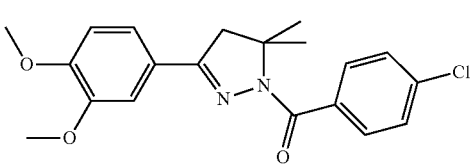 [SMILES: COc1ccc(C2=NN(C(=O)c3ccc(Cl)cc3)C(C)(C)C2)cc1OC]

(4-Chloro-phenyl)-[3-(3,4-dimethoxy-phenyl)-5,5-dimethyl-4,5-dihydro-pyrazol-1-yl]-methanone (247). Amount obtained: 139 mg, 0.37 mmol, 37% yield. LC-MS (ESI) 373 (M+H); $^1$H NMR (400 MHz, CHLOROFORM-d) δ ppm 1.78 (s, 6H) 3.16 (s, 2H) 3.89 (s, 3H) 3.93 (s, 3H) 6.87 (d, J=8.35 Hz, 1H) 7.11 (dd, J=8.32, 1.83 Hz, 1H) 7.25 (d, J=1.76 Hz, 1H) 7.38 (d, J=8.54 Hz, 2H) 7.84 (d, J=8.49 Hz, 2H).

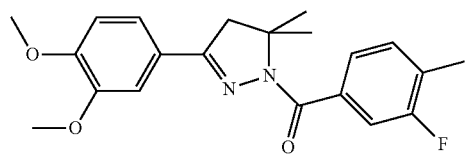

[3-(3,4-Dimethoxy-phenyl)-5,5-dimethyl-4,5-dihydro-pyrazol-1-yl]-(3-fluoro-4-methyl-phenyl)-methanone (249). Amount obtained: 154 mg, 0.42 mmol, 42% yield. LC-MS (ESI) 371 (M+H); ¹H NMR (400 MHz, CHLOROFORM-d) δ ppm 1.78 (s, 6H) 2.34 (d, J=1.12 Hz, 3H) 3.15 (s, 2H) 3.90 (s, 3H) 3.93 (s, 3H) 6.87 (d, J=8.35 Hz, 1H) 7.11 (dd, J=8.30, 1.85 Hz, 1H) 7.22 (t, J=7.76 Hz, 1H) 7.31 (d, J=1.76 Hz, 1H) 7.60-7.68 (m, 2H).

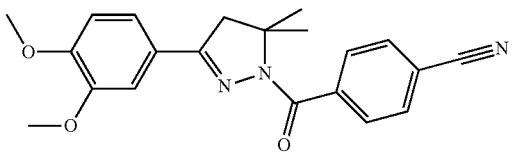 [SMILES: COc1ccc(C2=NN(C(=O)c3ccc(C#N)cc3)C(C)(C)C2)cc1OC]

4-[3-(3,4-Dimethoxy-phenyl)-5,5-dimethyl-4,5-dihydro-pyrazole-1-carbonyl]-benzonitrile (250). Amount obtained: 91 mg, 0.25 mmol, 25% yield. LC-MS (ESI) 364 (M+H); ¹H NMR (400 MHz, CHLOROFORM-d) δ ppm 1.79 (s, 6H) 3.19 (s, 2H) 3.87 (s, 3H) 3.93 (s, 3H) 6.87 (d, J=8.35 Hz, 1H) 7.10 (dd, J=8.30, 1.90 Hz, 1H) 7.19 (d, J=1.85 Hz, 1H) 7.71 (d, J=8.35 Hz, 2H) 7.93 (d, J=8.35 Hz, 2H).

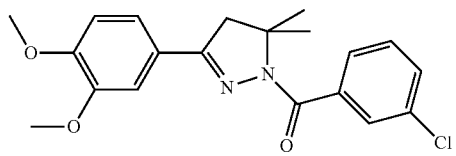

(3-Chloro-phenyl)-[3-(3,4-dimethoxy-phenyl)-5,5-dimethyl-4,5-dihydro-pyrazol-1-yl]-methanone (251). Amount obtained: 129 mg, 0.34 mmol, 34% yield. LC-MS (ESI) 373 (M+H); ¹H NMR (400 MHz, CHLOROFORM-d) δ ppm 1.79 (s, 6H) 3.17 (s, 2H) 3.90 (s, 3H) 3.93 (s, 3H) 6.87 (d, J=8.30 Hz, 1H) 7.07 (dd, J=8.30, 1.85 Hz, 1H) 7.33 (d, J=1.95 Hz, 1H) 7.36 (d, J=7.81 Hz, 1H) 7.40-7.46 (m, 1H) 7.77 (d, J=7.66 Hz, 1H) 7.97 (t, J=1.61 Hz, 1H).

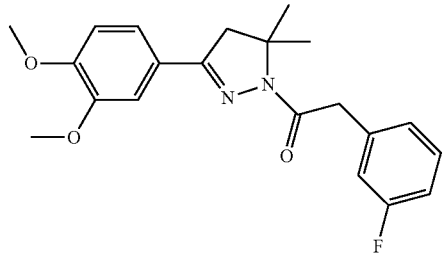 [SMILES: COc1ccc(C2=NN(C(=O)Cc3cccc(F)c3)C(C)(C)C2)cc1OC]

1-[3-(3,4-Dimethoxy-phenyl)-5,5-dimethyl-4,5-dihydro-pyrazol-1-yl]-2-(3-fluoro-phenyl)-ethanone (255). Amount obtained: 33 mg, 0.09 mmol, 9% yield. LC-MS (ESI) 371 (M+H); ¹H NMR (400 MHz, CHLOROFORM-d) δ ppm 1.65 (s, 6H) 3.10 (s, 2H) 3.94 (s, 3H) 3.96 (s, 3H) 4.05 (s, 2H) 6.88 (d, J=8.35 Hz, 1H) 6.92 (td, J=8.61, 2.29 Hz, 1H) 7.06-7.12 (m, 2H) 7.14 (d, J=7.66 Hz, 1H) 7.23-7.31 (m, 1H) 7.36 (d, J=1.76 Hz, 1H).

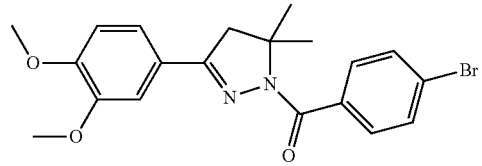 [SMILES: COc1ccc(C2=NN(C(=O)c3ccc(Br)cc3)C(C)(C)C2)cc1OC]

(4-Bromo-phenyl)-[3-(3,4-dimethoxy-phenyl)-5,5-dimethyl-4,5-dihydro-pyrazol-1-yl]-methanone (257). Amount obtained: 136 mg, 0.32 mmol, 7% yield. LC-MS (ESI) 417 & 419 (M+H); ¹H NMR (400 MHz, CHLOROFORM-d) δ ppm 1.78 (s, 6H) 3.16 (s, 2H) 3.89 (s, 3H) 3.93 (s, 3H) 6.87 (d, J=8.35 Hz, 1H) 7.11 (dd, J=8.30, 1.85 Hz, 1H) 7.24 (d, J=1.76 Hz, 1H) 7.54 (d, J=8.49 Hz, 2H) 7.77 (d, J=8.49 Hz, 2H).

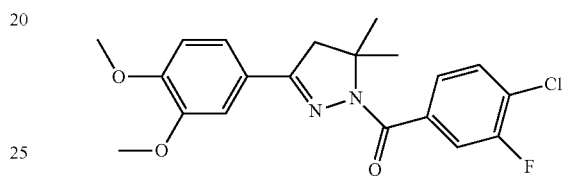

(4-Chloro-3-fluoro-phenyl)-[3-(3,4-dimethoxy-phenyl)-5,5-dimethyl-4,5-dihydro-pyrazol-1-yl]-methanone. Amount obtained: 18 mg, 0.05 mmol, 16% yield. LC-MS (ESI) 391 (M+H); ¹H NMR (400 MHz, CHLOROFORM-d) δ ppm 1.78 (s, 6H) 3.17 (s, 2H) 3.90 (s, 3H) 3.93 (s, 3H) 6.88 (d, J=8.35 Hz, 1H) 7.11 (dd, J=8.32, 1.88 Hz, 1H) 7.27 (s, 1H) 7.44 (t, J=7.86 Hz, 1H) 7.67 (dd, J=8.37, 1.00 Hz, 1H) 7.78 (dd, J=10.22, 1.83 Hz, 1H).

Example 2: Synthetic Route Towards (5,5-Dimethyl-3-o-tolyl-4,5-dihydro-pyrazol-1-yl)-(3-fluoro-phenyl)-methanone

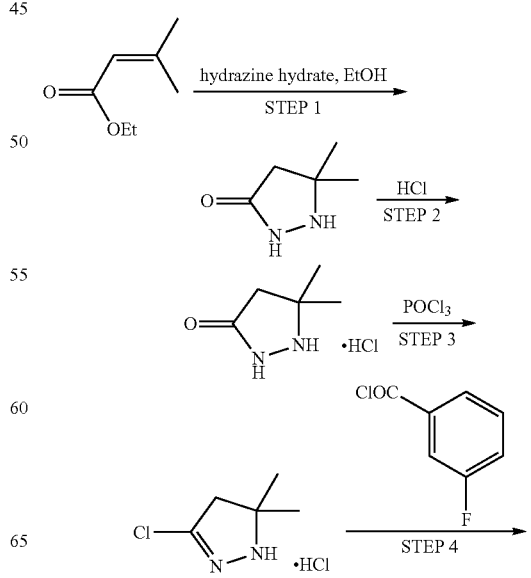

Scheme 2

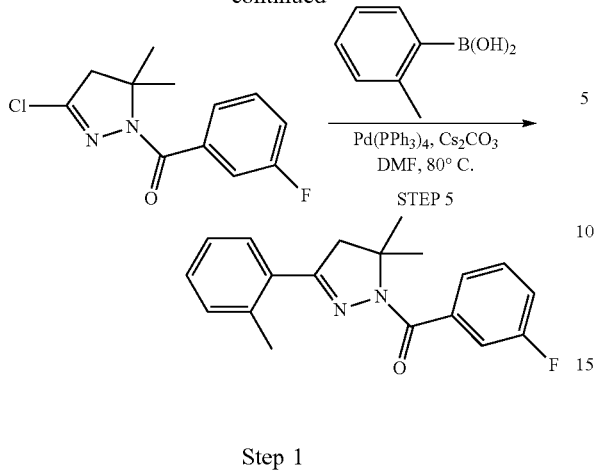

Step 1

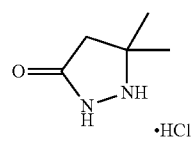

5,5-Dimethyl-pyrazolidin-3-one. A 100 mL round bottom flask equipped with a stir bar, Vigreux column and nitrogen inlet was charged with 3-methyl-but-2-enoic acid ethyl ester (1.4 mL, 10 mmol), EtOH (10 mL) and hydrazine monohydrate (0.58 mL, 12 mmol). The mixture was heated at 80° C. for 2 h. LC-MS and TLC analysis showed consumption of SM. The solvent was evaporated under reduced pressure and trace hydrazine and EtOH was removed under high vacuum for 30 min. The material was used as in the next step. Amount obtained: 1.1 g, 10 mmol, 100% yield. LC-MS (ESI) m/e 115 (M+H).

Step 2

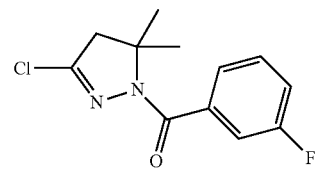

5,5-Dimethyl-pyrazolidin-3-one.Hydrochloride. A scintillation vial equipped with a stir bar was charged with 5,5-dimethyl-pyrazolidin-3-one (228 mg, 2.0 mmol) and 2.0 M HCl in Et$_2$O (2 mL) was added. A white PPT formed. This was filtered and washed with further Et$_2$O (20 mL). Amount obtained: 300 mg, 2.0 mmol, 100% yield.

Step 3

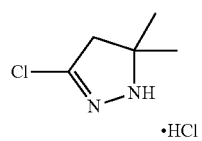

3-Chloro-5,5-dimethyl-4,5-dihydro-1H-pyrazole.Hydrochloride. A round 50 mL round bottom flask equipped with stir bar, Vigreux column and nitrogen inlet was charged with 5,5-dimethyl-pyrazolidin-3-one.Hydrochloride (300 mg, 2.0 mmol) and POCl$_3$ (4 mL). The mixture was heated at 90° C. for 3 h. LC-MS showed consumption of SM. The POCl$_3$ was evaporated under reduced pressure and trace POCl$_3$ was removed under high vacuum for 30 min. Amount obtained: 336 mg, 2.0 mmol, 100% yield. The material was used as in the next step.

Step 4

(3-Chloro-5,5-dimethyl-4,5-dihydro-pyrazol-1-yl)-(3-fluoro-phenyl)-methanone. A 250 mL round bottom flask equipped with a stir bar and nitrogen inlet was charged with dry CH$_2$Cl$_2$ (100 mL), Hunigs base (7.8 mL, 45 mmol) DMAP (5 mg) and 3-fluorobenzoyl chloride (1.8 mL. 15 mmol). The mixture was cooled to 0° C. To this mixture was added portionwise, 3-chloro-5,5-dimethyl-4,5-dihydro-1H-pyrazole.Hydrochloride (1.68 g, 10 mmol) and the reaction was allowed to warm to RT overnight. LC-MS showed consumption of SM. The reaction was added to water (100 mL), the phases were separated and the organic phase was washed with NaHCO$_3$ (100 mL), dried (Na$_2$SO$_4$) and the solvent was evaporated under reduced pressure. The material was purified by chromatography using a 40 g silica cartridge eluting with heptane-EtOAc, gradient 0 to 20% EtOAc. Amount obtained: 0.9 g, 3.7 mmol, 37% yield. LC-MS (ESI) m/e 255 (M+H). $^1$H NMR (400 MHz, CHLOROFORM-d) δ ppm 1.76 (s, 6H) 3.03 (s, 2H) 7.14 (td, J=8.36, 1.98 Hz, 1H) 7.36 (td, J=7.96, 5.71 Hz, 1H) 7.43 (dd, J=9.57, 2.25 Hz, 1H) 7.51 (d, J=7.76 Hz, 1H).

(5, 5-Dimethyl-3-o-tolyl-4, 5-dihydro-pyrazol-1-yl)-(3-fluoro-phenyl)-methanone. A scintillation vial equipped with a stir bar was charged with 3-chloro-5,5-dimethyl-4,5-dihydro-pyrazol-1-yl)-(3-fluoro-phenyl)-methanone (64 mg, 0.25 mmol), 3,4-dimethoxy boronic acid (40 mg, 0.3 mmol), Cs$_2$CO$_3$ (162 mg, 0.5 mmol) and DMF (5 mL). This mixture was degassed with nitrogen for 15 min and Pd(PPh$_3$)$_4$ (60 mg, 0.05 mmol) was added. The solution was further degassed for another 15 min and then it was heated at 80° C. for 2 h. LC-MS showed consumption of SM. The mixture was added to water (50 mL), extracted with EtOAc (50 mL), the organic phase washed with LiCl solution (50 mL), dried (Na$_2$SO$_4$) and the solvent was evaporated under reduced pressure. The material was purified by chromatography using a 12 g silica cartridge eluting with heptane-EtOAc, gradient 0 to 30% EtOAc. Amount obtained: 59 mg, 0.19 mmol, 76% yield. LC-MS (ESI) m/e 311 (M+H). $^1$H NMR (400 MHz, CHLOROFORM-d) δ ppm 1.57 (s, 6H) 1.95 (s, 1H) 3.77 (s, 3H) 3.82 (s, 3H) 4.16 (dd, J=12.25, 4.98 Hz, 1H) 4.57 (t, J=11.91 Hz, 1H) 4.68 (dd, 1H) 6.68 (d, J=8.39 Hz, 1H) 6.98 (dd, J=8.35, 1.85 Hz, 1H) 7.13-7.22 (m, 4H) 7.36 (d, J=8.20 Hz, 2H) 7.42 (td, J=8.07, 5.78 Hz, 1H) 7.81-7.87 (m, 2H).

Example 3: Synthetic Route Towards [3-(3,4-dimethoxy-phenyl)-4,4-dimethyl-4,5-dihydro-pyrazol-1-yl]-(phenyl)-methanones

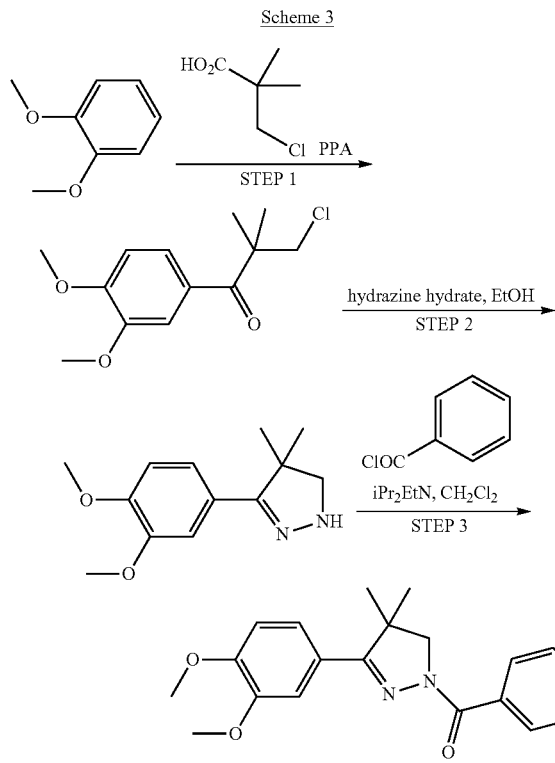

It shall be understood that the phenyl moiety (radical R) can be substituted in accordance with the Ar$^1$ definition as demonstrated below.

Step 1

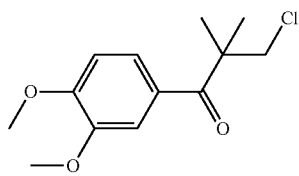 [SMILES: COc1ccc(C(=O)C(C)(C)CCl)cc1OC]

3-Chloro-1-(3,4-dimethoxy-phenyl)-2,2-dimethyl-propan-1-one. A 50 mL round bottom flask equipped with a stir bar was charged with veratrole (1.3 mL, 10 mmol) and 3-chloropivaloyl chloride (1.4 g, 10 mmol). To this mixture was added polyphosphoric acid (20 g). The mixture was heated at 70° C. for 2 h. [The progress of the reaction was followed by removing an aliquot for mini workup and NMR analysis.] The material was added to a mixture of ice water (100 mL)/EtOAc (100 mL) and stirred until the polyphosphoric acid had dissolved. The phases were separated and the EtOAc phase was washed with sat. NaHCO$_3$ (100 mL), dried (Na$_2$SO$_4$) and the solvent was evaporated under reduced pressure. The material was used as is in the next step. Amount obtained: 2.4 g, 9.3 mmol, 93% yield. LC-MS (ESI) m/e 257 (M+H). $^1$H NMR (400 MHz, CHLOROFORM-d) δ ppm 1.51 (s, 6H) 3.83 (s, 2H) 3.93 (s, 3H) 3.95 (s, 3H) 6.87 (d, J=8.44 Hz, 1H) 7.37 (d, J=1.95 Hz, 1H) 7.48 (dd, J=8.42, 1.98 Hz, 1H).

Step 2

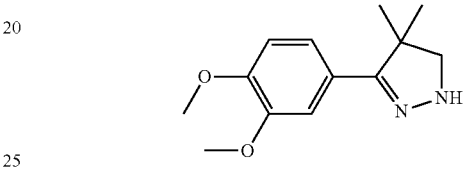

3-(3,4-Dimethoxy-phenyl)-4,4-dimethyl-4,5-dihydro-1H-pyrazole. A 100 mL round bottom flask equipped with a stir bar, Vigreux column and nitrogen inlet was charged with 3-chloro-1-(3,4-dimethoxy-phenyl)-2,2-dimethyl-propan-1-one (1.3 g, 5 mmol), EtOH (20 mL) and hydrazine monohydrate (0.3 mL, 6 mmol). The mixture was heated at 80° C. for 2 h. LC-MS and TLC analysis showed consumption of SM. The solvent was evaporated under reduced pressure and trace hydrazine and EtOH was removed under high vacuum for 30 min. The material was used as in the next step. Amount obtained: 1170 mg, 5 mmol, 100% yield. LC-MS (ESI) m/e 235 (M+H).

Step 3

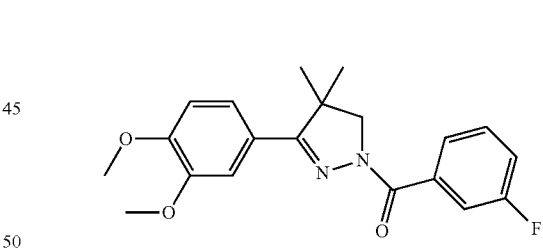

[3-(3,4-Dimethoxy-phenyl)-4,4-dimethyl-4,5-dihydro-pyrazol-1-yl]-(3-fluoro-phenyl)-methanone (149). A scintillation vial equipped with a stir bar was charged with 3-chloro-1-(3,4-dimethoxy-phenyl)-2,2-dimethyl-propan-1-one (469 mg, 2 mmol), Hunigs base (1 mL, 6 mmol) and dry CH$_2$Cl$_2$ (10 mL). To this mixture was added 3-fluorobenzoyl chloride (0.23 mL, 2 mmol) and the reaction was stirred at RT for 3 h. LC-MS indicated consumption of SM. The mixture was diluted with CH$_2$Cl$_2$ (50 mL) and added to water (50 mL). The phases were separated and the CH$_2$Cl$_2$ phase was washed with saturated Na$_2$CO$_3$, (50 mL), dried (Na$_2$SO$_4$) and the solvent was evaporated under reduced pressure. The material was purified using a 40 g silica cartridge eluting with heptane-EtOAc, gradient 0 to 50% EtOAc. Amount obtained: 350 mg, 1 mmol, 50% yield. LC-MS (ESI) m/e 357 (M+H). $^1$H NMR (400 MHz, CHLOROFORM-d) δ ppm 1.58 (s, 6H) 3.89 (s, 3H) 3.93 (s, 3H) 4.05 (s, 2H) 6.87 (d, J=8.39 Hz, 1H) 7.18 (td, J=8.31, 1.98 Hz, 1H) 7.30-7.43 (m, 3H) 7.80 (t, J=7.00 Hz, 2H).

The following compounds were prepared in a similar manner. LC-MS and HPLC analysis were performed as follows: Method: A—0.1% TFA in water, B—0.1% TFA in ACN: Flow—2 ml/min; Column: XBridge c8 (50×4.6 mm, 3.5 μm); unless stated otherwise.

(3-Bromo-phenyl)-[3-(3,4-dimethoxy-phenyl)-4,4-dimethyl-4,5-dihydro-pyrazol-1-yl]methanone

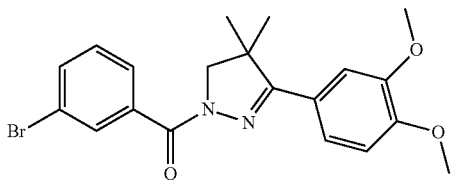 [SMILES: COc1ccc(C2=NN(C(=O)c3cccc(Br)c3)CC2(C)C)cc1OC]

White solid; 9.94% Yield

LC-MS: Mass found (M+, 419). Rt (min): 4.97; % Area: 95.97 (Max), 95.63 (220 nm).

HPLC—Rt (min): 4.94; % Area: 98.17 (Max), 97.86 (254 nm).

400 MHz, DMSO-d6: δ 8.12 (s, 1H), 7.85-7.83 (m, 1H), 7.73-7.71 (m, 1H), 7.44 (t, J=8.00 Hz, 1H), 7.35-7.33 (m, 1H), 7.27-7.26 (m, 1H), 6.98 (d, J=8.00 Hz, 1H), 3.92 (s, 2H), 3.78 (s, 3H), 3.76 (s, 3H), 1.48 (s, 6H).

(3-Chloro-phenyl)-[3-(3,4-dimethoxy-phenyl)-4,4-dimethyl-4,5-dihydro-pyrazol-1-yl]methanone

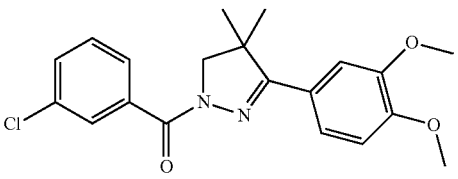 [SMILES: COc1ccc(C2=NN(C(=O)c3cccc(Cl)c3)CC2(C)C)cc1OC]

White solid; 6.98% Yield

LC-MS: Mass found (M+, 373). Rt (min): 4.88; % Area: 96.54 (Max), 96.77 (254 nm).

HPLC—Rt (min): 4.87; % Area: 98.76 (Max), 99.01 (254 nm).

400 MHz, DMSO-d6: δ 7.96 (s, 1H), 7.81-7.79 (m, 1H), 7.60-7.58 (m, 1H), 7.50 (t, J=8.00 Hz, 1H), 7.35-7.32 (m, 1H), 7.26-7.25 (m, 1H), 6.99 (d, J=12.00 Hz, 1H), 3.93 (s, 2H), 3.78 (s, 3H), 3.74 (s, 3H), 1.48 (s, 6H).

[3-(3,4-Dimethoxy-phenyl)-4,4-dimethyl-4,5-dihydro-pyrazol-1-yl]-(3-methoxy-phenyl)-methanone

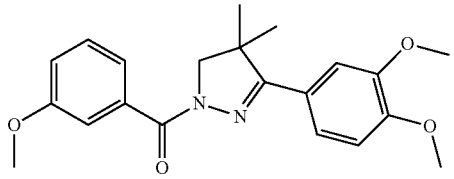 [SMILES: COc1cccc(C(=O)N2CC(C)(C)C(c3ccc(OC)c(OC)c3)=N2)c1]

White solid; 4.13% Yield

LC-MS: Mass found (M+, 369.3). Rt (min): 4.42; % Area: 95.08 (Max), 96.50 (254 nm).

HPLC—Rt (min): 4.39; % Area: 98.94 (Max), 98.15 (254 nm).

400 MHz, DMSO-d6: δ 7.44-7.42 (m, 2H), 7.38-7.31 (m, 2H), 7.23 (d, J=4.00 Hz, 1H), 7.09-7.06 (m, 1H), 6.99 (d, J=8.00 Hz, 1H), 3.91 (s, 2H), 3.78 (s, 6H), 3.73 (s, 3H), 1.47 (s, 6H).

[3-(3,4-Dimethoxy-phenyl)-4,4-dimethyl-4,5-dihydro-pyrazol-1-yl]-(3-ethoxy-phenyl)-methanone

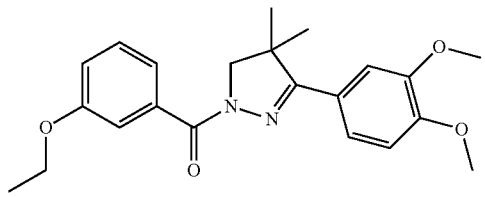 [SMILES: CCOc1cccc(C(=O)N2CC(C)(C)C(c3ccc(OC)c(OC)c3)=N2)c1]

White solid; 5.47% Yield

LC-MS: Mass found (M+, 383.3). Rt (min): 4.71; % Area: 97.98 (Max), 98.48 (220 nm).

HPLC—Rt (min): 4.7; % Area: 98.82 (Max), 98.31 (254 nm).

400 MHz, DMSO-d6: δ 7.42-7.40 (m, 2H), 7.37-7.31 (m, 2H), 7.24 (d, J=4.00 Hz, 1H), 7.07-7.04 (m, 1H), 6.98 (d, J=8.00 Hz, 1H), 4.07-4.02 (m, 2H), 3.91 (s, 2H), 3.78 (s, 3H), 3.73 (s, 3H), 1.47 (s, 6H), 1.31 (t, J=8.00 Hz, 3H).

[3-(3,4-Dimethoxy-phenyl)-4,4-dimethyl-4,5-dihydro-pyrazol-1-yl]-(3-trifluoromethyl-phenyl)-methanone

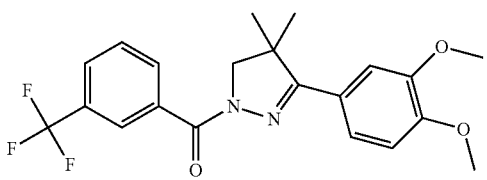 [SMILES: COc1ccc(C2=NN(C(=O)c3cccc(C(F)(F)F)c3)CC2(C)C)cc1OC]

Brown solid; 5.02% Yield

LC-MS: Mass found (M+, 407.3). Rt (min): 5.12; % Area: 96.50 (Max), 97.34 (254 nm).

HPLC—Rt (min): 5.3; % Area: 98.42 (Max), 98.15 (254 nm).

400 MHz, DMSO-d6: δ 8.29 (s, 1H), 8.15-8.13 (m, 1H), 7.91-7.89 (m, 1H), 7.72 (t, J=8.00 Hz, 1H), 7.36 (dd, J=8.00, 4.00 Hz, 1H), 7.25 (d, J=4.00 Hz, 1H), 6.98 (d, J=8.00 Hz, 1H), 3.96 (s, 2H), 3.78 (s, 3H), 3.71 (s, 3H), 1.50 (s, 6H).

[3-(3,4-Dimethoxy-phenyl)-4,4-dimethyl-4,5-di-hydro-pyrazol-1-yl]-m-tolyl-methanone

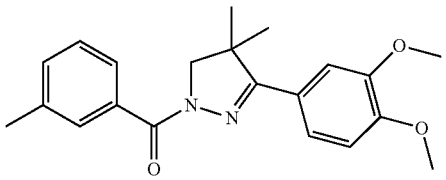

Brown gum; 15.29% Yield

LC-MS: Mass found (M+, 353.3). Rt (min): 4.66; % Area: 91.12 (Max), 92.42 (254 nm). HPLC—Rt (min): 4.64; % Area: 94.23 (Max), 95.13 (254 nm).

400 MHz, DMSO-d6: δ 7.71 (s, 1H), 7.64-7.62 (m, 1H), 7.35-7.31 (m, 3H), 7.25-7.24 (m, 1H), 6.98 (d, J=8.00 Hz, 1H), 3.91 (s, 2H), 3.78 (s, 3H), 3.73 (s, 3H), 2.35 (s, 3H), 1.47 (s, 6H).

3-[3-(3,4-Dimethoxy-phenyl)-4,4-dimethyl-4,5-di-hydro-pyrazole-1-carbonyl]benzonitrile

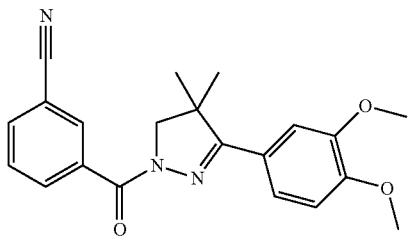 [SMILES: COc1ccc(C2=NN(C(=O)c3cccc(C#N)c3)CC2(C)C)cc1OC]

Brown solid; 28.18% Yield

LC-MS: Mass found (M+, 364.3). Rt (min): 4.36; % Area: 96.95 (Max), 96.43 (254 nm).

HPLC—Rt (min): 4.34; % Area: 97.62 (Max), 95.87 (254 nm).

400 MHz, DMSO-d6: δ 8.36 (s, 1H), 8.15-8.13 (m, 1H), 8.00-7.98 (m, 1H), 7.69 (t, J=8.00 Hz, 1H), 7.35-7.33 (m, 1H), 7.26-7.25 (m, 1H), 6.98 (d, J=8.00 Hz, 1H), 3.94 (s, 2H), 3.78 (s, 3H), 3.75 (s, 3H), 1.49 (s, 6H).

[3-(3,4-Dimethoxy-phenyl)-4,4-dimethyl-4,5-di-hydro-pyrazol-1-yl]-(3-trifluoromethoxy-phenyl)-methanone

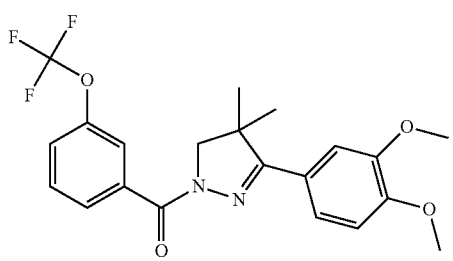 [SMILES: COc1ccc(C2=NN(C(=O)c3cccc(OC(F)(F)F)c3)CC2(C)C)cc1OC]

Brown solid; 7.82% Yield

LC-MS: Mass found (M+, 423.3). Rt (min): 5.24; % Area: 99.09 (Max), 98.87 (254 nm).

HPLC—Rt (min): 5.23; % Area: 99.18 (Max), 99.10 (254 nm). 400 MHz, DMSO-d6: δ 7.90-7.88 (m, 2H), 7.61 (t, J=8.00 Hz, 1H), 7.55-7.53 (m, 1H), 7.35 (dd, J=12.00, 4.00 Hz, 1H), 7.24-7.23 (m, 1H), 6.98 (d, J=8.00 Hz, 1H), 3.94 (s, 2H), 3.78 (s, 3H), 3.72 (s, 3H), 1.49 (s, 6H).

[3-(3,4-Dimethoxy-phenyl)-4,4-dimethyl-4,5-di-hydro-pyrazol-1-yl]-(3-dimethylamino-phenyl)-methanone

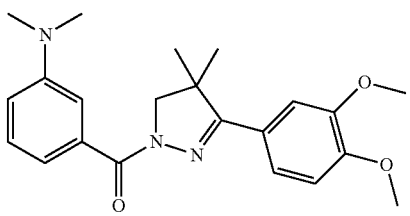 [SMILES: COc1ccc(C2=NN(C(=O)c3cccc(N(C)C)c3)CC2(C)C)cc1OC]

Yellow solid; 18.55% Yield

LC-MS: Mass found (M+, 382.3). Rt (min): 3.22; % Area: 91.47 (Max), 92.60 (254 nm).

HPLC—Rt (min): 3.18; % Area: 91.78 (Max), 91.41 (254 nm).

400 MHz, DMSO-d6: δ 7.33 (dd, J=8.00, 4.00 Hz, 1H), 7.26-7.22 (m, 3H), 7.14-7.12 (m, 1H), 6.98 (d, J=8.00 Hz, 1H), 6.87-6.84 (m, 1H), 3.90 (s, 2H), 3.78 (s, 3H), 3.72 (s, 3H), 2.91 (s, 6H), 1.47 (s, 6H).

(3-Benzyloxy-phenyl)-[3-(3,4-dimethoxy-phenyl)-4,4-dimethyl-4,5-dihydro-pyrazol-1-yl]-methanone

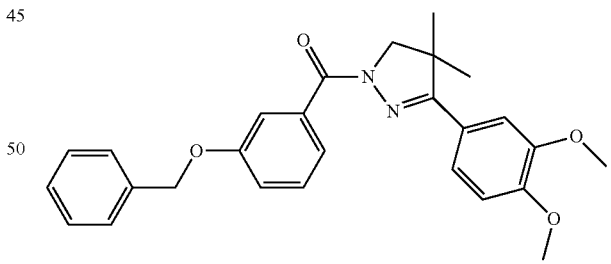

Brown solid; 16.34% Yield

LC-MS: Mass found (M+, 445.3). Rt (min): 5.29; % Area: 96.04 (Max), 96.50 (254 nm).

HPLC—Rt (min): 5.49; % Area: 98.40 (Max), 97.32 (254 nm).

400 MHz, DMSO-d6: δ 7.53-7.52 (m, 1H), 7.46-7.43 (m, 3H), 7.39-7.35 (m, 3H), 7.33-7.30 (m, 2H), 7.24 (s, 1H), 7.17 (dd, J=8.00, 4.00 Hz, 1H), 6.98 (d, J=12.00 Hz, 1H), 5.13 (s, 2H), 3.91 (s, 2H), 3.78 (s, 3H), 3.67 (s, 3H), 1.47 (s, 6H).

[3-(3,4-Dimethoxy-phenyl)-4,4-dimethyl-4,5-dihydro-pyrazol-1-yl]-(3-isopropoxy-phenyl)-methanone

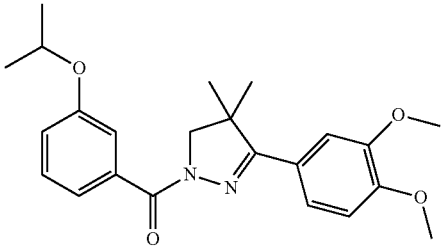 [SMILES: COc1ccc(C2=NN(C(=O)c3cccc(OC(C)C)c3)CC2(C)C)cc1OC]

Brown solid; 22.40% Yield

LC-MS: Mass found (M+, 397.3). Rt (min): 4.45; % Area: 95.91 (Max), 96.11 (254 nm).

HPLC—Rt (min): 5.11; % Area: 97.30 (Max), 96.48 (254 nm).

400 MHz, DMSO-d6: δ 7.40-7.31 (m, 4H), 7.24 (d, J=4.00 Hz, 1H), 7.06-7.03 (m, 1H), 6.98 (d, J=8.00 Hz, 1H), 4.65-4.59 (m, 1H), 3.91 (s, 2H), 3.78 (s, 3H), 3.73 (s, 3H), 1.47 (s, 6H), 1.25 (d, J=8.00 Hz, 6H).

[3-(3,4-Dimethoxy-phenyl)-4,4-dimethyl-4,5-dihydro-pyrazol-1-yl]-(3-phenoxy-phenyl)-methanone

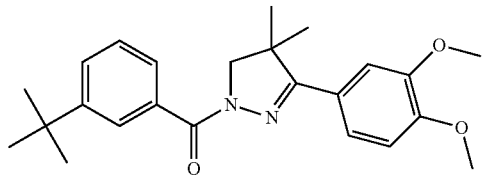 [SMILES: COc1ccc(C2=NN(C(=O)c3cccc(C(C)(C)C)c3)CC2(C)C)cc1OC]

White solid; 23.35% Yield

LC-MS: Mass found (M+, 431.3). Rt (min): 5.29; % Area: 98.33 (Max), 98.71 (254 nm).

HPLC—Rt (min): 5.47; % Area: 98.66 (Max), 99.24 (254 nm).

400 MHz, DMSO-d6: δ 7.65 (d, J=8.00 Hz, 1H), 7.51-7.47 (m, 2H), 7.39-7.35 (m, 2H), 7.28 (d, J=8.00 Hz, 1H), 7.21-7.12 (m, 3H), 7.03 (d, J=8.00 Hz, 2H), 6.97 (d, J=8.00 Hz, 1H), 3.90 (s, 2H), 3.79 (s, 3H), 3.69 (s, 3H), 1.46 (s, 6H).

Biphenyl-3-yl-[3-(3,4-dimethoxy-phenyl)-4,4-dimethyl-4,5-dihydro-pyrazol-1-yl]methanone

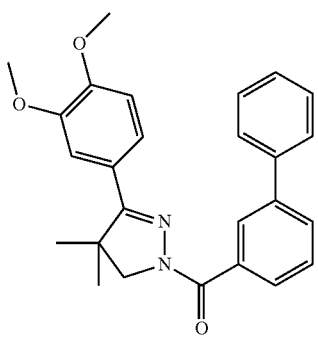 [SMILES: COc1ccc(C2=NN(C(=O)c3cccc(-c4ccccc4)c3)CC2(C)C)cc1OC]

White solid; 10.46% Yield

LC-MS: Mass found (M+, 415.3). Rt (min): 5.23; % Area: 97.14 (Max), 98.20 (254 nm).

HPLC—Rt (min): 5.22; % Area: 98.53 (Max), 98.97 (254 nm).

400 MHz, DMSO-d6: δ 8.20 (s, 1H), 7.83-7.79 (m, 2H), 7.69 (d, J=8.00 Hz, 2H), 7.56 (t, J=8.00 Hz, 1H), 7.48 (t, J=4.00 Hz, 2H), 7.41-7.33 (m, 2H), 7.20 (s, 1H), 6.97 (d, J=12.00 Hz, 1H), 3.96 (s, 2H), 3.77 (s, 3H), 3.50 (s, 3H), 1.50 (s, 6H).

(3-tert-Butyl-phenyl)-[3-(3,4-dimethoxy-phenyl)-4,4-dimethyl-4,5-dihydro-pyrazol-1-yl]-methanone

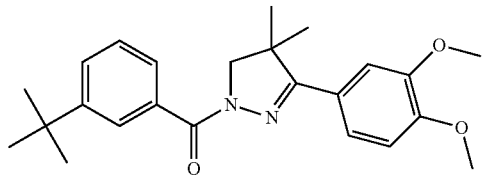 [SMILES: COc1ccc(C2=NN(C(=O)c3cccc(C(C)(C)C)c3)CC2(C)C)cc1OC]

White solid, 22.51% Yield

LC-MS: Mass found (M+, 395.3). Rt (min): 5.39; % Area: 96.81 (Max), 96.96 (220 nm).

HPLC—Rt (min): 5.57; % Area: 97.60 (Max), 97.74 (254 nm).

400 MHz, DMSO-d6: δ 7.91 (s, 1H), 7.66-7.64 (m, 1H), 7.56-7.53 (m, 1H), 7.40-7.34 (m, 2H), 7.24 (d, J=4.00 Hz, 1H), 6.98 (d, J=8.00 Hz, 1H), 3.92 (s, 2H), 3.78 (s, 3H), 3.71 (s, 3H), 1.48 (s, 6H), 1.30 (s, 9H).

[3-(3,4-Dimethoxy-phenyl)-4,4-dimethyl-4,5-dihydro-pyrazol-1-yl]-(3-methanesulfonyl-phenyl)-methanone

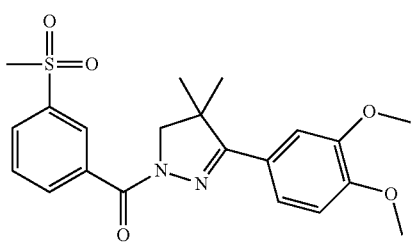

White solid; 23.85% Yield

LC-MS: Mass found (M+, 417.3). Rt (min): 3.89; % Area: 96.94 (Max), 96.17 (220 nm).

HPLC—Rt (min): 4.07; % Area: 98.57 (Max), 97.36 (254 nm).

400 MHz, DMSO-d6: δ 8.56 (s, 1H), 8.19-8.17 (m, 1H), 8.09-8.06 (m, 1H), 7.76 (t, J=8.00 Hz, 1H), 7.38 (dd, J=8.00, 4.00 Hz, 1H), 7.30 (d, J=4.00 Hz, 1H), 6.97 (d, J=8.00 Hz, 1H), 3.97 (s, 2H), 3.78 (s, 3H), 3.75 (s, 3H), 3.25 (s, 3H), 1.50 (s, 6H).

N-{3-[3-(3,4-Dimethoxy-phenyl)-4,4-dimethyl-4,5-dihydro-pyrazole-1-carbonyl]-phenyl}-acetamide

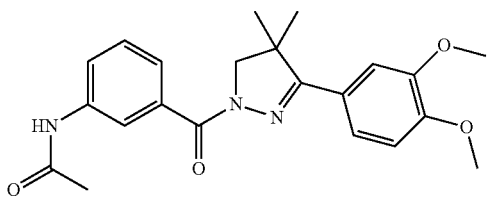 [SMILES: COc1ccc(C2=NN(C(=O)c3cccc(NC(C)=O)c3)CC2(C)C)cc1OC]

White solid; 6.40% Yield
LC-MS: Mass found (M+, 396.3). Rt (min): 3.62; % Area: 98.93 (Max), 99.25 (254 nm).
HPLC—Rt (min): 3.77; % Area: 99.61 (Max), 99.39 (254 nm).
400 MHz, DMSO-d6: δ 10.07 (s, 1H), 8.19 (s, 1H), 7.69-7.67 (m, 1H), 7.51-7.49 (m, 1H), 7.38-7.33 (m, 2H), 7.30 (d, J=4.00 Hz, 1H), 6.97 (d, J=8.00 Hz, 1H), 3.92 (s, 2H), 3.78 (s, 3H), 3.74 (s, 3H), 2.03 (s, 3H), 1.47 (s, 6H).

[3-(3,4-Dimethoxy-phenyl)-4,4-dimethyl-4,5-dihydro-pyrazol-1-yl]-(4-fluoro-phenyl)-methanone

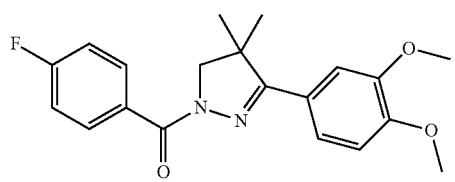 [SMILES: COc1ccc(C2=NN(C(=O)c3ccc(F)cc3)CC2(C)C)cc1OC]

Brown solid; 48.79% Yield
LC-MS: Mass found (M+, 357.2). Rt (min): 4.63; % Area: 97.62 (Max), 95.61 (254 nm).
HPLC—Rt (min): 4.56; % Area: 96.57 (Max), 95.51 (254 nm).
400 MHz, DMSO-d6: δ 7.97-7.94 (m, 2H), 7.34-7.27 (m, 3H), 7.23 (d, J=4.00 Hz, 1H), 6.98 (d, J=8.00 Hz, 1H), 3.91 (s, 2H), 3.78 (s, 3H), 3.74 (s, 3H), 1.47 (s, 6H).

(3,4-Difluoro-phenyl)-[3-(3,4-dimethoxy-phenyl)-4,4-dimethyl-4,5-dihydro-pyrazol-1-yl]-methanone

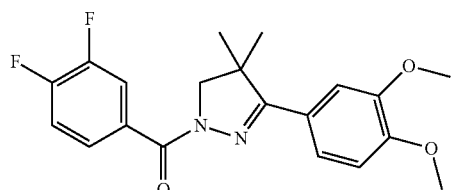

White solid; 18.49% Yield
LC-MS: Mass found (M+, 375). Rt (min): 4.80; % Area: 99.11 (Max), 99.31 (254 nm).
HPLC—Rt (min): 4.82; % Area: 97.49 (Max), 98.77 (254 nm).
400 MHz, DMSO-d6: δ 7.98-7.93 (m, 1H), 7.80-7.77 (m, 1H), 7.57-7.51 (m, 1H), 7.35 (dd, J=8.00, 4.00 Hz, 1H), 7.25 (d, J=4.00 Hz, 1H), 7.00 (d, J=12.00 Hz, 1H), 3.92 (s, 2H), 3.78 (s, 3H), 3.74 (s, 3H), 1.48 (s, 6H).

[3-(3,4-Dimethoxy-phenyl)-4,4-dimethyl-4,5-dihydro-pyrazol-1-yl]-(3-fluoro-4-trifluoromethyl-phenyl)-methanone

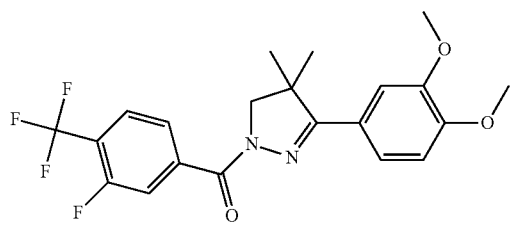 [SMILES: COc1ccc(C2=NN(C(=O)c3ccc(C(F)(F)F)c(F)c3)CC2(C)C)cc1OC]

White solid; 20.15% Yield
LC-MS: Mass found (M+, 425). Rt (min): 5.35; % Area: 99.05 (Max), 99.46 (254 nm).
HPLC—Rt (min): 5.34; % Area: 98.71 (Max), 98.93 (254 nm).
400 MHz, DMSO-d6: δ 7.84-7.79 (m, 2H), 7.35 (dd, J=8.00, 4.00 Hz, 1H), 7.27-7.22 (m, 2H), 7.00 (d, J=8.00 Hz, 1H), 3.90 (s, 2H), 3.79 (s, 3H), 3.76 (s, 3H), 1.47 (s, 6H).

[3-(3,4-Dimethoxy-phenyl)-4,4-dimethyl-4,5-dihydro-pyrazol-1-yl]-(3-fluoro-4-methyl-phenyl)-methanone

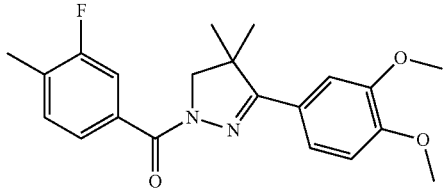

Brown solid; 5.82% Yield
LC-MS: Mass found (M+, 371.3). Rt (min): 4.87; % Area: 93.26 (Max), 94.56 (254 nm).
HPLC—Rt (min): 4.86; % Area: 95.35 (Max), 94.94 (254 nm).
400 MHz, DMSO-d6: δ 7.68-7.65 (m, 2H), 7.39-7.32 (m, 2H), 7.25 (d, J=4.00 Hz, 1H), 6.99 (d, J=8.00 Hz, 1H), 3.91 (s, 2H), 3.78 (s, 3H), 3.75 (s, 3H), 2.29 (d, J=4.00 Hz, 3H), 1.47 (s, 6H).

[3-(3,4-Dimethoxy-phenyl)-4,5-dihydro-pyrazol-1-yl]-(3-fluoro-4-methoxy-phenyl)-methanone

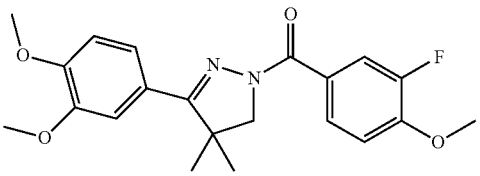

White solid; 9.50% Yield

LC-MS: Mass found (M+, 387.3). Rt (min): 4.53; % Area: 98.58 (Max), 99.07 (254 nm).

HPLC—Rt (min): 4.54; % Area: 98.67 (Max), 99.14 (254 nm).

400 MHz, DMSO-d6: δ 7.84-7.79 (m, 2H), 7.35 (dd, J=8.00, 4.00 Hz, 1H), 7.27-7.22 (m, 2H), 7.00 (d, J=8.00 Hz, 1H), 3.90 (d, J=4.00 Hz, 5H), 3.79 (s, 3H), 3.76 (s, 3H), 1.47 (s, 6H).

(4-Bromo-3-fluoro-phenyl)-[3-(3,4-dimethoxy-phenyl)-4,4-dimethyl-4,5-dihydro-pyrazol-1-yl]-methanone

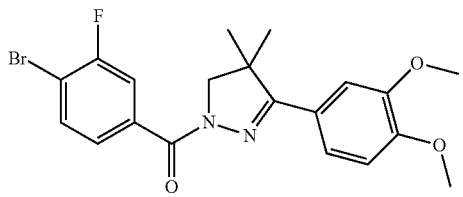 [SMILES: COc1ccc(C2=NN(C(=O)c3ccc(Br)c(F)c3)CC2(C)C)cc1OC]

White solid; 6.57% Yield

LC-MS: Mass found (M+, 437). Rt (min): 5.12; % Area: 97.72 (Max), 98.70 (254 nm).

HPLC—Rt (min): 5.11; % Area: 98.7 (Max), 98.93 (254 nm).

400 MHz, DMSO-d6: δ 7.87-7.81 (m, 2H), 7.69-7.67 (m, 1H), 7.34 (dd, J=8.00, 4.00 Hz, 1H), 7.24 (d, J=4.00 Hz, 1H), 6.99 (d, J=8.00 Hz, 1H), 3.92 (s, 2H), 3.78 (s, 3H), 3.75 (s, 3H), 1.48 (s, 6H).

(2,3-Difluoro-phenyl)-[3-(3,4-dimethoxy-phenyl)-4,4-dimethyl-4,5-dihydro-pyrazol-1-yl]-methanone

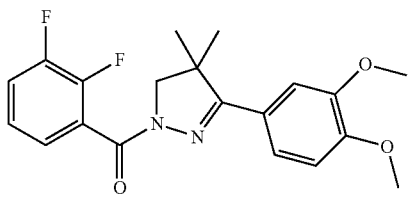 [SMILES: COc1ccc(C2=NN(C(=O)c3cccc(F)c3F)CC2(C)C)cc1OC]

White solid; 13.77% Yield

LC-MS: Mass found (M+, 375). Rt (min): 4.55; % Area: 97.31 (Max), 97.42 (254 nm).

HPLC—Rt (min): 4.54; % Area: 98.87 (Max), 99.13 (254 nm).

400 MHz, DMSO-d6: δ 7.59-7.52 (m, 1H), 7.38-7.35 (m, 1H), 7.31-7.28 (m, 1H), 7.25 (dd, J=8.00, 4.00 Hz, 1H), 7.10 (d, J=4.00 Hz, 1H), 6.97 (d, J=12.00 Hz, 1H), 3.93 (s, 2H), 3.76 (s, 3H), 3.67 (s, 3H), 1.46 (s, 6H).

[3-(3,4-Dimethoxy-phenyl)-4,4-dimethyl-4,5-di-hydro-pyrazol-1-yl]-(3-fluoro-2-methyl-phenyl)-methanone

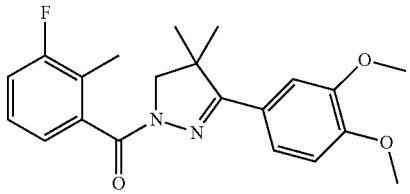 [SMILES: COc1ccc(C2=NN(C(=O)c3cccc(F)c3C)CC2(C)C)cc1OC]

Brown Gum; 13.85% Yield

LC-MS: Mass found (M+, 371.3). Rt (min): 4.60; % Area: 92.64 (Max), 94.86 (254 nm).

HPLC—Rt (min): 4.61; % Area: 95.70 (Max), 96.29 (254 nm).

400 MHz, DMSO-d6: δ 7.28-7.17 (m, 4H), 7.04 (d, J=4.00 Hz, 1H), 6.95 (d, J=8.00 Hz, 1H), 3.93 (s, 2H), 3.75 (s, 3H), 3.66 (s, 3H), 2.15 (d, J=4.00 Hz, 3H), 1.46 (s, 6H).

[3-(3,4-Dimethoxy-phenyl)-4,4-dimethyl-4,5-di-hydro-pyrazol-1-yl]-(3-fluoro-2-trifluoromethyl-phenyl)-methanone

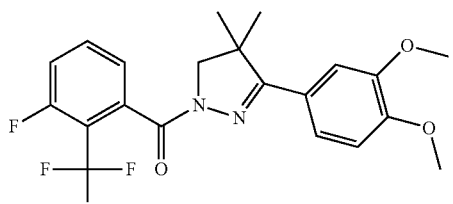

Brown solid; 9.11% Yield

LC-MS: Mass found (M+, 425.3). Rt (min): 4.89; % Area: 91.76 (Max), 93.89 (254 nm).

HPLC—Rt (min): 4.89; % Area: 93.92 (Max), 94.22 (254 nm).

400 MHz, DMSO-d6: δ 7.83-7.80 (m, 1H), 7.61-7.56 (m, 1H), 7.40-7.38 (m, 1H), 7.20 (dd, J=8.00, 4.00 Hz, 1H), 7.01 (d, J=4.00 Hz, 1H), 6.95 (d, J=8.00 Hz, 1H), 3.88 (s, 2H), 3.75 (s, 3H), 3.63 (s, 3H), 1.45 (s, 6H).

[3-(3,4-Dimethoxy-phenyl)-4,4-dimethyl-4,5-di-hydro-pyrazol-1-yl]-(3-fluoro-2-methoxy-phenyl)-methanone

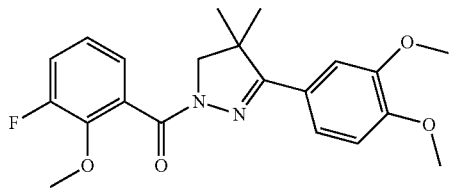 [SMILES: COc1ccc(C2=NN(C(=O)c3cccc(F)c3OC)CC2(C)C)cc1OC]

Yellow Gum; 24.56% Yield

LC-MS: Mass found (M+, 387.3). Rt (min): 4.40; % Area: 92.17 (Max), 92.25 (254 nm).

HPLC—Rt (min): 4.55; % Area: 93.05 (Max), 93.51 (254 nm).

400 MHz, DMSO-d6: δ 7.37-7.31 (m, 1H), 7.23 (dd, J=8.00, 4.00 Hz, 1H), 7.17-7.13 (m, 2H), 7.06 (s, 1H), 6.96 (d, J=12.00 Hz, 1H), 3.91 (s, 2H), 3.80 (s, 3H), 3.76 (s, 3H), 3.66 (s, 3H), 1.46 (s, 6H).

(2-Bromo-3-fluoro-phenyl)-[3-(3,4-dimethoxy-phenyl)-4,4-dimethyl-4,5-dihydro-pyrazol-1-yl]-methanone

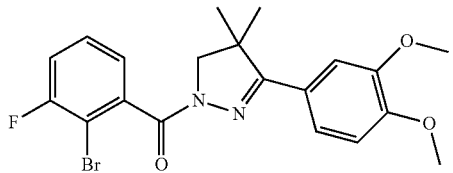 [SMILES: COc1ccc(C2=NN(C(=O)c3cccc(F)c3Br)CC2(C)C)cc1OC]

White solid; 17.60% Yield

LC-MS: Mass found (M+, 435). Rt (min): 4.62; % Area: 98.72 (Max), 98.38 (220 nm).

HPLC—Rt (min): 4.78; % Area: 98.25 (Max), 98.99 (254 nm).

400 MHz, DMSO-d6: δ 7.52-7.40 (m, 2H), 7.30 (dd, J=6.00, 0.00 Hz, 1H), 7.20 (dd, J=8.00, 4.00 Hz, 1H), 7.04 (d, J=4.00 Hz, 1H), 6.96 (d, J=12.00 Hz, 1H), 3.92 (s, 2H), 3.75 (s, 3H), 3.66 (s, 3H), 1.46 (s, 6H).

(2-Chloro-3-fluoro-phenyl)-[3-(3,4-dimethoxy-phenyl)-4,4-dimethyl-4,5-dihydro-pyrazol-1-yl]-methanone

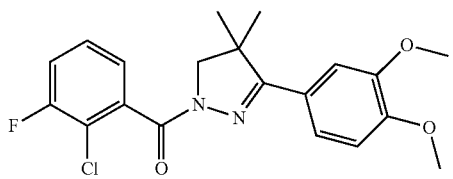 [SMILES: COc1ccc(C2=NN(C(=O)c3cccc(F)c3Cl)CC2(C)C)cc1OC]

White solid; 11.39% Yield

LC-MS: Mass found (M+, 391.3). Rt (min): 4.62; % Area: 93.71 (Max), 94.18 (220 nm).

HPLC—Rt (min): 4.77; % Area: 96.56 (Max), 96.01 (254 nm).

400 MHz, DMSO-d6: δ 7.51-7.45 (m, 2H), 7.36-7.33 (m, 1H), 7.21 (dd, J=8.00, 4.00 Hz, 1H), 7.04 (d, J=4.00 Hz, 1H), 6.96 (d, J=12.00 Hz, 1H), 3.93 (s, 2H), 3.75 (s, 3H), 3.65 (s, 3H), (s, 6H).

[3-(3,4-Dimethoxy-phenyl)-4,4-dimethyl-4,5-di-hydro-pyrazol-1-yl]-(2,3,4-trifluoro-phenyl)-methanone

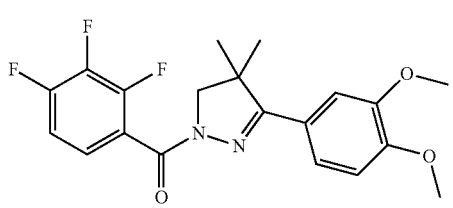 [SMILES: COc1ccc(C2=NN(C(=O)c3ccc(F)c(F)c3F)CC2(C)C)cc1OC]

Brown solid; 8.66% Yield

LC-MS: Mass found (M+, 393.3). Rt (min): 4.77; % Area: 94.01 (Max), 93.90 (254 nm).

HPLC—Rt (min): 4.78; % Area: 95.89 (Max), 95.68 (254 nm).

400 MHz, DMSO-d6: δ 7.46-7.40 (m, 2H), 7.27 (dd, J=8.00, 4.00 Hz, 1H), 7.11 (d, J=4.00 Hz, 1H), 6.97 (d, J=8.00 Hz, 1H), 3.92 (s, 2H), 3.77 (s, 3H), 3.69 (s, 3H), 1.46 (s, 6H).

(2,3-Difluoro-4-methyl-phenyl)-[3-(3,4-dimethoxy-phenyl)-4,4-dimethyl-4,5-dihydro-pyrazol-1-yl]-methanone

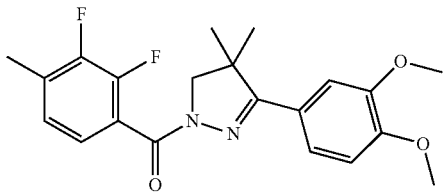

White solid; 29.86% Yield

LC-MS: Mass found (M+, 389.3). Rt (min): 4.79; % Area: 97.73 (Max), 97.21 (254 nm).

HPLC—Rt (min): 4.95; % Area: 97.84 (Max), 97.61 (254 nm).

400 MHz, DMSO-d6: δ 7.27-7.22 (m, 2H), 7.19-7.15 (m, 1H), 7.10 (d, J=4.00 Hz, 1H), 6.97 (d, J=8.00 Hz, 1H), 3.91 (s, 2H), 3.76 (s, 3H), 3.69 (s, 3H), 2.32 (d, J=4.00 Hz, 3H), 1.45 (s, 6H).

[3-(3,4-Dimethoxy-phenyl)-4,4-dimethyl-4,5-di-hydro-pyrazol-1-yl]-(2,3,4,5-tetrafluoro-phenyl)-methanone

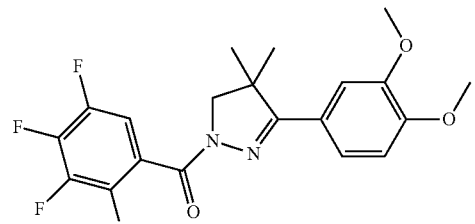

White solid; 3.94% Yield

LC-MS: Mass found (M+, 411.2). Rt (min): 5.04; % Area: 98.62 (Max), 98.04 (254 nm).

HPLC—Rt (min): 5.04; % Area: 98.61 (Max), 98.88 (254 nm).

400 MHz, DMSO-d6: δ 7.70-7.66 (m, 1H), 7.28 (dd, J=8.00, 4.00 Hz, 1H), 7.12 (d, J=4.00 Hz, 1H), 6.97 (d, J=8.00 Hz, 1H), 3.92 (s, 2H), 3.77 (s, 3H), 3.70 (s, 3H), 1.47 (s, 6H).

(6-Bromo-benzo[1,3]dioxol-5-yl)-[3-(3,4-dimethoxy-phenyl)-4,4-dimethyl-4,5-dihydro-pyrazol-1-yl]-methanone

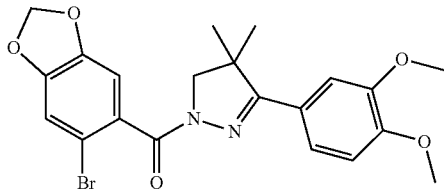 [SMILES: COc1ccc(C2=NN(C(=O)c3cc4c(cc3Br)OCO4)CC2(C)C)cc1OC]

Off-white solid; 26.16% Yield

LC-MS: Mass found (M+, 463). Rt (min): 4.49; % Area: 95.76 (Max), 96.08 (254 nm).

HPLC—Rt (min): 4.50; % Area: 98.26 (Max), 97.72 (254 nm). 400 MHz, DMSO-d6: δ 7.24-7.22 (m, 1H), 7.21-7.20 (m, 1H), 7.10 (d, J=4.00 Hz, 1H), 7.05 (s, 1H), 6.97 (d, J=12.00 Hz, 1H), 6.10 (s, 2H), 3.86 (s, 2H), 3.76 (s, 3H), 3.69 (s, 3H), 1.44 (s, 6H).

(2,2-Difluoro-benzo[1,3]dioxol-5-yl)-[3-(3,4-dimethoxy-phenyl)-4,4-dimethyl-4,5-dihydro-pyrazol-1-yl]-methanone

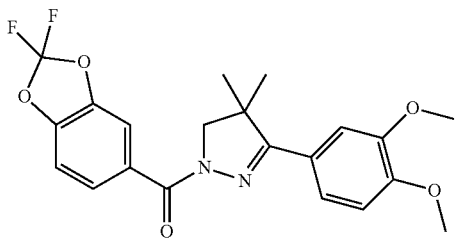 [SMILES: COc1ccc(C2=NN(C(=O)c3ccc4c(c3)OC(F)(F)O4)CC2(C)C)cc1OC]

Off-White solid; 17.98% Yield

LC-MS: Mass found (M+, 419). Rt (min): 5.17; % Area: 96.44 (Max), 97.53 (254 nm).

HPLC—Rt (min): 5.18; % Area: 97.36 (Max), 97.67 (254 nm).

400 MHz, DMSO-d6: δ 7.90 (s, 1H), 7.79 (d, J=8.00 Hz, 1H), 7.51 (d, J=12.00 Hz, 1H), 7.34 (dd, J=8.00, 4.00 Hz, 1H), 7.24-7.23 (m, 1H), 7.00 (d, J=12.00 Hz, 1H), 3.92 (s, 2H), 3.79 (s, 3H), 3.75 (s, 3H), 1.48 (s, 6H).

(2,5-Dimethoxy-phenyl)-[3-(3,4-dimethoxy-phenyl)-4,4-dimethyl-4,5-dihydro-pyrazol-1-yl]-methanone

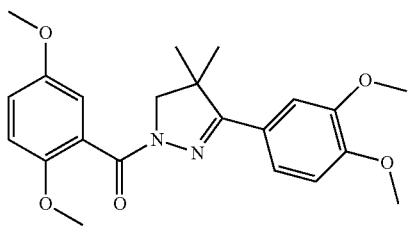 [SMILES: COc1ccc(OC)c(C(=O)N2CC(C)(C)C(c3ccc(OC)c(OC)c3)=N2)c1]

White solid; 11.23% Yield

LC-MS: Mass found (M+, 399.3). Rt (min): 4.14; % Area: 95.01 (Max), 96.10 (254 nm).

HPLC—Rt (min): 4.14; % Area: 95.86 (Max), 95.86 (254 nm).

400 MHz, DMSO-d6: δ 7.20 (dd, J=12.00, 4.00 Hz, 1H), 7.05 (d, J=4.00 Hz, 1H), 7.02-6.99 (m, 1H), 6.97-6.96 (m, 1H), 6.95-6.94 (m, 1H), 6.87 (d, J=4.00 Hz, 1H), 3.86 (s, 2H), 3.76 (s, 3H), 3.71 (s, 3H), 3.68 (s, 3H), 3.67 (s, 3H), 1.44 (s, 6H).

[3-(3,4-Dimethoxy-phenyl)-4,4-dimethyl-4,5-dihydro-pyrazol-1-yl]-(3-hydroxy-4-methoxy-phenyl)-methanone

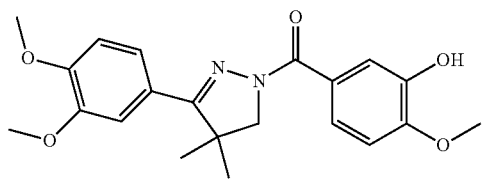

White solid; 30.78% Yield

LC-MS: Mass found (M+, 385.3). Rt (min): 3.78; % Area: 97.28 (Max), 96.55 (254 nm).

HPLC—Rt (min): 3.75; % Area: 98.10 (Max), 98.01 (254 nm).

400 MHz, DMSO-d6: δ 7.45 (s, 1H), 7.43 (d, J=4.00 Hz, 1H), 7.35 (dd, J=8.00, 4.00 Hz, 1H), 7.28 (d, J=4.00 Hz, 1H), 6.99 (d, J=8.00 Hz, 1H), 6.97 (d, J=4.00 Hz, 1H), 3.88 (s, 2H), 3.81 (s, 3H), 3.79 (s, 3H), 3.76 (s, 3H), 1.46 (s, 6H).

(2,3-Dihydro-benzofuran-5-yl)-[3-(3,4-dimethoxy-phenyl)-4,4-dimethyl-4,5-dihydro-pyrazol-1-yl]-methanone

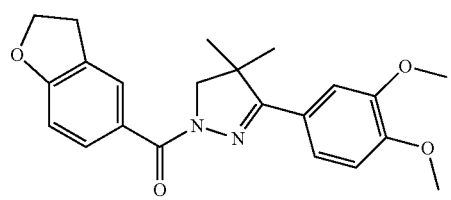 [SMILES: COc1ccc(C2=NN(C(=O)c3ccc4c(c3)CCO4)CC2(C)C)cc1OC]

Off-white solid; 44.35% Yield

LC-MS: Mass found (M+, 381.3). Rt (min): 4.34; % Area: 96.80 (Max), 97.33 (220 nm).

HPLC—Rt (min): 4.51; % Area: 96.93 (Max), 96.36 (254 nm).

400 MHz, DMSO-d6: δ 7.86 (s, 1H), 7.75-7.82 (m, 1H), 7.33 (d, J=8.00 Hz, 1H), 7.27 (d, J=4.00 Hz, 1H), 6.99 (d, J=8.00 Hz, 1H), 6.81 (d, J=8.00 Hz, 1H), 4.60 (t, J=8.00 Hz, 2H), 3.89 (s, 2H), 3.79 (s, 3H), 3.76 (s, 3H), 3.12 (t, J=8.00 Hz, 2H), 1.47 (s, 6H).

[3-(3,4-Dimethoxy-phenyl)-4,4-dimethyl-4,5-di-hydro-pyrazol-1-yl]indan-5-yl-methanone

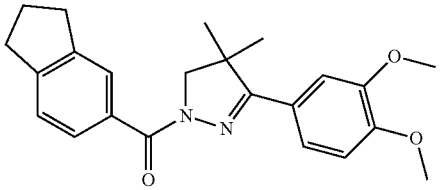 [SMILES: COc1ccc(C2=NN(C(=O)c3ccc4c(c3)CCC4)CC2(C)C)cc1OC]

Off-white solid; 16.78% Yield
LC-MS: Mass found (M+, 379.3). Rt (min): 5.00; % Area: 97.76 (Max), 97.82 (254 nm).
HPLC—Rt (min): 5.16; % Area: 98.08 (Max), 97.80 (254 nm).
400 MHz, DMSO-d6: δ 7.76 (s, 1H), 7.64 (d, J=8.00 Hz, 1H), 7.33-7.24 (m, 3H), 6.97 (d, J=4.00 Hz, 1H), 3.90 (s, 2H), 3.78 (s, 3H), 3.75 (s, 3H), 2.91-2.87 (m, 4H), 2.05 (q, J=8.00 Hz, 2H), 1.47 (s, 6H).

5-[3-(3,4-Dimethoxy-phenyl)-4,4-dimethyl-4,5-di-hydro-pyrazole-1-carbonyl]-2-methyl-isoindole-1,3-dione

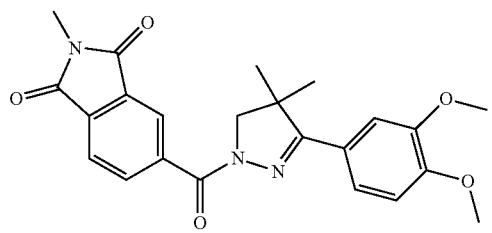 [SMILES: COc1ccc(C2=NN(C(=O)c3ccc4c(c3)C(=O)N(C)C4=O)CC2(C)C)cc1OC]

Yellow solid; 11.18% Yield
LC-MS: Mass found (M+, 422.2). Rt (min): 4.22; % Area: 99.08 (Max), 98.59 (254 nm).
HPLC—Rt (min): 4.21; % Area: 99.27 (Max), 98.91 (254 nm).
400 MHz, DMSO-d6: δ 8.34 (s, 1H), 8.23 (d, J=8.00 Hz, 1H), 7.95 (d, J=8.00 Hz, 1H), 7.34 (d, J=8.00 Hz, 1H), 7.26 (d, J=4.00 Hz, 1H), 6.98 (d, J=8.00 Hz, 1H), 3.97 (s, 2H), 3.79 (s, 3H), 3.74 (s, 3H), 3.05 (s, 3H), 1.51 (s, 6H).

5-[3-(3,4-Dimethoxy-phenyl)-4,4-dimethyl-4,5-di-hydro-pyrazole-1-carbonyl]-1,3-dihydro-indol-2-one

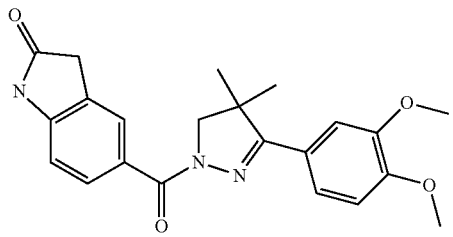 [SMILES: COc1ccc(C2=NN(C(=O)c3ccc4c(c3)CC(=O)N4)CC2(C)C)cc1OC]

Yellow solid; 14.71% Yield
LC-MS: Mass found (M+, 394.3). Rt (min): 2.94; % Area: 94.48 (Max), 95.26 (254 nm).
HPLC—Rt (min): 3.47; % Area: 95.98 (Max), 95.74 (254 nm).
400 MHz, DMSO-d6: δ 10.62 (s, 1H), 7.82 (s, 1H), 7.81 (d, J=8.00 Hz, 1H), 7.34 (dd, J=8.00, 4.00 Hz, 1H), 7.26 (s, 1H), 6.98 (d, J=8.00 Hz, 1H), 6.87 (d, J=8.00 Hz, 1H), 3.90 (s, 2H), 3.79 (s, 3H), 3.76 (s, 3H), 3.52 (s, 2H), 1.47 (s, 6H).

5-[3-(3,4-Dimethoxy-phenyl)-4,4-dimethyl-4,5-di-hydro-pyrazole-1-carbonyl]-2-methyl-isoindole-1,3-dione

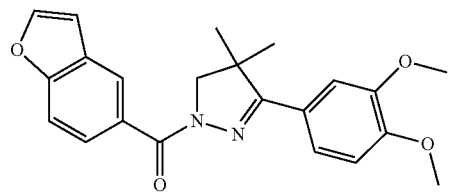 [SMILES: COc1ccc(C2=NN(C(=O)c3ccc4occc4c3)CC2(C)C)cc1OC]

Yellow solid; 14.49% Yield
LC-MS: Mass found (M+, 379.3). Rt (min): 4.56; % Area: 93.42 (Max), 95.41 (254 nm).
HPLC—Rt (min): 4.56; % Area: 96.17 (Max), 96.21 (254 nm).
400 MHz, DMSO-d6: δ 8.25 (s, 1H), 8.07 (d, J=4.00 Hz, 1H), 7.85 (d, J=8.00 Hz, 1H), 7.66 (d, J=8.00 Hz, 1H), 7.33 (d, J=8.00 Hz, 1H), 7.25 (s, 1H), 7.07-7.06 (m, 1H), 6.98 (d, J=8.00 Hz, 1H), 3.95 (s, 2H), 3.78 (s, 3H), 3.73 (s, 3H), 1.49 (s, 6H).

[3-(3,4-Dimethoxy-phenyl)-4,4-dimethyl-4,5-di-hydro-pyrazol-1-yl]-quinolin-6-yl-methanone

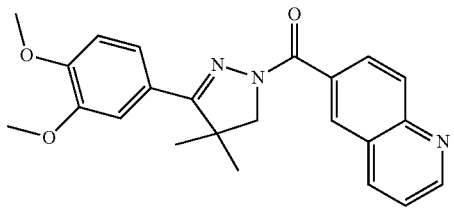 [SMILES: COc1ccc(C2=NN(C(=O)c3ccc4ncccc4c3)CC2(C)C)cc1OC]

Yellow solid; 9.45% Yield
LC-MS: Mass found (M+, 390). Rt (min): 3.11; % Area: 98.54 (Max), 98.14 (254 nm).
HPLC—Rt (min): 3.08; % Area: 99.10 (Max), 98.28 (254 nm).
400 MHz, DMSO-d6: δ 8.99-8.97 (m, 1H), 8.59 (s, 1H), 8.52 (d, J=8.00 Hz, 1H), 8.18 (d, J=12.00 Hz, 1H), 8.07 (d, J=8.00 Hz, 1H), 7.61-7.58 (m, 1H), 7.36 (dd, J=8.00, 4.00 Hz, 1H), 7.28 (s, 1H), 6.98 (d, J=8.00 Hz, 1H), 4.00 (s, 2H), 3.78 (s, 3H), 3.71 (s, 3H), 1.52 (s, 6H).

(2,3-Dihydro-benzo[1,4]dioxin-6-yl)-[3-(3,4-dimethoxy-phenyl)-4,4-dimethyl-4,5-dihydro-pyrazol-1-yl]-methanone

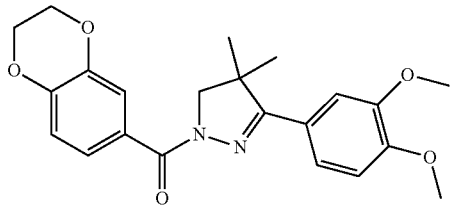 [SMILES: COc1ccc(C2=NN(C(=O)c3ccc4c(c3)OCCO4)CC2(C)C)cc1OC]

Brown solid; 11.58% Yield

LC-MS: Mass found (M+, 397.3). Rt (min): 4.31; % Area: 91.44 (Max), 93.57 (254 nm).

HPLC—Rt (min): 4.32; % Area: 91.86 (Max), 92.68 (254 nm).

400 MHz, DMSO-d6: δ 7.49-7.45 (m, 2H), 7.34-7.31 (m, 1H), 7.26 (d, J=4.00 Hz, 1H), 7.00 (d, J=8.00 Hz, 1H), 6.91 (d, J=8.00 Hz, 1H), 4.30-4.25 (m, 4H), 3.89 (s, 2H), 3.79 (s, 3H), 3.76 (s, 3H), 1.46 (s, 6H).

Example 4: Synthetic Route Towards 1-[3-(3,4-dimethoxy-phenyl)-4,5-dihydro-pyrazol-1-yl]-2-phenyl-ethanones

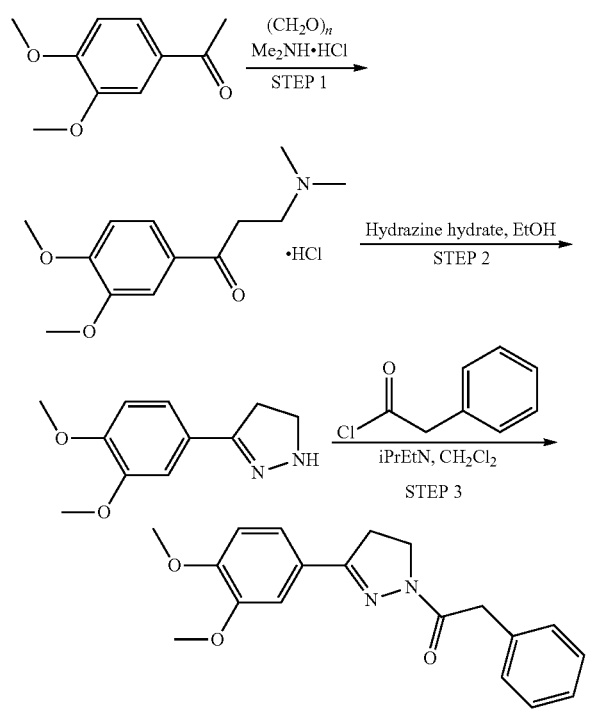

It shall be understood that the phenyl moiety (radical R) can be substituted in accordance with the Ar[1] definition as demonstrated below.

Step 1

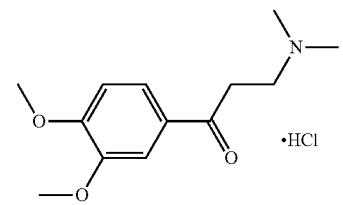

1-(3,4-Dimethoxy-phenyl)-3-dimethylamino-propan-1-one-.HCl. A round bottom flask equipped with a stir bar, Vigreux column and nitrogen inlet was charged with 1-(3,4-dimethoxy-phenyl)-ethanone (18.0 g, 100 mmol), paraformaldehyde (6 g, 200 mmol), dimethylamine.HCl (8.2 g, 100 mL) and EtOH, (50 mL). To this mixture was added 20 drops of conc. HCl and the reaction was heated at 80° C. for 18 h. TLC still showed consumption of SM. It was added to Et$_2$O causing a ppt to form. This was filtered and washed with Et$_2$O. Amount HCl salt obtained: 3.98 g, 13 mmol, 88% yield. Material was used as is in the next step. LC-MS (ESI) m/e 238 (M+H).

Step 2

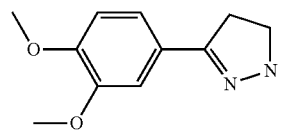

3-(3,4-Dimethoxy-phenyl)-4,5-dihydro-1H-pyrazole. A 100 mL round bottom flask equipped with a stir bar, Vigreux column and nitrogen inlet was charged with 1-(3,4-dimethoxy-phenyl)-3-dimethylamino-propan-1-one. HCl, (1.4 g, 5 mmol) EtOH, (20 mL) and hydrazine monohydrate, (0.3 mL, 6 mmol). The mixture was heated at 80° C. for 2 h. LC-MS and TLC analysis showed consumption of SM. The solvent was evaporated under reduced pressure and trace hydrazine and EtOH was removed under high vacuum for 30 min. The material was used as in the next step. Amount obtained 1030 mg, 5 mmol, 100% yield. LC-MS (ESI) m/e 207 (M+H).

Step 3

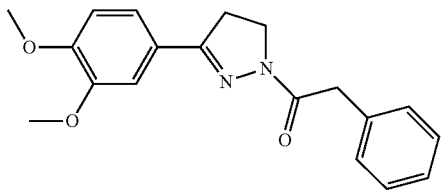 [SMILES: COc1ccc(C2=NN(C(=O)Cc3ccccc3)CC2)cc1OC]

1-[3-(3,4-Dimethoxy-phenyl)-4,5-dihydro-pyrazol-1-yl]-2-phenyl-ethanone (29). A scintillation vial equipped with a stir bar was charged with 3-(3,4-dimethoxy-phenyl)-4,5-dihydro-1H-pyrazole (412 mg, 2 mmol), Hunigs base (1 mL, 6 mmol) and dry CH$_2$Cl$_2$ (10 mL). To this mixture was added phenyl-acetyl chloride, (0.27 mL, 2 mmol) and the reaction was stirred at RT for 3 h. LC-MS indicated consumption of SM. The mixture was diluted with CH$_2$Cl$_2$ (50 mL) and added to water (50 mL). The phases were separated and the CH$_2$Cl$_2$ phase was washed with saturated Na$_2$CO$_3$, (50 mL), dried (Na$_2$SO$_4$) and the solvent was evaporated under reduced pressure. The material was purified using a 40 g silica cartridge eluting with heptane-EtOAc, gradient 0 to 100% EtOAc. Amount obtained: 123 mg, 0.37 mmol, 19% yield. LC-MS (ESI) m/e 325 (M+H). $^1$H NMR (400 MHz, CHLOROFORM-d) δ ppm 3.21 (t, J=10.03 Hz, 2H) 3.94 (s, 3H) 3.98 (s, 3H) 4.04 (t, J=10.03 Hz, 2H) 4.11 (s, 2H) 6.90 (d, J=8.35 Hz, 1H) 7.16 (dd, J=8.27, 1.88 Hz, 1H) 7.21-7.26 (m, 1H) 7.31 (t, J=7.42 Hz, 2H) 7.40-7.44 (m, 3H).

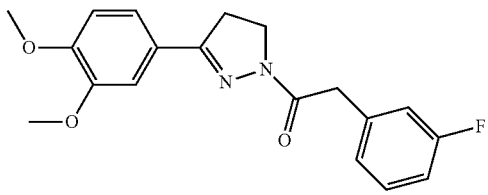 [SMILES: COc1ccc(C2=NN(C(=O)Cc3cccc(F)c3)CC2)cc1OC]

1-[3-(3,4-Dimethoxy-phenyl)-4,5-dihydro-pyrazol-1-yl]-2-(3-fluoro-phenyl)-ethanone (241). Prepared following the same procedure as 1-[3-(3,4-Dimethoxy-phenyl)-4,5-dihydro-pyrazol-1-yl]-2-phenyl-ethanone (29). Amount obtained: 50 mg, 0.15 mmol, 7% yield. LC-MS (ESI) m/e 343 (M+H). 1H NMR (400 MHz, CHLOROFORM-d) δ ppm 3.22 (t, J=10.01 Hz, 2H) 3.95 (s, 3H) 3.98 (s, 3H) 4.05 (t, J=10.03 Hz, 2H) 4.10 (s, 2H) 6.90 (d, J=8.39 Hz, 1H) 6.93-6.96 (m, 1H) 7.13-7.21 (m, 2H) 7.24-7.30 (m, 2H) 7.41 (d, J=1.85 Hz, 1H).

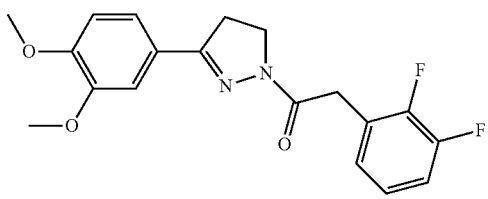 [SMILES: COc1ccc(C2=NN(C(=O)Cc3cccc(F)c3F)CC2)cc1OC]

2-(2,3-Difluoro-phenyl)-1-[3-(3,4-dimethoxy-phenyl)-4,5-dihydro-pyrazol-1-yl]-ethanone (261). Prepared following the same procedure as 1-[3-(3,4-Dimethoxy-phenyl)-4,5-dihydro-pyrazol-1-yl]-2-phenyl-ethanone (29). Amount obtained: 23 mg, 0.06 mmol, 3% yield. LC-MS (ESI) m/e 361 (M+H). $^1$H NMR (400 MHz, CHLOROFORM-d) δ ppm 3.22 (t, J=9.98 Hz, 2H) 3.94 (s, 3H) 3.98 (s, 3H) 4.05 (t, J=9.98 Hz, 2H) 4.16 (s, 2H) 6.88 (d, J=8.30 Hz, 1H) 6.99-7.08 (m, 2H) 7.10-7.17 (m, 2H) 7.47 (d, J=1.81 Hz, 1H).

Example 5: Synthetic Route Towards (3-Fluoro-phenyl)-(3-m-tolyl-4,5-dihydro-pyrazol-1-yl)-methanone Scheme 5

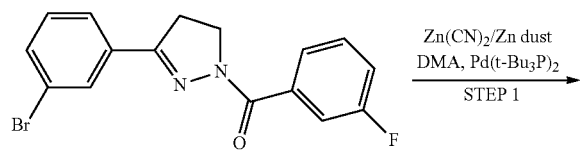

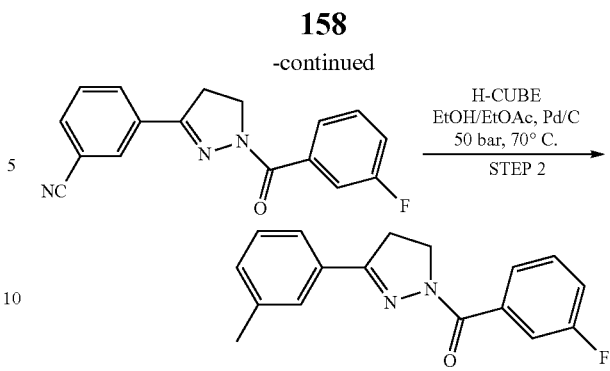

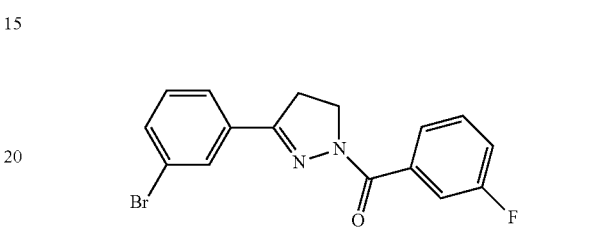

[3-(3-Bromo-phenyl)-4,5-dihydro-pyrazol-1-yl]-(3-fluoro-phenyl)-methanone. Prepared beginning with 1-(3-bromo-phenyl)-ethanone following the same procedure as 1-[3-(3,4-Dimethoxy-phenyl)-4,5-dihydro-pyrazol-1-yl]-2-phenyl-ethanone (29). LC-MS (ESI) m/e 347 & 349 (M+H). $^1$H NMR (CHLOROFORM-d) δ: 7.76-7.82 (m, 2H), 7.71 (d, J=9.7 Hz, 1H), 7.65 (d, J=7.8 Hz, 1H), 7.56 (d, J=8.0 Hz, 1H), 7.44 (td, J=8.0, 5.8 Hz, 1H), 7.30 (t, J=8.0 Hz, 1H), 7.22 (td, J=8.3, 2.1 Hz, 1H), 4.29 (t, 2H), 3.27 (t, 1H).

Step 1

3-[1-(3-Fluoro-benzoyl)-4,5-dihydro-1H-pyrazol-3-yl]-benzonitrile. A scintillation vial equipped with a stir bar was charged with [3-(3-bromo-phenyl)-4,5-dihydro-pyrazol-1-yl]-(3-fluoro-phenyl)-methanone (347 mg, 1.0 mmol), Zn(CN)$_2$ (234 mg, 2.0 mmol), Zn dust (65 mg, 1.0 mmol) and DMA (10 mL). The mixture was degassed and then Pd(t-Bu$_3$P)$_2$ (51 mg, 0.1 mmol) was added. The mixture was heated at 80° C. for 4 h. LC-MS showed consumption of SM. The material was filtered through a pad of Fluorosil and the solvent was evaporated under reduced pressure. It was purified by chromatography using a 12 g silica cartridge eluting with heptane-EtOAc, gradient 30 to 100% EtOAc. Amount obtained: 225 mg, 0.76 mmol, 76% yield. LC-MS (ESI) m/e 294 (M+H). $^1$H NMR (CHLOROFORM-d) δ: 7.92-7.97 (m, 2H), 7.76 (d, J=7.8 Hz, 1H), 7.66-7.74 (m, 2H), 7.52-7.59 (m, 1H), 7.45 (td, J=8.0, 5.8 Hz, 1H), 7.20-7.30 (m, 1H), 4.32 (t, J=10.1 Hz, 2H), 3.26-3.34 (m, 2H).

Step 2

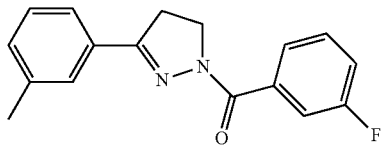 [SMILES: Cc1cccc(C2=NN(C(=O)c3cccc(F)c3)CC2)c1]

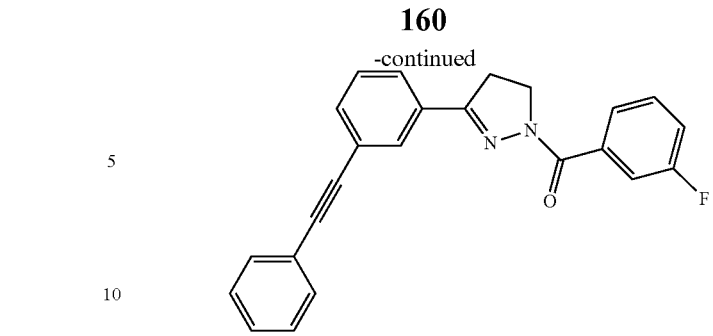

(3-Fluoro-phenyl)-[3-(3-phenylethynyl-phenyl)-4,5-dihydro-pyrazol-1-yl]-methanone (183). [3-(3-Bromo-phenyl)-4,5-dihydro-pyrazol-1-yl]-(3-fluoro-phenyl)-methanone was prepared beginning with 1-(3-bromo-phenyl)-ethanone following the same procedure as for 1-[3-(3,4-Dimethoxy-phenyl)-4,5-dihydro-pyrazol-1-yl]-2-phenyl-ethanone (29). A scintillation vial equipped with a stir bar was charged with the [3-(3-bromo-phenyl)-4,5-dihydro-pyrazol-1-yl]-(3-fluoro-phenyl)-methanone (138 mg, 0.40 mmol), phenyl acetylene (0.09 mL, 0.80 mmol) CuI (15 mg, 0.08 mmol), triethylamine (0.28 mL, 2.00 mmol) and acetonitrile (4 mL). The mixture was degassed with nitrogen and PdCl$_2$(PPh$_3$)$_2$ (56 mg, 0.08 mmol) was added. The reaction was heated at 80° C. under a nitrogen atmosphere for 5 h. LC-MS showed consumption of SM. The solvent was evaporated under reduced pressure. The material was dissolved in CH$_2$Cl$_2$ (50 mL) and passed through a pad of Fluorosil. The solvent was evaporated and the material was purified by chromatography using a 12 g silica cartridge eluting with heptane-EtOAc, gradient 0 to 50% EtOAc. Amount obtained: 13 mg, 0.04 mmol, 10% yield. LC-MS (ESI) m/e 369 (M+H). $^1$H NMR (400 MHz, CHLOROFORM-d) δ ppm 3.31 (t, J=10.01 Hz, 2H) 4.29 (t, J=10.01 Hz, 2H) 7.22 (td, J=8.32, 2.00 Hz, 1H) 7.36-7.48 (m, 5H) 7.54-7.62 (m, 3H) 7.70-7.77 (m, 2H) 7.79-7.83 (m, 2H).

(3-Fluoro-phenyl)-(3-m-tolyl-4,5-dihydro-pyrazol-1-yl)-methanone (179). 3-[1-(3-Fluoro-benzoyl)-4,5-dihydro-1H-pyrazol-3-yl]-benzonitrile (88 mg, 0.30 mmol), dissolved in EtOH (10 mL) and EtOAc (10 mL) was passed through the H-cube equipped with a 10% Pd/C cartridge. Temperature 80° C., 50 bar, flow rate, 1 mL/min. LC-MS showed consumption of SM. The solvent was evaporated under pressure and the material was purified by chromatography using a 12 g silica cartridge eluting with heptane-EtOAc, gradient 0 to 50% EtOAc. Amount obtained: 30 mg, 0.11 mmol, 35% yield. LC-MS (ESI) m/e 283 (M+H). $^1$H NMR (400 MHz, CHLOROFORM-d) δ ppm 2.40 (s, 3H) 3.26-3.33 (m, 2H) 4.27 (t, J=9.96 Hz, 2H) 7.17-7.26 (m, 2H) 7.32 (t, J=7.81 Hz, 1H) 7.43 (td, J=7.98, 5.81 Hz, 1H) 7.49-7.54 (m, 2H) 7.73-7.84 (m, 2H).

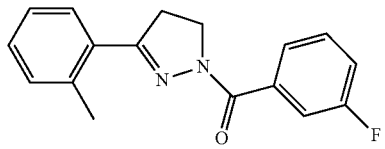 [SMILES: Cc1ccccc1C1=NN(C(=O)c2cccc(F)c2)CC1]

(3-Fluoro-phenyl)-(3-o-tolyl-4,5-dihydro-pyrazol-1-yl)-methanone (215). Prepared following the same procedure as (3-Fluoro-phenyl)-(3-m-tolyl-4,5-dihydro-pyrazol-1-yl)-methanone (29). Amount obtained: 33 mg, 0.12 mmol, 39% yield. LC-MS (ESI) m/e 283 (M+H). $^1$H NMR (400 MHz, CHLOROFORM-d) δ ppm 2.53 (s, 3H) 3.36 (t, 2H) 4.22 (t, J=9.96 Hz, 2H) 7.18 (td, J=8.36, 2.03 Hz, 1H) 7.28-7.34 (m, 3H) 7.36-7.41 (m, 1H) 7.41-7.45 (m, 1H) 7.72 (d, J=9.81 Hz, 1H) 7.77 (d, J=7.76 Hz, 1H).

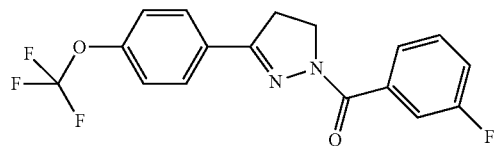 [SMILES: O=C(c1cccc(F)c1)N1CCC(c2ccc(OC(F)(F)F)cc2)=N1]

(3-Fluoro-phenyl)-[3-(4-trifluoromethoxy-phenyl)-4,5-dihydro-pyrazol-1-yl]-methanone (162). Prepared beginning with 1-(4-trifluoromethoxy-phenyl)-ethanone following the same procedure as 1-[3-(3,4-Dimethoxy-phenyl)-4,5-dihydro-pyrazol-1-yl]-2-phenyl-ethanone (29). Amount obtained: 103 mg, 0.29 mmol, 12% yield. LC-MS (ESI) m/e 353 (M+H). $^1$H NMR (400 MHz, CHLOROFORM-d) δ ppm 3.29 (t, 2H) 4.30 (t, 2H) 7.18-7.25 (m, 1H) 7.25-7.30 (m, 2H) 7.43 (td, J=7.99, 5.78 Hz, 1H) 7.66-7.85 (m, 4H).

Example 6: Synthetic Route Towards (3-Fluoro-phenyl)-[3-(3-phenylethynyl-phenyl)-4,5-dihydro-pyrazol-1-yl]-methanone Scheme 6

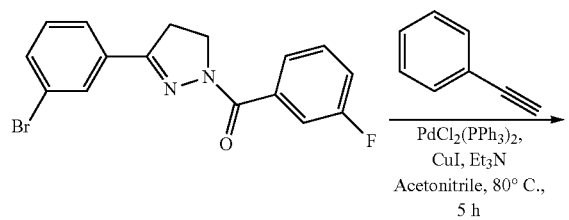

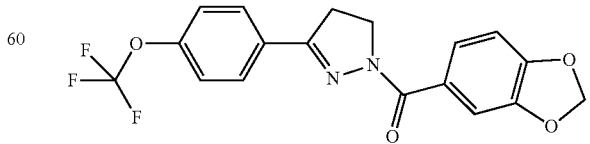

Benzo[1,3]dioxol-5-yl-[3-(4-trifluoromethoxy-phenyl)-4,5-dihydro-pyrazol-1-yl]-methanone (199). Prepared beginning with 1-(4-trifluoromethoxy-phenyl)-ethanone following the same procedure as 1-[3-(3,4-Dimethoxy-phenyl)-4,5-dihydro-pyrazol-1-yl]-2-phenyl-ethanone (29). Amount obtained 180 mg, 0.48 mmol, 19% yield. LC-MS (ESI) m/e 379 (M+H). ¹H NMR (400 MHz, CHLOROFORM-d) δ ppm 3.25 (t, J=10.08 Hz, 2H) 4.27 (t, J=10.08 Hz, 2H) 6.05 (s, 2H) 6.88 (d, J=8.20 Hz, 1H) 7.25-7.29 (m, 2H) 7.55 (d, J=1.46 Hz, 1H) 7.64 (dd, J=8.17, 1.54 Hz, 1H) 7.75 (d, J=8.79 Hz, 2H).

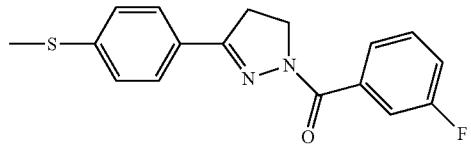 [SMILES: CSc1ccc(C2=NN(C(=O)c3cccc(F)c3)CC2)cc1]

(3-Fluoro-phenyl)-[3-(4-methylsulfanyl-phenyl)-4,5-dihydro-pyrazol-1-yl]methanone (204). Prepared beginning with 1-(4-methylsulfanyl-phenyl)-ethanone following the same procedure as 1-[3-(3,4-Dimethoxy-phenyl)-4,5-dihydro-pyrazol-1-yl]-2-phenyl-ethanone (29). Amount obtained: 178 mg, 0.57 mmol, 23% yield. LC-MS (ESI) m/e 315 (M+H). ¹H NMR (400 MHz, CHLOROFORM-d) δ ppm 2.52 (s, 3H) 3.27 (t, J=9.96 Hz, 2H) 4.27 (t, J=9.96 Hz, 2H) 7.20 (td, J=8.27, 2.34 Hz, 1H) 7.25 (s, 1H) 7.42 (td, J=7.97, 5.83 Hz, 2H) 7.62 (d, J=8.44 Hz, 2H) 7.75 (d, J=9.81 Hz, 1H) 7.80 (d, J=7.76 Hz, 1H).

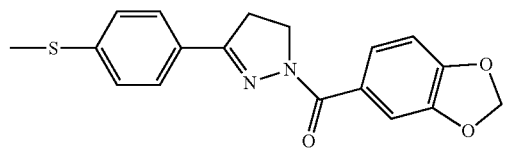 [SMILES: CSc1ccc(C2=NN(C(=O)c3ccc4c(c3)OCO4)CC2)cc1]

Benzo[1,3]dioxol-5-yl-[3-(4-methylsulfanyl-phenyl)-4,5-dihydro-pyrazol-1-yl]-methanone (205). Prepared beginning with 1-(4-methylsulfanyl-phenyl)-ethanone following the same procedure as 1-[3-(3,4-Dimethoxy-phenyl)-4,5-dihydro-pyrazol-1-yl]-2-phenyl-ethanone (29). Amount obtained: 53 mg, 0.16 mmol, 6% yield. LC-MS (ESI) m/e 341 (M+H). ¹H NMR (400 MHz, CHLOROFORM-d) δ ppm 2.52 (s, 3H) 3.23 (t, J=10.01 Hz, 2H) 4.24 (t, J=10.01 Hz, 2H) 6.05 (s, 2H) 6.88 (d, J=8.20 Hz, 1H) 7.25 (s, 1H) 7.27 (s, 1H) 7.58 (d, J=1.27 Hz, 1H) 7.63 (d, J=8.44 Hz, 2H) 7.67 (dd, J=8.20, 1.37 Hz, 1H).

Example 7: Synthetic Route Towards 3-(3,4 dimethoxyphenyl)-4,5-dihydro-1H-pyrazole-1 carbonyl derivatives Scheme 7

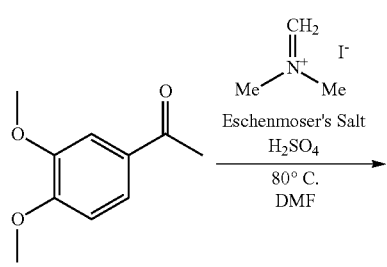

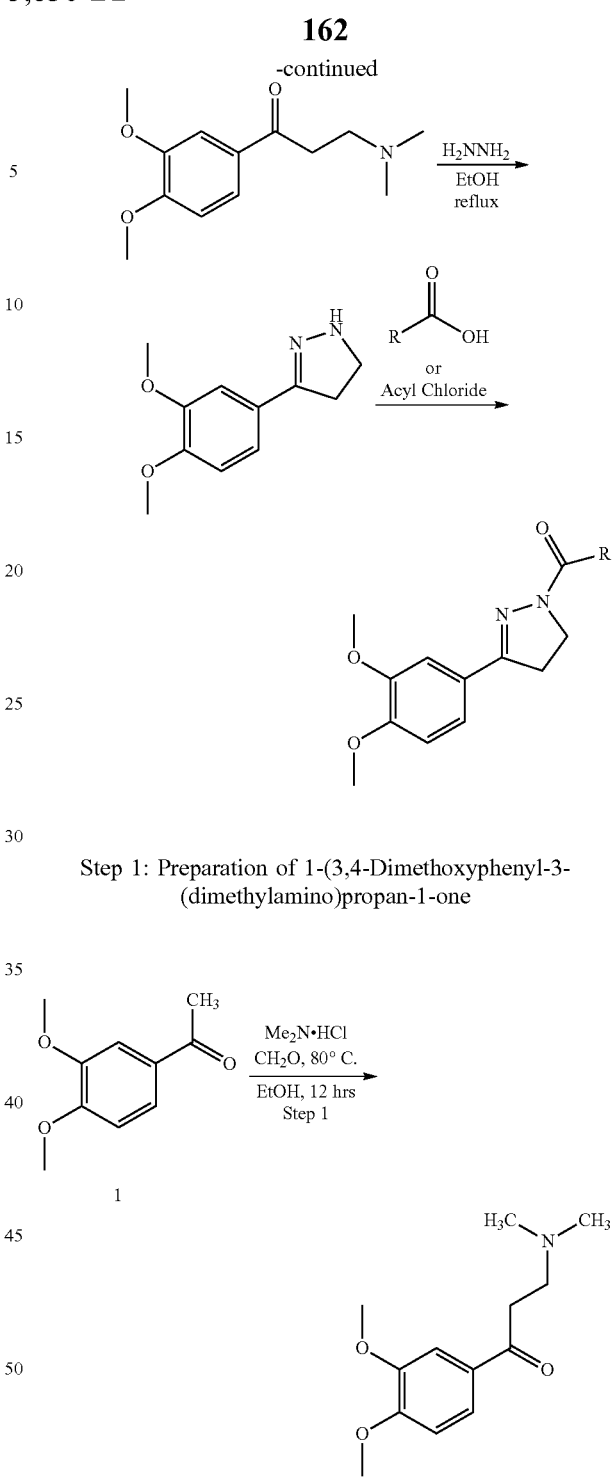

Step 1: Preparation of 1-(3,4-Dimethoxyphenyl-3-(dimethylamino)propan-1-one

To a stirred solution of 3,4-Dimethoxy acetophenone (3 g, 0.0166 moles, 1 equiv.) in ethanol was added paraformaldehyde (0.5 g, 0.0166 moles, 1 equiv.), dimethylamine hydrochloride (4.2 g, 0.0499 moles, 3 equiv.) and the reaction mixture was refluxed at 80° C. for 12 h. Consumption of starting materials was confirmed by LC-MS analysis and TLC. Ethanol was evaporated under reduced pressure; the crude solid residue was stirred with acetone at 0° C. for 1 h, filtered, washed with acetone, dried under vacuum. After that the solid was suspended in water, basified with 10% sodium bicarbonate solution (pH~8), extracted by dichloromethane (2×200 ml), washed with water followed by satd. Brine solution. The organic layer was dried over sodium sulfate and concentrated to get 2.9 g (73% yield) title compound as green oily liquid. It was taken forward for the next step without any further purification.

$R_f$=0.15

Green oily liquid; 73% Yield

LC-MS: Mass found (M+, 238.2)

Method: A—: 0.1% HCOOH, B—: MeOH Flow—1 ml/min. Atlantis dC18 (50×4.6 mm, 5 μm). Rt (min): 0.946; % Area: 96.97.

HPLC—Method: A—: 0.1% TFA in water, B—: 0.1% TFA in CAN: Flow—1 ml/min. Column: Xbridge C8 (50× 4.6 mm, 3.5 μm). Rt (min): 1.76; % Area: 95.21 (Max), 91.73 (254 nm).

$^1$H NMR 400 MHz, DMSO-d6: δ 7.65 (dd, J=8.00, 4.00 Hz, 1H), 7.44 (d, J=4.00 Hz, 1H), 7.04 (d, J=8.00 Hz, 1H), 3.85 (s, 3H), 3.80 (s, 3H), 3.07 (t, J=8.00 Hz, 2H), 2.57 (t, J=8.00 Hz, 2H), 2.14 (s, 6H).

Step 2: Preparation of 3-(3,4 dimethoxyphenyl)-4,5-dihydro-1H-pyrazole

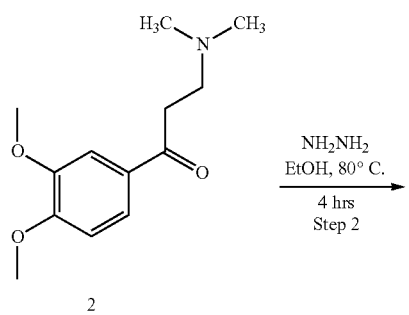

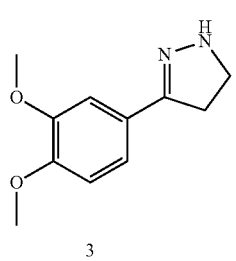

To a stirred solution of 1-(3,4-dimethoxyphenyl-3-(dimethylamino)propan-1-one (2.9 g, 0.0122 moles, 1 equiv.) in absolute ethanol was added hydrazine hydrate (99%-100%) (1.18 ml, 0.0244 moles, 2 equiv) drop wise. After that the reaction mixture was refluxed for 4 h at 80° C. under inert atmosphere. Consumption of starting materials was confirmed by LC-MS analysis and TLC. Ethanol and excess hydrazine hydrate was evaporated under reduced pressure and to the crude product was stirred with diethyl ether at RT for 30 mins, filtered washed with ether and finally dried under vacuum to get 2.4 g (95% yield) of the title product as yellow solid.

$R_f$=0.2

White solid; 95% Yield

LC-MS: Mass found (M+, 207)

Method: A—: 0.1% TFA in water, B—: 0.1% TFA in ACN: Flow—0.6 ml/min. Column: Xbridge C8 (50×4.6 mm, 3.5 μm). Rt (min): 1.49; % Area: 58.00.

$^1$H NMR 400 MHz, DMSO-d6: δ 7.25 (d, J=4.00 Hz, 1H), 7.04 (d, J=8.00 Hz, 1H), 6.93 (d, J=8.00 Hz, 1H), 3.83-3.80 (m, 1H), 3.75 (s, 6H), 3.31 (t, J=8.00 Hz, 2H), 2.82 (t, J=8.00 Hz, 2H).

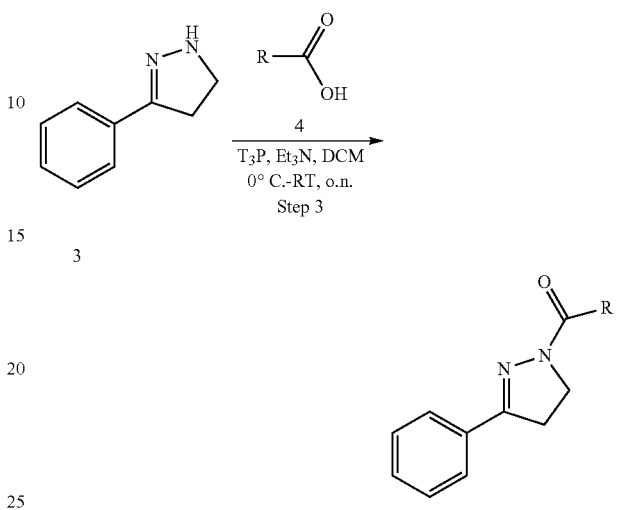

In an 8 ml vial, a solution of 3-(3,4-Dimethoxy-phenyl)-4,5-dihydro-1H-pyrazole (100 mg, 0.48 mmol, 1 equiv) in 5 ml dichloromethane was mixed with respective acid (4) (0.53 mmol, 1 equiv.) and triethylamine (147.3 mg, 1.4 mmol, 3 equiv). 1-propane phosphonic cyclic anhydride (60% in ethyl acetate) (309.46 mg, 0.97 mmol, 3 equiv) was added to this reaction mixture at 0° C. After the addition, reaction mixture was placed in the orbital shaker for about 12 h. Upon consumption of SM, reaction mixture was concentrated in Genvac to remove the solvent, dissolved in dichloromethane (4 ml) and washed with water (4 ml), the organic layer was evaporated in Genvac. The residue was passed through SPE-NH$_2$ column (2 g, 6 ml) to get the pure product. The solvents used for elution were pet ether/dichloromethane/methanol.

The following compounds were prepared in a similar manner. LC-MS and HPLC analysis were performed as follows: Method: A—0.1% TFA in water, B—0.1% TFA in ACN: Flow—2 ml/min; Column: XBridge c8 (50×4.6 mm, 3.5 μm); unless stated otherwise.

(3-Bromo-phenyl)-[3-(3,4-dimethoxy-phenyl)-4,5-dihydro-pyrazol-1-yl]-methanone

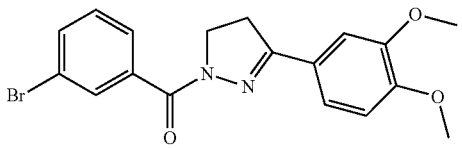

White solid; 30.17% Yield

LC-MS: Mass found (M+, 389). Rt (min): 4.44; % Area: 99.16 (Max), 99.30 (254 nm).

HPLC—Flow—1.0 ml/min. Rt (min): 4.50; % Area: 99.68 (Max), 99.20 (254 nm).

$^1$H NMR 400 MHz, CDCl3: δ 8.29 (s, 1H), 7.94 (d, J=8.00 Hz, 1H), 7.62 (td, J=2.00, 1.20 Hz, 1H), 7.40 (d, J=4.00 Hz, 1H), 7.33 (t, J=8.00 Hz, 1H), 7.14 (dd, J=8.40, 2.00 Hz, 1H), 6.89 (d, J=12.00 Hz, 1H), 4.26 (t, J=8.00 Hz, 2H), 3.93 (s, 6H), 3.28 (t, J=8.00 Hz, 2H).

(3-Chloro-phenyl)-[3-(3,4-dimethoxy-phenyl)-4,5-dihydro-pyrazol-1-yl]-methanone

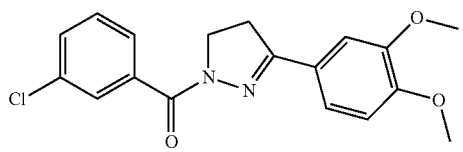 [SMILES: COc1ccc(C2=NN(C(=O)c3cccc(Cl)c3)CC2)cc1OC]

White solid; 21.38% Yield
LC-MS: Mass found (M+, 345). Rt (min): 4.36; % Area: 99.73 (Max), 99.54 (254 nm).
HPLC—Flow—1.0 ml/min. Rt (min): 4.44; % Area: 98.76 (Max), 98.44 (254 nm).
¹H NMR 400 MHz, DMSO-d6: δ 7.95 (s, 1H), 7.83 (d, J=8.00 Hz, 1H), 7.61-7.58 (m, 1H), 7.51 (t, J=8.00 Hz, 1H), 7.25-7.04 (m, 2H), 7.03 (d, J=8.00 Hz, 1H), 4.09 (t, J=12.00 Hz, 2H), 3.79 (s, 3H), 3.76 (s, 3H), 3.33 (t, J=12.00 Hz, 2H).

[3-(3,4-Dimethoxy-phenyl)-4,5-dihydro-pyrazol-1-yl]-(3-methoxy-phenyl)-methanone

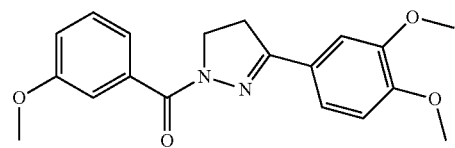 [SMILES: COc1cccc(C(=O)N2CCC(c3ccc(OC)c(OC)c3)=N2)c1]

Yellow solid; 35.81% Yield
LC-MS: Mass found (M+, 341). Rt (min): 3.87; % Area: 96.42 (Max), 96.54 (254 nm).
HPLC—Flow—1.0 ml/min. Rt (min): 3.88; % Area: 96.96 (Max), 95.83 (254 nm).
¹H NMR 400 MHz, CDCl3: δ 7.62-7.58 (m, 2H), 7.37-7.33 (m, 2H), 7.18 (d, J=8.00 Hz, 1H), 7.06-7.03 (m, 1H), 6.88 (d, J=8.00 Hz, 1H), 4.26 (t, J=12.00 Hz, 2H), 3.95 (s, 3H), 3.93 (s, 3H), 3.90 (s, 3H), 3.26 (t, J=12.00 Hz, 2H).

[3-(3,4-Dimethoxy-phenyl)-4,5-dihydro-pyrazol-1-yl]-(3-ethoxy-phenyl)-methanone

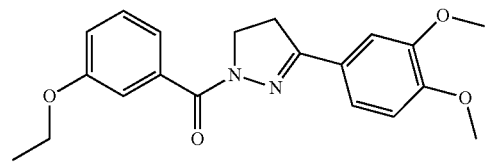 [SMILES: CCOc1cccc(C(=O)N2CCC(c3ccc(OC)c(OC)c3)=N2)c1]

Yellow solid; 37.36% Yield
LC-MS: Mass found (M+, 355). Rt (min): 4.21; % Area: 95.38 (Max), 94.61 (254 nm).
HPLC—Flow—1.0 ml/min. Rt (min): 4.21; % Area: 95.51 (Max), 93.71 (254 nm).
¹H NMR 400 MHz, CDCl3: δ 7.60-7.58 (m, 2H), 7.35-7.32 (m, 2H), 7.17 (dd, J=8.00, 4.00 Hz, 1H), 7.03 (td, J=5.00, 1.20 Hz, 1H), 6.88 (d, J=8.00 Hz, 1H), 4.26 (t, J=8.00 Hz, 2H), 4.09 (q, J=8.00 Hz, 2H), 3.93 (s, 3H), 3.90 (s, 3H), 3.26 (t, J=8.00 Hz, 2H), 1.42 (t, J=8.00 Hz, 3H).

[3-(3,4-Dimethoxy-phenyl)-4,5-dihydro-pyrazol-1-yl]-(3-trifluoromethyl-phenyl)-methanone

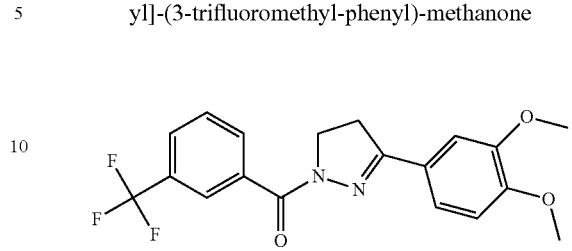

Yellow solid; 19.35% Yield
LC-MS: Mass found (M+, 379). Rt (min): 4.63; % Area: 99.37 (Max), 99.73 (254 nm).
HPLC—Rt (min): 4.64; % Area: 98.52 (Max), 98.24 (254 nm).
¹H NMR 400 MHz, DMSO-d6: δ 8.31 (d, J=8.00 Hz, 1H), 8.15 (d, J=8.00 Hz, 1H), 7.90 (d, J=8.00 Hz, 1H), 7.73 (t, J=8.00 Hz, 1H), 7.26-7.21 (m, 2H), 7.03 (d, J=8.00 Hz, 1H), 4.12 (t, J=12.00 Hz, 2H), 3.79 (s, 3H), 3.74 (s, 3H), 3.31 (t, J=12.00 Hz, 2H).

[3-(3,4-Dimethoxy-phenyl)-4,5-dihydro-pyrazol-1-yl]-m-tolyl-methanone

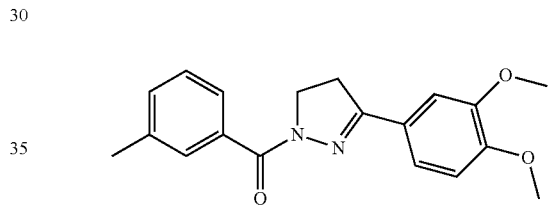

Brown gum; 13.86% Yield
LC-MS: Mass found (M+, 325). Rt (min): 4.14; % Area: 97.97 (Max), 97.64 (254 nm).
HPLC—Rt (min): 4.14; % Area: 96.54 (Max), 95.92 (254 nm).
¹H NMR 400 MHz, CDCl3: δ 7.83-7.79 (m, 2H), 7.35-7.29 (m, 3H), 7.16 (d, J=8.00 Hz, 1H), 6.88 (d, J=8.00 Hz, 1H), 4.26 (t, J=8.00 Hz, 2H), 3.95 (s, 3H), 3.90 (s, 3H), 3.26 (t, J=8.00 Hz, 2H), 2.42 (s, 3H).

3-[3-(3,4-Dimethoxy-phenyl)-4,5-dihydro-pyrazole-1-carbonyl]-benzonitrile

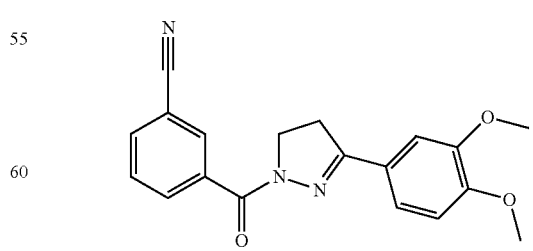

White solid; 82.23% Yield
LC-MS: Mass found (M+, 336). Rt (min): 3.84; % Area: 98.37 (Max), 98.63 (254 nm).

HPLC—Rt (min): 3.84; % Area: 97.96 (Max), 97.30 (254 nm).

¹H NMR 400 MHz, CDCl3: δ 8.46 (s, 1H), 8.24 (d, J=8.00 Hz, 1H), 7.78 (dt, J=7.73, 1.20 Hz, 1H), 7.58 (t, J=8.00 Hz, 1H), 7.34 (d, J=2.00 Hz, 1H), 7.17 (dd, J=8.40, 2.00 Hz, 1H), 6.90 (d, J=8.00 Hz, 1H), 4.28 (t, J=8.00 Hz, 2H), 3.94 (s, 3H), 3.93 (s, 3H), 3.30 (t, J=12.00 Hz, 2H).

[3-(3,4-Dimethoxy-phenyl)-4,5-dihydro-pyrazol-1-yl]-(3-trifluoromethoxy-phenyl)-methanone

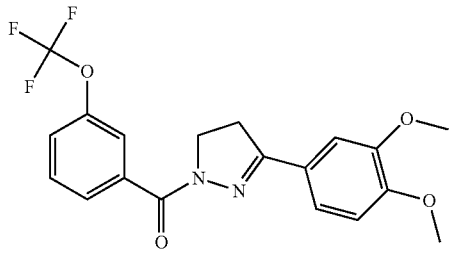 [SMILES: COc1ccc(C2=NN(C(=O)c3cccc(OC(F)(F)F)c3)CC2)cc1OC]

White solid; 20.97% Yield

LC-MS: Mass found (M+, 325). Rt (min): 4.74; % Area: 98.76 (Max), 98.56 (254 nm).

HPLC—Rt (min): 4.72; % Area: 97.48 (Max), 97.51 (254 nm).

¹H NMR 400 MHz, CDCl3: δ 8.00 (s, 1H), 7.95 (d, J=8.00 Hz, 1H), 7.49 (t, J=8.00 Hz, 1H), 7.36-7.34 (m, 2H), 7.16 (dd, J=8.00, 4.00 Hz, 1H), 6.89 (d, J=8.00 Hz, 1H), 4.27 (t, J=8.00 Hz, 2H), 3.93 (s, 3H), 3.90 (s, 3H), 3.29 (t, J=8.00 Hz, 2H).

[3-(3,4-Dimethoxy-phenyl)-4,5-dihydro-pyrazol-1-yl]-(3-dimethylamino-phenyl)-methanone

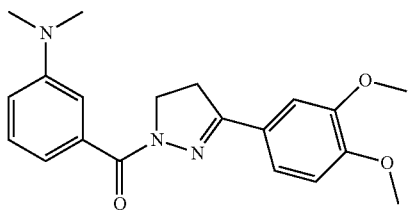 [SMILES: COc1ccc(C2=NN(C(=O)c3cccc(N(C)C)c3)CC2)cc1OC]

Yellow solid; 11.15% Yield

LC-MS: Mass found (M+, 354). Rt (min): 2.65; % Area: 98.79 (Max), 99.07 (254 nm).

HPLC—Rt (min): 2.65; % Area: 96.98 (Max), 96.66 (254 nm).

¹H NMR 400 MHz, DMSO-d6: δ 7.28-7.22 (m, 4H), 7.15 (d, J=4.00 Hz, 1H), 7.03 (d, J=12.00 Hz, 1H), 6.87 (dd, J=8.00, 4.00 Hz, 1H), 4.07 (t, J=8.00 Hz, 2H), 3.79 (s, 3H), 3.75 (s, 3H), 3.27 (t, J=12.00 Hz, 2H), 2.92 (s, 6H).

(3-Benzyloxy-phenyl)-[3-(3,4-dimethoxy-phenyl)-4,5-dihydro-pyrazol-1-yl]-methanone

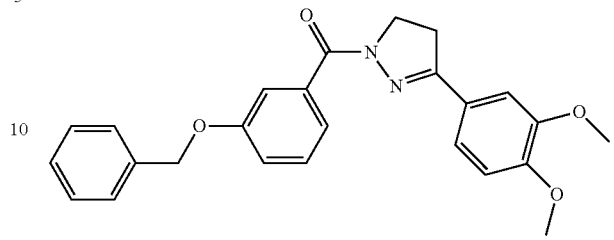

White solid; 33.15% Yield

LC-MS: Mass found (M+, 417). Rt (min): 4.87; % Area: 94.89 (Max), 93.72 (254 nm).

HPLC—Rt (min): 4.88; % Area: 94.10 (Max), 91.01 (254 nm).

¹H NMR 400 MHz, CDCl3: δ 7.80-7.70 (m, 1H), 7.64 (d, J=8.00 Hz, 1H), 7.45-7.32 (m, 7H), 7.17 (dd, J=8.00, 4.00 Hz, 1H), 7.12 (dd, J=4.60, 2.80 Hz, 1H), 6.88 (d, J=8.00 Hz, 1H), 5.12 (s, 2H), 4.26 (t, J=12.00 Hz, 2H), 3.95 (s, 3H), 3.99 (s, 3H), 3.26 (t, J=12.00 Hz, 2H).

[3-(3,4-Dimethoxy-phenyl)-4,5-dihydro-pyrazol-1-yl]-(3-isopropoxy-phenyl)-methanone

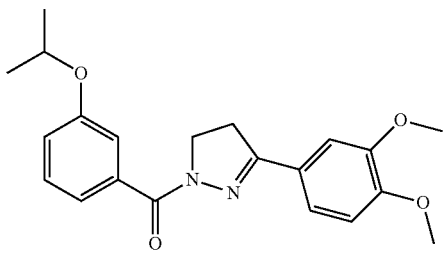 [SMILES: COc1ccc(C2=NN(C(=O)c3cccc(OC(C)C)c3)CC2)cc1OC]

Yellow solid; 18.81% Yield

LC-MS: Mass found (M+, 369). Rt (min): 4.45; % Area: 97.00 (Max), 96.31 (254 nm).

HPLC—Rt (min): 4.48; % Area: 97.23 (Max), 95.98 (254 nm).

¹H NMR 400 MHz, CDCl3: δ 7.56 (d, J=8.00 Hz, 2H), 7.35-7.27 (m, 2H), 7.02 (dt, J=8.13, 0.80 Hz, 1H), 6.88 (d, J=8.00 Hz, 1H), 4.62-4.59 (m, 1H), 4.26 (t, J=8.00 Hz, 2H), 3.93 (s, 3H), 3.89 (s, 3H), 3.26 (t, J=8.00 Hz, 2H), 1.36 (s, 3H), 1.35 (s, 3H).

[3-(3,4-Dimethoxy-phenyl)-4,5-dihydro-pyrazol-1-yl]-(3-phenoxy-phenyl)-methanone

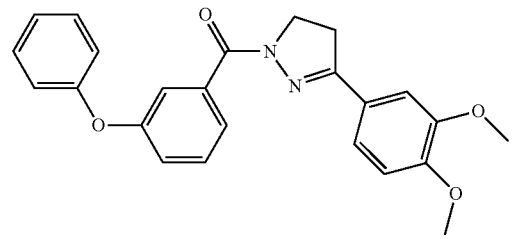 [SMILES: COc1ccc(C2=NN(C(=O)c3cccc(Oc4ccccc4)c3)CC2)cc1OC]

Brown gum; 35.41% Yield

LC-MS: Mass found (M+, 403). Rt (min): 4.80; % Area: 97.93 (Max), 96.41 (254 nm).

HPLC—Rt (min): 4.85; % Area: 97.21 (Max), 95.15 (254 nm).

$^1$H NMR 400 MHz, CDCl3: δ 7.77-7.73 (m, 2H), 7.42 (t, J=8.00 Hz, 1H), 7.34-7.30 (m, 3H), 7.17-7.03 (m, 5H), 6.87 (d, J=8.00 Hz, 1H), 4.24 (t, J=8.00 Hz, 2H), 3.93 (s, 3H), 3.83 (s, 3H), 3.25 (t, J=8.00 Hz, 2H).

Biphenyl-3-yl-[3-(3,4-dimethoxy-phenyl)-4,5-dihydro-pyrazol-1-yl]-methanone

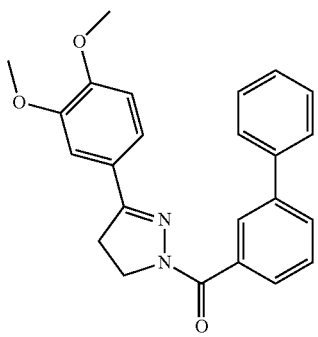 [SMILES: COc1ccc(C2=NN(C(=O)c3cccc(-c4ccccc4)c3)CC2)cc1OC]

White solid; 35.56% Yield

LC-MS: Mass found (M+, 387). Rt (min): 4.79; % Area: 99.10 (Max), 99.47 (254 nm).

HPLC—Rt (min): 4.85; % Area: 97.41 (Max), 98.79 (254 nm).

$^1$H NMR 400 MHz, CDCl3: δ 8.32 (s, 1H), 7.98 (d, J=8.00 Hz, 1H), 7.74-7.71 (m, 1H), 7.65 (d, J=8.00 Hz, 2H), 7.53 (t, J=4.00 Hz, 1H), 7.46-7.42 (m, 2H), 7.38-7.34 (m, 2H), 7.14 (dd, J=8.00, 4.00 Hz, 1H), 6.87 (d, J=8.00 Hz, 1H), 4.30 (t, J=8.00 Hz, 2H), 3.92 (s, 3H), 3.73 (s, 3H), 3.28 (t, J=12.00 Hz, 2H).

[3-(3,4-Dimethoxy-phenyl)-4,5-dihydro-pyrazol-1-yl]-[3-(2-methyl-thiazol-4-yl)-phenyl]-methanone

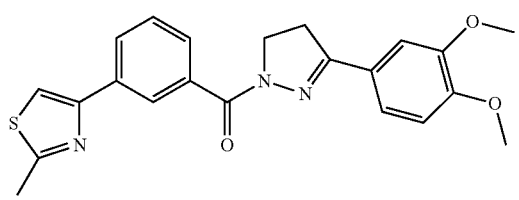 [SMILES: COc1ccc(C2=NN(C(=O)c3cccc(-c4csc(C)n4)c3)CC2)cc1OC]

White solid; 22.83% Yield

LC-MS: Mass found (M+, 408). Rt (min): 4.05; % Area: 98.13 (Max), 98.83 (254 nm).

HPLC—Rt (min): 4.05; % Area: 98.86 (Max), 99.07 (254 nm).

$^1$H NMR 400 MHz, CDCl3: δ 8.51 (s, 1H), 8.11 (d, J=8.00 Hz, 1H), 7.96 (d, J=8.00 Hz, 1H), 7.52 (t, J=4.00 Hz, 1H), 7.40-7.36 (m, 1H), 7.27-7.26 (m, 1H), 7.16 (d, J=8.00 Hz, 1H), 6.87 (d, J=8.00 Hz, 1H), 4.28 (t, J=12.00 Hz, 2H), 3.92 (s, 3H), 3.80 (s, 3H), 3.28 (t, J=12.00 Hz, 2H), 2.83 (s, 3H).

(3-tert-Butyl-phenyl)-[3-(3,4-dimethoxy-phenyl)-4,5-dihydro-pyrazol-1-yl]-methanone

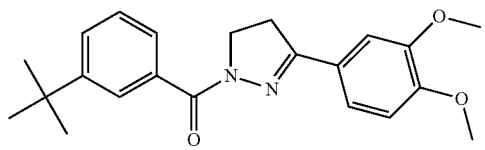 [SMILES: COc1ccc(C2=NN(C(=O)c3cccc(C(C)(C)C)c3)CC2)cc1OC]

Yellow solid, 12.55% Yield

LC-MS: Mass found (M+, 367). Rt (min): 4.91; % Area: 94.01 (Max), 92.83 (254 nm).

HPLC—Rt (min): 4.95; % Area: 97.22 (Max), 95.98 (254 nm).

$^1$H NMR 400 MHz, CDCl3: δ 8.08 (s, 1H), 7.80 (d, J=8.00 Hz, 1H), 7.51 (dd, J=5.00, 2.00 Hz, 1H), 7.38 (dd, J=10.00, 8.00 Hz, 2H), 7.15 (dd, J=11.00, 2.00 Hz, 1H), 6.88 (d, J=12.00 Hz, 1H), 4.27 (t, J=12.00 Hz, 2H), 3.93 (s, 3H), 3.87 (s, 3H), 3.27 (t, J=8.00 Hz, 2H), 1.38 (s, 9H).

[3-(3,4-Dimethoxy-phenyl)-4,5-dihydro-pyrazol-1-yl]-(3-ethyl-phenyl)-methanone

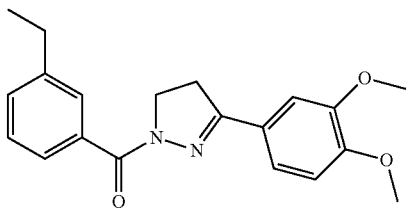 [SMILES: CCc1cccc(C(=O)N2CCC(c3ccc(OC)c(OC)c3)=N2)c1]

Yellow solid; 42.48% Yield

LC-MS: Mass found (M+, 339). Rt (min): 4.45; % Area: 92.47 (Max), 91.15 (220 nm).

HPLC—Rt (min): 4.46; % Area: 92.59 (Max), 91.02 (254 nm).

$^1$H NMR 400 MHz, CDCl3: δ 7.86 (s, 1H), 7.81 (d, J=8.00 Hz, 1H), 7.38-7.31 (m, 3H), 7.16 (dd, J=8.00, 4.00 Hz, 1H), 6.88 (d, J=8.00 Hz, 1H), 4.26 (t, J=12.00 Hz, 2H), 3.93 (s, 3H), 3.89 (s, 3H), 3.26 (t, J=12.00 Hz, 2H), 2.72 (q, J=8.00 Hz, 2H), 1.29 (t, J=8.00 Hz, 3H).

[3-(3,4-Dimethoxy-phenyl)-4,5-dihydro-pyrazol-1-yl]-(3-methanesulfonyl-phenyl)-methanone

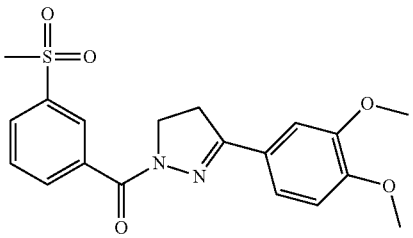

Yellow solid; 40.62% Yield

LC-MS: Mass found (M+, 389). Rt (min): 3.36; % Area: 98.64 (Max), 98.30 (254 nm).

HPLC—Rt (min): 3.35; % Area: 99.08 (Max), 98.77 (254 nm).

¹H NMR 400 MHz, CDCl3: δ 8.86 (s, 1H), 8.30 (d, J=8.00 Hz, 1H), 8.07 (dt, J=8.13, 1.20 Hz, 1H), 7.68 (t, J=8.00 Hz, 1H), 7.45 (d, J=1.60 Hz, 1H), 7.14 (dd, J=8.40, 2.00 Hz, 1H), 6.88 (d, J=8.00 Hz, 1H), 4.29 (t, J=8.00 Hz, 2H), 3.95 (s, 3H), 3.93 (s, 3H), 3.31 (t, J=8.00 Hz, 2H), 3.08 (s, 3H).

[3-(3,4-Dimethoxy-phenyl)-4,5-dihydro-pyrazol-1-yl]-(3-hydroxy-phenyl)-methanone

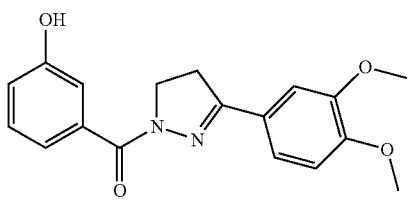 [SMILES: COc1ccc(C2=NN(C(=O)c3cccc(O)c3)CC2)cc1OC]

Yellow solid; 20.35% Yield

LC-MS: Mass found (M+, 327). Rt (min): 3.23; % Area: 97.80 (Max), 97.47 (254 nm).

HPLC—Rt (min): 3.24; % Area: 97.68 (Max), 96.88 (254 nm).

¹H NMR 400 MHz, CDCl3: δ 7.59 (s, 2H), 7.33-7.27 (m, 3H), 7.19 (d, J=8.00 Hz, 1H), 7.00-6.97 (m, 1H), 6.89-6.86 (m, 1H), 4.25 (t, J=12.00 Hz, 2H), 3.93 (s, 3H), 3.90 (s, 3H), 3.26 (t, J=12.00 Hz, 2H).

(3-Difluoromethoxy-phenyl)-[3-(3,4-dimethoxy-phenyl)-4,5-dihydro-pyrazol-1-yl]-methanone

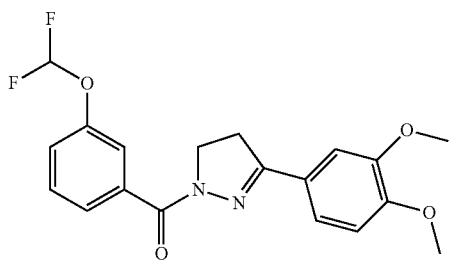 [SMILES: COc1ccc(C2=NN(C(=O)c3cccc(OC(F)F)c3)CC2)cc1OC]

Yellow solid; 7.18% Yield

LC-MS: Mass found (M+, 377). Rt (min): 4.28; % Area: 94.48 (Max), 93.62 (254 nm).

HPLC—Rt (min): 4.30; % Area: 97.41 (Max), 97.37 (254 nm).

¹H NMR 400 MHz, CDCl3: δ 7.90-7.86 (m, 2H), 7.45 (t, J=8.00 Hz, 1H), 7.36 (d, J=2.00 Hz, 1H), 7.25 (d, J=4.00 Hz, 1H), 7.17 (dd, J=8.00, 4.00 Hz, 1H), 6.88 (d, J=8.00 Hz, 1H), 6.76-6.39 (m, 1H), 4.26 (t, J=12.00 Hz, 2H), 3.93 (s, 3H), 3.90 (s, 3H), 3.28 (t, J=12.00 Hz, 2H).

N-{3-[3-(3,4-Dimethoxy-phenyl)-4,5-dihydro-pyrazole-1-carbonyl]-phenyl}-acetamide

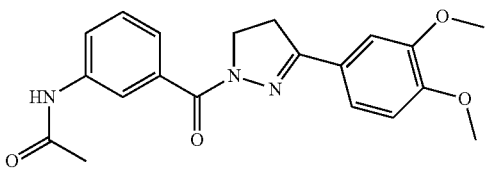 [SMILES: COc1ccc(C2=NN(C(=O)c3cccc(NC(C)=O)c3)CC2)cc1OC]

White solid; 20.93% Yield

LC-MS: Mass found (M+, 368). Rt (min): 3.13; % Area: 96.09 (Max), 96.43 (254 nm).

HPLC—Rt (min): 3.09; % Area: 98.62 (Max), 98.33 (254 nm).

¹H NMR 400 MHz, CDCl3: δ 8.12 (s, 1H), 7.76 (d, J=8.00 Hz, 1H), 7.71 (d, J=8.00 Hz, 1H), 7.42-7.37 (m, 2H), 7.33 (s, 1H), 7.17 (d, J=8.00 Hz, 1H), 6.88 (d, J=12.00 Hz, 1H), 4.25 (t, J=8.00 Hz, 2H), 3.93 (s, 3H), 3.92 (s, 3H), 3.26 (t, J=12.00 Hz, 2H), 2.19 (s, 3H).

[3-(3,4-Dimethoxy-phenyl)-4,5-dihydro-pyrazol-1-yl]-(4-fluoro-phenyl)-methanone

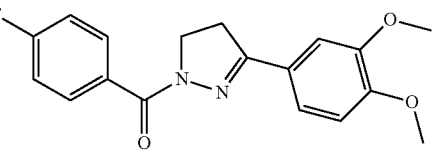

White solid; 59.29% Yield

LC-MS: Mass found (M+, 329). Rt (min): 4.06; % Area: 98.85 (Max), 98.98 (254 nm).

HPLC—Rt (min): 4.05; % Area: 98.89 (Max), 98.62 (254 nm).

¹H NMR 400 MHz, CDCl3: δ 8.07-8.04 (m, 2H), 7.31 (d, J=1.60 Hz, 1H), 7.19 (dd, J=8.00, 4.00 Hz, 1H), 7.14-7.10 (m, 2H), 6.89 (d, J=8.00 Hz, 1H), 4.26 (t, J=8.00 Hz, 2H), 3.93 (s, 3H), 3.91 (s, 3H), 3.27 (t, J=8.00 Hz, 2H).

(3,4-Difluoro-phenyl)-[3-(3,4-dimethoxy-phenyl)-4,5-dihydro-pyrazol-1-yl]-methanone

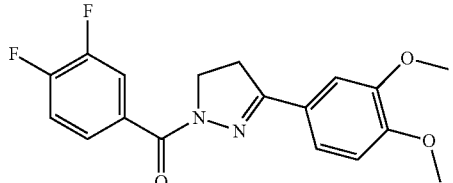

White solid; 53.59% Yield

LC-MS: Mass found (M+, 347). Rt (min): 4.29; % Area: 99.49 (Max), 99.34 (254 nm).

HPLC—Rt (min): 4.32; % Area: 99.39 (Max), 98.67 (254 nm).

¹H NMR 400 MHz, CDCl3: δ 8.02-7.97 (m, 1H), 7.86-7.83 (m, 1H), 7.33 (d, J=4.00 Hz, 1H), 7.24-7.21 (m, 1H), 7.19 (dd, J=8.00, 4.00 Hz, 1H), 6.90 (d, J=8.00 Hz, 1H), 4.25 (t, J=12.00 Hz, 2H), 3.94 (s, 3H), 3.92 (s, 3H), 3.28 (t, J=4.00 Hz, 2H).

[3-(3,4-Dimethoxy-phenyl)-4,5-dihydro-pyrazol-1-yl]-(3-fluoro-4-trifluoromethyl-phenyl)-methanone

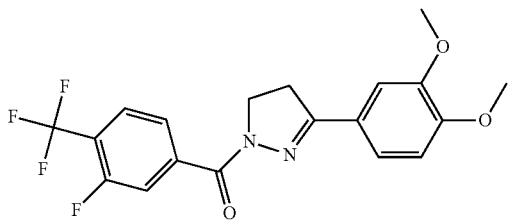 [SMILES: COc1ccc(C2=NN(C(=O)c3ccc(C(F)(F)F)c(F)c3)CC2)cc1OC]

White solid; 21.65% Yield

LC-MS: Mass found (M+, 397). Rt (min): 4.86; % Area: 97.60 (Max), 97.07 (254 nm).

HPLC—Rt (min): 4.97; % Area: 97.92 (Max), 97.38 (254 nm).

¹H NMR 400 MHz, CDCl3: δ 7.90 (t, J=12.00 Hz, 2H), 7.69 (t, J=4.00 Hz, 1H), 7.30 (d, J=4.00 Hz, 1H), 7.20 (dd, J=8.00, 4.00 Hz, 1H), 6.90 (d, J=8.00 Hz, 1H), 4.27 (t, J=8.00 Hz, 2H), 3.94 (s, 3H), 3.92 (s, 3H), 3.31 (t, J=8.00 Hz, 2H).

[3-(3,4-Dimethoxy-phenyl)-4,5-dihydro-pyrazol-1-yl]-(3-fluoro-4-methyl-phenyl)-methanone

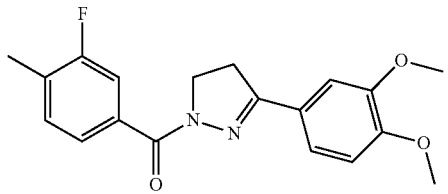

Yellow solid; 31.63% Yield

LC-MS: Mass found (M+, 343). Rt (min): 4.36; % Area: 96.11 (Max), 97.09 (254 nm).

HPLC—Rt (min): 4.37; % Area: 98.71 (Max), 98.42 (254 nm).

¹H NMR 400 MHz, CDCl3: δ 7.76 (dd, J=16.00, 8.00 Hz, 2H), 7.36 (d, J=1.60 Hz, 1H), 7.27-7.17 (m, 2H), 6.89 (d, J=8.00 Hz, 1H), 4.25 (t, J=12.00 Hz, 2H), 3.93 (s, 3H), 3.92 (s, 3H), 3.26 (t, J=12.00 Hz, 2H), 2.35 (s, 3H).

(4-Chloro-3-fluoro-phenyl)-[3-(3,4-dimethoxy-phenyl)-4,5-dihydro-pyrazol-1-yl]-methanone

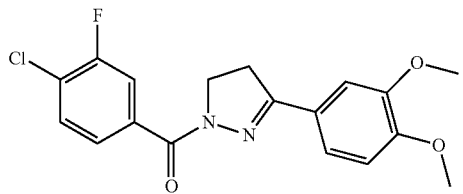 [SMILES: COc1ccc(C2=NN(C(=O)c3ccc(Cl)c(F)c3)CC2)cc1OC]

Brown solid; 33.64% Yield

LC-MS: Mass found (M+, 343). Rt (min): 4.36; % Area: 98.34 (Max), 98.75 (254 nm).

HPLC—Rt (min): 4.37; % Area: 99.08 (Max), 98.92 (254 nm).

¹H NMR 400 MHz, CDCl3: δ 7.93 (dd, J=9.20, 4.00 Hz, 1H), 7.80 (d, J=8.00 Hz, 1H), 7.47 (t, J=8.00 Hz, 1H), 7.33 (d, J=1.60 Hz, 1H), 7.19 (dd, J=8.00, 4.00 Hz, 1H), 6.90 (d, J=12.00 Hz, 1H), 4.25 (t, J=12.00 Hz, 2H), 3.94 (s, 3H), 3.92 (s, 3H), 3.28 (t, J=8.00 Hz, 2H).

[3-(3,4-Dimethoxy-phenyl)-4,5-dihydro-pyrazol-1-yl]-(3-fluoro-4-methoxy-phenyl)-methanone

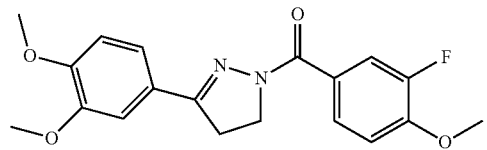

Yellow solid; 50.99% Yield

LC-MS: Mass found (M+, 359). Rt (min): 4.04; % Area: 98.61 (Max), 99.28 (254 nm).

HPLC—Rt (min): 4.03; % Area: 98.30 (Max), 97.91 (254 nm).

¹H NMR 400 MHz, CDCl3: δ 7.98 (dd, J=12.80, 1.60 Hz, 1H), 7.89 (d, J=8.00 Hz, 1H), 7.37 (d, J=2.00 Hz, 1H), 7.19 (dd, J=8.20, 2.00 Hz, 1H), 7.01 (t, J=8.00 Hz, 1H), 6.89 (d, J=8.00 Hz, 1H), 4.25 (t, J=12.00 Hz, 2H), 3.96 (s, 3H), 3.94 (s, 3H), 3.93 (s, 3H), 3.25 (t, J=12.00 Hz, 2H).

(4-Bromo-3-fluoro-phenyl)-[3-(3,4-dimethoxy-phenyl)-4,5-dihydro-pyrazol-1-yl]-methanone

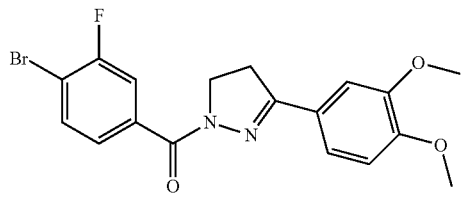 [SMILES: COc1ccc(C2=NN(C(=O)c3ccc(Br)c(F)c3)CC2)cc1OC]

Yellow solid; 25.12% Yield

LC-MS: Mass found (M+, 409). Rt (min): 4.62; % Area: 95.45 (Max), 96.43 (254 nm).

HPLC—Rt (min): 4.63; % Area: 95.39 (Max), 95.86 (254 nm).

¹H NMR 400 MHz, CDCl3: δ 7.90 (dd, J=9.60, 1.60 Hz, 1H), 7.73 (d, J=8.00 Hz, 1H), 7.63 (t, J=8.00 Hz, 1H), 7.32 (d, J=2.00 Hz, 1H), 7.19 (dd, J=8.20, 2.00 Hz, 1H), 6.89 (d, J=8.00 Hz, 1H), 4.25 (t, J=8.00 Hz, 2H), 3.94 (s, 3H), 3.92 (s, 3H), 3.28 (t, J=12.00 Hz, 2H).

(2,3-Difluoro-phenyl)-[3-(3,4-dimethoxy-phenyl)-4,5-dihydro-pyrazol-1-yl]-methanone

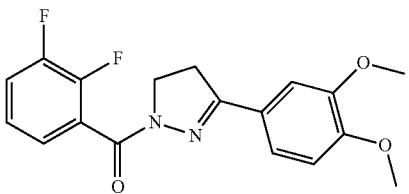 [SMILES: COc1ccc(C2=NN(C(=O)c3cccc(F)c3F)CC2)cc1OC]

Yellow solid; 14.83% Yield
LC-MS: Mass found (M+, 347). Rt (min): 3.99; % Area: 98.85 (Max), 99.26 (254 nm).
HPLC—Rt (min): 4.07; % Area: 98.85 (Max), 98.67 (254 nm).
$^1$H NMR 400 MHz, CDCl3: δ 7.36-7.33 (m, 1H), 7.28-7.27 (m, 1H), 7.22 (d, J=2.00 Hz, 1H), 7.18-7.12 (m, 2H), 6.85 (d, J=8.00 Hz, 1H), 4.25 (t, J=4.00 Hz, 2H), 3.91 (s, 3H), 3.85 (s, 3H), 3.32 (t, J=12.00 Hz, 2H).

[3-(3,4-Dimethoxy-phenyl)-4,5-dihydro-pyrazol-1-yl]-(3-fluoro-2-methyl-phenyl)-methanone

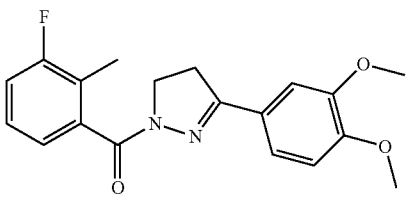 [SMILES: COc1ccc(C2=NN(C(=O)c3cccc(F)c3C)CC2)cc1OC]

Yellow solid; 28.49% Yield
LC-MS: Mass found (M+, 343). Rt (min): 4.05; % Area: 98.93 (Max), 99.15 (254 nm).
HPLC—Rt (min): 4.13; % Area: 98.99 (Max), 99.12 (254 nm).
$^1$H NMR 400 MHz, CDCl3: δ 7.22-7.20 (m, 2H), 7.16 (d, J=4.00 Hz, 1H), 7.13-7.07 (m, 2H), 6.84 (d, J=8.00 Hz, 1H), 4.26 (t, J=8.00 Hz, 2H), 3.90 (s, 3H), 3.83 (s, 3H), 3.30 (t, J=12.00 Hz, 2H), 2.27 (s, 3H).

[3-(3,4-Dimethoxy-phenyl)-4,5-dihydro-pyrazol-1-yl]-(3-fluoro-2-trifluoromethyl-phenyl)-methanone

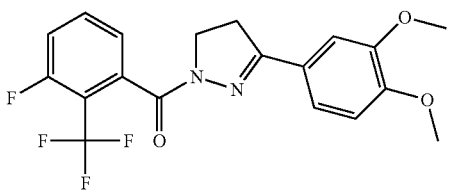 [SMILES: COc1ccc(C2=NN(C(=O)c3cccc(F)c3C(F)(F)F)CC2)cc1OC]

Brown solid; 24.46% Yield
LC-MS: Mass found (M+, 397). Rt (min): 4.39; % Area: 93.14 (Max), 92.71 (254 nm).
HPLC—Rt (min): 4.44; % Area: 93.80 (Max), 91.92 (254 nm).
$^1$H NMR 400 MHz, CDCl3: δ 7.61-7.60 (m, 1H), 7.30-7.28 (m, 2H), 7.16 (d, J=4.00 Hz, 1H), 7.08 (dd, J=8.00, 4.00 Hz, 1H), 6.83 (d, J=8.00 Hz, 1H), 4.21 (t, J=8.00 Hz, 2H), 3.90 (s, 3H), 3.82 (s, 3H), 3.31 (t, J=12.00 Hz, 2H).

(2-Chloro-3-fluoro-phenyl)-[3-(3,4-dimethoxy-phenyl)-4,5-dihydro-pyrazol-1-yl]-methanone

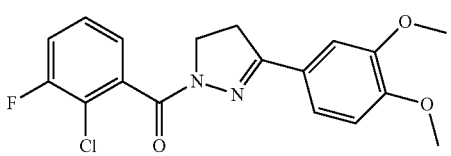 [SMILES: COc1ccc(C2=NN(C(=O)c3cccc(F)c3Cl)CC2)cc1OC]

White solid; 33.69% Yield
LC-MS: Mass found (M+, 363). Rt (min): 4.09; % Area: 96.66 (Max), 95.86 (254 nm).
HPLC—Rt (min): 4.12; % Area: 97.87 (Max), 97.52 (254 nm).
$^1$H NMR 400 MHz, CDCl3: δ 7.34-7.28 (m, 2H), 7.24-7.19 (m, 1H), 7.16 (d, J=4.00 Hz, 1H), 7.12 (dd, J=8.00, 4.00 Hz, 1H), 6.84 (d, J=8.00 Hz, 1H), 4.26 (t, J=8.00 Hz, 2H), 3.90 (s, 3H), 3.83 (s, 3H), 3.32 (t, J=12.00 Hz, 2H).

[3-(3,4-Dimethoxy-phenyl)-4,5-dihydro-pyrazol-1-yl]-(2,3,4-trifluoro-phenyl)-methanone

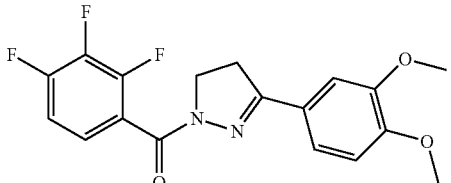

White solid; 58.13% Yield
LC-MS: Mass found (M+, 365). Rt (min): 4.27; % Area: 99.31 (Max), 99.04 (254 nm).
HPLC—Rt (min): 4.30; % Area: 99.02 (Max), 98.68 (254 nm).
$^1$H NMR 400 MHz, CDCl3: δ 7.38-7.30 (m, 1H), 7.22 (d, J=4.00 Hz, 1H), 7.14 (dd, J=8.00, 4.00 Hz, 1H), 7.08-7.01 (m, 1H), 6.86 (d, J=8.00 Hz, 1H), 4.23 (t, J=12.00 Hz, 2H), 3.92 (s, 3H), 3.87 (s, 3H), 3.32 (t, J=12.00 Hz, 2H).

(2,3-Difluoro-4-methyl-phenyl)-[3-(3,4-dimethoxy-phenyl)-4,5-dihydro-pyrazol-1-yl]-methanone

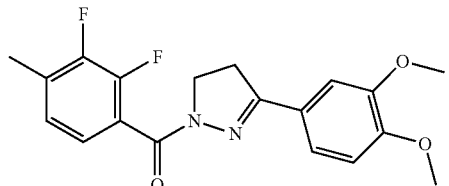

White solid; 33.53% Yield
LC-MS: Mass found (M+, 361). Rt (min): 4.29; % Area: 97.01 (Max), 96.49 (220 nm).
HPLC—Rt (min): 4.35; % Area: 98.83 (Max), 98.99 (254 nm).

¹H NMR 400 MHz, CDCl3: δ 7.26-7.24 (m, 2H), 7.24 (d, J=2.00 Hz, 1H), 7.14 (dd, J=8.40, 2.00 Hz, 1H), 7.00 (t, J=8.00 Hz, 1H), 4.24 (t, J=8.00 Hz, 2H), 3.91 (s, 3H), 3.87 (s, 3H), 3.31 (t, J=8.00 Hz, 2H), 2.37 (s, 3H).

(2,3-Difluoro-4-methoxy-phenyl)-[3-(3,4-dimethoxy-phenyl)-4,5-dihydro-pyrazol-1-yl]-methanone

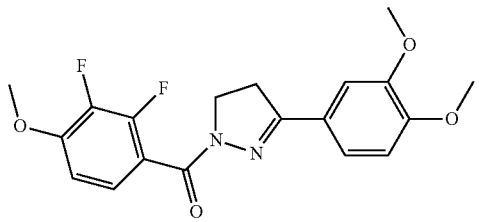

Yellow solid; 5.26% Yield

LC-MS: Mass found (M+, 377). Rt (min): 4.02; % Area: 97.62 (Max), 97.66 (254 nm).

HPLC—Rt (min): 4.05; % Area: 97.43 (Max), 97.79 (254 nm).

¹H NMR 400 MHz, CDCl3: δ 7.37-7.33 (m, 1H), 7.26 (d, J=1.60 Hz, 1H), 7.14 (dd, J=8.00, 4.00 Hz, 1H), 6.86 (d, J=8.00 Hz, 1H), 6.83-6.79 (m, 1H), 4.23 (t, J=8.00 Hz, 2H), 3.96 (s, 3H), 3.91 (s, 3H), 3.87 (s, 3H), 3.30 (t, J=12.00 Hz, 2H).

[3-(3,4-Dimethoxy-phenyl)-4,5-dihydro-pyrazol-1-yl]-(2,3,4,5-tetrafluoro-phenyl)-methanone

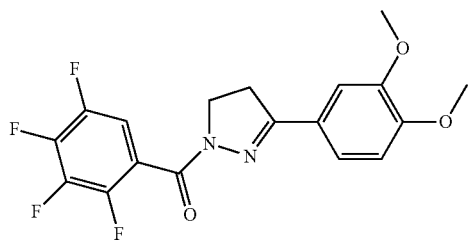 [SMILES: COc1ccc(C2=NN(C(=O)c3cc(F)c(F)c(F)c3F)CC2)cc1OC]

White solid; 21.79% Yield

LC-MS: Mass found (M+, 383). Rt (min): 4.52; % Area: 97.94 (Max), 97.96 (254 nm).

HPLC—Rt (min): 4.63; % Area: 97.82 (Max), 97.91 (254 nm).

¹H NMR 400 MHz, DMSO-d6: δ 7.64-7.59 (m, 1H), 7.21 (d, J=8.00 Hz, 1H), 7.14 (d, J=1.60 Hz, 1H), 7.01 (d, J=12.00 Hz, 1H), 4.09 (t, J=8.00 Hz, 2H), 3.78 (s, 3H), 3.72 (s, 3H), 3.38 (t, J=8.00 Hz, 2H).

(7-Chloro-benzo[1,3]dioxol-5-yl)-[3-(3,4-dimethoxy-phenyl)-4,5-dihydro-pyrazol-1-yl]-methanone

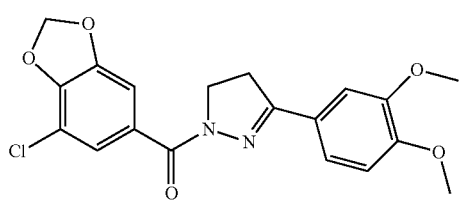 [SMILES: COc1ccc(C2=NN(C(=O)c3cc(Cl)c4c(c3)OCO4)CC2)cc1OC]

Brown solid; 5.47% Yield

LC-MS: Mass found (M+, 389). Rt (min): 4.33; % Area: 98.31 (Max), 98.28 (220 nm).

HPLC—Rt (min): 4.34; % Area: 97.52 (Max), 98.07 (254 nm).

¹H NMR 400 MHz, CDCl3: δ 7.82 (s, 1H), 7.51 (d, J=8.00 Hz, 1H), 7.40 (d, J=4.00 Hz, 1H), 7.17 (dd, J=8.40, 2.00 Hz, 1H), 6.89 (d, J=8.00 Hz, 1H), 6.12 (s, 2H), 4.24 (t, J=8.00 Hz, 2H), 3.94 (s, 3H), 3.92 (s, 3H), 3.25 (t, J=12.00 Hz, 2H).

(6-Bromo-benzo[1,3]dioxol-5-yl)-[3-(3,4-dimethoxy-phenyl)-4,5-dihydro-pyrazol-1-yl]-methanone

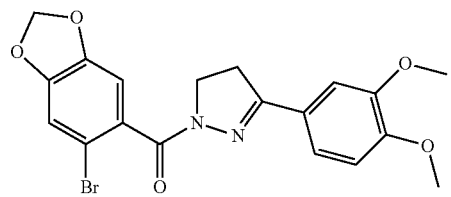 [SMILES: COc1ccc(C2=NN(C(=O)c3cc4c(cc3Br)OCO4)CC2)cc1OC]

Brown solid; 23.85% Yield

LC-MS: Mass found (M+, 433). Rt (min): 3.95; % Area: 98.38 (Max), 98.32 (254 nm).

HPLC—Rt (min): 3.94; % Area: 97.76 (Max), 98.98 (254 nm).

¹H NMR 400 MHz, CDCl3: δ 7.22 (d, J=4.00 Hz, 1H), 7.15 (dd, J=8.00, 4.00 Hz, 1H), 7.04 (s, 1H), 6.93 (s, 1H), 6.85 (d, J=8.00 Hz, 1H), 6.03 (s, 2H), 4.22 (t, J=12.00 Hz, 2H), 3.91 (s, 3H), 3.87 (s, 3H), 3.29 (t, J=12.00 Hz, 2H).

[3-(3,4-Dimethoxy-phenyl)-4,5-dihydro-pyrazol-1-yl]-(6-nitro-benzo[1,3]dioxol-5-yl)-methanone

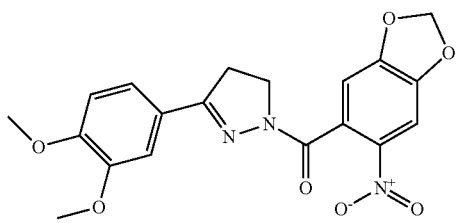 [SMILES: COc1ccc(C2=NN(C(=O)c3cc4c(cc3[N+](=O)[O-])OCO4)CC2)cc1OC]

Brown solid; 6.97% Yield

LC-MS: Mass found (M+, 400). Rt (min): 3.75; % Area: 94.53 (Max), 92.65 (254 nm).

HPLC—Rt (min): 3.78; % Area: 93.42 (Max), 91.57 (254 nm).

¹H NMR 400 MHz, CDCl3: δ 7.56 (s, 1H), 7.12 (d, J=2.00 Hz, 1H), 7.05-7.01 (m, 2H), 6.82 (d, J=8.00 Hz, 1H), 6.18 (s, 2H), 4.20 (t, J=12.00 Hz, 2H), 3.94 (s, 3H), 3.89 (s, 3H), 3.27 (t, J=8.00 Hz, 2H).

(2,2-Difluoro-benzo[1,3]dioxol-5-yl)-[3-(3,4-dimethoxy-phenyl)-4,5-dihydro-pyrazol-1-yl]-methanone

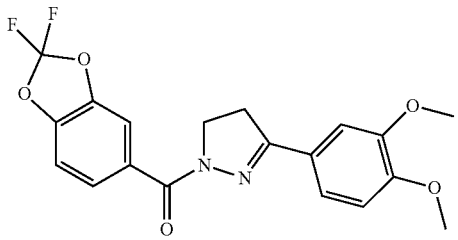 [SMILES: COc1ccc(C2=NN(C(=O)c3ccc4c(c3)OC(F)(F)O4)CC2)cc1OC]

Yellow solid; 9.62% Yield
LC-MS: Mass found (M+, 391). Rt (min): 4.69; % Area: 93.95 (Max), 93.64 (220 nm).
HPLC—Rt (min): 4.72; % Area: 97.44 (Max), 97.76 (254 nm).
$^1$H NMR 400 MHz, CDCl3: δ 7.86 (d, J=8.00 Hz, 2H), 7.31 (d, J=4.00 Hz, 1H), 7.20 (d, J=8.00 Hz, 1H), 7.13 (d, J=8.00 Hz, 1H), 6.90 (d, J=8.00 Hz, 1H), 4.26 (t, J=8.00 Hz, 2H), 3.94 (s, 3H), 3.92 (s, 3H), 3.28 (t, J=8.00 Hz, 2H).

(2,3-Dimethoxy-phenyl)-[3-(3,4-dimethoxy-phenyl)-4,5-dihydro-pyrazol-1-yl]-methanone

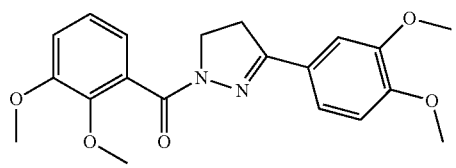 [SMILES: COc1ccc(C2=NN(C(=O)c3cccc(OC)c3OC)CC2)cc1OC]

Brown solid; 5.68% Yield
LC-MS: Mass found (M+, 371). Rt (min): 3.62; % Area: 95.22 (Max), 95.61 (254 nm).
HPLC—Rt (min): 3.62; % Area: 95.26 (Max), 95.30 (254 nm).
$^1$H NMR 400 MHz, CDCl3: δ 7.17-7.07 (m, 3H), 6.99 (d, J=8.00 Hz, 2H), 6.82 (d, J=8.00 Hz, 1H), 4.26 (t, J=8.00 Hz, 2H), 3.90 (s, 9H), 3.76 (s, 3H), 3.28 (t, J=12.00 Hz, 2H).

(2,5-Dimethoxy-phenyl)-[3-(3,4-dimethoxy-phenyl)-4,5-dihydro-pyrazol-1-yl]-methanone

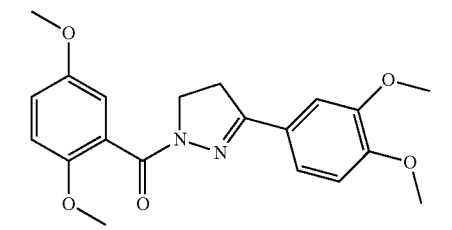 [SMILES: COc1ccc(OC)c(C(=O)N2CCC(c3ccc(OC)c(OC)c3)=N2)c1]

Yellow gum; 10.02% Yield
LC-MS: Mass found (M+, 371). Rt (min): 3.59; % Area: 96.83 (Max), 96.46 (254 nm).
HPLC—Rt (min): 3.61; % Area: 96.33 (Max), 96.54 (254 nm).
$^1$H NMR 400 MHz, CDCl3: δ 7.20 (d, J=1.60 Hz, 1H), 7.11 (dd, J=8.20, 2.00 Hz, 1H), 7.01 (d, J=2.40 Hz, 1H), 6.96-6.88 (m, 2H), 6.84 (d, J=8.00 Hz, 1H), 4.25 (t, J=8.00 Hz, 2H), 3.93 (s, 3H), 3.90 (s, 3H), 3.79 (s, 3H), 3.78 (s, 3H), 3.27 (t, J=12.00 Hz, 2H).

[3-(3,4-Dimethoxy-phenyl)-4,5-dihydro-pyrazol-1-yl]-(4-hydroxy-3-methoxy-phenyl)-methanone

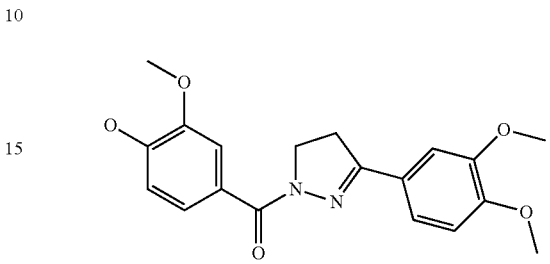

Brown solid; 9.02% Yield
LC-MS: Mass found (M+, 357). Rt (min): 3.22; % Area: 90.88 (Max), 90.37 (254 nm).
HPLC—Rt (min): 3.19; % Area: 91.29 (Max), 90.03 (254 nm).
$^1$H NMR 400 MHz, CDCl3: δ 7.74 (d, J=8.00 Hz, 1H), 7.68 (d, J=2.00 Hz, 1H), 7.36 (d, J=4.00 Hz, 1H), 7.19 (dd, J=8.00, 4.00 Hz, 1H), 6.97 (d, J=12.00 Hz, 1H), 6.89 (d, J=8.00 Hz, 1H), 5.89 (s, 1H), 4.26 (t, J=8.00 Hz, 2H), 3.94 (s, 3H), 3.92 (s, 3H), 3.91 (s, 3H), 3.25 (t, J=8.00 Hz, 2H).

[3-(3,4-Dimethoxy-phenyl)-4,5-dihydro-pyrazol-1-yl]-(3-hydroxy-4-methoxy-phenyl)-methanone

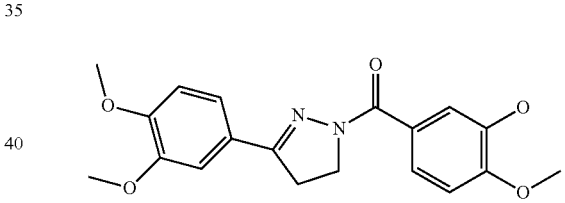

White solid; 37.84% Yield
LC-MS: Mass found (M+, 357). Rt (min): 3.23; % Area: 97.05 (Max), 97.01 (254 nm).
HPLC—Rt (min): 3.19; % Area: 97.08 (Max), 97.03 (254 nm).
$^1$H NMR 400 MHz, CDCl3: δ 7.75 (s, 1H), 7.65 (d, J=−4.00 Hz, 1H), 7.38 (s, 1H), 7.19 (dd, J=−4.00, −8.00 Hz, 1H), 6.90 (t, J=−8.00 Hz, 2H), 4.25 (t, J=−8.00 Hz, 2H), 3.96 (s, 3H), 3.93 (s, 6H), 3.24 (t, J=−12.00 Hz, 2H).

(2,3-Dihydro-benzofuran-5-yl)-[3-(3,4-dimethoxy-phenyl)-4,5-dihydro-pyrazol-1-yl]-methanone

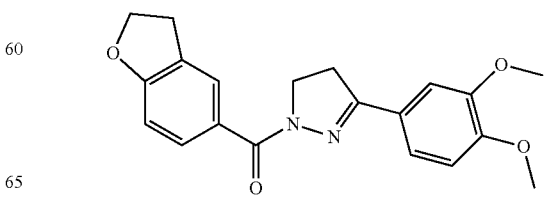

Brown solid; 44.59% Yield

LC-MS: Mass found (M+, 353). Rt (min): 3.85; % Area: 97.90 (Max), 98.57 (254 nm).

HPLC—Rt (min): 3.84; % Area: 97.54 (Max), 98.84 (254 nm).

$^1$H NMR 400 MHz, CDCl3: δ 7.93-7.90 (m, 2H), 7.36 (d, J=2.00 Hz, 1H), 7.18 (dd, J=8.00, 4.00 Hz, 1H), 6.89 (d, J=8.00 Hz, 1H), 6.82 (d, J=8.00 Hz, 1H), 4.65 (t, J=8.00 Hz, 2H), 4.25 (t, J=8.00 Hz, 2H), 3.93 (s, 3H), 3.91 (s, 3H), 3.25 (q, J=8.00 Hz, 4H).

[3-(3,4-Dimethoxy-phenyl)-4,5-dihydro-pyrazol-1-yl]-indan-5-yl-methanone

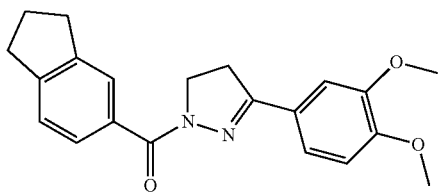 [SMILES: COc1ccc(C2=NN(C(=O)c3ccc4c(c3)CCC4)CC2)cc1OC]

Brown solid; 12.12% Yield

LC-MS: Mass found (M+, 351). Rt (min): 4.54; % Area: 97.17 (Max), 98.23 (254 nm).

HPLC—Rt (min): 4.52; % Area: 98.03 (Max), 98.59 (254 nm).

$^1$H NMR 400 MHz, CDCl3: δ 7.88 (s, 1H), 7.80 (d, J=8.00 Hz, 1H), 7.36 (s, 1H), 7.29 (s, 1H), 7.17 (dd, J=8.00, 4.00 Hz, 1H), 6.88 (d, J=8.00 Hz, 1H), 4.26 (t, J=8.00 Hz, 2H), 3.93 (s, 3H), 3.91 (s, 3H), 3.25 (t, J=8.00 Hz, 2H), 2.96 (t, J=8.00 Hz, 4H), 2.16-2.10 (m, 2H).

5-[3-(3,4-Dimethoxy-phenyl)-4,5-dihydro-pyrazole-1-carbonyl]-2-methyl-isoindole-1,3-dione

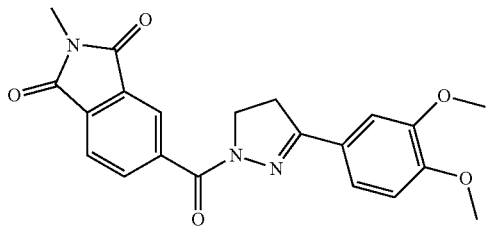 [SMILES: COc1ccc(C2=NN(C(=O)c3ccc4c(c3)C(=O)N(C)C4=O)CC2)cc1OC]

Yellow solid; 4.29% Yield

LC-MS: Mass found (M+, 394). Rt (min): 3.68; % Area: 96.28 (Max), 95.65 (220 nm).

HPLC—Rt (min): 3.68; % Area: 98.12 (Max), 98.84 (254 nm).

$^1$H NMR 400 MHz, CDCl3: δ 8.58 (s, 1H), 8.33 (d, J=8.00 Hz, 1H), 7.92 (d, J=8.00 Hz, 1H), 7.34 (s, 1H), 7.16 (d, J=8.00 Hz, 1H), 6.89 (d, J=12.00 Hz, 1H), 4.29 (t, J=12.00 Hz, 2H), 3.93 (s, 3H), 3.91 (s, 3H), 3.32 (t, J=8.00 Hz, 2H), 3.22 (s, 3H).

6-[3-(3,4-Dimethoxy-phenyl)-4,5-dihydro-pyrazole-1-carbonyl]-1,3-dihydro-indol-2-one

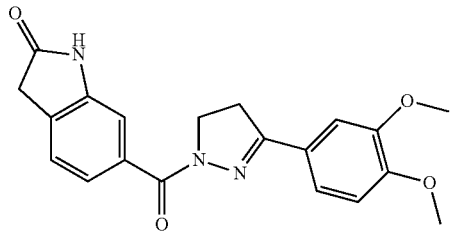 [SMILES: COc1ccc(C2=NN(C(=O)c3ccc4c(c3)NC(=O)C4)CC2)cc1OC]

Brown solid; 6.72% Yield

LC-MS: Mass found (M+, 366). Rt (min): 2.95; % Area: 98.45 (Max), 98.53 (254 nm).

HPLC—Rt (min): 3.00; % Area: 98.86 (Max), 99.05 (254 nm).

$^1$H NMR 400 MHz, CDCl3: δ 7.80-7.60 (m, 1H), 7.52-7.31 (m, 2H), 7.29-7.27 (m, 2H), 7.25-7.00 (m, 1H), 6.89 (d, J=8.00 Hz, 1H), 4.26 (t, J=8.00 Hz, 2H), 3.93 (s, 3H), 3.90 (s, 3H), 3.60 (s, 2H), 3.28 (t, J=8.00 Hz, 2H).

1-{5-[3-(3,4-Dimethoxy-phenyl)-4,5-dihydro-pyrazole-1-carbonyl]-2,3-dihydro-indol-1-yl}-ethanone

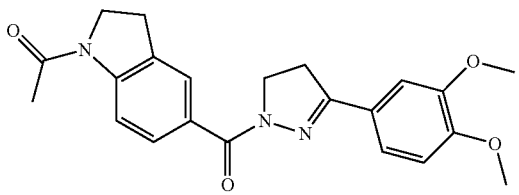 [SMILES: COc1ccc(C2=NN(C(=O)c3ccc4c(c3)CCN4C(C)=O)CC2)cc1OC]

Yellow solid; 13.73% Yield

LC-MS: Mass found (M+, 394). Rt (min): 3.44; % Area: 90.94 (Max), 92.33 (254 nm).

HPLC—Rt (min): 3.37; % Area: 90.93 (Max), 90.20 (254 nm).

$^1$H NMR 400 MHz, CDCl3: δ 8.24 (d, J=8.00 Hz, 1H), 7.98 (d, J=8.00 Hz, 1H), 7.86 (s, 1H), 7.34 (s, 1H), 7.17 (d, J=8.00 Hz, 1H), 6.88 (d, J=8.00 Hz, 1H), 4.25 (t, J=8.00 Hz, 2H), 4.13 (t, J=8.00 Hz, 2H), 3.95 (s, 3H), 3.93 (s, 3H), 3.25 (q, J=8.00 Hz, 4H), 2.27 (s, 3H).

5-[3-(3,4-Dimethoxy-phenyl)-4,5-dihydro-pyrazole-1-carbonyl]-1,3-dihydro-indol-2-one

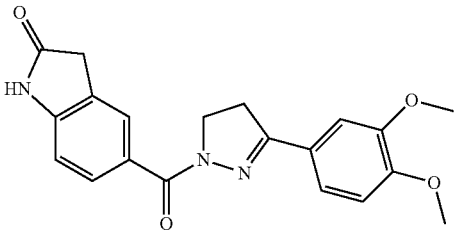 [SMILES: COc1ccc(C2=NN(C(=O)c3ccc4c(c3)CC(=O)N4)CC2)cc1OC]

Yellow solid; 9.14% Yield

LC-MS: Mass found (M+, 366). Rt (min): 2.94; % Area: 90.16 (Max), 90.02 (254 nm).

HPLC—Rt (min): 2.93; % Area: 92.14 (Max), 90.70 (254 nm).

¹H NMR 400 MHz, CDCl3: δ 7.99 (d, J=8.00 Hz, 1H), 7.97 (s, 1H), 7.54 (d, J=4.00 Hz, 1H), 7.32 (d, J=4.00 Hz, 1H), 7.19 (d, J=8.00 Hz, 1H), 6.90 (t, J=8.00 Hz, 2H), 4.26 (t, J=8.00 Hz, 2H), 3.93 (s, 3H), 3.91 (s, 3H), 3.59 (s, 2H), 3.26 (t, J=12.00 Hz, 2H).

5-[3-(3,4-Dimethoxy-phenyl)-4,5-dihydro-pyrazole-1-carbonyl]-3H-benzooxazol-2-one

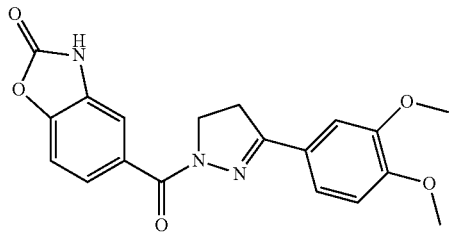 [SMILES: COc1ccc(C2=NN(C(=O)c3ccc4oc(=O)[nH]c4c3)CC2)cc1OC]

Yellow solid; 8.25% Yield

LC-MS: Mass found (M+, 368). Rt (min): 3.25; % Area: 98.89 (Max), 98.63 (254 nm).

HPLC—Rt (min): 3.27; % Area: 98.75 (Max), 98.64 (254 nm).

¹H NMR 400 MHz, CDCl3: δ 7.99 (s, 1H), 7.90 (d, J=8.00 Hz, 1H), 7.75 (s, 1H), 7.29-7.19 (m, 3H), 6.90 (d, J=8.00 Hz, 1H), 4.27 (t, J=12.00 Hz, 2H), 3.94 (s, 3H), 3.90 (s, 3H), 3.29 (t, J=8.00 Hz, 2H).

6-[3-(3,4-Dimethoxy-phenyl)-4,5-dihydro-pyrazole-1-carbonyl]-2,3-dihydro-isoindol-1-one

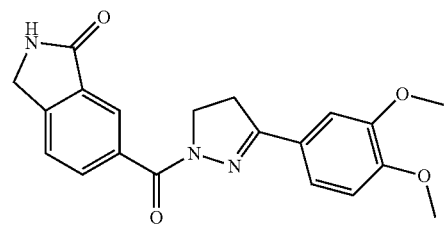 [SMILES: COc1ccc(C2=NN(C(=O)c3ccc4c(c3)C(=O)NC4)CC2)cc1OC]

Yellow solid; 4.85% Yield

LC-MS: Mass found (M+, 366). Rt (min): 2.82; % Area: 93.91 (Max), 94.20 (220 nm).

HPLC—Rt (min): 2.82; % Area: 96.33 (Max), 96.44 (254 nm).

¹H NMR 400 MHz, CDCl3: δ 8.71 (s, 1H), 8.25-8.22 (m, 1H), 7.56 (d, J=8.00 Hz, 1H), 7.42 (d, J=4.00 Hz, 1H), 7.15 (d, J=8.00 Hz, 1H), 6.87 (d, J=8.00 Hz, 1H), 6.18 (s, 1H), 4.53 (s, 2H), 4.30 (t, J=8.00 Hz, 2H), 3.94 (s, 3H), 3.93 (s, 3H), 3.29 (t, J=12.00 Hz, 2H).

Benzofuran-5-yl-[3-(3,4-dimethoxy-phenyl)-4,5-dihydro-pyrazol-1-yl]-methanone

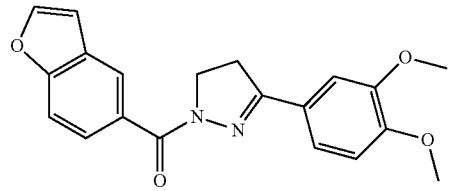 [SMILES: COc1ccc(C2=NN(C(=O)c3ccc4occc4c3)CC2)cc1OC]

Brown solid; 13.89% Yield

LC-MS: Mass found (M+, 351). Rt (min): 4.07; % Area: 97.88 (Max), 98.80 (254 nm).

HPLC—Rt (min): 4.06; % Area: 97.93 (Max), 98.39 (254 nm).

¹H NMR 400 MHz, CDCl3: δ 8.32 (s, 1H), 8.00 (d, J=8.00 Hz, 1H), 7.69 (d, J=4.00 Hz, 1H), 7.54 (d, J=8.00 Hz, 1H), 7.33 (s, 1H), 7.19 (dd, J=8.00, 4.00 Hz, 1H), 6.88 (d, J=8.00 Hz, 1H), 6.85 (dd, J=2.00, 0.80 Hz, 1H), 4.29 (t, J=12.00 Hz, 2H), 3.93 (s, 3H), 3.88 (s, 3H), 3.28 (t, J=12.00 Hz, 2H).

[3-(3,4-Dimethoxy-phenyl)-4,5-dihydro-pyrazol-1-yl]-quinolin-6-yl-methanone

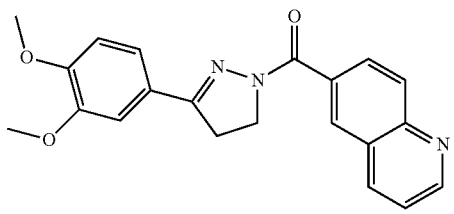 [SMILES: COc1ccc(C2=NN(C(=O)c3ccc4ncccc4c3)CC2)cc1OC]

Yellow solid; 14.32% Yield

LC-MS: Mass found (M+, 362). Rt (min): 2.56; % Area: 98.56 (Max), 99.01 (254 nm).

HPLC—Rt (min): 2.61; % Area: 99.09 (Max), 99.08 (254 nm).

¹H NMR 400 MHz, CDCl3: δ 9.02 (d, J=3.20 Hz, 1H), 8.56 (s, 1H), 8.40-8.36 (m, 2H), 8.30-8.28 (m, 1H), 7.58-7.52 (m, 1H), 7.31 (d, J=4.00 Hz, 1H), 7.20 (dd, J=8.20, 1.60 Hz, 1H), 6.89 (d, J=8.00 Hz, 1H), 4.33 (t, J=8.00 Hz, 2H), 3.95 (s, 3H), 3.86 (s, 3H), 3.33 (t, J=8.00 Hz, 2H).

(2,3-Dihydro-benzo[1,4]dioxin-6-yl)-[3-(3,4-dimethoxy-phenyl)-4,5-dihydro-pyrazol-1-yl]-methanone

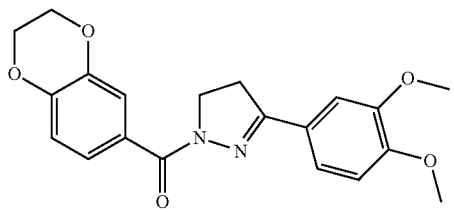 [SMILES: COc1ccc(C2=NN(C(=O)c3ccc4c(c3)OCCO4)CC2)cc1OC]

Yellow solid; 25.87% Yield

LC-MS: Mass found (M+, 369). Rt (min): 3.79; % Area: 98.91 (Max), 99.13 (254 nm).

HPLC—Rt (min): 3.86; % Area: 99.02 (Max), 99.47 (254 nm).

$^1$H NMR 400 MHz, CDCl3: δ 7.69 (s, 1H), 7.62 (d, J=8.00 Hz, 1H), 7.37 (s, 1H), 7.19 (dd, J=10.80, 1.60 Hz, 1H), 6.90 (dd, J=8.00, 4.00 Hz, 2H), 4.33-4.28 (m, 4H), 4.24 (t, J=8.00 Hz, 2H), 3.93 (s, 3H), 3.92 (s, 3H), 3.23 (t, J=12.00 Hz, 2H).

Example 8: Synthetic Route Towards (3-Benzylamino-4,5-dihydro-pyrazol-1-yl)-(3-fluoro-phenyl)-methanones, [3-(Benzyl-methyl-amino)-4,5-dihydro-pyrazol-1-yl]-(3-fluoro-phenyl)-methanones and (3-Benzyloxy-4,5-dihydro-pyrazol-1-yl)-(3-fluoro-phenyl)-methanones Scheme 8

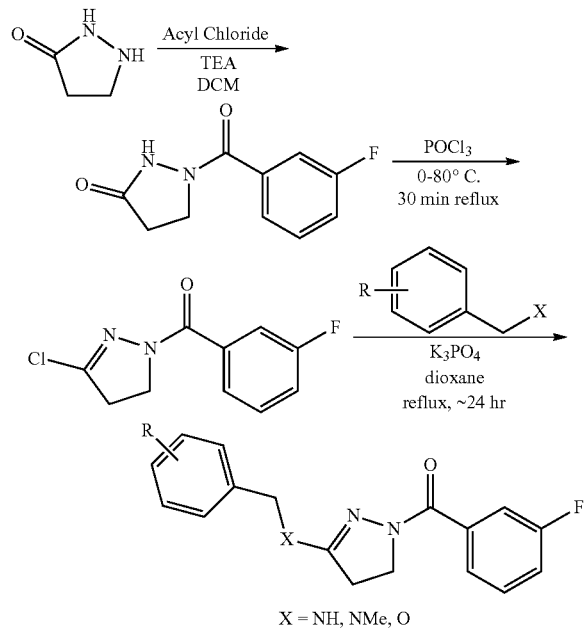

X = NH, NMe, O

It shall be understood that the phenyl moiety (radical L) can be substituted in accordance with the Ar$^1$ definition as demonstrated below.

Step 1: Preparation of pyrazolidin-3-one

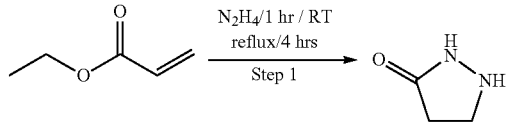

To a solution of hydrazine hydrate (6.67 ml, 0.14 mmol, 1 equiv.) in 75 ml of absolute ethanol was added drop-wise, ethyl acrylate (13.53 ml, 0.125 mmol, 1.12 equiv.) in 50 ml of absolute ethanol. The resulting solution was stirred for 1 h at ambient temperature and then at reflux for 4 h. The reaction mixture was concentrated in vacuum to get viscous oil. The crude product obtained was purified by silica gel column using (60-120) mesh to afford the titled product as pale yellow oil (7 gm, 50% yield).

Yellow oily liquid; 46.13% Yield

400 MHz, CDCl3: δ 7.06 (s, 1H), 5.50 (s, 1H), 3.52 (t, J=8.00 Hz, 2H), 2.50 (t, J=8.00 Hz, 2H).

Step 2: Preparation of 1-(3-fluorobenzoyl)pyrazolidin-3-one

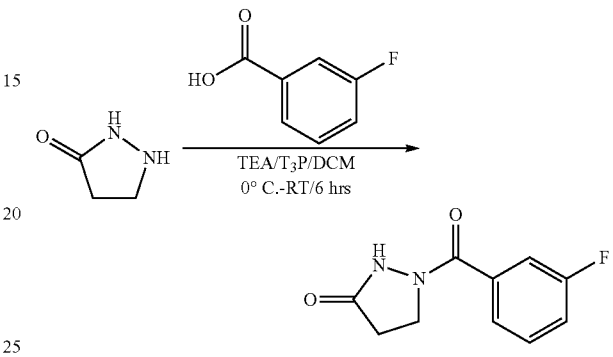

To a solution of pyrazolidin-3-one (6.9 gm, 0.080 mmol, 1 equiv.) in dry dichloromethane (70 ml), 3-fluorobenzoic acid (12.3 gm, 0.088 mmol, 1.1 equiv.), triethylamine (24.3 gm, 0.240 mmol, 3 equiv.) and 1-propane phosphonic acid cyclic anhydride (60% by weight in ethyl acetate) (51 gm, 0.16 mmol, 2 equiv.) were added in cooling condition and stirred for overnight at room temperature. The reaction mixture was concentrated and the residue was poured in water (500 ml), extracted with dichloromethane (100 ml×2) and concentrated. The crude product was purified by silica gel column using (60-120) mesh to get the pure product as yellow oil (5.4 gm, 32% yield).

Yellow oil; 32% Yield

LC-MS: Mass found (M+, 209)

Method: A—0.1% HCOOH, B—MeOH—1 ml/min. Atlantis dC18 (50×4.6 mm, 5 μm). Rt (min): 1.64; % Area: 98.34.

400 MHz, CDCl3: δ 9.20 (s, 1H), 7.47-7.38 (m, 2H), 7.34-7.31 (m, 1H), 7.27-7.21 (m, 1H), 4.17 (t, J=8.00 Hz, 2H), 2.81 (t, J=4.00 Hz, 2H).

Step 3: Synthesis of 3-chloro-1-(3-fluorobenzoyl)-4,5-dihydro-1H-pyrazole

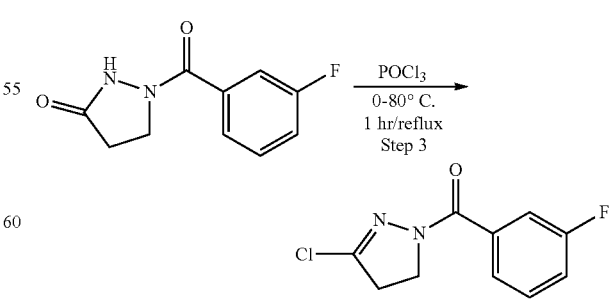

Phosphorus oxychloride (54 ml for 5.4 gm of SM, 10 volume) was added drop wise directly to 1-(3-fluorobenzoyl) pyrazolidin-3-one (5.4 gm, 0.0238 mmol, 1 equiv.) at 0° C. and then refluxed at 85° C. for an hour. The reaction mixture was cooled to RT, concentrated and basified with solid NaCO₃ (pH: 8-9), extracted with dichloromethane (100 ml×2) and concentrated. The crude product was purified by silica gel column using (60-120) mesh to get the pure product as off green solid (4.8, 88.9% yield).

Off green solid; 88.9% Yield

LC-MS: Mass found (M+, 227)

Method: A—0.1% TFA in water, B—0.1% TFA in ACN: Flow—0.6 ml/min. Column: Xbridge C8 (50×4.6 mm, 3.5 µm). Rt (min): 3.57; % Area: 97.92 (Max), 97.52 (254 nm).

400 MHz, CDCl3: δ 7.65 (d, J=1.60 Hz, 1H), 7.59-7.55 (m, 1H), 7.42-7.37 (m, 1H), 7.21-7.16 (m, 1H), 4.26 (t, J=4.00 Hz, 2H), 3.19 (t, J=4.00 Hz, 2H).

Compounds of the invention can be subsequently prepared according to the general method:

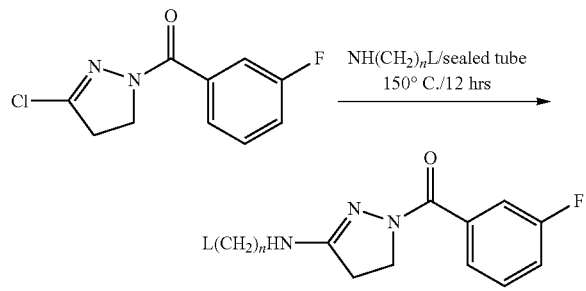

SC02 (1 eq) and amine (3 eq) were taken in a 8 ml vial and heated at 150° C. for 12 hours. The reaction mixture was taken in saturated bicarbonate (5 ml) and extracted with dichloromethane (5 ml×2) and concentrated in Genevac overnight. The crude product was purified by column chromatography (230-400 mesh) to get the pure target product.

The following compounds were prepared in a similar manner. LC-MS and HPLC analysis were performed as follows: Method: A—0.1% TFA in water, B—0.1% TFA in ACN: Flow—2 ml/min; Column: XBridge c8 (50×4.6 mm, 3.5 µm); unless stated otherwise.

(3-Benzylamino-4,5-dihydro-pyrazol-1-yl)-(3-fluoro-phenyl)-methanone

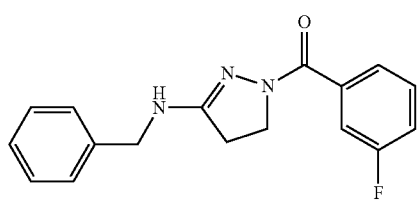 [SMILES: O=C(c1cccc(F)c1)N1CCC(NCc2ccccc2)=N1]

Yellow solid; 11.51% Yield

LC-MS: Mass found (M+, 298.3). Rt (min): 3.91; % Area: 92.20 (Max), 92.90 (254 nm).

HPLC—Flow—1.0 ml/min. Rt (min): 3.96; % Area: 93.79 (Max), 92.74 (254 nm).

400 MHz, CDCl3: δ 7.71-7.69 (m, 2H), 7.39-7.27 (m, 6H), 7.25-7.09 (m, 1H), 4.38 (s, 2H), 4.15 (t, J=8.00 Hz, 2H), 2.89 (t, J=12.00 Hz, 2H).

[3-(4-Fluoro-benzylamino)-4,5-dihydro-pyrazol-1-yl]-(3-fluoro-phenyl)-methanone

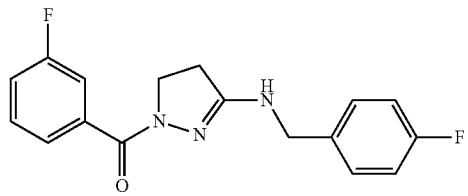 [SMILES: O=C(c1cccc(F)c1)N1CCC(NCc2ccc(F)cc2)=N1]

Brown solid; 40.36% Yield

LC-MS: Mass found (M+, 316). Rt (min): 3.99; % Area: 97.94 (Max), 97.97 (254 nm).

HPLC—Flow—1.0 ml/min. Rt (min): 4.03; % Area: 96.51 (Max), 97.27 (254 nm).

400 MHz, CDCl3: δ 7.71-7.69 (m, 2H), 7.35-7.26 (m, 3H), 7.15-7.11 (m, 1H), 7.05 (t, J=4.00 Hz, 2H), 4.35 (s, 1H), 4.34 (s, 2H), 4.16 (t, J=4.00 Hz, 2H), 2.89 (t, J=12.00 Hz, 2H).

[3-(2,4-Difluoro-benzylamino)-4,5-dihydro-pyrazol-1-yl]-(3-fluoro-phenyl)-methanone

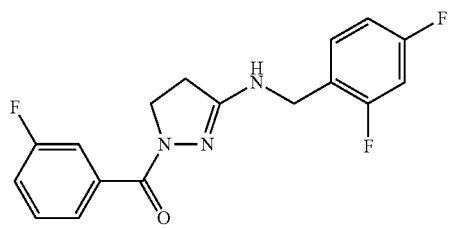 [SMILES: O=C(c1cccc(F)c1)N1CCC(NCc2ccc(F)cc2F)=N1]

Orange solid; 59.43% Yield

LC-MS: Mass found (M+, 334). Rt (min): 4.14; % Area: 96.06 (Max), 97.06 (254 nm).

HPLC—Flow—1.0 ml/min. Rt (min): 4.14; % Area: 98.13 (Max), 98.46 (254 nm).

400 MHz, DMSO-d6: δ 7.61 (d, J=8.00 Hz, 1H), 7.56-7.53 (m, 1H), 7.43-7.32 (m, 3H), 7.28-7.17 (m, 2H), 7.05-7.01 (m, 1H), 4.22 (d, J=8.00 Hz, 2H), 3.90 (t, J=8.00 Hz, 2H), 2.84 (t, J=12.00 Hz, 2H).

[3-(3,4-Difluoro-benzylamino)-4,5-dihydro-pyrazol-1-yl]-(3-fluoro-phenyl)-methanone

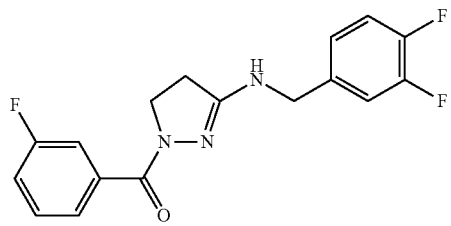 [SMILES: O=C(c1cccc(F)c1)N1CCC(NCc2ccc(F)c(F)c2)=N1]

Yellow solid; 53.07% Yield

LC-MS: Mass found (M+, 334). Rt (min): 4.11; % Area: 90.56 (Max), 91.60 (254 nm).

HPLC—Flow—1.0 ml/min. Rt (min): 4.18; % Area: 93.32 (Max), 92.10 (254 nm).

400 MHz, CDCl3: δ 7.67-7.61 (m, 2H), 7.33 (dd, J=16.00, 8.00 Hz, 1H), 7.17-7.10 (m, 3H), 7.04 (s, 1H), 4.47 (s, 1H), 4.31 (d, J=8.00 Hz, 2H), 4.15 (t, J=8.00 Hz, 2H), 2.89 (t, J=8.00 Hz, 2H).

{3-[(4-Fluoro-benzyl)-methyl-amino]-4,5-dihydro-pyrazol-1-yl}-(3-fluoro-phenyl)-methanone

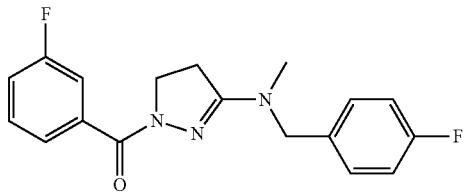 [SMILES: CN(Cc1ccc(F)cc1)C1=NN(C(=O)c2cccc(F)c2)CC1]

Yellow gum; 16.14% Yield

LC-MS: Mass found (M+, 330.3). Rt (min): 4.36; % Area: 91.22 (Max), 95.34 (254 nm).

HPLC—Flow—1.0 ml/min. Rt (min): 4.38; % Area: 93.82 (Max), 95.05 (254 nm).

400 MHz, CDCl3: δ 7.79-7.74 (m, 2H), 7.35-7.30 (m, 1H), 7.21-7.17 (m, 2H), 7.12-7.01 (m, 3H), 4.37 (s, 2H), 4.19 (t, J=8.00 Hz, 2H), 2.96 (t, J=12.00 Hz, 2H), 2.91 (s, 3H).

(3-Fluoro-phenyl)-{3-[(3-methoxy-benzyl)-methyl-amino]-4,5-dihydro-pyrazol-1-yl}-methanone

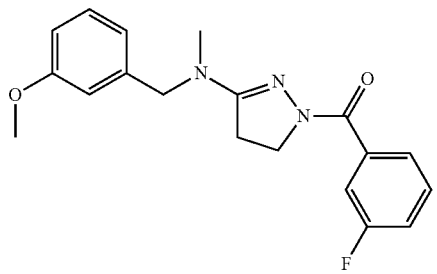 [SMILES: COc1cccc(CN(C)C2=NN(C(=O)c3cccc(F)c3)CC2)c1]

Yellow gum; 8.46% Yield

LC-MS: Mass found (M+, 342.3). Rt (min): 4.26; % Area: 95.68 (Max), 96.68 (254 nm).

HPLC—Flow—1.0 ml/min. Rt (min): 4.27; % Area: 93.14 (Max), 95.01 (254 nm).

400 MHz, CDCl3: δ 7.81 (t, J=8.00 Hz, 2H), 7.36-7.26 (m, 2H), 7.12-7.07 (m, 1H), 6.85-6.76 (m, 3H), 4.40 (s, 2H), 4.21 (t, J=8.00 Hz, 2H), 3.78 (s, 3H), 2.98 (t, J=8.00 Hz, 2H), 2.94 (s, 3H).

{3-[(3-Fluoro-benzyl)-methyl-amino]-4,5-dihydro-pyrazol-1-yl}-(3-fluoro-phenyl)-methanone

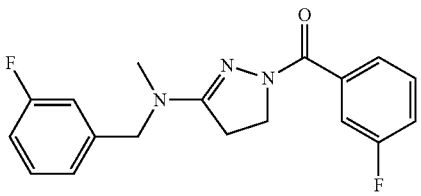 [SMILES: CN(Cc1cccc(F)c1)C1=NN(C(=O)c2cccc(F)c2)CC1]

Yellow gum; 11.97% Yield

LC-MS: Mass found (M+, 330.3). Rt (min): 4.34; % Area: 91.12 (Max), 94.21 (254 nm).

HPLC—Flow—1.0 ml/min. Rt (min): 4.37; % Area: 91.70 (Max), 94.99 (254 nm).

400 MHz, CDCl3: δ 7.79-7.74 (m, 2H), 7.35-7.27 (m, 2H), 7.13-7.08 (m, 1H), 7.01-6.92 (m, 3H), 4.42 (s, 2H), 4.21 (t, J=8.00 Hz, 2H), 3.02 (t, J=8.00 Hz, 2H), 2.96 (s, 3H).

Example 9: General Method for the Preparation of the Following Compounds

Scheme 9

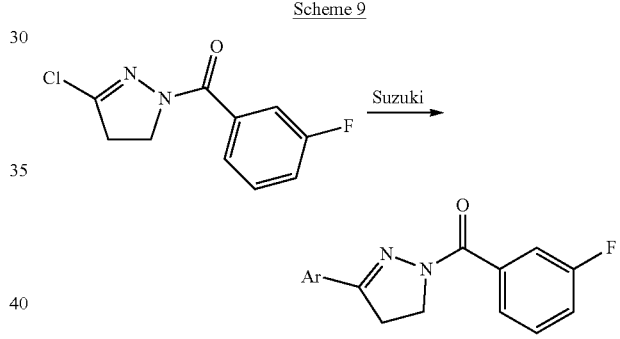

It shall be understood that Ar includes Ar¹ and Ar².

Taking the example of 4-methoxyphenylboronic acid, the Suzuki reaction is performed as follows:

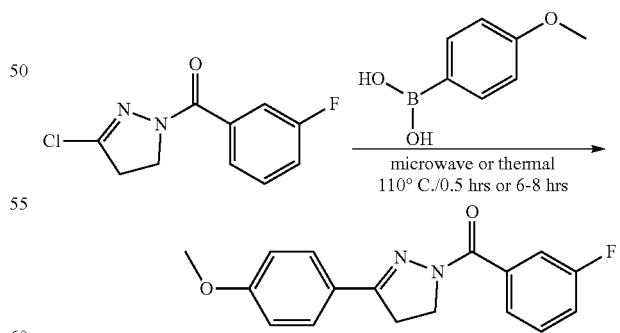

To a degassed solution of (3-Chloro-4,5-dihydro-pyrazol-1-yl)-(3-fluoro-phenyl)-methanone (0.19 g, 0.0008 moles, 1 equiv) in dry 1,2-DME-water, 5 mL, (4:1) was added 4-Methoxyphenylboronic acid (0.17 g, 0.0112 moles, 1.4 equiv), anhydrous sodium carbonate (0.17 g, 0.0016 moles, 2 equiv) and Tetrakis-(triphenylphosphine)-palladium(0)

(0.092 g, 0.00008 moles, 0.1 equiv). The reaction mixture was heated at 110° C. for 0.5 h under nitrogen atmosphere in microwave conditions or 6-8 h in thermal conditions. Consumption of starting material was confirmed by TLC and LC-MS. 1,2-DME was distilled under reduced pressure, the crude residue was dissolved in dichloromethane (25 mL), washed with water, saturated brine, dried over anhydrous sodium sulfate. The crude product was purified by column chromatography to get the pure compound (3-Fluorophenyl)-[3-(4-methoxyphenyl)-4,5-dihydropyrazol-1-yl]-methanone in 0.100 g. P.S.: (a) In case of Carboxy boronic acid, LiCl (3 eq) was added to the reaction mixture as an additive. (b) In Case of Cyano boronic acid, $K_3PO_4$ (2 eq) was used as base.

The following compounds were prepared in a similar manner. LC-MS and HPLC analysis were performed as follows: Method: A—0.1% TFA in water, B—0.1% TFA in ACN: Flow—2 ml/min; Column: XBridge c8 (50×4.6 mm, 3.5 μm); unless stated otherwise.

(3-Fluoro-phenyl)-(3-phenyl-4, 5-dihydro-pyrazol-1-yl)-methanone

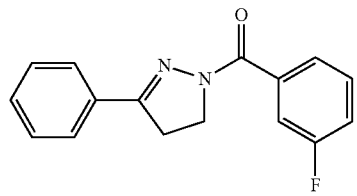 [SMILES: O=C(c1cccc(F)c1)N1CCC(c2ccccc2)=N1]

Off white solid; 46.81% Yield

LC-MS: Mass found (M+, 269.0). Rt (min): 4.47; % Area: 99.47 (Max), 99.55 (220 nm).

HPLC—Rt (min): 4.55; % Area: 98.88 (Max), 99.70 (254 nm).

400 MHz, CDCl3: δ 7.76-7.70 (m, 4H), 7.45-7.40 (m, 4H), 7.23-7.18 (m, 1H), 4.28 (t, J=8.00 Hz, 2H), 3.30 (t, J=12.00 Hz, 2H).

(3-Fluoro-phenyl)-(3-p-tolyl-4,5-dihydro-pyrazol-1-yl)-methanone

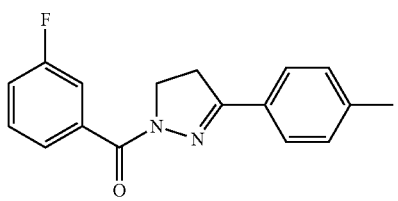 [SMILES: Cc1ccc(C2=NN(C(=O)c3cccc(F)c3)CC2)cc1]

Off white solid; 30.31% Yield

LC-MS: Mass found (M+, 283.0). Rt (min): 4.80; % Area: 97.87 (Max), 97.31 (254 nm).

HPLC—Rt (min): 4.87; % Area: 99.21 (Max), 99.0 (254 nm).

400 MHz, CDCl3: δ 7.82-7.80 (m, 1H), 7.77-7.75 (m, 1H), 7.61-7.59 (m, 2H), 7.45-7.40 (m, 1H), 7.24-7.18 (m, 3H), 4.26 (t, J=9.76 Hz, 2H), 3.28 (t, J=10.12 Hz, 2H), 2.40 (s, 3H).

(3-Biphenyl-4-yl-4,5-dihydro-pyrazol-1-yl)-(3-fluoro-phenyl)-methanone

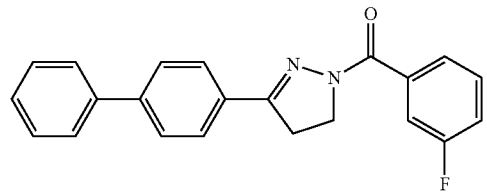 [SMILES: O=C(c1cccc(F)c1)N1CCC(c2ccc(-c3ccccc3)cc2)=N1]

Yellow solid; 52.83% Yield

LC-MS: Mass found (M+, 345.3). Rt (min): 5.35; % Area: 98.25 (Max), 94.69 (254 nm).

HPLC—Rt (min): 5.43; % Area: 98.34 (Max), 95.50 (254 nm).

400 MHz, CDCl3: δ 7.82-7.76 (m, 4H), 7.68-7.62 (m, 4H), 7.50-7.40 (m, 4H), 7.38-7.21 (m, 1H), 4.30 (t, J=9.60 Hz, 2H), 3.37-3.32 (m, 2H).

(3-Fluoro-phenyl)-[3-(4-phenoxy-phenyl)-4,5-dihydro-pyrazol-1-yl]-methanone

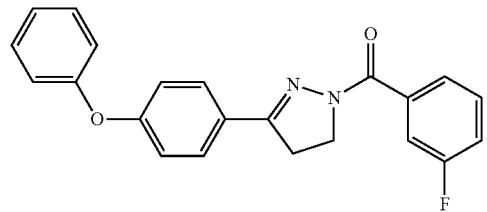 [SMILES: O=C(c1cccc(F)c1)N1CCC(c2ccc(Oc3ccccc3)cc2)=N1]

White solid; 69.10% Yield

LC-MS: Mass found (M+, 361). Flow—0.6 ml/min. Rt (min): 5.40; % Area: 95.59 (Max), 94.88 (220 nm).

HPLC—Rt (min): 3.45; % Area: 97.77 (Max), 97.44 (220 nm).

400 MHz, CDCl3: δ 7.80 (d, J=8.00 Hz, 1H), 7.75-7.73 (m, 1H), 7.69-7.66 (m, 2H), 7.44-7.37 (m, 3H), 7.22-7.16 (m, 2H), 7.07-7.00 (m, 4H), 4.27 (t, J=8.00 Hz, 2H), 3.28 (t, J=12.00 Hz, 2H).

4-[1-(3-Fluoro-benzoyl)-4,5-dihydro-1H-pyrazol-3-yl]-benzoic acid

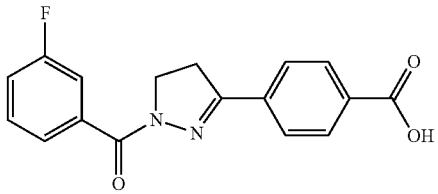 [SMILES: O=C(O)c1ccc(C2=NN(C(=O)c3cccc(F)c3)CC2)cc1]

Off white solid; 100% Yield

LC-MS: Mass found (M+, 313). Flow—0.6 ml/min. Rt (min): 3.65; % Area: 98.41 (Max), 97.27 (220 nm).

HPLC—Rt (min): 3.60; % Area: 97.42 (Max), 94.73 (254 nm).

400 MHz, DMSO-d6: δ 13.00 (brs, 1H), (8.00 (d, J=8.00 Hz, 2H), 7.79 (d, J=12.00 Hz, 2H), 7.70 (d, J=8.00 Hz, 1H), 7.64-7.60 (m, 1H), 7.57-7.52 (m, 1H), 7.42-7.37 (m, 1H), 4.14 (t, J=12.00 Hz, 2H), 3.36-3.34 (m, 2H).

(3-Fluoro-phenyl)-[3-(4-trifluoromethyl-phenyl)-4,5-dihydro-pyrazol-1-yl]-methanone

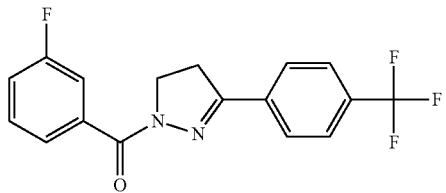

Off white solid; 38.73% Yield
LC-MS: Mass found (M+, 337.0). Flow—0.6 ml/min. Rt (min): 5.22; % Area: 98.50 (Max), 97.31 (254 nm).
HPLC—Rt (min): 5.28; % Area: 98.50 (Max), 99.20 (254 nm).
400 MHz, CDCl3: δ 7.80-7.73 (m, 3H), 7.71-7.67 (m, 3H), 7.47-7.42 (m, 1H), 7.25-7.20 (m, 1H), 4.32 (t, J=9.76 Hz, 2H), 3.32 (t, J=10.36 Hz, 2H).

(3-Fluoro-phenyl)-[3-(4-vinyl-phenyl)-4,5-dihydro-pyrazol-1-yl]-methanone

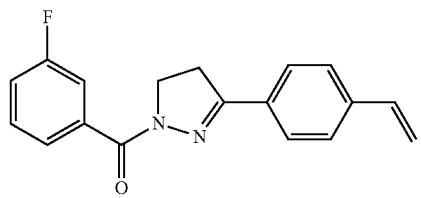 [SMILES: C=Cc1ccc(C2=NN(C(=O)c3cccc(F)c3)CC2)cc1]

Off white solid; 2.06% Yield
LC-MS: Mass found (M+, 295.0). Rt (min): 4.90; % Area: 97.52 (Max), 95.52 (220 nm).
HPLC—Rt (min): 5.02; % Area: 96.52 (Max), 96.25 (220 nm).
400 MHz, CDCl3: δ 7.80-7.77 (m, 1H), 7.74-7.68 (m, 1H), 7.66-7.47 (m, 2H), 7.46-7.41 (m, 3H), 7.24-7.19 (m, 1H), 6.78-6.71 (m, 1H), 5.84 (d, J=16.96 Hz, 1H), 5.35 (d, J=11.28 Hz, 1H), 4.28 (t, J=9.72 Hz, 2H), 3.30 (t, J=10.36 Hz, 2H).

(3-Fluoro-phenyl)-[3-(4-hydroxymethyl-phenyl)-4,5-dihydro-pyrazol-1-yl]-methanone

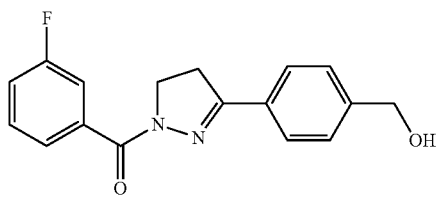 [SMILES: O=C(c1cccc(F)c1)N1CCC(c2ccc(CO)cc2)=N1]

White Solid; 58.71% Yield
LC-MS: Mass found (M+, 299.0). Rt (min): 3.36; % Area: 98.53 (Max), 96.80 (220 nm).
HPLC—Rt (min): 3.45; % Area: 99.82 (Max), 99.46 (254 nm).
400 MHz, CDCl3: δ 7.82-7.76 (m, 1H), 7.74-7.33 (m, 1H), 7.70-7.68 (m, 2H), 7.46-7.40 (m, 3H), 7.23-7.18 (m, 1H), 4.75 (s, 2H), 4.24 (t, J=9.64 Hz, 2H), 3.30-3.25 (m, 2H).

[3-(4-Ethyl-phenyl)-4,5-dihydro-pyrazol-1-yl]-(3-fluoro-phenyl)-methanone

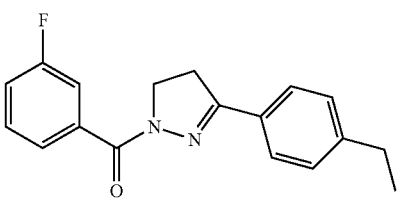 [SMILES: CCc1ccc(C2=NN(C(=O)c3cccc(F)c3)CC2)cc1]

Green solid; 31.13% Yield
LC-MS: Mass found (M+, 297.2). Rt (min): 5.13; % Area: 99.3 (Max), 99.21 (254 nm).
HPLC—Rt (min): 5.21; % Area: 99.42 (Max), 98.15 (254 nm).
400 MHz, CDCl3: δ 7.82-7.80 (m, 1H), 7.77-7.74 (m, 1H), 7.64-7.62 (m, 2H), 7.45-7.39 (m, 1H), 7.24-7.22 (m, 2H), 7.21-7.17 (m, 1H), 4.26 (t, J=8.00 Hz, 2H), 3.31-3.26 (m, 2H), 2.72-2.66 (m, 2H), 1.26 (t, J=4.00 Hz, 3H).

[3-(4-tert-Butyl-phenyl)-4,5-dihydro-pyrazol-1-yl]-(3-fluoro-phenyl)-methanone

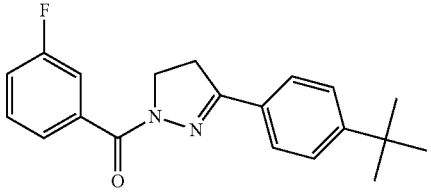 [SMILES: CC(C)(C)c1ccc(C2=NN(C(=O)c3cccc(F)c3)CC2)cc1]

White solid; 68.24% Yield
LC-MS: Mass found (M+, 325.3). Flow—0.6 ml/min. Rt (min): 5.64; % Area: 91.91 (Max), 90.29 (220 nm).
HPLC—Rt (min): 5.67; % Area: 99.16 (Max), 99.52 (254 nm).
400 MHz, CDCl3: δ 7.82 (d, J=8.00 Hz, 1H), 7.77 (d, J=12.00 Hz, 1H), 7.66 (d, J=12.00 Hz, 2H), 7.46-7.40 (m, 3H), 7.23-7.18 (m, 1H), 4.27 (t, J=8.00 Hz, 2H), 3.29 (t, J=12.00 Hz, 2H), 1.35 (s, 9H).

(3-Fluoro-phenyl)-[3-(4-isopropyl-phenyl)-4,5-dihydro-pyrazol-1-yl]-methanone

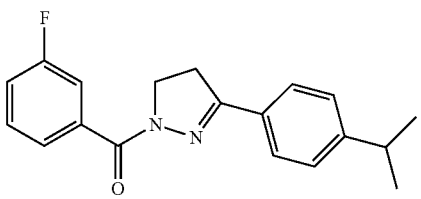 [SMILES: CC(C)c1ccc(C2=NN(C(=O)c3cccc(F)c3)CC2)cc1]

White solid; 32.35% Yield

LC-MS: Mass found (M+, 311.3). Rt (min): 5.39; % Area: 98.99 (Max), 99.09 (254 nm).

HPLC—Rt (min): 5.49; % Area: 99.35 (Max), 98.07 (254 nm).

400 MHz, CDCl3: δ 7.82-7.80 (m, 1H), 7.77-7.74 (m, 1H), 7.65-7.63 (m, 2H), 7.44-7.39 (m, 1H), 7.28-7.27 (m, 2H), 7.22-7.17 (m, 1H), 4.26 (t, J=9.60 Hz, 2H), 3.30 (t, J=3.60 Hz, 2H), 2.98-2.91 (m, 1H), 1.28 (s, 3H), 1.27 (d, J=8 Hz, 3H).

(3-Fluoro-phenyl)-[3-(4-hydroxy-phenyl)-4,5-di-hydro-pyrazol-1-yl]-methanone

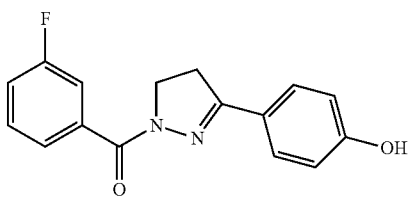 [SMILES: O=C(c1cccc(F)c1)N1CCC(c2ccc(O)cc2)=N1]

White solid; 76.73% Yield

LC-MS: Mass found (M+, 285.2). Flow—0.6 ml/min. Rt (min): 4.26; % Area: 92.32 (Max), 98.21 (254 nm).

HPLC—Rt (min): 4.29; % Area: 95.02 (Max), 97.61 (254 nm).

400 MHz, CDCl3: δ 7.57 (d, J=8.00 Hz, 1H), 7.50-7.47 (m, 1H), 7.41-7.37 (m, 2H), 7.36-7.29 (m, 3H), 7.25-7.22 (m, 1H), 7.17-7.13 (m, 1H), 4.25 (t, J=8.00 Hz, 2H), 3.21 (t, J=8.00 Hz, 2H).

(3-Fluoro-phenyl)-[3-(4-trifluoromethoxy-phenyl)-4,5-dihydro-pyrazol-1-yl]-methanone

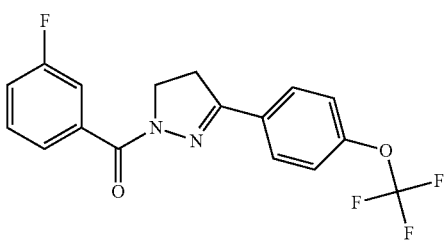 [SMILES: O=C(c1cccc(F)c1)N1CCC(c2ccc(OC(F)(F)F)cc2)=N1]

White solid; 48.11% Yield

LC-MS: Mass found (M+, 353.0). Rt (min): 5.28; % Area: 98.08 (Max), 98.31 (254 nm).

HPLC—Rt (min): 5.34; % Area: 98.97 (Max), 98.90 (254 nm).

400 MHz, CDCl3: δ 7.75-7.71 (m, 4H), 7.46-7.44 (m, 1H), 7.43-7.41 (m, 1H), 7.24-7.19 (m, 2H), 4.32-4.27 (m, 2H), 3.32-3.27 (m, 2H).

1-{4-[1-(3-Fluoro-benzoyl)-4,5-dihydro-1H-pyrazol-3-yl]-phenyl}-ethanone

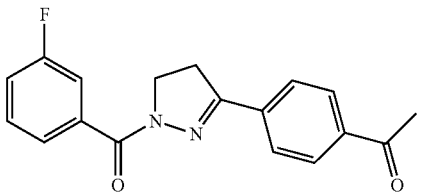 [SMILES: CC(=O)c1ccc(C2=NN(C(=O)c3cccc(F)c3)CC2)cc1]

Off white solid; 53.87% Yield

LC-MS: Mass found (M+, 311.3). Flow—0.6 ml/min. Rt (min): 4.10; % Area: 98.68 (Max), 97.93 (254 nm).

HPLC—Rt (min): 4.13; % Area: 99.20 (Max), 98.38 (254 nm).

400 MHz, CDCl3: δ 8.01 (d, J=8.00 Hz, 2H), 7.81-7.72 (m, 4H), 7.47-7.42 (m, 1H), 7.23-7.21 (m, 1H), 4.32 (t, J=8.00 Hz, 2H), 3.33 (t, J=12.00 Hz, 2H), 2.64 (s, 3H).

[3-(4-Dimethylaminomethyl-phenyl)-4,5-dihydro-pyrazol-1-yl]-(3-fluoro-phenyl)-methanone

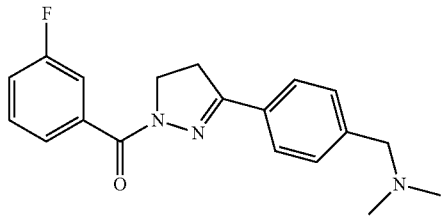 [SMILES: CN(C)Cc1ccc(C2=NN(C(=O)c3cccc(F)c3)CC2)cc1]

White solid; 77.26% Yield

LC-MS: Mass found (M+, 326.3). Flow—0.6 ml/min. Rt (min): 2.75; % Area: 97.95 (Max), 97.13 (254 nm).

HPLC—Rt (min): 2.71; % Area: 98.51 (Max), 97.78 (254 nm).

400 MHz, CDCl3: δ 7.81 (d, J=8.00 Hz, 1H), 7.76-7.74 (m, 1H), 7.67 (d, J=8.00 Hz, 2H), 7.45-7.40 (m, 1H), 7.37 (d, J=8.00 Hz, 2H), 7.23-7.18 (m, 1H), 4.27 (t, J=12.00 Hz, 2H), 3.47 (s, 2H), 3.30 (t, J=8.00 Hz, 2H), 2.26 (s, 6H).

(3-Fluoro-phenyl)-[3-(4-methanesulfonyl-phenyl)-4,5-dihydro-pyrazol-1-yl]-methanone

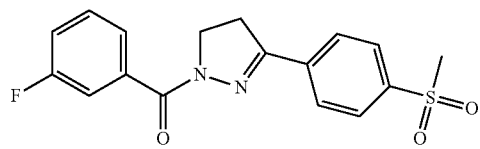 [SMILES: CS(=O)(=O)c1ccc(C2=NN(C(=O)c3cccc(F)c3)CC2)cc1]

Off white solid; 1.93% Yield

LC-MS: Mass found (M+, 347.0). Rt (min): 3.60; % Area: 97.31 (Max), 96.0 (220 nm).

HPLC—Rt (min): 3.73; % Area: 98.07 (Max), 96.61 (254 nm).

400 MHz, CDCl3: δ 8.01-7.99 (m, 2H), 7.89-7.87 (m, 2H), 7.78-7.76 (m, 1H), 7.72-7.69 (m, 1H), 7.48-7.42 (m, 1H), 7.28-7.23 (m, 1H), 4.34 (t, J=9.80 Hz, 2H), 3.36-3.31 (m, 2H), 3.08 (s, 3H).

4-[1-(3-Fluoro-benzoyl)-4,5-dihydro-1H-pyrazol-3-yl]-N,N-dimethyl-benzamide

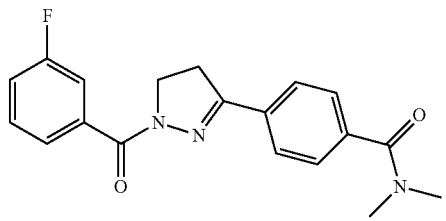 [SMILES: CN(C)C(=O)c1ccc(C2=NN(C(=O)c3cccc(F)c3)CC2)cc1]

White Solid; 92.16% Yield

LC-MS: Mass found (M+, 340.0). Rt (min): 3.44; % Area: 97.35 (Max), 98.22 (254 nm).

HPLC—Rt (min): 3.56; % Area: 97.53 (Max), 97.70 (254 nm).

400 MHz, CDCl3: δ 7.75-7.73 (m, 1H), 7.73-7.72 (m, 3H), 7.50-7.47 (m, 2H), 7.46-7.41 (m, 1H), 7.24-7.19 (m, 1H), 4.32-4.27 (m, 2H), 3.34-3.29 (m, 2H), 3.06 (brs, 6H).

[3-(4-tert-Butoxy-phenyl)-4,5-dihydro-pyrazol-1-yl]-(3-fluoro-phenyl)-methanone

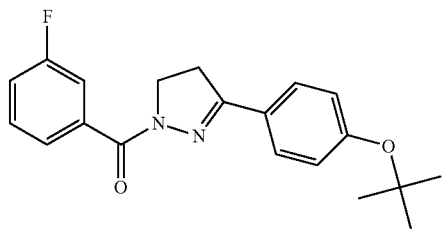 [SMILES: CC(C)(C)Oc1ccc(C2=NN(C(=O)c3cccc(F)c3)CC2)cc1]

Off white Solid; 71.83% Yield

LC-MS: Mass found (M+, 341.0). Rt (min): 5.21; % Area: 95.26 (Max), 95.0 (254 nm).

HPLC—Rt (min): 5.31; % Area: 95.36 (Max), 95.12 (254 nm).

400 MHz, CDCl3: δ 7.80 (d, J=8.00 Hz, 1H), 7.76-7.73 (m, 1H), 7.64-7.61 (m, 2H), 7.44-7.39 (m, 1H), 7.22-7.17 (m, 1H), 7.05-7.01 (m, 2H), 4.25 (t, J=12.00 Hz, 2H), 3.27 (t, J=12.00 Hz, 2H), 1.39 (s, 9H).

4-[1-(3-Fluoro-benzoyl)-4,5-dihydro-1H-pyrazol-3-yl]-N,N-dimethyl-benzenesulfonamide

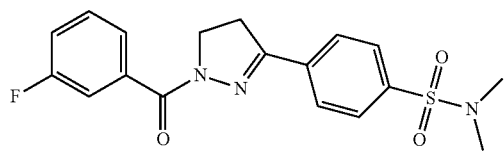 [SMILES: CN(C)S(=O)(=O)c1ccc(C2=NN(C(=O)c3cccc(F)c3)CC2)cc1]

White solid; 1.93% Yield

LC-MS: Mass found (M+, 376.0). Rt (min): 4.21; % Area: 99.06 (Max), 98.96 (220 nm).

HPLC—Rt (min): 4.32; % Area: 99.11 (Max), 98.07 (254 nm).

400 MHz, CDCl3: δ 7.87-7.84 (m, 4H), 7.83-7.77 (m, 1H), 7.73-7.72 (m, 1H), 7.48-7.42 (m, 1H), 7.28-7.23 (m, 1H), 4.33 (t, J=9.76 Hz, 2H), 3.33 (t, J=10.56 Hz, 2H), 2.74 (s, 6H).

3-[1-(3-Fluoro-benzoyl)-4,5-dihydro-1H-pyrazol-3-yl]-benzoic acid

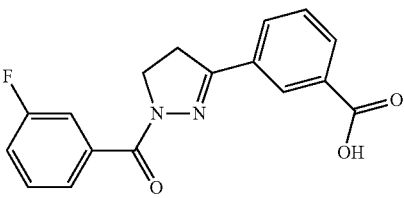 [SMILES: O=C(O)c1cccc(C2=NN(C(=O)c3cccc(F)c3)CC2)c1]

Grey solid; 100% Yield

LC-MS: Mass found (M+, 313.3). Flow—0.6 ml/min. Rt (min): 3.68; % Area: 96.31 (Max), 97.70 (254 nm).

HPLC—Rt (min): 3.66; % Area: 96.38 (Max), 97.14 (254 nm).

400 MHz, DMSO-d6: δ 13.25 (brs, 1H), 8.18 (brs, 1H), 8.01 (d, J=8.00 Hz, 1H), 7.92 (d, J=8.00 Hz, 1H), 7.69 (d, J=8.00 Hz, 1H), 7.64-7.52 (m, 3H), 7.42-7.37 (m, 1H), 4.14 (t, J=8.00 Hz, 2H), 3.41-3.32 (m, 2H).

(3-Fluoro-phenyl)-(3-m-tolyl-4,5-dihydro-pyrazol-1-yl)-methanone

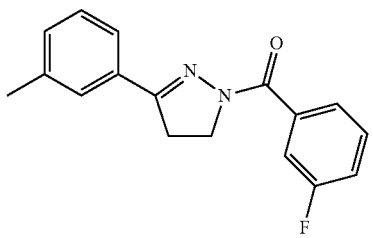 [SMILES: Cc1cccc(C2=NN(C(=O)c3cccc(F)c3)CC2)c1]

Off white solid; 57.44% Yield

LC-MS: Mass found (M+, 283.0). Rt (min): 4.77; % Area: 96.24 (Max), 97.25 (254 nm).

HPLC—Rt (min): 4.88; % Area: 96.34 (Max), 96.52 (254 nm).

400 MHz, CDCl3: δ 7.81 (d, J=8.00 Hz, 1H), 7.76-7.74 (m, 1H), 7.52-7.50 (m, 2H), 7.46-7.42 (m, 1H), 7.33-7.29 (m, 1H), 7.24-7.18 (m, 2H), 4.26 (t, J=12.00 Hz, 2H), 3.29 (t, J=8.00 Hz, 2H), 2.40 (s, 3H).

(3-Fluoro-phenyl)-[3-(3-trifluoromethyl-phenyl)-4,5-dihydro-pyrazol-1-yl]-methanone

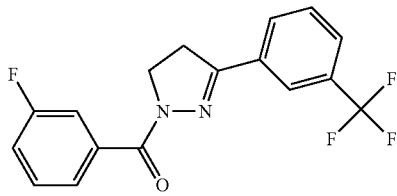 [SMILES: O=C(c1cccc(F)c1)N1CCC(c2cccc(C(F)(F)F)c2)=N1]

Yellow solid; 59.97% Yield
LC-MS: Mass found (M+, 337.0). Rt (min): 5.12; % Area: 98.56 (Max), 98.32 (254 nm).
HPLC—Rt (min): 5.22; % Area: 99.58 (Max), 99.09 (254 nm).
400 MHz, CDCl3: δ 7.93 (d, J=8.00 Hz, 1H), 7.88 (brs, 1H), 7.78 (d, J=8.00 Hz, 1H), 7.72-7.68 (m, 2H), 7.58-7.54 (m, 1H), 7.47-7.41 (m, 1H), 7.25-7.20 (m, 1H), 4.32 (t, J=8.00 Hz, 2H), 3.33 (t, J=8.00 Hz, 2H).

[3-(3-Amino-phenyl)-4,5-dihydro-pyrazol-1-yl]-(3-fluoro-phenyl)-methanone

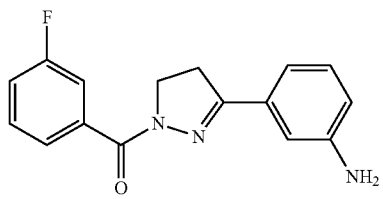 [SMILES: Nc1cccc(C2=NN(C(=O)c3cccc(F)c3)CC2)c1]

Off white solid; 42.93% Yield
LC-MS: Mass found (M+, 284). Rt (min): 2.61; % Area: 96.86 (Max), 93.73 (254 nm).
HPLC—Rt (min): 2.60; % Area: 96.52 (Max), 93.72 (254 nm).
400 MHz, CDCl3: δ 7.79 (d, J=8.00 Hz, 1H), 7.75-7.72 (m, 1H), 7.45-7.40 (m, 1H), 7.23-7.18 (m, 2H), 7.07-7.01 (m, 2H), 6.78-6.75 (m, 1H), 4.25 (t, J=12.00 Hz, 2H), 3.78 (brs, 2H), 3.26 (t, J=12.00 Hz, 2H).

N-{3-[1-(3-Fluoro-benzoyl)-4,5-dihydro-1H-pyrazol-3-yl]-phenyl}-acetamide

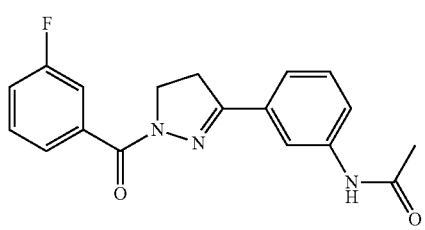 [SMILES: CC(=O)Nc1cccc(C2=NN(C(=O)c3cccc(F)c3)CC2)c1]

White solid; 15.45% Yield
LC-MS: Mass found (M+, 326.3). Rt (min): 3.51; % Area: 98.63 (Max), 99.22 (254 nm).
HPLC—Rt (min): 3.50; % Area: 98.69 (Max), 99.55 (254 nm).
400 MHz, CDCl3: δ 7.79 (d, J=8.00 Hz, 1H), 7.74-7.71 (m, 1H), 7.66 (d, J=8.00 Hz, 1H), 7.47-7.36 (m, 3H), 7.24-7.21 (m, 2H), 4.28 (t, J=8.00 Hz, 2H), 3.30 (t, J=12.00 Hz, 2H), 2.21 (s, 3H).

(3-Fluoro-phenyl)-[3-(3-fluoro-phenyl)-4,5-dihydro-pyrazol-1-yl]-methanone

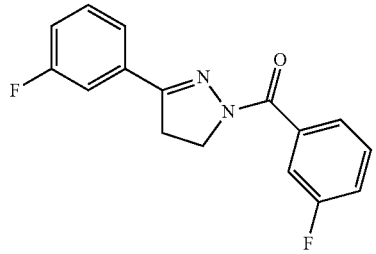 [SMILES: O=C(c1cccc(F)c1)N1CCC(c2cccc(F)c2)=N1]

White solid; 60.45% Yield
LC-MS: Mass found (M+, 326.3). Rt (min): 4.61; % Area: 99.22 (Max), 98.49 (254 nm).
HPLC—Rt (min): 4.63; % Area: 99.50 (Max), 98.40 (254 nm).
400 MHz, CDCl3: δ 7.79 (d, J=4.00 Hz, 1H), 7.73-7.70 (m, 1H), 7.48-7.38 (m, 4H), 7.24-7.19 (m, 1H), 7.17-7.12 (m, 1H), 4.29 (t, J=12.00 Hz, 2H), 3.31-3.26 (m, 2H).

[3-(3-Ethoxy-phenyl)-4,5-dihydro-pyrazol-1-yl]-(3-fluoro-phenyl)-methanone

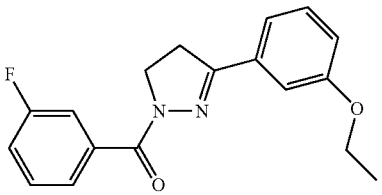 [SMILES: CCOc1cccc(C2=NN(C(=O)c3cccc(F)c3)CC2)c1]

Yellow solid; 41.55% Yield
LC-MS: Mass found (M+, 313.0). Rt (min): 4.83; % Area: 97.72 (Max), 98.24 (254 nm).
HPLC—Rt (min): 4.91; % Area: 98.07 (Max), 98.95 (254 nm).
400 MHz, CDCl3: δ 7.94-7.74 (m, 2H), 7.45-7.39 (m, 2H), 7.35-7.31 (m, 1H), 7.28-7.24 (m, 1H), 7.22-7.19 (m, 1H), 6.98-6.95 (m, 1H), 4.26 (t, J=12.00 Hz, 2H), 4.09-4.04 (m, 2H), 3.28 (t, J=8.00 Hz, 2H), 1.44 (t, J=8.00 Hz, 3H).

(3-Fluoro-phenyl)-[3-(3-hydroxy-phenyl)-4,5-dihydro-pyrazol-1-yl]-methanone

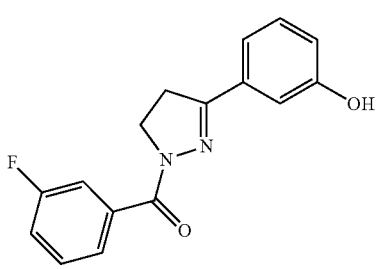 [SMILES: O=C(c1cccc(F)c1)N1CCC(c2cccc(O)c2)=N1]

White Solid; 11.26% Yield

LC-MS: Mass found (M+, 285.3). Rt (min): 3.70; % Area: 93.85 (Max), 95.49 (254 nm).

HPLC—Rt (min): 3.72; % Area: 97.02 (Max), 96.72 (254 nm).

400 MHz, DMSO-d6: δ 7.69 (d, J=8.00 Hz, 1H), 7.63-7.61 (m, 1H), 7.56-7.51 (m, 1H), 7.41-7.36 (m, 1H), 7.26 (t, J=8.00 Hz, 1H), 7.11-7.10 (m, 2H), 6.86-6.84 (m, 1H), 4.09 (t, J=12.00 Hz, 2H), 3.32-3.26 (m, 2H).

(3-Fluoro-phenyl)-[3-(3-isopropyl-phenyl)-4,5-dihydro-pyrazol-1-yl]-methanone

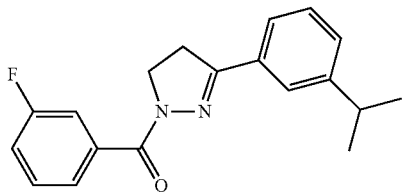

Yellow gum; 7.50% Yield

LC-MS: Mass found (M+, 311.3). Rt (min): 5.39; % Area: 98.67 (Max), 97.0 (254 nm).

HPLC—Rt (min): 5.49; % Area: 98.55 (Max), 96.42 (254 nm).

400 MHz, CDCl3: δ 7.89-7.86 (m, 1H), 7.82-7.79 (m, 1H), 7.54-7.52 (m, 2H), 7.43-7.42 (m, 1H), 7.35-7.30 (m, 2H), 7.26-7.20 (m, 1H), 4.27 (t, J=8.00 Hz, 2H), 3.30 (t, J=12.00 Hz, 2H), 2.97-2.93 (m, 1H), 1.28 (s, 3H), 1.26 (s, 3H).

(3-Fluoro-phenyl)-[3-(3-hydroxymethyl-phenyl)-4,5-dihydro-pyrazol-1-yl]-methanone

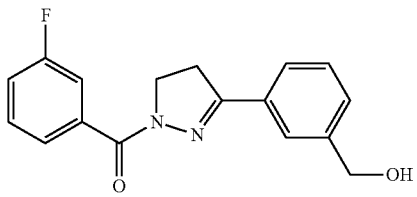 [SMILES: O=C(c1cccc(F)c1)N1CCC(c2cccc(CO)c2)=N1]

White Solid; 43.46% Yield

LC-MS: Mass found (M+, 299.3). Rt (min): 3.51; % Area: 97.69 (Max), 95.92 (254 nm).

HPLC—Rt (min): 3.52; % Area: 97.98 (Max), 95.78 (254 nm).

400 MHz, CDCl3: δ 7.80 (d, J=8.00 Hz, 1H), 7.75-7.72 (m, 1H), 7.69-7.65 (m, 2H), 7.46-7.41 (m, 3H), 7.24-7.18 (m, 1H), 4.76 (d, J=4.00 Hz, 2H), 4.28 (t, J=8.00 Hz, 2H), 3.31 (t, J=12.00 Hz, 2H), 1.80 (t, J=8.00 Hz, 1H).

(3-Biphenyl-3-yl-4,5-dihydro-pyrazol-1-yl)-(3-fluoro-phenyl)-methanone

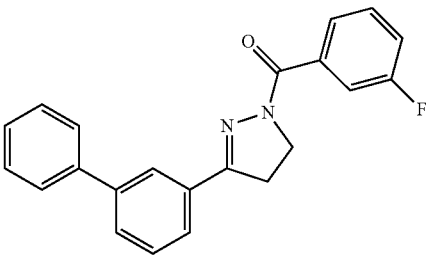 [SMILES: O=C(c1cccc(F)c1)N1CCC(c2cccc(-c3ccccc3)c2)=N1]

White Solid; 71.85% Yield

LC-MS: Mass found (M+, 345.3). Rt (min): 5.40; % Area: 98.51 (Max), 99.15 (254 nm).

HPLC—Rt (min): 5.42; % Area: 99.52 (Max), 98.95 (254 nm).

400 MHz, CDCl3: δ 7.88 (brs, 1H), 7.82 (d, J=8.00 Hz, 1H), 7.78-7.71 (m, 2H), 7.68-7.65 (m, 1H), 7.62-7.60 (m, 2H), 7.52-7.38 (m, 5H), 7.24-7.19 (m, 1H), 4.31 (t, J=8.00 Hz, 2H), 3.36 (t, J=12.00 Hz, 2H).

3-[1-(3-Fluoro-benzoyl)-4,5-dihydro-1H-pyrazol-3-yl]-benzonitrile

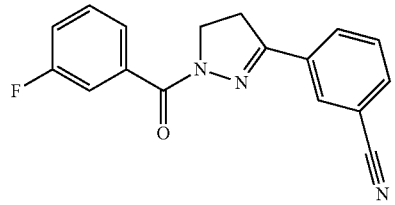 [SMILES: N#Cc1cccc(C2=NN(C(=O)c3cccc(F)c3)CC2)c1]

White Solid; 100% Yield

LC-MS: Mass found (M+, 294.0). Rt (min): 4.22; % Area: 97.71 (Max), 98.24 (254 nm).

HPLC—Rt (min): 4.25; % Area: 98.09 (Max), 98.66 (254 nm).

400 MHz, CDCl3: δ 7.95-7.93 (m, 2H), 7.77-7.66 (m, 3H), 7.58-7.53 (m, 1H), 7.49-7.43 (m, 1H), 7.24-7.21 (m, 1H), 4.33 (t, J=8.00 Hz, 2H), 3.31 (t, J=8.00 Hz, 2H).

[3-(3-Dimethylamino-phenyl)-4,5-dihydro-pyrazol-1-yl]-(3-fluoro-phenyl)-methanone

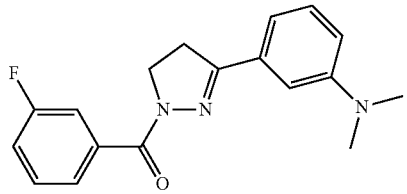 [SMILES: CN(C)c1cccc(C2=NN(C(=O)c3cccc(F)c3)CC2)c1]

Off white solid; 8.80% Yield

LC-MS: Mass found (M+, 312.3). Rt (min): 3.0; % Area: 98.03 (Max), 96.58 (254 nm).

HPLC—Rt (min): 3.01; % Area: 98.58 (Max), 97.49 (254 nm).

400 MHz, CDCl3: δ 7.83-7.78 (m, 2H), 7.43-7.38 (m, 1H), 7.30-7.27 (m, 1H), 7.21-7.16 (m, 1H), 7.08 (brs, 1H), 7.04-7.02 (m, 1H), 6.83-6.80 (m, 1H), 4.26 (t, J=−8.00 Hz, 2H), 3.32-3.27 (m, 2H), 2.98 (s, 6H).

(3-Fluoro-phenyl)-[3-(3-methylsulfanyl-phenyl)-4,5-dihydro-pyrazol-1-yl]-methanone

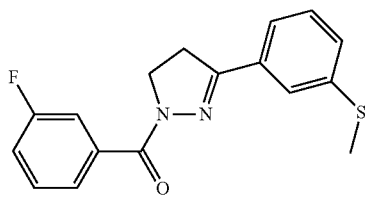

Off White Solid; 73.81% Yield

LC-MS: Mass found (M+, 315.3). Rt (min): 4.89; % Area: 95.38 (Max), 94.13 (254 nm).

HPLC—Rt (min): 4.90; % Area: 96.80 (Max), 95.64 (254 nm).

400 MHz, CDCl3: δ 7.80 (d, J=8.00 Hz, 1H), 7.77-7.74 (m, 1H), 7.58 (brs, 1H), 7.48-7.42 (m, 2H), 7.37-7.30 (m, 2H), 7.24-7.21 (m, 1H), 4.28 (t, J=12.00 Hz, 2H), 3.29 (t, J=8.00 Hz, 2H), 2.52 (s, 3H).

(3-Fluoro-phenyl)-[3-(3-trifluoromethoxy-phenyl)-4,5-dihydro-pyrazol-1-yl]-methanone

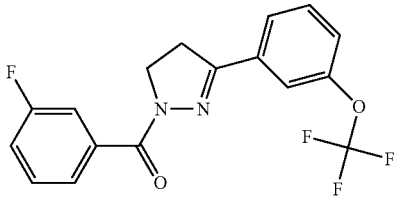 [SMILES: O=C(c1cccc(F)c1)N1CCC(c2cccc(OC(F)(F)F)c2)=N1]

White solid; 48.57% Yield

LC-MS: Mass found (M+, 353.0). Rt (min): 5.26; % Area: 99.73 (Max), 99.55 (254 nm).

HPLC—Rt (min): 5.34; % Area: 99.59 (Max), 98.97 (254 nm).

400 MHz, CDCl3: δ 7.78 (d, J=8.00 Hz, 1H), 7.71 (d, J=8.00 Hz, 1H), 7.63 (d, J=8.00 Hz, 1H), 7.53 (brs, 1H), 7.48-7.41 (m, 2H), 7.30-7.28 (m, 1H), 7.24-7.19 (m, 1H), 4.30 (t, J=8.00 Hz, 2H), 3.29 (t, J=12.00 Hz, 2H).

N-{3-[1-(3-Fluoro-benzoyl)-4,5-dihydro-1H-pyrazol-3-yl]-phenyl}-methanesulfonamide

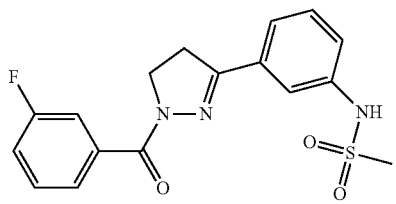 [SMILES: CS(=O)(=O)Nc1cccc(C2=NN(C(=O)c3cccc(F)c3)CC2)c1]

Off white Solid; 67.48% Yield

LC-MS: Mass found (M+, 362.0). Rt (min): 3.62; % Area: 99.17 (Max), 98.40 (254 nm).

HPLC—Rt (min): 3.77; % Area: 99.44 (Max), 99.11 (254 nm).

400 MHz, CDCl3: δ 7.78 (d, J=8.00 Hz, 1H), 7.72 (d, J=8.00 Hz, 1H), 7.54-7.53 (m, 1H), 7.51-7.48 (m, 1H), 7.45-7.41 (m, 2H), 7.34-7.32 (m, 1H), 7.24-7.19 (m, 1H), 6.56 (brs, 1H), 4.29 (t, J=8.00 Hz, 2H), 3.29 (t, J=12.00 Hz, 2H), 3.04 (s, 3H).

3-[1-(3-Fluoro-benzoyl)-4,5-dihydro-1H-pyrazol-3-yl]-N-methyl-benzamide

White solid; 46.40% Yield

LC-MS: Mass found (M+, 326.0). Rt (min): 3.31; % Area: 98.77 (Max), 99.10 (254 nm).

HPLC—Rt (min): 3.40; % Area: 98.47 (Max), 99.25 (254 nm).

400 MHz, CDCl3: δ 8.05 (brs, 1H), 7.90-7.88 (m, 1H), 7.79-7.77 (m, 2H), 7.72 (d, J=12.00 Hz, 1H), 7.51-7.41 (m, 2H), 7.24-7.19 (m, 1H), 6.19 (brs, 1H), 4.29 (t, J=12.00 Hz, 2H), 3.33 (t, J=12.00 Hz, 2H), 3.05 (d, J=4.00 Hz, 3H).

N-Cyclopentyl-3-[1-(3-fluoro-benzoyl)-4,5-dihydro-1H-pyrazol-3-yl]-benzamide

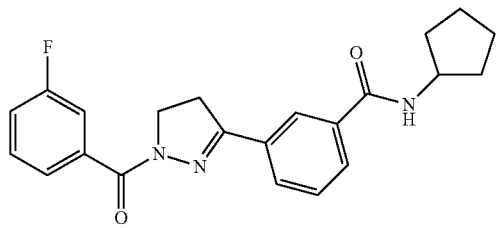 [SMILES: O=C(NC1CCCC1)c1cccc(C2=NN(C(=O)c3cccc(F)c3)CC2)c1]

Off white solid; 4.15% Yield

LC-MS: Mass found (M+, 380.0). Rt (min): 4.32; % Area: 93.75 (Max), 94.50 (254 nm).

HPLC—Rt (min): 4.44; % Area: 93.94 (Max), 94.41 (254 nm).

400 MHz, CDCl3: δ 8.05 (brs, 1H), 7.88-7.86 (m, 1H), 7.80-7.75 (m, 3H), 7.50-7.40 (m, 2H), 7.24-7.19 (m, 1H), 4.45-4.39 (m, 1H), 4.30 (t, J=8.00 Hz, 2H), 3.36-3.31 (m, 2H), 2.15-2.08 (m, 2H), 1.77-1.68 (m, 4H), 1.56-1.49 (m, 2H).

(3-Fluoro-phenyl)-[3-(3-pyrazol-1-yl-phenyl)-4,5-dihydro-pyrazol-1-yl]-methanone

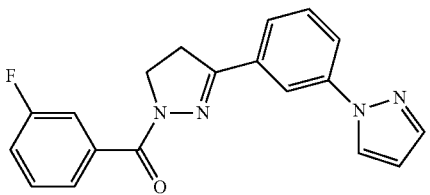 [SMILES: O=C(c1cccc(F)c1)N1CCC(c2cccc(-n3cccn3)c2)=N1]

Off White Solid; 80.01% Yield
LC-MS: Mass found (M+, 335.0). Rt (min): 4.33; % Area: 98.42 (Max), 98.52 (254 nm).
HPLC—Rt (min): 4.35; % Area: 98.50 (Max), 98.49 (254 nm).
400 MHz, CDCl3: δ 8.01 (brs, 1H), 7.97 (d, J=4.00 Hz, 1H), 7.81-7.66 (m, 5H), 7.53-7.47 (m, 1H), 7.46-7.42 (m, 1H), 7.25-7.20 (m, 1H), 6.52-6.51 (m, 1H), 4.31 (t, J=12.00 Hz, 2H), 3.36 (t, J=12.00 Hz, 2H).

[3-(3-Fluoro-4-methoxy-phenyl)-4,5-dihydro-pyrazol-1-yl]-(3-fluoro-phenyl)-methanone

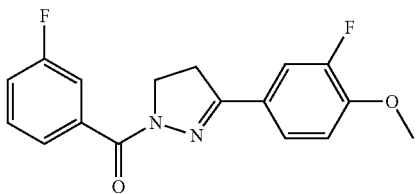 [SMILES: COc1ccc(C2=NN(C(=O)c3cccc(F)c3)CC2)cc1F]

Off White Solid; 18.58% Yield
LC-MS: Mass found (M+, 317.3). Rt (min): 4.49; % Area: 99.44 (Max), 99.09 (254 nm).
HPLC—Rt (min): 4.50; % Area: 99.48 (Max), 99.51 (254 nm).
400 MHz, CDCl3: δ 7.72-7.70 (m, 2H), 7.53-7.40 (m, 3H), 7.23-7.18 (m, 1H), 7.00-6.96 (m, 1H), 4.26 (t, J=12.00 Hz, 2H), 3.94 (s, 3H), 3.27-3.22 (m, 2H).

(3-Fluoro-phenyl)-[3-(4-methoxy-3-methyl-phenyl)-4,5-dihydro-pyrazol-1-yl]-methanone

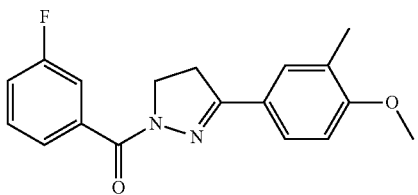 [SMILES: COc1ccc(C2=NN(C(=O)c3cccc(F)c3)CC2)cc1C]

Grey solid; 44.61% Yield
LC-MS: Mass found (M+, 313.0). Rt (min): 4.18; % Area: 99.32 (Max), 99.31 (254 nm).
HPLC—Rt (min): 4.98; % Area: 97.95 (Max), 99.85 (254 nm).
400 MHz, CDCl3: δ 7.81 (d, J=8.00 Hz, 1H), 7.76 (d, J=8.00 Hz, 1H), 7.52-7.50 (m, 2H), 7.45-7.40 (m, 1H), 7.22-7.17 (m, 1H), 6.85 (d, J=8.00 Hz, 1H), 4.24 (t, J=12.00 Hz, 2H), 3.88 (s, 3H), 3.26 (t, J=12.00 Hz, 2H), 2.24 (s, 3H).

[3-(3-Nitro-4-methoxy-phenyl)-4,5-dihydro-pyrazol-1-yl]-(3-fluoro-phenyl)-methanone

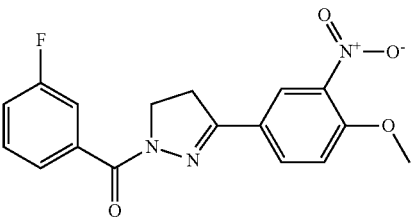 [SMILES: COc1ccc(C2=NN(C(=O)c3cccc(F)c3)CC2)cc1[N+](=O)[O-]]

Yellow solid; 12.69% Yield
LC-MS: Mass found (M+, 344.0). Rt (min): 4.45; % Area: 93.51 (Max), 91.34 (254 nm).
HPLC—Rt (min): 4.40; % Area: 94.94 (Max), 94.32 (220 nm).
400 MHz, CDCl3: δ 7.94 (s, 1H), 7.76 (d, J=8.00 Hz, 1H), 7.69 (d, J=8.00 Hz, 1H), 7.53-7.41 (m, 1H), 7.72-7.14 (m, 3H), 4.30 (t, J=12.00 Hz, 2H), 4.02 (s, 3H), 3.29 (t, J=8.00 Hz, 2H).

[3-(3-Cyclopentyloxy-4-methoxy-phenyl)-4,5-dihydro-pyrazol-1-yl]-(3-fluoro-phenyl)-methanone

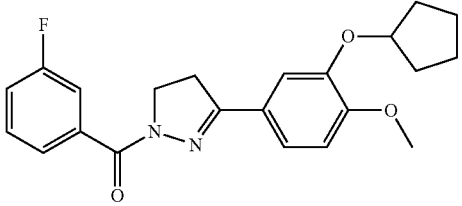 [SMILES: COc1ccc(C2=NN(C(=O)c3cccc(F)c3)CC2)cc1OC1CCCC1]

White Solid; 36.55% Yield
LC-MS: Mass found (M+, 383.0). Rt (min): 5.14; % Area: 97.77 (Max), 98.83 (254 nm).
HPLC—Rt (min): 5.13; % Area: 98.99 (Max), 98.49 (254 nm).
400 MHz, CDCl3: δ 7.83 (d, J=8.00 Hz, 2H), 7.44-7.38 (m, 2H), 7.22-7.17 (m, 1H), 7.15-7.13 (m, 1H), 6.87 (d, J=8.00 Hz, 1H), 4.80-4.76 (m, 1H), 4.26 (t, J=12.00 Hz, 2H), 3.90 (s, 3H), 3.27 (t, J=8.00 Hz, 2H), 2.02-1.83 (m, 6H), 1.66-1.65 (m, 2H).

[3-(3-Chloro-4-methoxy-phenyl)-4,5-dihydro-pyrazol-1-yl]-(3-fluoro-phenyl)-methanone

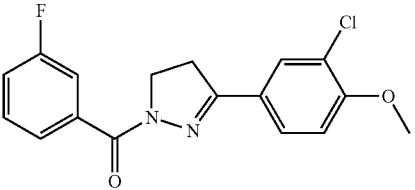 [SMILES: COc1ccc(C2=NN(C(=O)c3cccc(F)c3)CC2)cc1Cl]

Off white solid; 12.22% Yield

LC-MS: Mass found (M+, 333.0). Rt (min): 4.74; % Area: 97.19 (Max), 95.73 (254 nm).

HPLC—Rt (min): 4.74; % Area: 96.09 (Max), 95.64 (254 nm).

400 MHz, CDCl3: δ 7.79 (d, J=4.00 Hz, 1H), 7.73-7.71 (m, 2H), 7.60-7.57 (m, 1H), 7.46-7.41 (m, 1H), 7.24-7.19 (m, 1H), 6.98-6.96 (m, 1H), 4.27 (t, J=8.00 Hz, 2H), 3.92 (s, 3H), 3.25 (t, J=12.00 Hz, 2H).

[3-(3-Amino-4-methoxy-phenyl)-4,5-dihydro-pyrazol-1-yl]-(3-fluoro-phenyl)-methanone

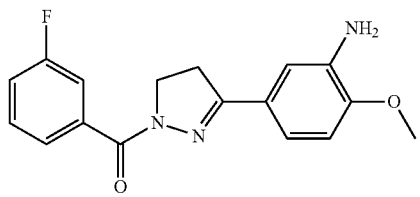 [SMILES: COc1ccc(C2=NN(C(=O)c3cccc(F)c3)CC2)cc1N]

White solid; 24.94% Yield

LC-MS: Mass found (M+, 314.0). Rt (min): 2.72; % Area: 96.03 (Max), 93.93 (220 nm).

HPLC—Rt (min): 2.70; % Area: 96.75 (Max), 94.64 (254 nm).

400 MHz, CDCl3: δ 7.80 (d, J=8.00 Hz, 1H), 7.75 (d, J=8.00 Hz, 1H), 7.45-7.39 (m, 1H), 7.22-7.17 (m, 1H), 7.15-7.12 (m, 1H), 7.03-7.01 (m, 1H), 6.80 (d, J=12.00 Hz, 1H), 4.23 (t, J=12.00 Hz, 2H), 3.90 (s, 5H), 3.24 (t, J=12.00 Hz, 2H).

5-[1-(3-Fluoro-benzoyl)-4,5-dihydro-1H-pyrazol-3-yl]-2-methoxy-benzoic acid

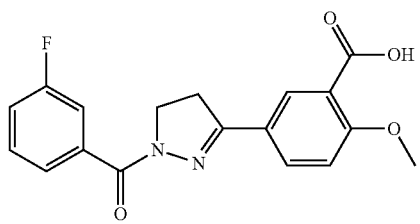 [SMILES: COc1ccc(C2=NN(C(=O)c3cccc(F)c3)CC2)cc1C(=O)O]

White solid; 100% Yield

LC-MS: Mass found (M+, 343.3). Rt (min): 3.39; % Area: 92.46 (Max), 92.31 (254 nm).

HPLC—Rt (min): 3.40; % Area: 94.26 (Max), 93.30 (220 nm).

400 MHz, DMSO-d6: δ 12.87 (brs, 1H), 7.91 (d, J=4.00 Hz, 1H), 7.83-7.80 (m, 1H), 7.69 (d, J=8.00 Hz, 1H), 7.64-7.61 (m, 1H), 7.56-7.50 (m, 1H), 7.40-7.35 (m, 1H), 7.23 (d, J=12.00 Hz, 1H), 4.10 (t, J=12.00 Hz, 2H), 3.86 (s, 3H), 3.32 (m, 2H).

(3-Fluoro-phenyl)-[3-(4-methoxy-3-trifluoromethyl-phenyl)-4,5-dihydro-pyrazol-1-yl]-methanone

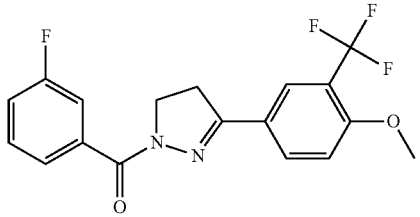 [SMILES: COc1ccc(C2=NN(C(=O)c3cccc(F)c3)CC2)cc1C(F)(F)F]

Grey solid; 91.22% Yield

LC-MS: Mass found (M+, 367.0). Rt (min): 5.06; % Area: 98.62 (Max), 98.09 (254 nm).

HPLC—Rt (min): 5.07; % Area: 98.87 (Max), 98.88 (254 nm).

400 MHz, CDCl3: δ 7.91-7.90 (m, 1H), 7.88 (brs, 1H), 7.79 (d, J=8.00 Hz, 1H), 7.73 (d, J=12.00 Hz, 1H), 7.46-7.40 (m, 1H), 7.24-7.19 (m, 1H), 7.06 (d, J=8.00 Hz, 1H), 4.29 (t, J=8.00 Hz, 2H), 3.97 (s, 3H), 3.29 (t, J=8.00 Hz, 2H).

(3-Fluoro-phenyl)-{3-[4-methoxy-3-(morpholine-4-sulfonyl)-phenyl]-4,5-dihydro-pyrazol-1-yl}-methanone

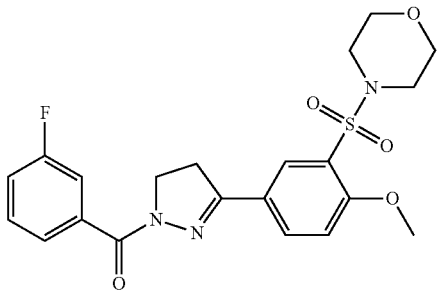 [SMILES: COc1ccc(C2=NN(C(=O)c3cccc(F)c3)CC2)cc1S(=O)(=O)N1CCOCC1]

Grey solid; 13.95% Yield

LC-MS: Mass found (M+, 448.0). Rt (min): 3.87; % Area: 99.57 (Max), 99.73 (220 nm).

HPLC—Rt (min): 3.93; % Area: 96.23 (Max), 98.86 (254 nm).

400 MHz, CDCl3: δ 8.08-8.07 (m, 1H), 8.02-7.99 (m, 1H), 7.78 (d, J=8.00 Hz, 1H), 7.75-7.70 (m, 1H), 7.46-7.41 (m, 1H), 7.23-7.18 (m, 1H), 6.99-6.97 (m, 1H), 4.29 (t, J=8.00 Hz, 2H), 4.00-3.99 (m, 4H), 3.76-3.73 (m, 4H), 3.32-3.26 (m, 5H).

N,N-Diethyl-5-[1-(3-fluoro-benzoyl)-4,5-dihydro-1H-pyrazol-3-yl]-2-methoxy-benzenesulfonamide

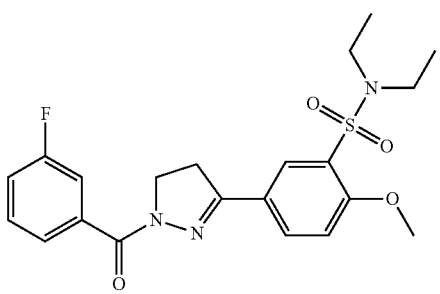 [SMILES: CCN(CC)S(=O)(=O)c1cc(C2=NN(C(=O)c3cccc(F)c3)CC2)ccc1OC]

White solid; 22.14% Yield

LC-MS: Mass found (M+, 434.0). Rt (min): 4.54; % Area: 98.98 (Max), 98.55 (254 nm).

HPLC—Rt (min): 4.60; % Area: 98.91 (Max), 98.61 (254 nm).

400 MHz, CDCl3: δ 8.12 (d, J=4.00 Hz, 1H), 7.98-7.96 (m, 1H), 7.79 (d, J=8.00 Hz, 1H), 7.72 (d, J=8.00 Hz, 1H), 7.46-7.40 (m, 1H), 7.23-7.18 (m, 1H), 7.05 (d, J=12.00 Hz, 1H), 4.28 (t, J=12.00 Hz, 2H), 3.99 (s, 3H), 3.39-3.28 (m, 6H), 1.15-1.11 (m, 6H).

5-[1-(3-Fluoro-benzoyl)4,5-dihydro-1-H-pyrazole-3-yl]-2-methoxy-N-phenyl-benzenesulfonamide

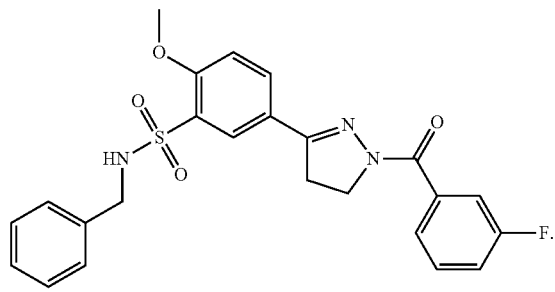 [SMILES: COc1ccc(C2=NN(C(=O)c3cccc(F)c3)CC2)cc1S(=O)(=O)NCc1ccccc1]

Off white solid; 5.89% Yield

LC-MS: Mass found (M+, 468.0). Rt (min): 4.46; % Area: 98.14 (Max), 98.48 (254 nm).

HPLC—Rt (min): 4.57; % Area: 98.34 (Max), 98.23 (220 nm).

400 MHz, CDCl3: δ 8.07-0.00 (m, 1H), 8.02-8.01 (m, 1H), 8.00-7.99 (m, 1H), 7.81-7.79 (m, 1H), 7.47-7.42 (m, 1H), 7.28-7.21 (m, 4H), 7.21-7.12 (m, 2H), 7.00-6.98 (m, 1H), 5.15-5.12 (m, 1H), 4.33-4.28 (m, 2H), 4.14-4.13 (m, 2H), 3.89 (s, 3H), 3.33-3.29 (m, 2H).

[3-(3-Ethoxy-4-methoxy-phenyl)-4,5-dihydro-pyrazol-1-yl]-(3-fluoro-phenyl)-methanone

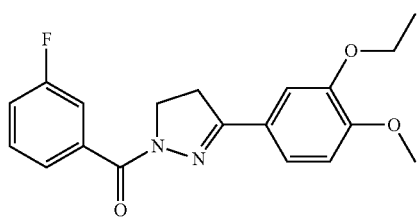 [SMILES: CCOc1cc(C2=NN(C(=O)c3cccc(F)c3)CC2)ccc1OC]

Off white solid; 47.07% Yield

LC-MS: Mass found (M+, 343.0). Rt (min): 4.34; % Area: 91.93 (Max), 93.17 (254 nm).

HPLC—Rt (min): 4.42; % Area: 92.49 (Max), 94.39 (254 nm).

400 MHz, CDCl3: δ 7.82-7.78 (m, 2H), 7.54-7.42 (m, 1H), 7.41-7.39 (m, 1H), 7.20-7.16 (m, 2H), 6.90-6.88 (m, 1H), 4.26 (t, J=9.60 Hz, 2H), 4.16-4.11 (m, 2H), 3.92 (s, 3H), 3.27 (t, J=10.00 Hz, 2H), 1.49 (t, J=−6.40 Hz, 3H).

[3-(3-Benzyloxy-4-methoxy-phenyl)-4,5-dihydro-pyrazol-1-yl]-(3-fluoro-phenyl)-methanone

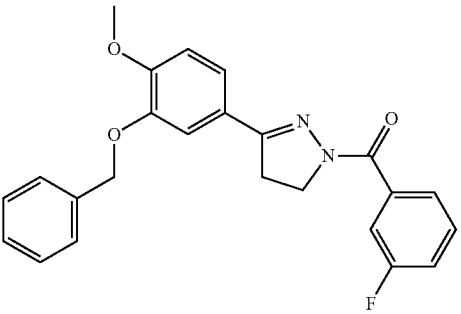 [SMILES: COc1ccc(C2=NN(C(=O)c3cccc(F)c3)CC2)cc1OCc1ccccc1]

Brown solid; 6.01% Yield

LC-MS: Mass found (M+, 405.0). Rt (min): 5.03; % Area: 95.97 (Max), 95.98 (220 nm).

HPLC—Rt (min): 5.09; % Area: 95.49 (Max), 93.96 (254 nm).

400 MHz, CDCl3: δ 7.76-7.74 (m, 2H), 7.45-7.40 (m, 3H), 7.36-7.31 (m, 4H), 7.31-7.27 (m, 1H), 7.23-7.21 (m, 1H), 7.18-6.89 (m, 1H), 5.31-5.19 (m, 2H), 4.23 (t, J=9.60 Hz, 2H), 3.94 (s, 3H), 3.21 (t, J=10.00 Hz, 2H).

(3-Fluoro-phenyl)-[3-(3-isopropoxy-4-methoxy-phenyl)-4,5-dihydro-pyrazol-1-yl]-methanone

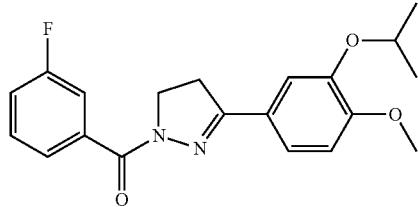 [SMILES: COc1ccc(C2=NN(C(=O)c3cccc(F)c3)CC2)cc1OC(C)C]

Off white solid; 2.47% Yield

LC-MS: Mass found (M+, 357.3). Rt (min): 4.66; % Area: 98.26 (Max), 98.37 (254 nm).

HPLC—Rt (min): 4.72; % Area: 90.49 (Max), 91.41 (254 nm).

400 MHz, CDCl3: δ 7.82-7.78 (m, 2H), 7.44-7.40 (m, 1H), 7.38-7.36 (m, 1H), 7.20-7.18 (m, 2H), 6.90-6.88 (m, 1H), 4.59-4.53 (m, 1H), 4.28-4.23 (m, 2H), 3.90 (s, 3H), 3.28-3.23 (m, 2H), 1.40-1.38 (m, 6H).

(3-Fluoro-phenyl)-[3-(3-hydroxy-4-methoxy-phenyl)-4,5-dihydro-pyrazol-1-yl]-methanone

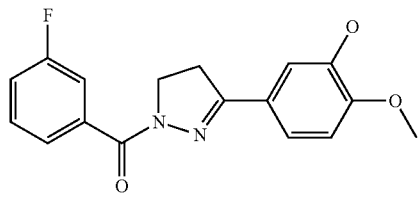

Yellow solid; 100% Yield

LC-MS: Mass found (M+, 315). Rt (min): 3.68; % Area: 94.03 (Max), 97.23 (254 nm).

HPLC—Rt (min): 3.63; % Area: 95.31 (Max), 97.24 (254 nm).

400 MHz, DMSO-d6: δ 9.32 (brs, 1H), 7.69 (d, J=8.00 Hz, 1H), 7.63-7.61 (m, 1H), 7.56-7.50 (m, 1H), 7.40-7.35 (m, 1H), 7.16-7.15 (m, 1H), 7.10-7.07 (m, 1H), 6.98 (d, J=12.00 Hz, 1H), 4.07 (t, J=8.00 Hz, 2H), 3.79 (s, 3H), 3.26 (t, J=8.00 Hz, 2H).

(3-Fluoro-phenyl)-(3-o-tolyl-4,5-dihydro-pyrazol-1-yl)-methanone

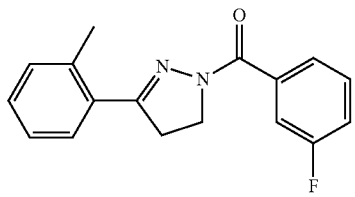 [SMILES: Cc1ccccc1C1=NN(C(=O)c2cccc(F)c2)CC1]

Off white solid; 28.90% Yield

LC-MS: Mass found (M+, 283.0). Rt (min): 4.80; % Area: 99.36 (Max), 99.56 (254 nm).

HPLC—Rt (min): 4.83; % Area: 99.10 (Max), 99.04 (254 nm).

400 MHz, CDCl3: δ 7.78-7.70 (m, 2H), 7.45-7.37 (m, 2H), 7.32-7.29 (m, 2H), 7.28-7.27 (m, 1H), 7.20-7.16 (m, 1H), 4.22 (t, J=8.00 Hz, 2H), 3.37 (t, J=8.00 Hz, 2H), 2.52 (s, 3H).

(3-Biphenyl-2-yl-4,5-dihydro-pyrazol-1-yl)-(3-fluoro-phenyl)-methanone

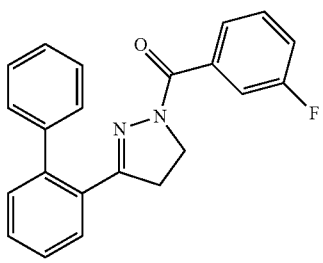 [SMILES: O=C(c1cccc(F)c1)N1CCC(c2ccccc2-c2ccccc2)=N1]

Off white solid; 43.67% Yield

LC-MS: Mass found (M+, 345.3). Rt (min): 5.26; % Area: 97.11 (Max), 97.01 (254 nm).

HPLC—Rt (min): 5.27; % Area: 97.08 (Max), 97.44 (254 nm).

400 MHz, CDCl3: δ 7.53-7.50 (m, 1H), 7.48-7.40 (m, 8H), 7.39-7.31 (m, 3H), 7.14-7.13 (m, 1H), 4.03 (t, J=8.00 Hz, 2H), 2.67 (t, J=8.00 Hz, 2H).

(3-Fluoro-phenyl)-[3-(2-methoxy-phenyl)-4,5-dihydro-pyrazol-1-yl]-methanone

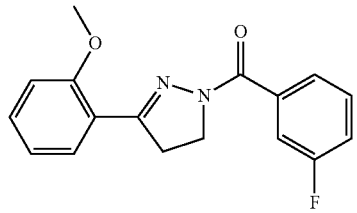 [SMILES: COc1ccccc1C1=NN(C(=O)c2cccc(F)c2)CC1]

Off white solid; 40.13% Yield

LC-MS: Mass found (M+, 299.0). Rt (min): 4.52; % Area: 98.52 (Max), 99.25 (254 nm).

HPLC—Rt (min): 4.58; % Area: 99.29 (Max), 99.59 (254 nm).

400 MHz, CDCl3: δ 7.83 (d, J=8.00 Hz, 2H), 7.74-7.72 (m, 1H), 7.43-7.38 (m, 2H), 7.21-7.16 (m, 1H), 7.01-6.97 (m, 2H), 4.21 (t, J=12.00 Hz, 2H), 3.91 (s, 3H), 3.43 (t, J=8.00 Hz, 2H).

(3-Fluoro-phenyl)-[3-(2-trifluoromethyl-phenyl)-4,5-dihydro-pyrazol-1-yl]-methanone

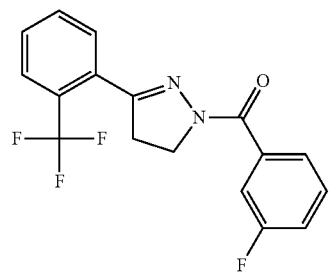 [SMILES: O=C(c1cccc(F)c1)N1CCC(c2ccccc2C(F)(F)F)=N1]

White solid; 66.60% Yield

LC-MS: Mass found (M+, 337.3). Rt (min): 4.85; % Area: 99.10 (Max), 99.46 (254 nm).

HPLC—Rt (min): 4.87; % Area: 97.36 (Max), 98.45 (254 nm).

400 MHz, CDCl3: δ 7.78 (d, J=8.00 Hz, 1H), 7.73 (d, J=8.00 Hz, 1H), 7.68-7.64 (m, 1H), 7.62-7.60 (m, 1H), 7.57-7.53 (m, 2H), 7.40-7.34 (m, 1H), 7.18-7.13 (m, 1H), 4.30 (t, J=8.00 Hz, 2H), 3.31 (t, J=8.00 Hz, 2H).

(3-Fluoro-phenyl)-[3-(2-hydroxy-phenyl)-4,5-dihydro-pyrazol-1-yl]-methanone

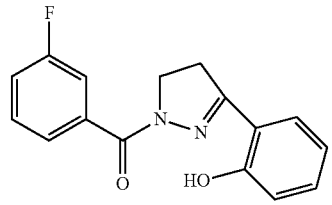 [SMILES: O=C(c1cccc(F)c1)N1CCC(c2ccccc2O)=N1]

Off white solid; 8.03% Yield

LC-MS: Mass found (M−, 283). Method: A—10 mM NH$_4$HCO$_3$, B: ACN; Flow Rate: 1.0 ml/min. Rt (min): 5.68; % Area: 93.65 (Max), 93.47 (220 nm).

HPLC—Rt (min): 4.36; % Area: 95.36 (Max), 96.10 (254 nm).

400 MHz, DMSO-d6: δ 10.04 (brs, 1H), 7.60-7.48 (m, 4H), 7.41-7.31 (m, 2H), 6.95-6.90 (m, 2H), 4.07 (t, J=12.00 Hz, 2H), 3.46 (t, J=8.00 Hz, 2H).

[3-(2-Amino-phenyl)-4,5-dihydro-pyrazol-1-yl]-(3-fluoro-phenyl)-methanone

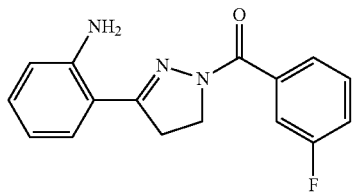 [SMILES: Nc1ccccc1C1=NN(C(=O)c2cccc(F)c2)CC1]

Brown solid; 4.30% Yield

LC-MS: Mass found (M+, 284.2). Rt (min): 3.96; % Area: 98.39 (Max), 100.0 (254 nm).

HPLC—Rt (min): 3.90; % Area: 97.96 (Max), 98.62 (254 nm).

400 MHz, DMSO-d6: δ 7.52-7.50 (m, 3H), 7.48-7.34 (m, 1H), 7.28-7.25 (m, 1H), 7.13-7.09 (m, 1H), 6.70-6.68 (m, 1H), 6.60-6.56 (m, 1H), 4.48 (m, 2H), 4.00 (t, J=8.00 Hz, 2H), 3.42-3.31 (m, 2H).

(3-Fluoro-phenyl)-[3-(2-methylsulfanyl-phenyl)-4,5-dihydro-pyrazol-1-yl]-methanone

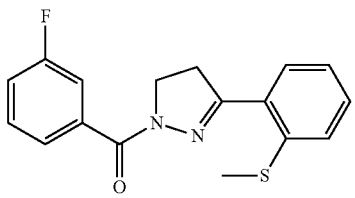 [SMILES: CSc1ccccc1C1=NN(C(=O)c2cccc(F)c2)CC1]

White Solid; 66.36% Yield

LC-MS: Mass found (M+, 315). Rt (min): 4.69; % Area: 98.74 (Max), 99.16 (254 nm).

HPLC—Rt (min): 4.61; % Area: 98.13 (Max), 99.03 (254 nm).

400 MHz, CDCl3: δ 7.98-7.95 (m, 1H), 7.90-7.88 (m, 1H), 7.46-7.37 (m, 3H), 7.31-7.29 (m, 1H), 7.22-7.19 (m, 2H), 4.25 (t, J=8.00 Hz, 2H), 3.39 (t, J=8.00 Hz, 2H), 2.48 (s, 3H).

[3-(2-Dimethylamino-phenyl)-4,5-dihydro-pyrazol-1-yl]-(3-fluoro-phenyl)-methanone

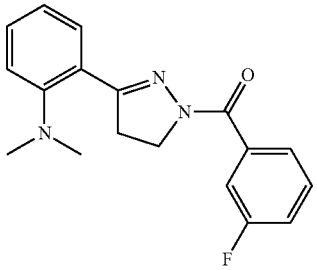 [SMILES: CN(C)c1ccccc1C1=NN(C(=O)c2cccc(F)c2)CC1]

Red gum; 22.62% Yield

LC-MS: Mass found (M+, 312.3). Rt (min): 2.24; % Area: 98.61 (Max), 95.58 (254 nm).

HPLC—Rt (min): 2.32; % Area: 99.74 (Max), 96.54 (254 nm).

400 MHz, CDCl3: δ 7.83-7.78 (m, 2H), 7.55-7.52 (m, 1H), 7.43-7.35 (m, 2H), 7.20-7.15 (m, 1H), 7.12-7.10 (m, 1H), 7.05-7.03 (m, 1H), 4.23 (t, J=8.00 Hz, 2H), 3.42 (t, J=12.00 Hz, 2H), 2.73 (s, 6H).

2-[1-(3-Fluoro-benzoyl)-4,5-dihydro-1H-pyrazol-3-yl]-benzonitrile

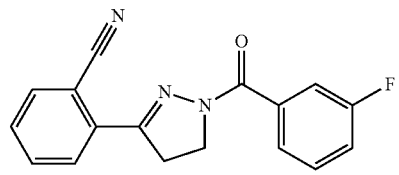 [SMILES: N#Cc1ccccc1C1=NN(C(=O)c2cccc(F)c2)CC1]

Off white solid; 20.21% Yield

LC-MS: Mass found (M+, 294.0). Rt (min): 3.96; % Area: 94.87 (Max), 96.73 (254 nm).

HPLC—Rt (min): 4.00; % Area: 94.56 (Max), 96.71 (254 nm).

400 MHz, CDCl3: δ 7.91 (d, J=8.00 Hz, 1H), 7.80-7.78 (m, 2H), 7.72 (d, J=8.00 Hz, 1H), 7.67-7.64 (m, 1H), 7.54-7.51 (m, 1H), 7.47-7.41 (m, 1H), 7.24-7.19 (m, 1H), 4.34 (t, J=12.00 Hz, 2H), 3.46 (t, J=12.00 Hz, 2H).

N-{2-[1-(3-Fluoro-benzoyl)-4,5-dihydro-1H-pyrazol-3-yl]-phenyl}-methanesulfonamide

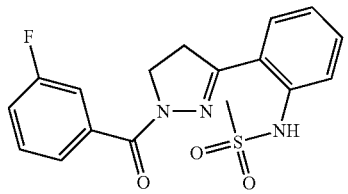 [SMILES: CS(=O)(=O)Nc1ccccc1C1=NN(C(=O)c2cccc(F)c2)CC1]

White Solid; 4.75% Yield

LC-MS: Mass found (M+, 362). Rt (min): 3.87; % Area: 97.67 (Max), 98.43 (254 nm).

HPLC—Rt (min): 3.94; % Area: 99.54 (Max), 99.61 (254 nm).

400 MHz, CDCl3: δ 7.73 (d, J=8.00 Hz, 1H), 7.62-7.60 (m, 1H), 7.55-7.42 (m, 4H), 7.25-7.24 (m, 1H), 7.19-7.14 (m, 1H), 4.24 (t, J=12.00 Hz, 2H), 3.45 (t, J=12.00 Hz, 2H), 2.97 (s, 3H).

2-[1-(3-Fluoro-benzoyl)-4,5-dihydro-1H-pyrazol-3-yl]-N,N-dimethyl-benzamide

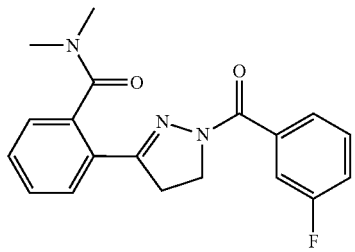 [SMILES: CN(C)C(=O)c1ccccc1C1=NN(C(=O)c2cccc(F)c2)CC1]

Off white solid; 52.29% Yield

LC-MS: Mass found (M+, 340.0). Rt (min): 3.33; % Area: 99.53 (Max), 99.21 (254 nm).

HPLC—Rt (min): 3.39; % Area: 99.31 (Max), 99.28 (254 nm).

400 MHz, CDCl3: δ 7.66-7.63 (m, 1H), 7.56-7.52 (m, 2H), 7.46-7.40 (m, 3H), 7.27-7.24 (m, 1H), 7.21-7.18 (m, 1H), 4.22 (t, J=12.00 Hz, 2H), 3.31 (t, J=12.00 Hz, 2H), 2.69 (s, 3H), 2.57 (s, 3H).

[3-(4-Chloro-3-methoxy-phenyl)-4,5-dihydro-pyrazol-1-yl]-(3-fluoro-phenyl)-methanone

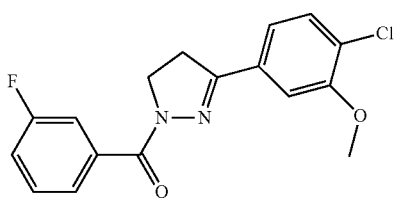 [SMILES: COc1cc(C2=NN(C(=O)c3cccc(F)c3)CC2)ccc1Cl]

White solid; 50.44% Yield

LC-MS: Mass found (M+, 333.0). Rt (min): 4.96; % Area: 96.37 (Max), 96.96 (254 nm).

HPLC—Rt (min): 4.92; % Area: 97.08 (Max), 96.70 (254 nm).

400 MHz, CDCl3: δ 7.80-7.74 (m, 2H), 7.45-7.40 (m, 2H), 7.33-0.00 (m, 1H), 7.24-7.21 (m, 1H), 7.17-7.14 (m, 1H), 4.29 (t, J=12.00 Hz, 2H), 3.93 (s, 3H), 3.29 (t, J=8.00 Hz, 2H).

4-[1-(3-Fluoro-benzoyl)-4,5-dihydro-1H-pyrazol-3-yl]-2-methoxy-benzoic acid

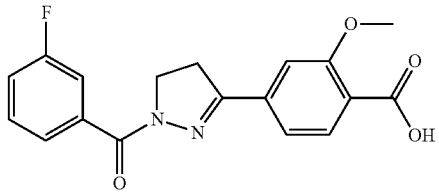 [SMILES: COc1cc(C2=NN(C(=O)c3cccc(F)c3)CC2)ccc1C(=O)O]

Grey solid; 100% Yield

LC-MS: Mass found (M+, 343.0). Rt (min): 3.50; % Area: 91.12 (Max), 90.07 (254 nm).

HPLC—Rt (min): 3.53; % Area: 92.15 (Max), 90.03 (254 nm).

400 MHz, DMSO-d6: δ 12.81 (brs, 1H), 7.75-7.64 (m, 3H), 7.57-7.52 (m, 1H), 7.42-7.37 (m, 1H), 7.33-7.31 (m, 2H), 4.15 (t, J=8.00 Hz, 2H), 3.84 (s, 3H), 3.40-3.32 (m, 2H).

[3-(4-Fluoro-3-methoxy-phenyl)-4,5-dihydro-pyrazol-1-yl]-(3-fluoro-phenyl)-methanone

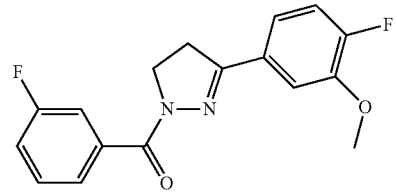 [SMILES: COc1cc(C2=NN(C(=O)c3cccc(F)c3)CC2)ccc1F]

White solid; 100% Yield

LC-MS: Mass found (M+, 317.0). Rt (min): 4.56; % Area: 91.74 (Max), 97.03 (254 nm).

HPLC—Rt (min): 4.61; % Area: 94.59 (Max), 98.11 (254 nm).

400 MHz, CDCl3: δ 7.80-7.74 (m, 2H), 7.45-7.38 (m, 2H), 7.23-7.12 (m, 3H), 4.29 (t, J=8.00 Hz, 2H), 3.94-3.92 (m, 3H), 3.28 (t, J=12.00 Hz, 2H).

(3-Fluoro-phenyl)-[3-(3-methoxy-4-methyl-phenyl)-4,5-dihydro-pyrazol-1-yl]-methanone

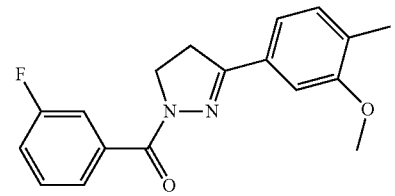 [SMILES: COc1cc(C2=NN(C(=O)c3cccc(F)c3)CC2)ccc1C]

White solid; 9.55% Yield

LC-MS: Mass found (M+, 313.0). Rt (min): 4.93; % Area: 96.69 (Max), 97.70 (254 nm).

HPLC—Rt (min): 4.99; % Area: 96.88 (Max), 97.19 (254 nm).

400 MHz, CDCl3: δ 7.81 (t, J=8.00 Hz, 2H), 7.45-7.39 (m, 1H), 7.24-7.19 (m, 3H), 7.18-7.17 (m, 2H), 4.27 (t, J=8.00 Hz, 2H), 3.86 (s, 3H), 3.29 (t, J=12.00 Hz, 2H), 2.26 (s, 3H).

[3-(4-Benzyloxy-3-methoxy-phenyl)-4,5-dihydro-pyrazol-1-yl]-(3-fluoro-phenyl)-methanone

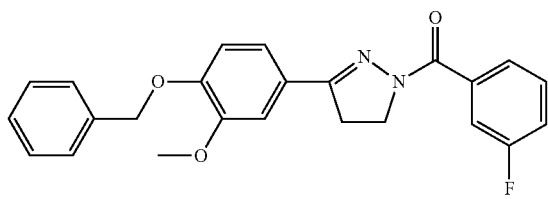 [SMILES: COc1cc(C2=NN(C(=O)c3cccc(F)c3)CC2)ccc1OCc1ccccc1]

White solid; 10.72% Yield

LC-MS: Mass found (M+, 405.0). Rt (min): 5.18; % Area: 98.51 (Max), 97.41 (220 nm).

HPLC—Rt (min): 5.19; % Area: 97.35 (Max), 99.08 (254 nm).

400 MHz, CDCl3: δ 7.79 (t, J=8.00 Hz, 2H), 7.45-7.31 (m, 7H), 7.22-7.18 (m, 1H), 7.13-7.10 (m, 1H), 6.89 (d, J=8.00 Hz, 1H), 5.22 (s, 2H), 4.25 (t, J=12.00 Hz, 2H), 3.92 (s, 3H), 3.26 (t, J=8.00 Hz, 2H).

4-[1-(3-Fluoro-benzoyl)-4,5-dihydro-1H-pyrazol-3-yl]-2-methoxy-benzonitrile

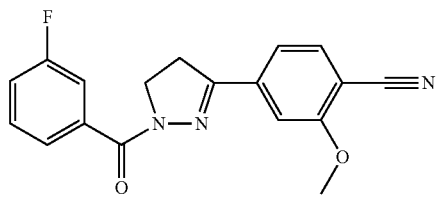 [SMILES: COc1cc(C2=NN(C(=O)c3cccc(F)c3)CC2)ccc1C#N]

Off white solid; 71.84% Yield

LC-MS: Mass found (M+, 324.0). Rt (min): 4.41; % Area: 99.68 (Max), 99.45 (254 nm).

HPLC—Rt (min): 4.49; % Area: 99.48 (Max), 99.19 (254 nm).

400 MHz, CDCl3: δ 7.62-7.60 (m, 2H), 7.46-7.44 (m, 1H), 7.42-7.40 (m, 1H), 7.32-7.26 (m, 1H), 7.24-7.20 (m, 2H), 4.32 (t, J=12.00 Hz, 2H), 3.96 (s, 3H), 3.30 (t, J=8.00 Hz, 2H).

[3-(2,4-Dimethoxy-phenyl)-4,5-dihydro-pyrazol-1-yl]-(3-fluoro-phenyl)-methanone

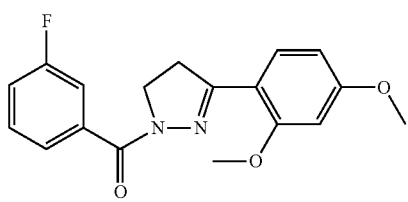 [SMILES: COc1ccc(C2=NN(C(=O)c3cccc(F)c3)CC2)c(OC)c1]

Grey solid; 72.76% Yield

LC-MS: Mass found (M+, 329.0). Rt (min): 4.47; % Area: 97.16 (Max), 98.36 (254 nm).

HPLC—Rt (min): 4.54; % Area: 96.70 (Max), 98.61 (254 nm).

400 MHz, CDCl3: δ 7.87-7.83 (m, 2H), 7.68 (d, J=12.00 Hz, 1H), 7.43-7.37 (m, 1H), 7.20-7.15 (m, 1H), 6.54 (dd, J=8.00, 4.00 Hz, 1H), 6.50 (d, J=4.00 Hz, 1H), 4.18 (t, J=12.00 Hz, 2H), 3.88 (s, 3H), 3.86 (s, 3H), 3.38 (t, J=12.00 Hz, 2H).

(3-Fluoro-phenyl)-[3-(4-methoxy-2-methyl-phenyl)-4,5-dihydro-pyrazol-1-yl]-methanone

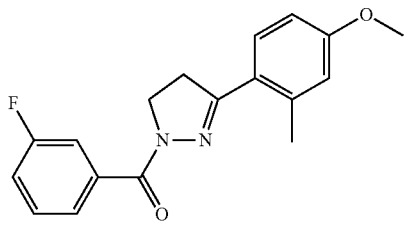 [SMILES: COc1ccc(C2=NN(C(=O)c3cccc(F)c3)CC2)c(C)c1]

White Solid; 44.94% Yield

LC-MS: Mass found (M+, 313.3). Rt (min): 4.71; % Area: 99.43 (Max), 99.14 (254 nm).

HPLC—Rt (min): 4.74; % Area: 98.94 (Max), 98.51 (220 nm).

400 MHz, CDCl3: δ 7.78-7.71 (m, 2H), 7.42-7.36 (m, 2H), 7.19-7.14 (m, 1H), 6.80-6.78 (m, 1H), 4.19 (t, J=8.00 Hz, 2H), 3.84 (s, 3H), 3.33 (t, J=12.00 Hz, 2H), 2.51 (s, 3H).

(3-Fluoro-phenyl)-[3-(4-methoxy-2-trifluoromethyl-phenyl)-4,5-dihydro-pyrazol-1-yl]-methanone

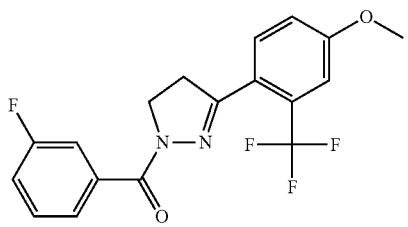 [SMILES: COc1ccc(C2=NN(C(=O)c3cccc(F)c3)CC2)c(C(F)(F)F)c1]

Yellow gum; 43.71% Yield

LC-MS: Mass found (M+, 367.0). Rt (min): 4.90; % Area: 95.75 (Max), 97.14 (254 nm).

HPLC—Rt (min): 4.97; % Area: 92.76 (Max), 96.42 (254 nm).

400 MHz, CDCl3: δ 7.74 (d, J=8.00 Hz, 1H), 7.69-7.66 (m, 1H), 7.50 (d, J=8.00 Hz, 1H), 7.40-7.34 (m, 1H), 7.28-7.27 (m, 1H), 7.18-7.14 (m, 1H), 7.10-7.07 (m, 1H), 4.27 (t, J=8.00 Hz, 2H), 3.89 (s, 3H), 3.27 (t, J=12.00 Hz, 2H).

[3-(2-Chloro-4-methoxy-phenyl)-4,5-dihydro-pyrazol-1-yl]-(3-fluoro-phenyl)-methanone

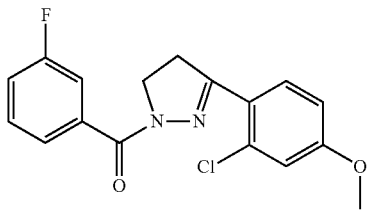 [SMILES: COc1ccc(C2=NN(C(=O)c3cccc(F)c3)CC2)c(Cl)c1]

White Solid; 8.75% Yield
LC-MS: Mass found (M+, 333). Rt (min): 4.80; % Area: 96.09 (Max), 93.73 (254 nm).
HPLC—Rt (min): 4.79; % Area: 96.35 (Max), 94.47 (254 nm).
400 MHz, CDCl3: δ 7.82-7.75 (m, 2H), 7.62 (d, J=12.00 Hz, 1H), 7.43-7.37 (m, 1H), 7.21-7.15 (m, 1H), 6.98 (d, J=4.00 Hz, 1H), 6.87-6.84 (m, 1H), 4.25 (t, J=8.00 Hz, 2H), 3.85 (s, 3H), 3.45 (t, J=12.00 Hz, 2H).

[3-(2-Fluoro-4-methoxy-phenyl)-4,5-dihydro-pyrazol-1-yl]-(3-fluoro-phenyl)-methanone

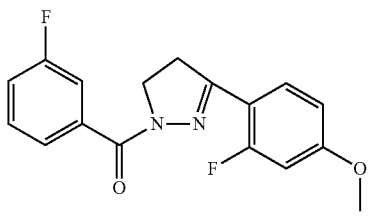

White Solid; 72.23% Yield
LC-MS: Mass found (M+, 317.3). Rt (min): 4.70; % Area: 96.67 (Max), 95.03 (220 nm).
HPLC—Rt (min): 4.62; % Area: 98.12 (Max), 97.77 (254 nm).
400 MHz, CDCl3: δ 7.81-7.74 (m, 3H), 7.44-7.39 (m, 1H), 7.22-7.17 (m, 1H), 6.75 (dd, J=8.00 Hz, 4.00, Hz, 1H), 6.67-6.63 (m, 1H), 4.23 (t, J=12.00 Hz, 2H), 3.85 (s, 3H), 3.40-3.34 (m, 2H).

(3-Fluoro-phenyl)-[3-(4-methoxy-2-trifluoromethoxy-phenyl)-4,5-dihydro-pyrazol-1-yl]-methanone

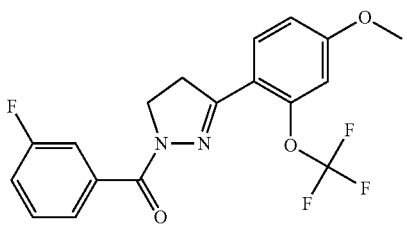 [SMILES: COc1ccc(C2=NN(C(=O)c3cccc(F)c3)CC2)c(OC(F)(F)F)c1]

White solid; 29.40% Yield
LC-MS: Mass found (M+, 383.3). Rt (min): 5.16; % Area: 98.97 (Max), 98.63 (254 nm).
HPLC—Rt (min): 5.16; % Area: 99.47 (Max), 99.84 (254 nm).
400 MHz, CDCl3: δ 7.79-7.69 (m, 2H), 7.72-7.69 (m, 1H), 7.43-7.38 (m, 1H), 7.21-7.16 (m, 1H), 6.89-6.84 (m, 2H), 4.24 (t, J=8.00 Hz, 2H), 3.87 (s, 3H), 3.35 (t, J=8.00 Hz, 2H).

(3-Fluoro-phenyl)-[3-(2-hydroxymethyl-4-methoxy-phenyl)-4,5-dihydro-pyrazol-1-yl]-methanone

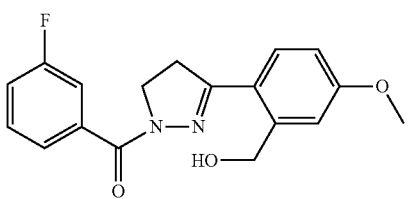 [SMILES: COc1ccc(C2=NN(C(=O)c3cccc(F)c3)CC2)c(CO)c1]

Off white solid; 43.16% Yield
LC-MS: Mass found (M+, 329.0). Rt (min): 3.48; % Area: 99.68 (Max), 99.46 (254 nm).
HPLC—Rt (min): 3.60; % Area: 99.78 (Max), 99.67 (254 nm).
400 MHz, CDCl3: δ 7.52-7.47 (m, 1H), 7.46-7.40 (m, 3H), 7.22-7.20 (m, 1H), 7.19-7.17 (m, 1H), 6.96-6.88 (m, 1H), 4.51 (s, 2H), 4.23 (t, J=8.00 Hz, 2H), 3.86 (s, 3H), 3.41 (t, J=8.00 Hz, 2H).

[3-(2-Fluoro-3-methoxy-phenyl)-4,5-dihydro-pyrazol-1-yl]-(3-fluoro-phenyl)-methanone

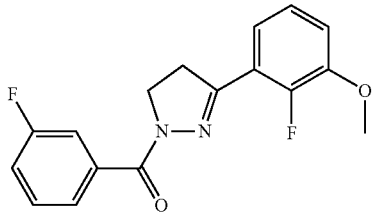 [SMILES: COc1cccc(C2=NN(C(=O)c3cccc(F)c3)CC2)c1F]

Off white solid; 33.35% Yield
LC-MS: Mass found (M+, 317.0). Rt (min): 4.41; % Area: 99.73 (Max), 99.92 (254 nm).
HPLC—Rt (min): 4.54; % Area: 99.51 (Max), 99.65 (254 nm).
400 MHz, CDCl3: δ 7.79-7.72 (m, 1H), 7.44-7.42 (m, 1H), 7.40-7.36 (m, 2H), 7.22-7.19 (m, 1H), 7.17-7.10 (m, 1H), 7.10-7.00 (m, 1H), 4.26 (t, J=8.00 Hz, 2H), 3.92 (s, 3H), 3.44-3.38 (m, 2H).

[3-(2,3-Dimethoxy-phenyl)-4,5-dihydro-pyrazol-1-yl]-(3-fluoro-phenyl)-methanone

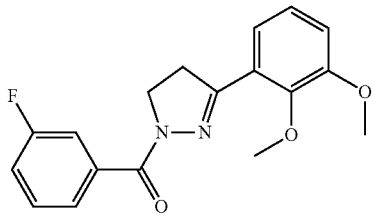 [SMILES: COc1cccc(C2=NN(C(=O)c3cccc(F)c3)CC2)c1OC]

Off white solid; 59.74% Yield

LC-MS: Mass found (M+, 329.0). Rt (min): 4.45; % Area: 97.93 (Max), 98.83 (254 nm).

HPLC—Rt (min): 4.46; % Area: 97.56 (Max), 98.13 (254 nm).

400 MHz, CDCl3: δ 7.80 (d, J=8.00 Hz, 1H), 7.76-7.73 (m, 1H), 7.43-7.38 (m, 1H), 7.34-7.32 (m, 1H), 7.21-7.15 (m, 1H), 7.08 (t, J=8.00 Hz, 1H), 6.99 (dd, J=8.00, 4.00 Hz, 1H), 4.23 (t, J=12.00 Hz, 2H), 3.90 (s, 3H), 3.85 (s, 3H), 3.43 (t, J=8.00 Hz, 2H).

(3-Fluoro-phenyl)-[3-(2-hydroxy-3-methoxy-phenyl)-4,5-dihydro-pyrazol-1-yl]-methanone

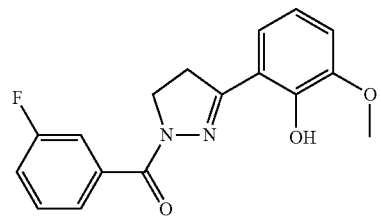 [SMILES: COc1cccc(C2=NN(C(=O)c3cccc(F)c3)CC2)c1O]

Off white solid; 21.92% Yield

LC-MS: Mass found (M+, 315.0). Rt (min): 3.95; % Area: 97.35 (Max), 97.55 (254 nm).

HPLC—Rt (min): 4.04; % Area: 98.52 (Max), 98.60 (220 nm).

400 MHz, CDCl3: δ 7.58-7.56 (m, 1H), 7.49-7.42 (m, 2H), 7.21-7.16 (m, 1H), 7.01-6.95 (m, 1H), 6.94-6.89 (m, 2H), 4.24 (t, J=8.00 Hz, 2H), 3.91 (s, 3H), 3.44 (t, J=12.00 Hz, 2H).

(3-Fluoro-phenyl)-[3-(2,3,4-trimethoxy-phenyl)-4,5-dihydro-pyrazol-1-yl]-methanone

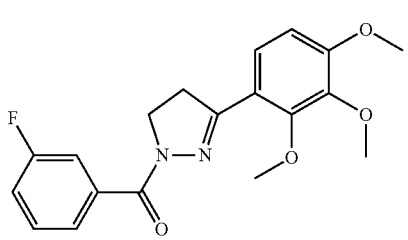 [SMILES: COc1ccc(C2=NN(C(=O)c3cccc(F)c3)CC2)c(OC)c1OC]

White solid; 49.44% Yield

LC-MS: Mass found (M+, 359.0). Rt (min): 4.38; % Area: 95.44 (Max), 97.08 (254 nm).

HPLC—Rt (min): 4.40; % Area: 95.40 (Max), 96.51 (254 nm).

400 MHz, CDCl3: δ 7.81-7.75 (m, 2H), 7.46-7.37 (m, 2H), 7.20-7.15 (m, 2H), 4.21 (t, J=8.00 Hz, 2H), 3.91 (s, 6H), 3.88 (s, 3H), 3.38 (t, J=12.00 Hz, 2H).

(3-Fluoro-phenyl)-[3-(1H-indol-5-yl)-4,5-dihydro-pyrazol-1-yl]-methanone

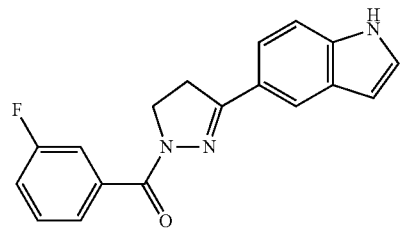 [SMILES: O=C(c1cccc(F)c1)N1CCC(c2ccc3[nH]ccc3c2)=N1]

Off white solid; 12.44% Yield

LC-MS: Mass found (M+, 308.3). Rt (min): 4.09; % Area: 98.67 (Max), 99.43 (254 nm).

HPLC—Rt (min): 4.10; % Area: 98.73 (Max), 99.13 (254 nm).

400 MHz, CDCl3: δ 8.32 (brs, 1H), 7.91 (brs, 1H), 7.87-7.80 (m, 2H), 7.72 (d, J=8.00 Hz, 1H), 7.53-7.42 (m, 2H), 7.27 (s, 1H), 7.23-7.19 (m, 1H), 6.63 (brs, 1H), 4.29 (t, J=8.00 Hz, 2H), 3.39 (t, J=8.00 Hz, 2H).

[3-(2,3-Dihydro-benzofuran-5-yl)-4,5-dihydro-pyrazol-1-yl]-(3-fluoro-phenyl)-methanone

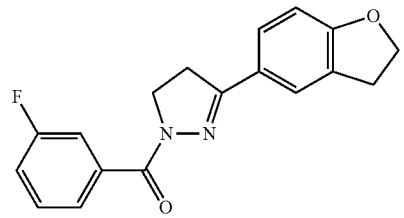 [SMILES: O=C(c1cccc(F)c1)N1CCC(c2ccc3c(c2)CCO3)=N1]

White solid; 40.77% Yield

LC-MS: Mass found (M+, 311.0). Rt (min): 4.33; % Area: 98.26 (Max), 97.53 (254 nm).

HPLC—Rt (min): 4.44; % Area: 98.34 (Max), 97.57 (254 nm).

400 MHz, CDCl3: δ 7.60-7.73 (m, 1H), 7.45-7.45 (m, 1H), 7.44-7.43 (m, 1H), 7.42-7.39 (m, 2H), 7.22-7.16 (m, 1H), 6.81 (d, J=8.40 Hz, 1H), 4.64 (t, J=8.00 Hz, 2H), 4.24 (t, J=8.00 Hz, 2H), 3.28-3.23 (m, 4H).

(3-Fluoro-phenyl)-[3-(1H-indol-6-yl)-4,5-dihydro-pyrazol-1-yl]-methanone

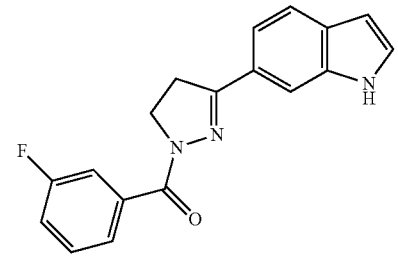 [SMILES: O=C(c1cccc(F)c1)N1CCC(c2ccc3cc[nH]c3c2)=N1]

Off white solid; 58.08% Yield

LC-MS: Mass found (M+, 308.0). Rt (min): 4.35; % Area: 94.89 (Max), 98.41 (254 nm).

HPLC—Rt (min): 4.45; % Area: 96.20 (Max), 99.28 (254 nm).

400 MHz, CDCl3: δ 8.35 (brs, 1H), 7.83-7.82 (m, 3H), 7.79-7.76 (m, 1H), 7.68-7.65 (m, 1H), 7.54-7.51 (m, 1H), 7.47-7.41 (m, 1H), 7.27-7.21 (m, 1H), 6.61-6.69 (m, 1H), 4.31-4.26 (m, 2H), 3.39-3.34 (m, 2H).

(3-Fluoro-phenyl)-[3-(1-methyl-1H-indol-5-yl)-4,5-dihydro-pyrazol-1-yl]-methanone

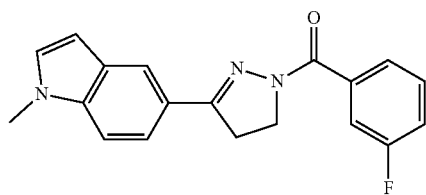 [SMILES: Cn1ccc2cc(C3=NN(C(=O)c4cccc(F)c4)CC3)ccc21]

White solid; 35.36% Yield

LC-MS: Mass found (M+, 322.0). Rt (min): 4.53; % Area: 98.26 (Max), 98.89 (254 nm).

HPLC—Rt (min): 4.70; % Area: 97.78 (Max), 98.34 (254 nm).

400 MHz, CDCl3: δ 7.88-7.78 (m, 4H), 7.47-7.45 (m, 1H), 7.43-7.41 (m, 1H), 7.35-7.33 (m, 1H), 7.23-7.19 (m, 1H), 7.11-7.10 (m, 1H), 4.32-4.25 (m, 2H), 3.83-3.79 (m, 3H), 3.44-3.36 (m, 2H).

[3-(1-Benzenesulfonyl-1H-indol-6-yl)-4,5-dihydro-pyrazol-1-yl]-(3-fluoro-phenyl)-methanone

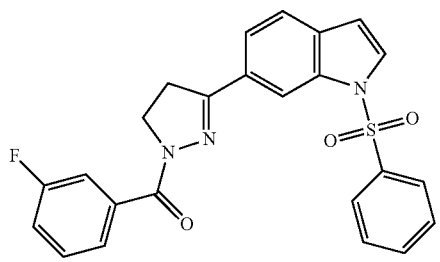 [SMILES: O=C(c1cccc(F)c1)N1CCC(c2ccc3ccn(S(=O)(=O)c4ccccc4)c3c2)=N1]

White solid; 1.91% Yield

LC-MS: Mass found (M+, 448.0). Rt (min): 5.15; % Area: 96.93 (Max), 98.12 (254 nm).

HPLC—Rt (min): 5.16; % Area: 97.39 (Max), 98.18 (254 nm).

400 MHz, CDCl3: δ 8.26 (s, 1H), 7.89-7.82 (m, 4H), 7.68-7.65 (m, 2H), 7.57-7.55 (m, 2H), 7.48-7.44 (m, 3H), 7.24-7.21 (m, 1H), 6.71 (d, J=4.00 Hz, 1H), 4.32 (t, J=8.00 Hz, 2H), 3.39 (t, J=8.00 Hz, 2H).

(3-Benzofuran-5-yl-4,5-dihydro-pyrazol-1-yl)-(3-fluoro-phenyl)-methanone

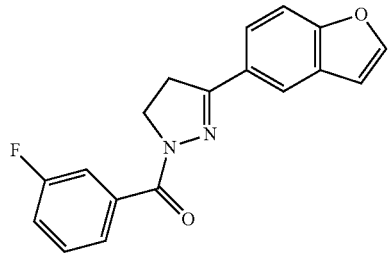 [SMILES: O=C(c1cccc(F)c1)N1CCC(c2ccc3occc3c2)=N1]

Off white solid; 95.49% Yield

LC-MS: Mass found (M+, 309.0). Rt (min): 4.76; % Area: 99.04 (Max), 97.95 (254 nm).

HPLC—Rt (min): 4.76; % Area: 98.86 (Max), 99.18 (254 nm).

400 MHz, CDCl3: δ 7.82-7.80 (m, 1H), 7.76-7.73 (m, 2H), 7.68-7.55 (m, 1H), 7.53-7.47 (m, 1H), 7.46-7.45 (m, 1H), 7.44-7.42 (m, 1H), 7.24-7.19 (m, 1H), 6.83-6.80 (m, 1H), 4.32-4.27 (m, 2H), 3.37 (t, J=10.40 Hz, 2H).

(3-Benzo[b]thiophen-5-yl-4,5-dihydro-pyrazol-1-yl)-(3-fluoro-phenyl)-methanone

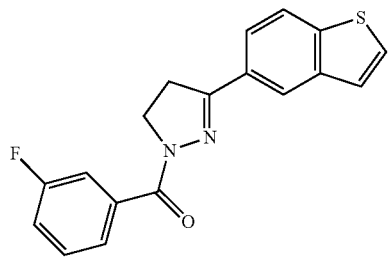 [SMILES: O=C(c1cccc(F)c1)N1CCC(c2ccc3sccc3c2)=N1]

Off white solid; 79.55% Yield

LC-MS: Mass found (M+, 325.0). Rt (min): 4.92; % Area: 91.98 (Max), 94.40 (254 nm).

HPLC—Rt (min): 4.92; % Area: 91.38 (Max), 93.89 (254 nm).

400 MHz, CDCl3: δ 7.82-7.81 (m, 1H), 7.75-7.73 (m, 2H), 7.65-7.56 (m, 1H), 7.53-7.47 (m, 1H), 7.46-7.43 (m, 1H), 7.44-7.40 (m, 1H), 7.24-7.19 (d, J=8 Hz, 1H), 6.83 (d, J=8 Hz, 1H), 4.32-4.27 (m, 2H), 3.35 (t, J=10.40 Hz, 2H).

(3-Fluoro-phenyl)-[3-(1-methyl-1H-indazol-6-yl)-4,5-dihydro-pyrazol-1-yl]-methanone

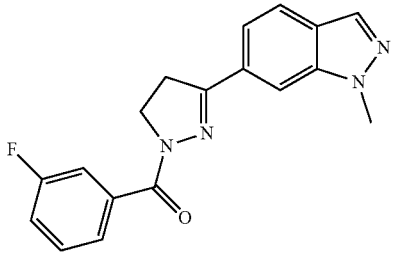 [SMILES: Cn1ncc2ccc(C3=NN(C(=O)c4cccc(F)c4)CC3)cc21]

Off white solid; 25.17% Yield

LC-MS: Mass found (M+, 323.0). Rt (min): 4.04; % Area: 94.55 (Max), 91.93 (254 nm).

HPLC—Rt (min): 4.12; % Area: 96.92 (Max), 96.75 (254 nm).

400 MHz, CDCl3: δ 8.00 (s, 1H), 7.84-7.76 (m, 1H), 7.74-7.73 (m, 2H), 7.63-7.60 (m, 2H), 7.48-7.42 (m, 1H), 7.27-7.20 (m, 1H), 4.33 (t, J=8.00 Hz, 2H), 4.13 (s, 3H), 3.43-3.38 (m, 2H).

(3-Fluoro-phenyl)-[3-(3-methyl-3H-benzoimidazol-5-yl)-4,5-dihydro-pyrazol-1-yl]-methanone

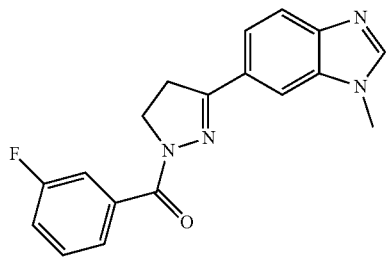 [SMILES: Cn1cnc2ccc(C3=NN(C(=O)c4cccc(F)c4)CC3)cc21]

White solid; 37.75% Yield

LC-MS: Mass found (M+, 323.0). Rt (min): 3.26; % Area: 94.53 (Max), 96.10 (220 nm).

HPLC—Rt (min): 2.67; % Area: 98.44 (Max), 97.92 (254 nm).

400 MHz, CDCl3: δ 10.23-10.21 (s, 1H), 8.08-8.05 (m, 1H), 7.95-7.93 (m, 1H), 7.89-7.88 (m, 1H), 7.77-7.76 (m, 1H), 7.71-7.69 (m, 1H), 7.52-7.45 (m, 1H), 7.27-7.22 (m, 1H), 4.36 (t, J=12.00 Hz, 2H), 4.27 (s, 3H), 3.40 (t, J=12.00 Hz, 2H).

(3-Fluoro-phenyl)-[3-(2-methyl-benzooxazol-6-yl)-4,5-dihydro-pyrazol-1-yl]-methanone

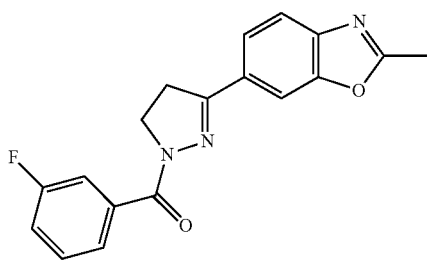 [SMILES: Cc1nc2ccc(C3=NN(C(=O)c4cccc(F)c4)CC3)cc2o1]

Brown solid; 70.60% Yield

LC-MS: Mass found (M+, 324.0). Rt (min): 3.94; % Area: 98.34 (Max), 97.96 (220 nm).

HPLC—Rt (min): 3.93; % Area: 99.03 (Max), 97.94 (254 nm).

400 MHz, CDCl3: δ 7.83-7.80 (m, 2H), 7.76-7.74 (m, 1H), 7.68 (d, J=4.00 Hz, 2H), 7.47-7.42 (m, 1H), 7.25-7.20 (m, 1H), 4.31 (t, J=12.00 Hz, 2H), 3.36 (t, J=8.00 Hz, 2H), 2.68 (s, 3H).

(3-Fluoro-phenyl)-(3-indan-5-yl-4,5-dihydro-pyrazol-1-yl)-methanone

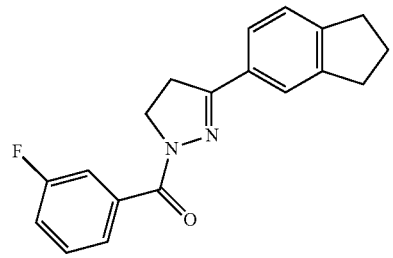 [SMILES: O=C(c1cccc(F)c1)N1CCC(c2ccc3c(c2)CCC3)=N1]

Light brown solid; 19.19% Yield

LC-MS: Mass found (M+, 309.2). Rt (min): 5.19; % Area: 96.85 (Max), 98.04 (254 nm).

HPLC—Rt (min): 5.21; % Area: 96.41 (Max), 98.34 (254 nm).

400 MHz, CDCl3: δ 7.81 (d, J=8.00 Hz, 1H), 7.77-7.74 (m, 1H), 7.49-7.40 (m, 2H), 7.26-7.25 (m, 2H), 7.23-7.18 (m, 1H), 4.26 (t, J=8.00 Hz, 2H), 3.29 (t, J=8.00 Hz, 2H), 2.96-2.93 (m, 4H), 2.15-2.08 (m, 2H).

6-[1-(3-Fluoro-benzoyl)-4,5-dihydro-1H-pyrazol-3-yl]-2,3-dihydro-isoindol-1-one

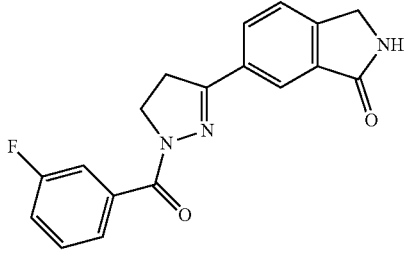 [SMILES: O=C1NCc2ccc(C3=NN(C(=O)c4cccc(F)c4)CC3)cc21]

White solid; 38.84% Yield

LC-MS: Mass found (M+, 324.0). Rt (min): 3.11; % Area: 97.97 (Max), 98.73 (254 nm).

HPLC—Rt (min): 3.11; % Area: 99.20 (Max), 99.38 (254 nm).

400 MHz, CDCl3: δ 8.09-8.06 (m, 2H), 7.79 (d, J=8.00 Hz, 1H), 7.73-7.71 (m, 1H), 7.54 (d, J=8.00 Hz, 1H), 7.48-7.42 (m, 1H), 7.24-7.20 (m, 1H), 4.53 (s, 2H), 4.34-4.29 (m, 2H), 3.38-3.33 (m, 2H).

(3-Fluoro-phenyl)-(3-naphthalen-2-yl-4,5-dihydro-pyrazol-1-yl)-methanone

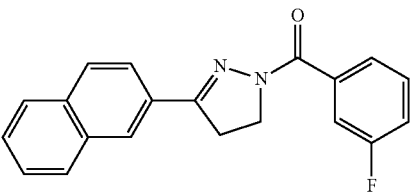 [SMILES: O=C(c1cccc(F)c1)N1CCC(c2ccc3ccccc3c2)=N1]

227

White solid; 76.65% Yield

LC-MS: Mass found (M+, 319.0). Rt (min): 5.05; % Area: 98.80 (Max), 99.47 (254 nm).

HPLC—Rt (min): 5.10; % Area: 99.48 (Max), 99.72 (254 nm).

400 MHz, CDCl3: δ 7.98-7.96 (m, 2H), 7.91-7.84 (m, 4H), 7.81-7.79 (m, 1H), 7.58-7.53 (m, 2H), 7.49-7.43 (m, 1H), 7.26-7.21 (m, 1H), 4.34 (t, J=8.00 Hz, 2H), 3.46-3.41 (m, 2H).

[3-(2,3-Dihydro-benzo[1,4]dioxin-6-yl)-4,5-dihydro-pyrazol-1-yl]-(3-fluoro-phenyl)-methanone

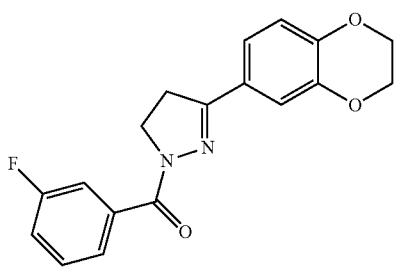 [SMILES: O=C(c1cccc(F)c1)N1CCC(c2ccc3c(c2)OCCO3)=N1]

White solid; 80.13% Yield

LC-MS: Mass found (M+, 327.0). Rt (min): 4.34; % Area: 95.92 (Max), 98.10 (254 nm).

HPLC—Rt (min): 4.42; % Area: 95.32 (Max), 97.92 (254 nm).

400 MHz, CDCl3: δ 7.80-7.78 (m, 1H), 7.73-7.71 (m, 1H), 7.42-7.38 (m, 1H), 7.26-7.16 (m, 3H), 6.95-6.88 (m, 1H), 4.31-4.26 (m, 4H), 4.23-4.21 (m, 2H), 3.23 (t, J=8.00 Hz, 2H).

(3-Fluoro-phenyl)-(3-quinolin-6-yl-4,5-dihydro-pyrazol-1-yl)-methanone

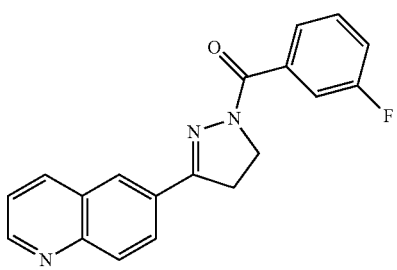 [SMILES: O=C(c1cccc(F)c1)N1CCC(c2ccc3ncccc3c2)=N1]

White solid; 14.02% Yield

LC-MS: Mass found (M+, 320.0). Rt (min): 2.75; % Area: 94.85 (Max), 96.42 (254 nm).

HPLC—Rt (min): 2.77; % Area: 96.57 (Max), 98.30 (254 nm).

400 MHz, CDCl3: δ 9.02-9.00 (m, 1H), 8.68-8.66 (m, 2H), 8.40-8.37 (m, 1H), 8.14 (s, 1H), 7.82-7.79 (m, 2H), 7.73-7.71 (m, 1H), 7.75-7.45 (m, 1H), 7.28-7.23 (m, 1H), 4.39 (t, J=8.00 Hz, 2H), 3.44 (t, J=12.00 Hz, 2H).

228

(3-Chroman-6-yl-4,5-dihydro-pyrazol-1-yl)-(3-fluoro-phenyl)-methanone

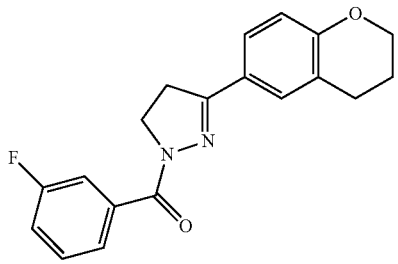 [SMILES: O=C(c1cccc(F)c1)N1CCC(c2ccc3c(c2)CCCO3)=N1]

White solid; 18.10% Yield

LC-MS: Mass found (M+, 325.3). Rt (min): 4.68; % Area: 96.60 (Max), 94.10 (220 nm).

HPLC—Rt (min): 2.41; % Area: 99.93 (Max), 99.28 (254 nm).

400 MHz, CDCl3: δ 7.81 (d, J=4.00 Hz, 1H), 7.76-7.74 (m, 1H), 7.47-7.38 (m, 3H), 7.22-7.17 (m, 1H), 6.82 (d, J=8.00 Hz, 1H), 4.26-4.21 (m, 4H), 3.27-3.22 (m, 2H), 2.82 (t, J=8.00 Hz, 2H), 2.07-2.01 (m, 2H).

(3-Fluoro-phenyl)-(3-pyridin-4-yl-4,5-dihydro-pyrazol-1-yl)-methanone

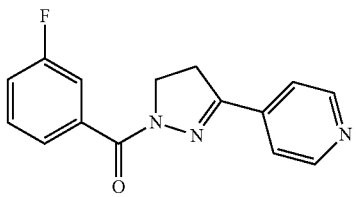 [SMILES: O=C(c1cccc(F)c1)N1CCC(c2ccncc2)=N1]

White solid; 12.99% Yield

LC-MS: Mass found (M+, 270.0). Rt (min): 2.23; % Area: 98.21 (Max), 96.25 (220 nm).

HPLC—Rt (min): 2.27; % Area: 98.52 (Max), 95.92 (254 nm).

400 MHz, CDCl3: δ 8.71-8.69 (m, 2H), 7.77 (d, J=8.00 Hz, 1H), 7.72-7.69 (m, 1H), 7.55-7.54 (m, 2H), 7.47-7.42 (m, 1H), 7.24-7.21 (m, 1H), 4.33 (t, J=8.00 Hz, 2H), 3.30 (t, J=12.00 Hz, 2H).

[3-(5-Fluoro-2-methoxy-pyridin-4-yl)-4,5-dihydro-pyrazol-1-yl]-(3-fluoro-phenyl)-methanone

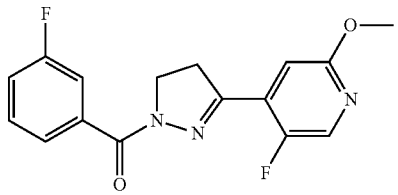 [SMILES: COc1cc(C2=NN(C(=O)c3cccc(F)c3)CC2)c(F)cn1]

Light brown solid; 20.33% Yield

LC-MS: Mass found (M+, 318.0). Rt (min): 4.36; % Area: 97.91 (Max), 95.52 (220 nm).

HPLC—Rt (min): 4.36; % Area: 97.83 (Max), 96.12 (254 nm).
400 MHz, CDCl3: δ 8.10 (d, J=4.00 Hz, 1H), 7.79-7.76 (m, 1H), 7.72-7.68 (m, 1H), 7.46-7.40 (m, 1H), 7.24-7.19 (m, 1H), 7.06 (d, J=4.00 Hz, 1H), 4.29 (t, J=8.00 Hz, 2H), 3.93 (s, 3H), 3.40-3.34 (m, 2H).

[3-(3-Chloro-2-methoxy-pyridin-4-yl)-4,5-dihydro-pyrazol-1-yl]-(3-fluoro-phenyl)-methanone

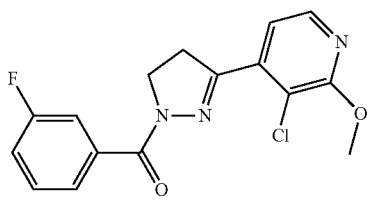 [SMILES: COc1nccc(C2=NN(C(=O)c3cccc(F)c3)CC2)c1Cl]

Off white solid; 43.85% Yield
LC-MS: Mass found (M+, 334.0). Rt (min): 4.56; % Area: 97.24 (Max), 97.32 (220 nm).
HPLC—Rt (min): 4.62; % Area: 98.91 (Max), 98.79 (254 nm).
400 MHz, CDCl3: δ 8.06 (d, J=8.00 Hz, 1H), 7.78-7.76 (m, 1H), 7.73-7.69 (m, 1H), 7.44-7.39 (m, 1H), 7.23-7.17 (m, 2H), 4.30 (t, J=8.00 Hz, 2H), 4.06 (s, 3H), 3.51 (t, J=12.00 Hz, 2H).

(3-Fluoro-phenyl)-[3-(3-methoxy-pyridin-4-yl)-4,5-dihydro-pyrazol-1-yl]-methanone

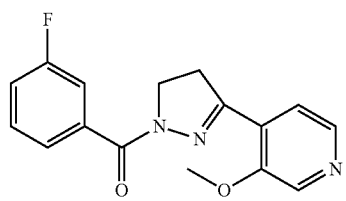 [SMILES: COc1cnccc1C1=NN(C(=O)c2cccc(F)c2)CC1]

White Solid; 38.60% Yield
LC-MS: Mass found (M+, 300). Rt (min): 2.49; % Area: 99.66 (Max), 99.21 (254 nm).
HPLC—Rt (min): 2.55; % Area: 98.14 (Max), 98.58 (254 nm).
400 MHz, CDCl3: δ 8.42 (s, 1H), 8.30 (d, J=4.00 Hz, 1H), 7.80-7.76 (m, 2H), 7.59 (d, J=4.00 Hz, 2H), 7.45-7.41 (m, 1H), 7.24-7.19 (m, 1H), 4.25 (t, J=12.00 Hz, 2H), 4.02 (s, 3H), 3.43 (t, J=8.00 Hz, 2H).

(3-Fluoro-phenyl)-[3-(2-methoxy-pyridin-4-yl)-4,5-dihydro-pyrazol-1-yl]-methanone

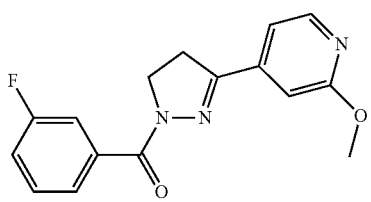 [SMILES: COc1cc(C2=NN(C(=O)c3cccc(F)c3)CC2)ccn1]

Off white solid; 8.49% Yield
LC-MS: Mass found (M+, 300.3). Rt (min): 3.87; % Area: 94.48 (Max), 90.84 (220 nm).
HPLC—Rt (min): 3.74; % Area: 96.03 (Max), 93.16 (254 nm).
400 MHz, CDCl3: δ 8.26-8.24 (m, 1H), 7.76-7.74 (m, 1H), 7.69-7.66 (m, 1H), 7.47-7.41 (m, 1H), 7.31-7.27 (m, 1H), 7.23-7.21 (m, 1H), 6.99 (s, 1H), 4.32 (t, J=12.00 Hz, 2H), 4.14-4.10 (m, 3H), 3.27 (t, J=8.00 Hz, 2H).

(3-Fluoro-phenyl)-[3-(6-methoxy-pyridin-3-yl)-4,5-dihydro-pyrazol-1-yl]-methanone

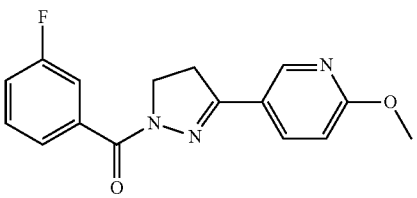 [SMILES: COc1ccc(C2=NN(C(=O)c3cccc(F)c3)CC2)cn1]

White solid; 61.49% Yield
LC-MS: Mass found (M+, 300.0). Rt (min): 3.95; % Area: 98.57 (Max), 96.66 (220 nm).
HPLC—Rt (min): 3.94; % Area: 98.84 (Max), 98.34 (254 nm).
400 MHz, CDCl3: δ 8.40-8.39 (m, 1H), 8.01-7.99 (m, 1H), 7.79-7.71 (m, 2H), 7.45-7.39 (m, 1H), 7.23-7.18 (m, 1H), 6.80 (d, J=8.00 Hz, 1H), 4.28 (t, J=8.00 Hz, 2H), 3.99 (s, 3H), 3.28 (t, J=12.00 Hz, 2H).

(3-Fluoro-phenyl)-[3-(2-methoxy-pyridin-3-yl)-4,5-dihydro-pyrazol-1-yl]-methanone

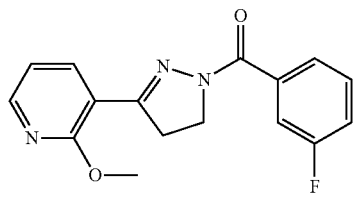 [SMILES: COc1ncccc1C1=NN(C(=O)c2cccc(F)c2)CC1]

White solid; 4.35% Yield
LC-MS: Mass found (M+, 300.3). Rt (min): 4.14; % Area: 96.89 (Max), 98.37 (220 nm).
HPLC—Rt (min): 4.05; % Area: 99.08 (Max), 99.25 (254 nm).
400 MHz, CDCl3: δ 8.24-8.22 (m, 1H), 8.04-8.02 (m, 1H), 7.81-7.78 (m, 2H), 7.44-7.39 (m, 1H), 7.22-7.17 (m, 1H), 6.97-6.94 (m, 1H), 4.23 (t, J=12.00 Hz, 2H), 4.04 (s, 3H), 3.43 (t, J=12.00 Hz, 2H).

(3-Fluoro-phenyl)-[3-(5-methoxy-pyridin-3-yl)-4,5-dihydro-pyrazol-1-yl]-methanone

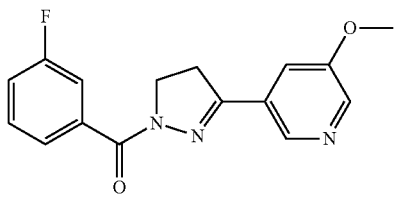 [SMILES: COc1cncc(C2=NN(C(=O)c3cccc(F)c3)CC2)c1]

Off white solid; 66.64% Yield
LC-MS: Mass found (M+, 300.0). Rt (min): 2.81; % Area: 97.26 (Max), 99.15 (254 nm).
HPLC—Rt (min): 2.81; % Area: 99.26 (Max), 99.24 (254 nm).
400 MHz, CDCl3: δ 8.61-8.54 (m, 1H), 8.45-8.37 (m, 1H), 7.95-7.91 (m, 1H), 7.71-7.65 (m, 1H), 7.64-7.61 (m, 1H), 7.48-7.42 (m, 1H), 7.27-7.22 (m, 1H), 4.37 (t, J=8.00 Hz, 2H), 4.00 (s, 3H), 3.33 (t, J=12.00 Hz, 2H).

[3-(5-Fluoro-6-methoxy-pyridin-3-yl)-4,5-dihydro-pyrazol-1-yl]-(3-fluoro-phenyl)-methanone

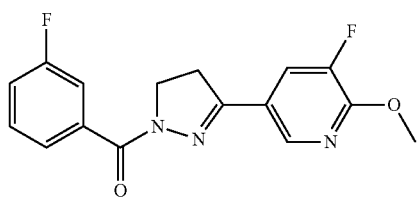 [SMILES: COc1ncc(C2=NN(C(=O)c3cccc(F)c3)CC2)cc1F]

White solid; 7.91% Yield
LC-MS: Mass found (M+, 318.0). Rt (min): 4.24; % Area: 95.74 (Max), 90.08 (220 nm).
HPLC—Rt (min): 4.44; % Area: 97.55 (Max), 95.14 (254 nm).
400 MHz, CDCl3: δ 8.13 (d, J=4.00 Hz, 1H), 7.76-7.73 (m, 2H), 7.69-7.66 (m, 1H), 7.45-7.40 (m, 1H), 7.23-7.19 (m, 1H), 4.29 (t, J=8.00 Hz, 2H), 4.08 (s, 3H), 3.27 (t, J=12.00 Hz, 2H).

[3-(5-Chloro-2-methoxy-pyridin-3-yl)-4,5-dihydro-pyrazol-1-yl]-(3-fluoro-phenyl)-methanone

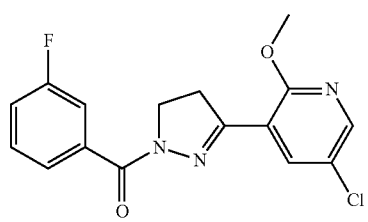 [SMILES: COc1ncc(Cl)cc1C1=NN(C(=O)c2cccc(F)c2)CC1]

White solid; 31.93% Yield
LC-MS: Mass found (M+, 334.0). Rt (min): 4.87; % Area: 92.17 (Max), 93.85 (254 nm).
HPLC—Rt (min): 4.88; % Area: 92.21 (Max), 93.13 (254 nm).
400 MHz, CDCl3: δ 8.16-8.15 (m, 1H), 7.97 (d, J=4.00 Hz, 1H), 7.76 (t, J=8.00 Hz, 2H), 7.46-7.41 (m, 1H), 7.24-7.19 (m, 1H), 4.24 (t, J=8.00 Hz, 2H), 4.02 (s, 3H), 3.41 (t, J=8.00 Hz, 2H).

[3-(5-Chloro-6-methoxy-pyridin-3-yl)-4,5-dihydro-pyrazol-1-yl]-(3-fluoro-phenyl)-methanone

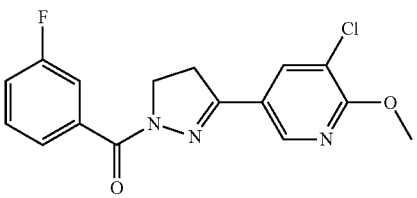 [SMILES: COc1ncc(C2=NN(C(=O)c3cccc(F)c3)CC2)cc1Cl]

Off white solid; 4.62% Yield
LC-MS: Mass found (M+, 334.0). Rt (min): 4.81; % Area: 92.84 (Max), 93.84 (254 nm).
HPLC—Rt (min): 4.93; % Area: 94.76 (Max), 94.37 (254 nm).
400 MHz, CDCl3: δ 8.16-8.15 (m, 1H), 7.97 (d, J=4.00 Hz, 1H), 7.75 (t, J=8.00 Hz, 2H), 7.45-7.40 (m, 1H), 7.23-7.18 (m, 1H), 4.23 (t, J=12.00 Hz, 2H), 4.01 (s, 3H), 3.40 (t, J=12.00 Hz, 2H).

(3-Fluoro-phenyl)-[3-(6-methoxy-2-methyl-pyridin-3-yl)-4,5-dihydro-pyrazol-1-yl]-methanone

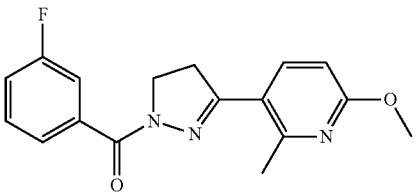 [SMILES: COc1ccc(C2=NN(C(=O)c3cccc(F)c3)CC2)c(C)n1]

White solid; 13.88% Yield
LC-MS: Mass found (M+, 314.0). Rt (min): 3.78; % Area: 97.78 (Max), 98.61 (254 nm).
HPLC—Rt (min): 3.75; % Area: 97.99 (Max), 98.66 (254 nm).
400 MHz, CDCl3: δ 7.77 (d, J=8.00 Hz, 1H), 7.73-7.70 (m, 1H), 7.61 (d, J=8.00 Hz, 1H), 7.43-7.37 (m, 1H), 7.21-7.16 (m, 1H), 6.64 (d, J=8.00 Hz, 1H), 4.22 (t, J=8.00 Hz, 2H), 3.97 (s, 3H), 3.30 (t, J=8.00 Hz, 2H), 2.67 (s, 3H).

[3-(6-Dimethylamino-pyridin-3-yl)-4,5-dihydro-pyrazol-1-yl]-(3-fluoro-phenyl)-methanone

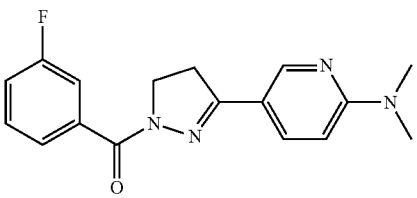 [SMILES: CN(C)c1ccc(C2=NN(C(=O)c3cccc(F)c3)CC2)cn1]

White solid; 60.38% Yield

LC-MS: Mass found (M+, 313.0). Rt (min): 2.50; % Area: 99.51 (Max), 99.73 (254 nm).

HPLC—Rt (min): 2.55; % Area: 99.37 (Max), 99.47 (254 nm).

400 MHz, CDCl3: δ 8.40-8.39 (m, 1H), 7.87-7.74 (m, 3H), 7.43-7.38 (m, 1H), 7.21-7.16 (m, 1H), 6.55 (d, J=12.00 Hz, 1H), 4.23 (t, J=12.00 Hz, 2H), 3.24 (t, J=12.00 Hz, 2H), 3.16 (s, 6H).

(3-Fluoro-phenyl)-[3-(1H-pyrrolo[2,3-b]pyridin-5-yl)-4,5-dihydro-pyrazol-1-yl]-methanone

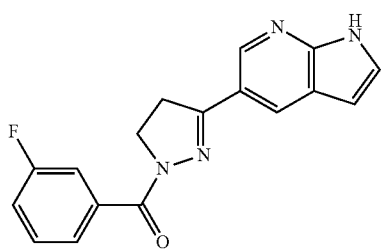 [SMILES: O=C(c1cccc(F)c1)N1CCC(c2cnc3[nH]ccc3c2)=N1]

Off white solid; 65.27% Yield

LC-MS: Mass found (M+, 309.0). Rt (min): 3.11; % Area: 96.77 (Max), 96.14 (254 nm).

HPLC—Rt (min): 3.10; % Area: 98.69 (Max), 99.09 (254 nm).

400 MHz, CDCl3: δ 8.71-0.00 (m, 1H), 8.27 (s, 1H), 7.85-7.83 (m, 1H), 7.79-7.76 (m, 1H), 7.48-7.42 (m, 1H), 7.39-7.38 (m, 1H), 7.24-7.20 (m, 1H), 6.60-6.59 (m, 1H), 4.32 (t, J=8.00 Hz, 2H), 3.40 (t, J=8.00 Hz, 2H).

[3-(6-Amino-pyridin-3-yl)-4,5-dihydro-pyrazol-1-yl]-(3-fluoro-phenyl)-methanone

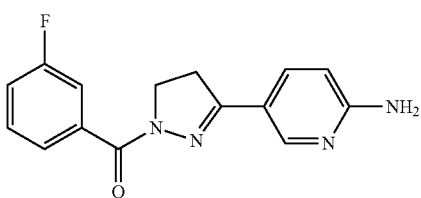 [SMILES: Nc1ccc(C2=NN(C(=O)c3cccc(F)c3)CC2)cn1]

Off white solid; 11.10% Yield

LC-MS: Mass found (M+, 285.0). Rt (min): 2.35; % Area: 99.45 (Max), 98.80 (254 nm).

HPLC—Rt (min): 2.33; % Area: 98.97 (Max), 98.92 (254 nm).

400 MHz, DMSO-d6: δ 8.19-8.18 (m, 1H), 7.72-7.66 (m, 2H), 7.63-7.61 (m, 1H), 7.54-7.49 (m, 1H), 7.39-7.33 (m, 1H), 6.55 (s, 2H), 6.48 (d, J=8.00 Hz, 1H), 4.05 (t, J=8.00 Hz, 2H), 3.25 (t, J=8.00 Hz, 2H).

(3-Fluoro-phenyl)-(3-pyrimidin-5-yl-4,5-dihydro-pyrazol-1-yl)-methanone

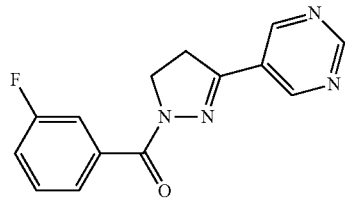 [SMILES: O=C(c1cccc(F)c1)N1CCC(c2cncnc2)=N1]

White Solid; 11.71% Yield

LC-MS: Mass found (M+, 271). Rt (min): 2.80; % Area: 95.20 (Max), 96.55 (254 nm).

HPLC—Rt (min): 2.81; % Area: 96.24 (Max), 94.46 (254 nm).

400 MHz, CDCl3: δ 9.26 (s, 1H), 9.04 (s, 2H), 7.76 (d, J=8.00 Hz, 1H), 7.70-7.66 (m, 1H), 7.47-7.42 (m, 1H), 7.28-7.22 (m, 1H), 4.35 (t, J=8.00 Hz, 2H), 3.33 (t, J=12.00 Hz, 2H).

(3-Fluoro-phenyl)-[3-(2-methoxy-pyrimidin-5-yl)-4,5-dihydro-pyrazol-1-yl]methanone

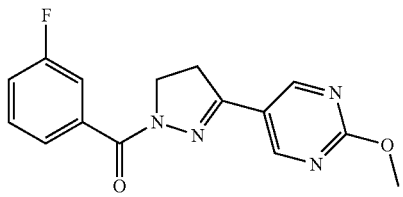 [SMILES: COc1ncc(C2=NN(C(=O)c3cccc(F)c3)CC2)cn1]

White solid; 40.79% Yield

LC-MS: Mass found (M+, 301.2). Rt (min): 2.80; % Area: 98.80 (Max), 98.32 (254 nm).

HPLC—Rt (min): 3.34; % Area: 99.20 (Max), 98.82 (254 nm).

400 MHz, CDCl3: δ 8.83 (s, 2H), 7.76 (d, J=8.00 Hz, 1H), 7.70-7.67 (m, 1H), 7.45-7.40 (m, 1H), 7.24-7.19 (m, 1H), 4.30 (t, J=12.00 Hz, 2H), 4.08 (s, 3H), 3.28 (t, J=12.00 Hz, 2H).

(3-Fluoro-phenyl)-[3-(2-methyl-pyrimidin-5-yl)-4,5-dihydro-pyrazol-1-yl]-methanone

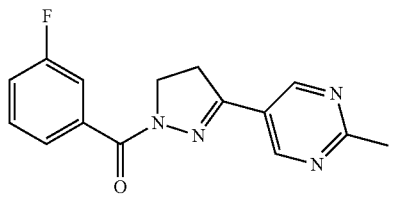 [SMILES: Cc1ncc(C2=NN(C(=O)c3cccc(F)c3)CC2)cn1]

White Solid; 14.21% Yield

LC-MS: Mass found (M+, 285.0). Rt (min): 4.19; % Area: 99.30 (Max), 98.66 (254 nm).

HPLC—Rt (min): 4.33; % Area: 98.83 (Max), 97.31 (254 nm).

400 MHz, CDCl3: δ 8.92 (s, 2H), 7.76 (d, J=8.00 Hz, 1H), 7.71-7.67 (m, 1H), 7.46-7.40 (m, 1H), 7.25-7.20 (m, 1H), 4.32 (t, J=12.00 Hz, 2H), 3.31 (t, J=8.00 Hz, 2H), 2.80 (s, 3H).

[3-(2-Amino-pyrimidin-5-yl)-4,5-dihydro-pyrazol-1-yl]-(3-fluoro-phenyl)-methanone

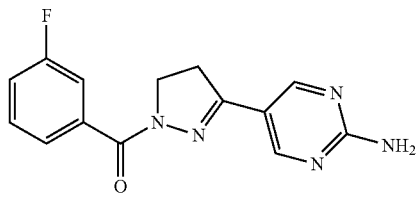 [SMILES: Nc1ncc(C2=NN(C(=O)c3cccc(F)c3)CC2)cn1]

Yellow solid; 14.88% Yield

LC-MS: Mass found (M+, 286.2). Rt (min): 2.48; % Area: 99.76 (Max), 97.20 (254 nm).

HPLC—Rt (min): 2.43; % Area: 98.82 (Max), 96.54 (254 nm).

400 MHz, CDCl3: δ 8.61 (s, 2H), 7.76 (d, J=8.00 Hz, 1H), 7.69 (d, J=8.00 Hz, 1H), 7.44-7.39 (m, 1H), 7.23-7.18 (m, 1H), 5.34-5.30 (m, 2H), 4.26 (t, J=12.00 Hz, 2H), 3.23 (t, J=12.00 Hz, 2H).

[3-(2-Dimethylamino-pyrimidin-5-yl)-4,5-dihydro-pyrazol-1-yl]-(3-fluoro-phenyl)-methanone

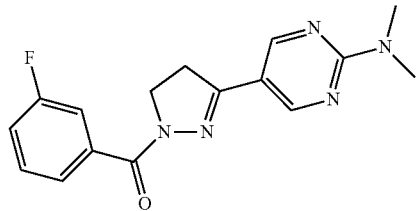 [SMILES: CN(C)c1ncc(C2=NN(C(=O)c3cccc(F)c3)CC2)cn1]

White Solid; 7.79% Yield

LC-MS: Mass found (M+, 314.3). Rt (min): 3.49; % Area: 99.52 (Max), 98.83 (254 nm).

HPLC—Rt (min): 4.62; % Area: 99.60 (Max), 97.57 (254 nm).

400 MHz, CDCl3: δ 8.63 (s, 2H), 7.79 (d, J=8.00 Hz, 1H), 7.73 (d, J=12.00 Hz, 1H), 7.42-7.37 (m, 1H), 7.22-7.17 (m, 1H), 4.24 (t, J=12.00 Hz, 2H), 3.26 (s, 6H), 3.22 (t, J=8.00 Hz, 2H).

(3-Fluoro-phenyl)-(3-thiophen-3-yl-4,5-dihydro-pyrazol-1-yl)-methanone

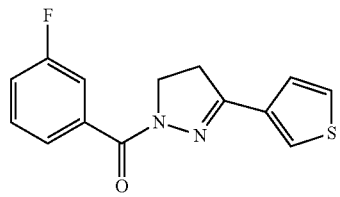 [SMILES: O=C(c1cccc(F)c1)N1CCC(c2ccsc2)=N1]

Brown solid; 14.46% Yield

LC-MS: Mass found (M+, 275.0). Rt (min): 4.27; % Area: 98.69 (Max), 99.55 (254 nm).

HPLC—Rt (min): 4.27; % Area: 97.97 (Max), 98.53 (254 nm).

400 MHz, DMSO-d6: δ 7.98-7.97 (m, 1H), 7.71 (d, J=8.00 Hz, 1H), 7.65-7.61 (m, 2H), 7.55-7.49 (m, 1H), 7.40-7.35 (m, 2H), 4.08 (t, J=8.00 Hz, 2H), 3.32-3.27 (m, 2H).

(3-Benzofuran-2-yl-4,5-dihydro-pyrazol-1-yl)-(3-fluoro-phenyl)-methanone

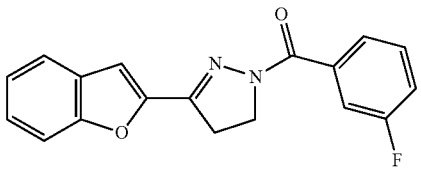 [SMILES: O=C(c1cccc(F)c1)N1CCC(c2cc3ccccc3o2)=N1]

White solid; 29.06% Yield

LC-MS: Mass found (M+, 309.0). Rt (min): 4.70; % Area: 98.71 (Max), 98.00 (220 nm).

HPLC—Rt (min): 4.72; % Area: 98.56 (Max), 98.68 (220 nm).

400 MHz, CDCl3: δ 7.83 (d, J=4.00 Hz, 1H), 7.77-7.74 (m, 1H), 7.63 (d, J=8.00 Hz, 1H), 7.56 (d, J=8.00 Hz, 1H), 7.48-7.37 (m, 2H), 7.31-7.29 (m, 1H), 7.25-7.21 (m, 1H), 7.17-7.10 (m, 1H), 4.31 (t, J=12.00 Hz, 2H), 3.36 (t, J=12.00 Hz, 2H).

(3-Fluoro-phenyl)-[3-(5-phenyl-thiophen-2-yl)-4,5-dihydro-pyrazol-1-yl]-methanone

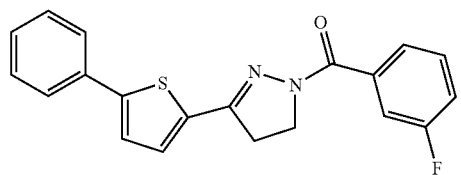 [SMILES: O=C(c1cccc(F)c1)N1CCC(c2ccc(-c3ccccc3)s2)=N1]

Yellow solid; 48.86% Yield

LC-MS: Mass found (M+, 351.0). Rt (min): 5.24; % Area: 98.94 (Max), 98.59 (254 nm).

HPLC—Rt (min): 5.26; % Area: 99.31 (Max), 97.80 (254 nm).

400 MHz, CDCl3: δ 7.83 (d, J=4.00 Hz, 1H), 7.76 (d, J=8.00 Hz, 1H), 7.65-7.63 (m, 2H), 7.47-7.39 (m, 3H), 7.36-7.32 (m, 1H), 7.30-7.29 (m, 1H), 7.27-7.26 (m, 1H), 7.24-7.19 (m, 1H), 4.29 (t, J=12.00 Hz, 2H), 3.31 (t, J=12.00 Hz, 2H).

(4,5-Dihydro-1'H-[3,3']bipyrazolyl-1-yl)-(3-fluoro-phenyl)-methanone

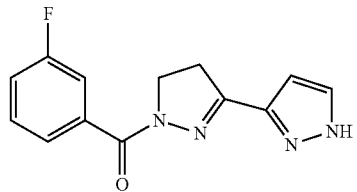 [SMILES: O=C(c1cccc(F)c1)N1CCC(c2cc[nH]n2)=N1]

White Solid; 69.02% Yield
LC-MS: Mass found (M+, 259.0). Rt (min): 3.30; % Area: 94.11 (Max), 96.78 (254 nm).
HPLC—Rt (min): 3.36; % Area: 96.98 (Max), 97.91 (254 nm).
400 MHz, CDCl3: δ 8.12 (d, J=4.00 Hz, 1H), 7.73-7.71 (m, 2H), 7.69-7.64 (m, 1H), 7.44-7.39 (m, 1H), 7.23-7.18 (m, 1H), 6.49-6.47 (m, 1H), 4.36 (t, J=12.00 Hz, 2H), 3.59 (t, J=8.00 Hz, 2H).

[3-(3,5-Dimethyl-isoxazol-4-yl)-4,5-dihydro-pyrazol-1-yl]-(3-fluoro-phenyl)-methanone

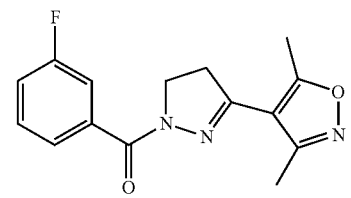 [SMILES: Cc1noc(C)c1C1=NN(C(=O)c2cccc(F)c2)CC1]

Off white solid; 26.69% Yield
LC-MS: Mass found (M+, 288.0). Rt (min): 3.82; % Area: 98.67 (Max), 99.34 (254 nm).
HPLC—Rt (min): 3.85; % Area: 99.67 (Max), 99.65 (254 nm).
400 MHz, CDCl3: δ 7.72-7.70 (m, 1H), 7.68-7.64 (m, 1H), 7.43-7.37 (m, 1H), 7.21-7.16 (m, 1H), 4.22 (t, J=12.00 Hz, 2H), 3.26 (t, J=12.00 Hz, 2H), 2.58 (s, 3H), 2.37 (s, 3H).

(1'-Benzyl-4,5-dihydro-1'H-[3,4']bipyrazolyl-1-yl)-(3-fluoro-phenyl)-methanone

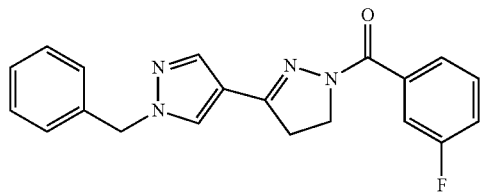 [SMILES: O=C(c1cccc(F)c1)N1CCC(c2cnn(Cc3ccccc3)c2)=N1]

Off white solid; 35.08% Yield
LC-MS: Mass found (M+, 349.0). Rt (min): 4.20; % Area: 98.60 (Max), 98.61 (254 nm).
HPLC—Rt (min): 4.31; % Area: 99.31 (Max), 98.84 (254 nm).
400 MHz, CDCl3: δ 8.85-8.81 (m, 1H), 8.80-8.72 (m, 1H), 8.71-8.65 (m, 2H), 7.42-7.33 (m, 4H), 7.27-7.23 (m, 2H), 7.20-7.14 (m, 1H), 5.33 (s, 2H), 4.18 (t, J=8.00 Hz, 2H), 3.14 (t, J=12.00 Hz, 2H).

(3-Fluoro-phenyl)-[3-(5-methoxy-benzofuran-2-yl)-4,5-dihydro-pyrazol-1-yl]-methanone

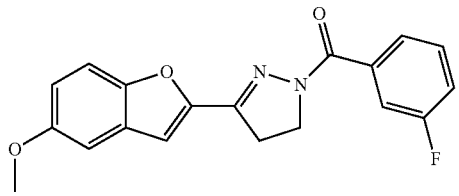 [SMILES: COc1ccc2oc(C3=NN(C(=O)c4cccc(F)c4)CC3)cc2c1]

Off white solid; 36.53% Yield
LC-MS: Mass found (M+, 339.0). Rt (min): 4.64; % Area: 97.45 (Max), 96.85 (254 nm).
HPLC—Rt (min): 4.66; % Area: 97.47 (Max), 96.13 (254 nm).
400 MHz, CDCl3: δ 7.82 (d, J=8.00 Hz, 1H), 7.76-7.73 (m, 1H), 7.47-7.42 (m, 2H), 7.25-7.20 (m, 1H), 7.07-7.04 (m, 2H), 7.00 (dd, J=8.00, 4.00 Hz, 1H), 4.30 (t, J=8.00 Hz, 2H), 3.86 (s, 3H), 3.34 (t, J=12.00 Hz, 2H).

(4,5-Dihydro-2'H-[3,3']bipyrazolyl-1-yl)-(3-fluoro-phenyl)-methanone

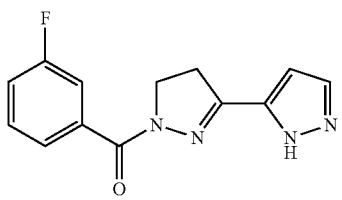 [SMILES: O=C(c1cccc(F)c1)N1CCC(c2ccn[nH]2)=N1]

Off white solid; 85.33% Yield
LC-MS: Mass found (M+, 259.0). Rt (min): 3.31; % Area: 97.42 (Max), 96.70 (254 nm).
HPLC—Rt (min): 3.36; % Area: 97.17 (Max), 95.99 (254 nm).
400 MHz, CDCl3: δ 8.12-8.11 (m, 1H), 7.73-7.71 (m, 2H), 7.65 (d, J=8.00 Hz, 1H), 7.45-7.39 (m, 1H), 7.23-7.18 (m, 1H), 4.36 (t, J=12.00 Hz, 2H), 3.59 (t, J=8.00 Hz, 2H).

(4,5-Dihydro-1'H-[3,4']bipyrazolyl-1-yl)-(3-fluoro-phenyl)-methanone

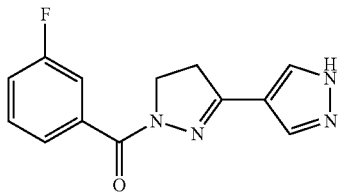 [SMILES: O=C(c1cccc(F)c1)N1CCC(c2cn[nH]c2)=N1]

White solid; 18.88% Yield
LC-MS: Mass found (M+, 259). Rt (min): 3.35; % Area: 96.38 (Max), 92.65 (220 nm).

HPLC—Rt (min): 3.34; % Area: 99.36 (Max), 99.07 (254 nm).

400 MHz, CDCl3: δ 8.12-8.11 (m, 1H), 7.73-7.71 (m, 2H), 7.65 (d, J=8.00 Hz, 1H), 7.45-7.39 (m, 1H), 7.23-7.18 (m, 1H), 6.49-6.47 (m, 1H), 4.36 (t, J=12.00 Hz, 2H), 3.59 (t, J=8.00 Hz, 2H).

(3-Fluoro-phenyl)-(1'-pyridin-4-ylmethyl-4,5-dihydro-1'H-[3,4']bipyrazolyl-1-yl)-methanone

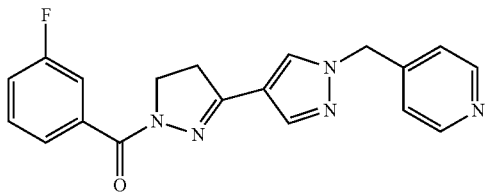 [SMILES: O=C(c1cccc(F)c1)N1CCC(c2cnn(Cc3ccncc3)c2)=N1]

Off white solid; 23.01% Yield

LC-MS: Mass found (M+, 350.0). Rt (min): 2.33; % Area: 98.97 (Max), 99.03 (254 nm).

HPLC—Rt (min): 2.46; % Area: 98.16 (Max), 98.27 (254 nm).

400 MHz, CDCl3: δ 8.54 (brs, 2H), 7.79-7.76 (m, 2H), 7.69-7.67 (m, 1H), 7.63-7.61 (m, 1H), 7.36-7.27 (m, 1H), 7.13-7.08 (m, 1H), 7.03-7.02 (m, 2H), 5.31 (s, 2H), 4.13 (t, J=8.00 Hz, 2H), 3.14-3.04 (m, 2H).

Example 10: $EC_{50}$ of Cyclic AMP Production in CHO FSHR Cells+$EC_{20}$ FSH (Assay A)

2500 Cho-FSHR-LUC-1-1-43 cells were plated per well in 5 µl of phenol red free DMEM/F12+1% FBS. Cells were plated in 384 well, solid white low volume plates (Greiner 784075) by Multidrop. Cells were assayed by adding 100 µl of 2× $EC_{20}$ FSH/IBMX in DMEM/F12+0.1% BSA) by Multidrop to 2 µl of test compound stamped in 384 well plates (compounds are diluted 1:50). The final FSH concentration was 0.265 pM, and the final IBMX concentration was 200 µM. The compound plate map was as follows: Column 1: 2 µl of DMSO; Column 2: 2 µl of DMSO; Columns 3-12 and 13-24: 2 µl of test compound, diluted 1:4 in 100% DMSO, or 2 µl of FSH, diluted 1:4 in DMEM/F12+0.1% BSA. The starting concentration for FSH was 50 nM (final concentration was 0.5 nM). Furthermore, Column 23 contained 2 µl of $EC_{100}$ FSH reference (100×) (diluted in DMEM/F12+0.1% BSA) at a final concentration of 0.5 nM, and Column 24 contained 2 µl of 1 mM AS707664/2 reference compound 2.5 µl of compound +$EC_{20}$ FSH mixture were transferred to cell plates (1:2 dilution into 5 µl of cell media). The plates were incubated at 37° C. for 1 h. 10 µl of mixed HTRF (CisBio #62AM4PEC) reagents were added per well and incubated at room temperature for 1 h. The plates were read on Envision using the cAMP HTRF—low volume 384 well protocol. The readout was the calculated fluorescence ratio (665 nm/620 nm). Results are given in Table 1.

Example 11: Rat Granulosa $EC_{50}$ FSH (Assay B)

The assay was performed pursuant to the teaching of Yanofsky et al. (2006) Allosteric activation of the follicle-stimulating hormone (FSH) receptor by selective, nonpeptide agonists. JBC 281(19): 13226-13233, which is incorporated by reference in the disclosure of the invention. Results are given in Table 1.

Example 12: Pharmaceutical Preparations (A) Injection vials: A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

The invention claimed is:

1. A method of treating fertility disorders, wherein an effective amount of at least one compound of formula I, or a physiologically acceptable salt thereof, is administered to a mammal in need of such treatment:

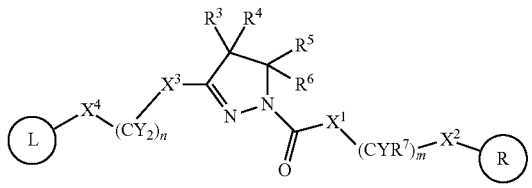

(I)

wherein

R, L each independently denote $Ar^1$ or $Het^1$;

$R^1$ denotes Hal, A, —$(CY_2)_p$—OY, —$(CY_2)_p$—$NY_2$, COOY, $CONY_2$, NHCOY, CN, $SO_2Y$, -E-$(CY_2)_p$—$Ar^2$, -E-$(CY_2)_p$-$Het^1$ or -E-$(CY_2)_p$-$Het^3$;

$R^2$ denotes Hal, A, —$(CY_2)_p$—OY, —$(CY_2)_p$—$NY_2$, COY, COOY, $CONY_2$, —CONY—Cyc, —O-Cyc, $NO_2$, CN, SY, SOY, $SO_2Y$, $SO_2NY_2$, $NHSO_2Y$, alkenyl or -E-$(CY_2)_p$—$Ar^2$;

$R^3$, $R^4$, $R^5$, $R^6$ denote independently from one another H, A or $Ar^2$;

$R^7$ denotes Y, OY or $NY_2$;

$X^1$, $X^2$, $X^3$, $X^4$ denote independently from one another a single bond,

E denotes —C≡C—, $SO_2$, —$SO_2$—NY—, O, NY or a single bond;

Y denotes H or A;

A denotes unbranched or branched alkyl having 1-10 C atoms, in which 1-7 H atoms can be replaced by Hal;

Cyc denotes cycloalkyl having 3-7 C atoms,
  in which 1-4 H atoms can be replaced independently from one another by Hal or A;

$Ar^1$ denotes a saturated, unsaturated or aromatic, mono- or bicyclic carbocycle having 3-10 C atoms,
  which can be substituted by at least one substituent selected from the group of $R^1$, $R^2$ and —C≡C—C$(A)_2$OH, and/or which can be fused to Cyc, $Het^1$ or $Het^3$;

$Ar^2$ denotes an aromatic, mono- or bicyclic carbocycle having 6-10 C atoms, which can be substituted by at least one substituent selected from the group of Hal, A and —$(CY_2)_p$—OY;

$Het^1$ denotes an unsaturated or aromatic mono- or bicyclic heterocycle having 3-8 C atoms and 1-4 N, O and/or S atoms,
  which can be substituted by at least one substituent selected from the group of Hal, A, —$(CY_2)_p$—OY, —(CY$_2$)$_p$—NY$_2$, —(CY$_2$)$_p$—Ar$^2$, —CO—Ar$^2$, SO$_2$—Ar$^2$, —(CY$_2$)$_p$-Het$^2$, Het$^3$ and CN;

Het$^2$ denotes an aromatic monocyclic heterocycle having 5-7 C atoms and 1-3 N atoms,
 which can be substituted by at least one substituent selected from the group of Hal, A and —(CY$_2$)$_p$—OY;

Het$^3$ denotes a saturated monocyclic heterocycle having 3-7 C atoms and 1-4 N, O and/or S atoms,
 which can be substituted by at least one substituent selected from the group of Hal, A, —(CY$_2$)$_p$—OY, —(CY$_2$)$_p$—NY$_2$, COOY, COY, —CONY$_2$, =O and CN;

Hal denotes F, Cl, Br or I;
m is 0;
n is 0; and
p is 0, 1, 2, 3 or 4;

or
 wherein
 R, L each independently denote Ar$^1$ or Het$^1$;
 R$^1$ denotes Hal, A, —(CY$_2$)$_p$—OY, —(CY$_2$)$_p$—NY$_2$, COOY, CONY$_2$, NHCOY, CN, SO$_2$Y, -E-(CY$_2$)$_p$—Ar$^2$, -E-(CY$_2$)$_p$-Het$^1$ or -E-(CY$_2$)$_p$-Het$^3$;
 R$^2$ denotes Hal, A, —(CY$_2$)$_p$—OY, —(CY$_2$)$_p$—NY$_2$, COY, COOY, CONY$_2$, —CONY—Cyc, —O-Cyc, NO$_2$, CN, SY, SOY, SO$_2$Y, SO$_2$NY$_2$, NHSO$_2$Y, alkenyl or -E-(CY$_2$)$_p$—Ar$^2$;
 R$^3$, R$^4$, R$^5$, R$^6$ denote independently from one another H, A or Ar$^2$;
 R$^7$ denotes Y, OY or NY$_2$;
 X$^1$ denotes a single bond;
 X$^2$ denotes O or a single bond;
 X$^3$ denotes O, NY or a single bond;
 X$^4$ denotes a single bond;
  with the proviso that m denotes 0 if X$^1$ and X$^2$ denote a single bond;
 E denotes —C≡C—, SO$_2$, —SO$_2$—NY—, O, NY or a single bond;
 Y denotes H or A;
 A denotes unbranched or branched alkyl having 1-10 C atoms, in which 1-7 H atoms can be replaced by Hal;
 Cyc denotes cycloalkyl having 3-7 C atoms,
  in which 1-4 H atoms can be replaced independently from one another by Hal or A;
 Ar$^1$ denotes a saturated, unsaturated or aromatic, mono- or bicyclic carbocycle having 3-10 C atoms,
  which can be substituted by at least one substituent selected from the group of R$^1$, R$^2$ and —C≡C—C(A)$_2$OH, and/or which can be fused to Cyc, Het$^1$ or Het$^3$;
 Ar$^2$ denotes an aromatic, mono- or bicyclic carbocycle having 6-10 C atoms, which can be substituted by at least one substituent selected from the group of Hal, A and —(CY$_2$)$_p$—OY;
 Het$^1$ denotes an unsaturated or aromatic mono- or bicyclic heterocycle having 3-8 C atoms and 1-4 N, O and/or S atoms,
  which can be substituted by at least one substituent selected from the group of Hal, A, —(CY$_2$)$_p$—OY, —(CY$_2$)$_p$—NY$_2$, —(CY$_2$)$_p$—Ar$^2$, —CO—Ar$^2$, SO$_2$—Ar$^2$, —(CY$_2$)$_p$-Het$^2$, Het$^3$ and CN;
 Het$^2$ denotes an aromatic monocyclic heterocycle having 5-7 C atoms and 1-3 N atoms,
  which can be substituted by at least one substituent selected from the group of Hal, A and —(CY$_2$)$_p$—OY;
 Het$^3$ denotes a saturated monocyclic heterocycle having 3-7 C atoms and 1-4 N, O and/or S atoms,
  which can be substituted by at least one substituent selected from the group of Hal, A, —(CY$_2$)$_p$—OY, —(CY$_2$)$_p$—NY$_2$, COOY, COY, —CONY$_2$, =O and CN;

Hal denotes F, Cl, Br or I; and
m is 0 or 1;
n is 0 or 1;
p is 0, 1, 2, 3 or 4
wherein at least one of m or n is not 0.

2. The method of claim 1, wherein the compound is selected from:

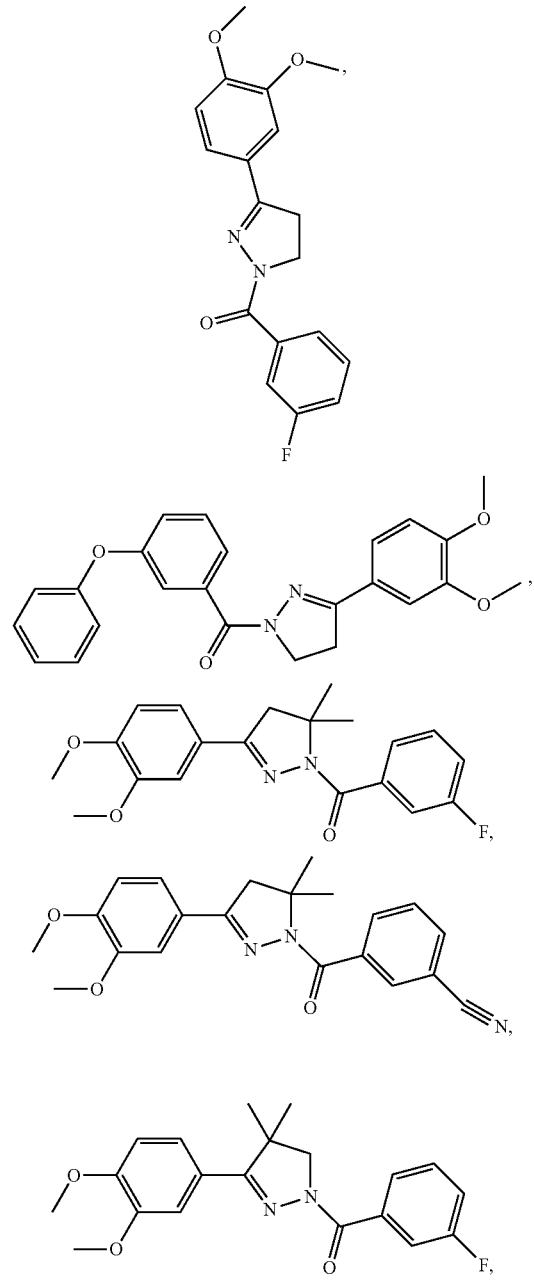

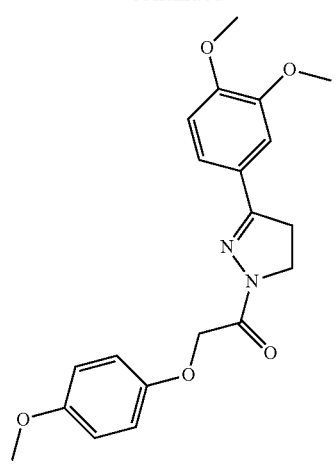
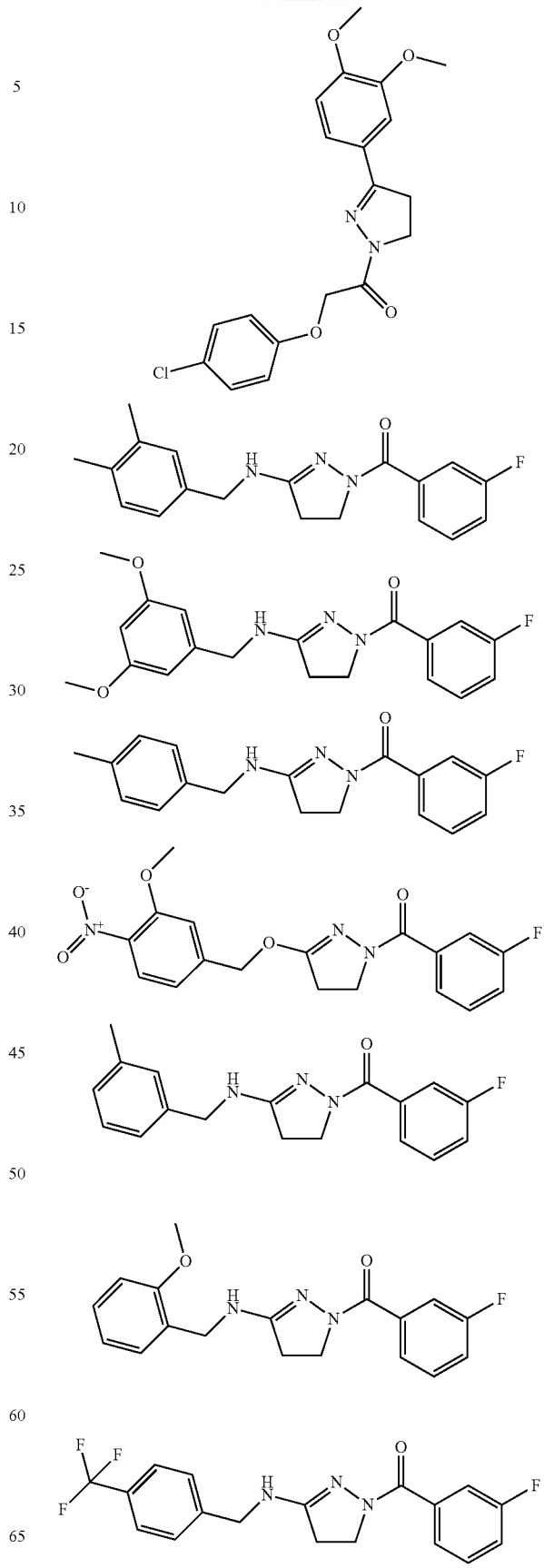

-continued
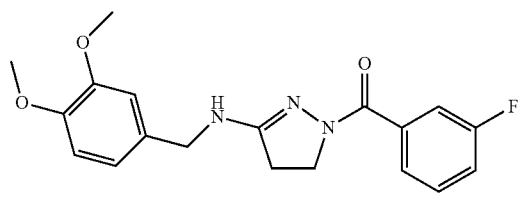
or a physiologically acceptable salt thereof.
3. A method for in-vitro fertilization comprising the steps of:
   (a) treating a mammal according to the method of claim 1,
   (b) collecting ova from said mammal,
   (c) fertilizing said ova, and
   (d) implanting said fertilized ova into a host mammal.
4. The method of claim 3, wherein the compound is selected from:
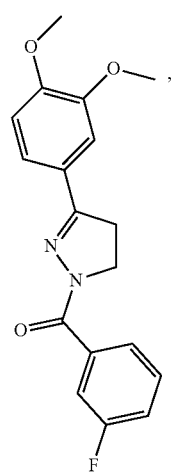
-continued
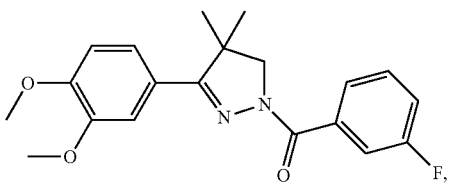
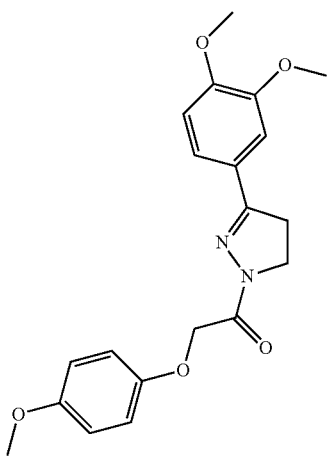
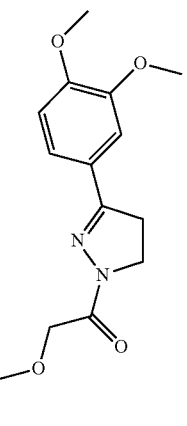
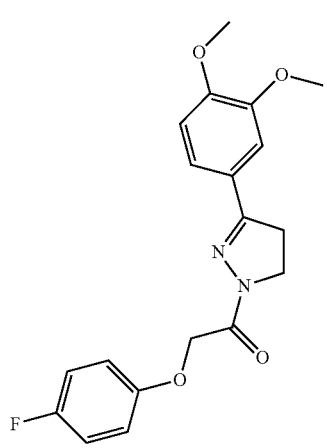

-continued
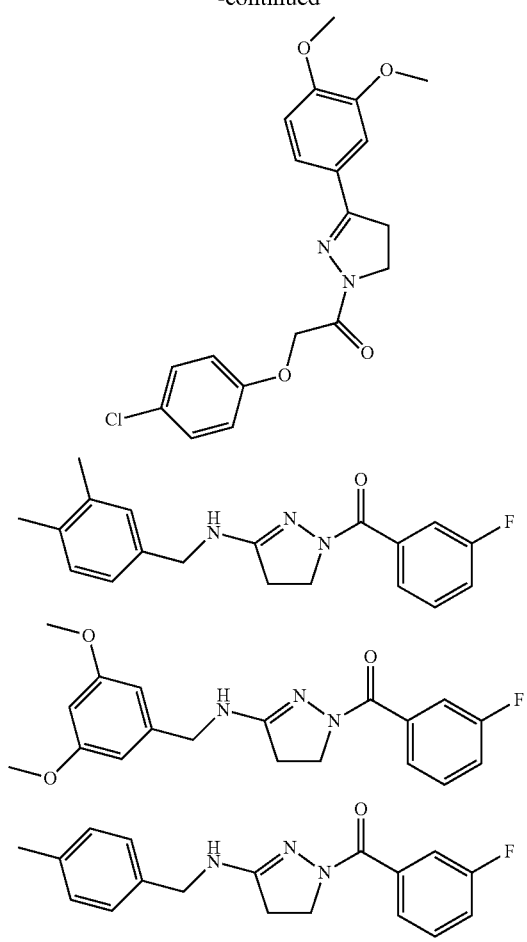
-continued
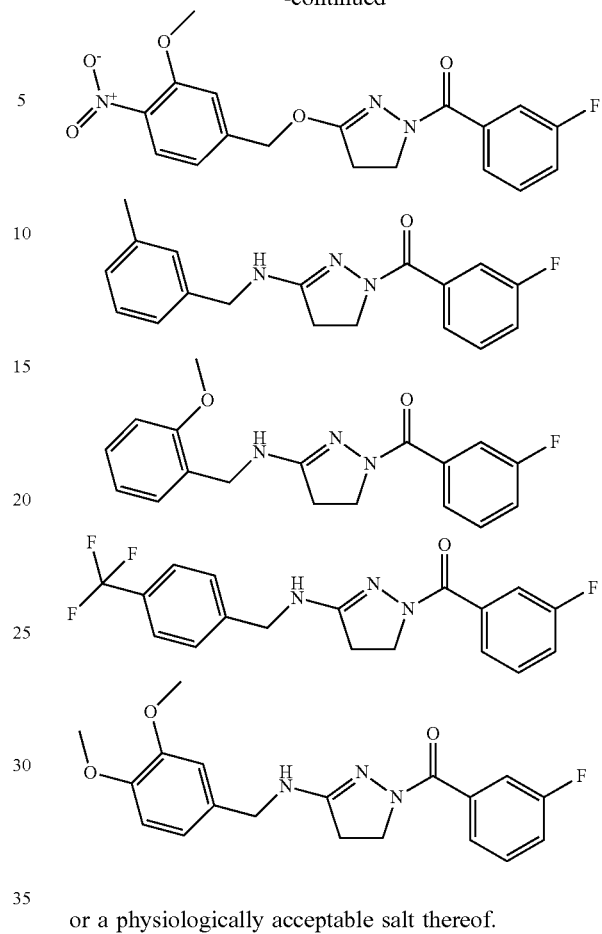
or a physiologically acceptable salt thereof.
* * * * *